United States Patent
Singh et al.

(10) Patent No.: US 9,169,249 B2
(45) Date of Patent: Oct. 27, 2015

(54) PROTEIN KINASE C INHIBITORS AND USES THEREOF

(71) Applicant: Rigel Pharmaceuticals, Inc., South San Francisco, CA (US)

(72) Inventors: Rajinder Singh, Belmont, CA (US); Matthew Duncton, San Bruno, CA (US); Jing Zhang, Mercer Island, WA (US); Salvador Alvarez, Fremont, CA (US); Kin Tso, San Francisco, CA (US); Sacha Holland, San Francisco, CA (US); Rose Yen, San Francisco, CA (US); Rao Kolluri, Foster City, CA (US); Thilo Heckrodt, San Francisco, CA (US); Yan Chen, Foster City, CA (US); Esteban Masuda, Menlo Park, CA (US); Hui Li, Santa Clara, CA (US); Donald G. Payan, Hillsborough, CA (US)

(73) Assignee: Rigel Pharmaceuticals, Inc., South San Francisco, CA (US)

( * ) Notice: Subject to any disclaimer, the term of this patent is extended or adjusted under 35 U.S.C. 154(b) by 0 days.

(21) Appl. No.: 14/209,997

(22) Filed: Mar. 13, 2014

(65) Prior Publication Data
US 2014/0275055 A1    Sep. 18, 2014

Related U.S. Application Data

(60) Provisional application No. 61/783,647, filed on Mar. 14, 2013.

(51) Int. Cl.
*C07D 471/04* (2006.01)
*C07D 498/04* (2006.01)

(52) U.S. Cl.
CPC ............ *C07D 471/04* (2013.01); *C07D 498/04* (2013.01)

(58) Field of Classification Search
CPC .................... C07D 471/04; C07D 498/04
See application file for complete search history.

(56) References Cited

U.S. PATENT DOCUMENTS

| | | | |
|---|---|---|---|
| 5,843,935 A * | 12/1998 | Heath et al. ............... | 514/183 |
| 6,235,746 B1 | 5/2001 | Davis et al. | |
| 2005/0054701 A1 | 3/2005 | Wallace et al. | |
| 2010/0130501 A1 | 5/2010 | Li et al. | |
| 2010/0204208 A1 | 8/2010 | Singh et al. | |
| 2011/0130415 A1 | 6/2011 | Singh et al. | |
| 2012/0022092 A1 | 1/2012 | Holland et al. | |
| 2012/0028923 A1 | 2/2012 | Li et al. | |

FOREIGN PATENT DOCUMENTS

| | | |
|---|---|---|
| WO | 2010083207 | 7/2010 |
| WO | 2010090875 | 8/2010 |
| WO | 2011068898 | 9/2011 |
| WO | 2012012619 | 1/2012 |
| WO | 2013152198 | 10/2013 |

OTHER PUBLICATIONS

Fellah et al., "Total Synthesis of Indolizidine," Eur. J. Org. Chem, 463-465 (2012).
King, et al. "Synthesis of quinolizidines and indolizidines via an intramolecular Mannich reaction," J. Chem. Soc., Perkin Trans. 1:447-453 (1986).
Strong et al., "In Vitro Stimulation of Murine Spleen Cells Usings a Microculture System and a Multiple Automated Sample Harvester," J. Immunol. Methods, 2:279-291 (1973).

* cited by examiner

*Primary Examiner* — Gina Justice
(74) *Attorney, Agent, or Firm* — Rudy J. Ng; Carol L. Francis; Bozicevic, Field, Francis LLP

(57) ABSTRACT

This disclosure concerns compounds which are useful as inhibitors of protein kinase C (PKC) and are thus useful for treating a variety of diseases and disorders that are mediated or sustained through the activity of PKC. This disclosure also relates to pharmaceutical compositions comprising these compounds, methods of using these compounds in the treatment of various diseases and disorders, processes for preparing these compounds and intermediates useful in these processes.

17 Claims, No Drawings

SEQUENCE LISTING

<160> NUMBER OF SEQ ID NOS: 1

<210> SEQ ID NO 1
<211> LENGTH: 13
<212> TYPE: PRT
<213> ORGANISM: Artificial Sequence
<220> FEATURE:
<223> OTHER INFORMATION: Synthetic polypeptide

<400> SEQUENCE: 1

Arg Phe Ala Arg Lys Gly Ser Leu Arg Gln Lys Asn Val
1               5                   10

PROTEIN KINASE C INHIBITORS AND USES THEREOF

CROSS-REFERENCE TO RELATED APPLICATION

Pursuant to 35 U.S.C. §119(e), this application claims priority to the filing date of U.S. Provisional Application No. 61/783,647, filed Mar. 14, 2013, the disclosure of which is incorporated herein by reference.

BACKGROUND

Protein kinase C ("PKC") is a key enzyme in signal transduction involved in a variety of cellular functions, including cell growth, regulation of gene expression, and ion channel activity. The PKC family of isozymes includes at least 11 different protein kinases that can be divided into at least three subfamilies based on their homology and sensitivity to activators. Each isozyme includes a number of homologous ("conserved" or "C") domains interspersed with isozyme-unique ("variable" or "V") domains. Members of the "classical" or "cPKC" subfamily, PKC α, $β_i$, $β_{ii}$ and γ, contain four homologous domains (C1, C2, C3 and C4) and require calcium, phosphatidylserine, and diacylglycerol or phorbol esters for activation. Members of the "novel" or "nPKC" subfamily, PKC δ, ε, η and θ, lack the C2 homologous domain and do not require calcium for activation. Finally, members of the "atypical" or "αPKC" subfamily, PKC ζ and λ/i, lack both the C2 and one-half of the C1 homologous domains and are insensitive to diacylglycerol, phorbol esters and calcium.

SUMMARY

This disclosure concerns compounds which are useful as inhibitors of protein kinase C (PKC) and are thus useful for treating a variety of diseases and disorders that are mediated or sustained through the activity of PKC. This disclosure also relates to pharmaceutical compositions comprising these compounds, methods of using these compounds in the treatment of various diseases and disorders, processes for preparing these compounds and intermediates useful in these processes.

Exemplary chemical structures are provided throughout the disclosure. By way of example, such compounds are represented by the following formula (I):

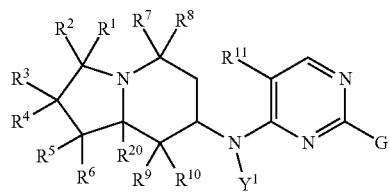

wherein $R^1$, $R^2$, $R^3$, $R^4$, $R^5$, and $R^6$ are independently selected from hydrogen, alkyl, substituted alkyl, alkoxy, substituted alkoxy, acyl, acylamino, acyloxy, amino, substituted amino, aminoacyl, aminoacyloxy, oxyaminoacyl, azido, cyano, halogen, hydroxyl, carboxyl, carboxylalkyl, thiol, thioalkoxy, substituted thioalkoxy, aryl, aryloxy, hydroxyamino, alkoxyamino, nitro, —SO-alkyl, —SO-substituted alkyl, —SO-aryl, —SO-heteroaryl, —$SO_2$-alkyl, —$SO_2$-substituted alkyl, —$SO_2$-aryl and —$SO_2$-heteroaryl; or $R^1$ and $R^2$ together form an oxo group; or $R^3$ and $R^4$ together form an oxo group; or $R^5$ and $R^6$ together form an oxo group;

$R^7$, $R^8$, $R^9$, and $R^{10}$ are independently selected from hydrogen, alkyl, substituted alkyl, alkoxy, substituted alkoxy, acyl, acylamino, acyloxy, amino, substituted amino, aminoacyl, aminoacyloxy, oxyaminoacyl, azido, cyano, halogen, hydroxyl, carboxyl, carboxylalkyl, thiol, thioalkoxy, substituted thioalkoxy, aryl, aryloxy, hydroxyamino, alkoxyamino, nitro, —SO-alkyl, —SO-substituted alkyl, —SO-aryl, —SO-heteroaryl, —$SO_2$-alkyl, —$SO_2$-substituted alkyl, —$SO_2$-aryl and —$SO_2$-heteroaryl; or $R^7$ and $R^8$ together form an oxo group; or $R^9$ and $R^{10}$ together form an oxo group;

$R^{11}$ is selected from alkyl, substituted alkyl, hydroxy, alkoxy, substituted alkoxy, amino, substituted amino, carboxyl, carboxyl ester, cyano, halogen, acyl, aminoacyl, nitro, alkenyl, substituted alkenyl, alkynyl, and substituted alkynyl;

$R^{20}$ is selected from hydrogen, alkyl, and substituted alkyl;

G is halogen or —$NY^2Ar^1$;

$Y^1$ and $Y^2$ are independently selected from hydrogen and alkyl; and $Ar^1$ is selected from aryl, substituted aryl, heteroaryl, and substituted heteroaryl;

or a salt or stereoisomer thereof.

DETAILED DESCRIPTION

This disclosure concerns compounds which are useful as inhibitors of protein kinase C (PKC) and are thus useful for treating a variety of diseases and disorders that are mediated or sustained through the activity of PKC. This disclosure also relates to pharmaceutical compositions comprising these compounds, methods of using these compounds in the treatment of various diseases and disorders, processes for preparing these compounds and intermediates useful in these processes.

Before the present invention is further described, it is to be understood that this invention is not limited to particular embodiments described, as such may, of course, vary. It is also to be understood that the terminology used herein is for the purpose of describing particular embodiments only, and is not intended to be limiting, since the scope of the present invention will be limited only by the appended claims.

It must be noted that as used herein and in the appended claims, the singular forms "a," "an," and "the" include plural referents unless the context clearly dictates otherwise. It is further noted that the claims may be drafted to exclude any optional element. As such, this statement is intended to serve as antecedent basis for use of such exclusive terminology as "solely," "only" and the like in connection with the recitation of claim elements, or use of a "negative" limitation.

Where a range of values is provided, it is understood that each intervening value, to the tenth of the unit of the lower limit unless the context clearly dictates otherwise, between the upper and lower limit of that range and any other stated or intervening value in that stated range, is specifically contemplated. The upper and lower limits of these smaller ranges may independently be included in the smaller ranges, and are also encompassed within the invention, subject to any specifically excluded limit in the stated range. Where the stated range includes one or both of the limits, ranges excluding either or both of those included limits are also included in the invention.

The publications discussed herein are provided solely for their disclosure prior to the filing date of the present application. Nothing herein is to be construed as an admission that the present invention is not entitled to antedate such publication by virtue of prior invention. Further, the dates of publication provided may be different from the actual publication dates which may need to be independently confirmed.

Unless defined otherwise, all technical and scientific terms used herein have the same meaning as commonly understood by one of ordinary skill in the art to which this invention belongs. Although any methods and materials similar or equivalent to those described herein can also be used in the practice or testing of the present invention, the preferred methods and materials are now described. All publications mentioned herein are incorporated herein by reference to disclose and describe the methods and/or materials in connection with which the publications are cited.

Except as otherwise noted, the methods and techniques of the present embodiments are generally performed according to conventional methods well known in the art and as described in various general and more specific references that are cited and discussed throughout the present specification. See, e.g., Loudon, Organic Chemistry, Fourth Edition, New York: Oxford University Press, 2002, pp. 360-361, 1084-1085; Smith and March, March's Advanced Organic Chemistry: Reactions, Mechanisms, and Structure, Fifth Edition, Wiley-Interscience, 2001; or Vogel, A Textbook of Practical Organic Chemistry, Including Qualitative Organic Analysis, Fourth Edition, New York: Longman, 1978.

The nomenclature used herein to name the subject compounds is illustrated in the Examples herein. This nomenclature has generally been derived using the commercially-available AutoNom software (MDL, San Leandro, Calif.).

TERMS

The following terms have the following meanings unless otherwise indicated. Any undefined terms have their art recognized meanings.

"Alkyl" refers to monovalent saturated aliphatic hydrocarbyl groups having from 1 to 10 carbon atoms and preferably 1 to 6 carbon atoms. This term includes, by way of example, linear and branched hydrocarbyl groups such as methyl (—$CH_3$—), ethyl (—$CH_3CH_2$—), n-propyl (—$CH_3CH_2CH_2$—), isopropyl ((—$CH_3$)$_2$CH—), n-butyl (—$CH_3CH_2CH_2CH_2$—), isobutyl ((—$CH_3$)$_2$CHCH$_2$—), sec-butyl ((—$CH_3$)(—$CH_3CH_2$)CH—), t-butyl ((—$CH_3$)$_3$C—), n-pentyl (—$CH_3CH_2CH_2CH_2CH_2$—), and neopentyl ((—$CH_3$)$_3$CCH$_2$—).

The term "substituted alkyl" refers to an alkyl group as defined herein wherein one or more carbon atoms in the alkyl chain have been optionally replaced with a heteroatom such as —O—, —N—, —S—, —S(O)$_n$— (where n is 0 to 2), —NR— (where R is hydrogen or alkyl) and having from 1 to 5 substituents selected from the group consisting of alkoxy, substituted alkoxy, cycloalkyl, substituted cycloalkyl, cycloalkenyl, substituted cycloalkenyl, acyl, acylamino, acyloxy, amino, aminoacyl, aminoacyloxy, oxyaminoacyl, azido, cyano, halogen, hydroxyl, oxo, thioketo, carboxyl, carboxylalkyl, thioaryloxy, thioheteroaryloxy, thioheterocyclooxy, thiol, thioalkoxy, substituted thioalkoxy, aryl, aryloxy, heteroaryl, heteroaryloxy, heterocyclyl, heterocyclooxy, hydroxyamino, alkoxyamino, nitro, —SO-alkyl, —SO-aryl, —SO-heteroaryl, —SO$_2$-alkyl, —SO$_2$-aryl, —SO$_2$-heteroaryl, and —NR$^a$R$^b$, wherein R$^a$ and R$^b$ may be the same or different and are chosen from hydrogen, optionally substituted alkyl, cycloalkyl, alkenyl, cycloalkenyl, alkynyl, aryl, heteroaryl and heterocyclic.

"Alkylene" refers to divalent aliphatic hydrocarbyl groups preferably having from 1 to 6 and more preferably 1 to 3 carbon atoms that are either straight-chained or branched, and which are optionally interrupted with one or more groups selected from —O—, —NR$^{10}$—, —NR$^{10}$C(O)—, —C(O)NR$^{10}$— and the like. This term includes, by way of example, methylene (—$CH_2$—), ethylene (—$CH_2CH_2$—), n-propylene (—$CH_2CH_2CH_2$—), iso-propylene (—$CH_2CH$(CH$_3$)—), (—$C$(CH$_3$)$_2$CH$_2$CH$_2$—), (—$C$(CH$_3$)$_2$CH$_2$C(O)—), (—$C$(CH$_3$)$_2$CH$_2$C(O)NH—), (—$CH$(CH$_3$)CH$_2$—), and the like.

"Substituted alkylene" refers to an alkylene group having from 1 to 3 hydrogens replaced with substituents as described for carbons in the definition of "substituted" below.

The term "alkane" refers to alkyl group and alkylene group, as defined herein.

The term "alkylaminoalkyl", "alkylaminoalkenyl" and "alkylaminoalkynyl" refers to the groups R'NHR"— where R' is alkyl group as defined herein and R" is alkylene, alkenylene or alkynylene group as defined herein.

The term "alkaryl" or "aralkyl" refers to the groups -alkylene-aryl and -substituted alkylene-aryl where alkylene, substituted alkylene and aryl are defined herein.

"Alkoxy" refers to the group —O-alkyl, wherein alkyl is as defined herein. Alkoxy includes, by way of example, methoxy, ethoxy, n-propoxy, isopropoxy, n-butoxy, t-butoxy, sec-butoxy, n-pentoxy, and the like. The term "alkoxy" also refers to the groups alkenyl-O—, cycloalkyl-O—, cycloalkenyl-O—, and alkynyl-O—, where alkenyl, cycloalkyl, cycloalkenyl, and alkynyl are as defined herein.

The term "substituted alkoxy" refers to the groups substituted alkyl-O—, substituted alkenyl-O—, substituted cycloalkyl-O—, substituted cycloalkenyl-O—, and substituted alkynyl-O— where substituted alkyl, substituted alkenyl, substituted cycloalkyl, substituted cycloalkenyl and substituted alkynyl are as defined herein.

The term "alkoxyamino" refers to the group —NH-alkoxy, wherein alkoxy is defined herein.

The term "haloalkoxy" refers to the groups alkyl-O— wherein one or more hydrogen atoms on the alkyl group have been substituted with a halo group and include, by way of examples, groups such as trifluoromethoxy, and the like.

The term "haloalkyl" refers to a substituted alkyl group as described above, wherein one or more hydrogen atoms on the alkyl group have been substituted with a halo group. Examples of such groups include, without limitation, fluoroalkyl groups, such as trifluoromethyl, difluoromethyl, trifluoroethyl and the like.

The term "alkylalkoxy" refers to the groups -alkylene-O-alkyl, alkylene-β-substituted alkyl, substituted alkylene-O-alkyl, and substituted alkylene-O-substituted alkyl wherein alkyl, substituted alkyl, alkylene and substituted alkylene are as defined herein.

The term "alkylthioalkoxy" refers to the group -alkylene-S-alkyl, alkylene-S-substituted alkyl, substituted alkylene-S-alkyl and substituted alkylene-S-substituted alkyl wherein alkyl, substituted alkyl, alkylene and substituted alkylene are as defined herein.

"Alkenyl" refers to straight chain or branched hydrocarbyl groups having from 2 to 6 carbon atoms and preferably 2 to 4 carbon atoms and having at least 1 and preferably from 1 to 2 sites of double bond unsaturation. This term includes, by way of example, bi-vinyl, allyl, and but-3-en-1-yl. Included within this term are the cis and trans isomers or mixtures of these isomers.

The term "substituted alkenyl" refers to an alkenyl group as defined herein having from 1 to 5 substituents, or from 1 to 3 substituents, selected from alkoxy, substituted alkoxy, cycloalkyl, substituted cycloalkyl, cycloalkenyl, substituted cycloalkenyl, acyl, acylamino, acyloxy, amino, substituted amino, aminoacyl, aminoacyloxy, oxyaminoacyl, azido, cyano, halogen, hydroxyl, oxo, thioketo, carboxyl, carboxylalkyl, thioaryloxy, thioheteroaryloxy, thioheterocyclooxy, thiol, thioalkoxy, substituted thioalkoxy, aryl, aryloxy, heteroaryl, heteroaryloxy, heterocyclyl, heterocyclooxy, hydroxyamino, alkoxyamino, nitro, —SO-alkyl, —SO-substituted alkyl, —SO-aryl, —SO-heteroaryl, —SO$_2$-alkyl, —SO$_2$-substituted alkyl, —SO$_2$-aryl and —SO$_2$-heteroaryl.

"Alkynyl" refers to straight or branched monovalent hydrocarbyl groups having from 2 to 6 carbon atoms and preferably 2 to 3 carbon atoms and having at least 1 and preferably from 1 to 2 sites of triple bond unsaturation. Examples of such alkynyl groups include acetylenyl (—C≡CH), and propargyl (—CH$_2$C≡CH).

The term "substituted alkynyl" refers to an alkynyl group as defined herein having from 1 to 5 substituents, or from 1 to 3 substituents, selected from alkoxy, substituted alkoxy, cycloalkyl, substituted cycloalkyl, cycloalkenyl, substituted cycloalkenyl, acyl, acylamino, acyloxy, amino, substituted amino, aminoacyl, aminoacyloxy, oxyaminoacyl, azido, cyano, halogen, hydroxyl, oxo, thioketo, carboxyl, carboxylalkyl, thioaryloxy, thioheteroaryloxy, thioheterocyclooxy, thiol, thioalkoxy, substituted thioalkoxy, aryl, aryloxy, heteroaryl, heteroaryloxy, heterocyclyl, heterocyclooxy, hydroxyamino, alkoxyamino, nitro, —SO-alkyl, —SO-substituted alkyl, —SO-aryl, —SO-heteroaryl, —SO$_2$-alkyl, —SO$_2$-substituted alkyl, —SO$_2$-aryl, and —SO$_2$-heteroaryl.

"Alkynyloxy" refers to the group —O-alkynyl, wherein alkynyl is as defined herein. Alkynyloxy includes, by way of example, ethynyloxy, propynyloxy, and the like.

"Acyl" refers to the groups H—C(O)—, alkyl-C(O)—, substituted alkyl-C(O)—, alkenyl-C(O)—, substituted alkenyl-C(O)—, alkynyl-C(O)—, substituted alkynyl-C(O)—, cycloalkyl-C(O)—, substituted cycloalkyl-C(O)—, cycloalkenyl-C(O)—, substituted cycloalkenyl-C(O)—, aryl-C(O)—, substituted aryl-C(O)—, heteroaryl-C(O)—, substituted heteroaryl-C(O)—, heterocyclyl-C(O)—, and substituted heterocyclyl-C(O)—, wherein alkyl, substituted alkyl, alkenyl, substituted alkenyl, alkynyl, substituted alkynyl, cycloalkyl, substituted cycloalkyl, cycloalkenyl, substituted cycloalkenyl, aryl, substituted aryl, heteroaryl, substituted heteroaryl, heterocyclic, and substituted heterocyclic are as defined herein. For example, acyl includes the "acetyl" group CH$_3$C(O)—

"Acylamino" refers to the groups —NR$^{20}$C(O)alkyl, —NR$^{20}$C(O)substituted alkyl, NR$^{20}$C(O)cycloalkyl, —NR$^{20}$C(O)substituted cycloalkyl, —NR$^{20}$C(O)cycloalkenyl, —NR$^{20}$C(O)substituted cycloalkenyl, —NR$^{20}$C(O)alkenyl, —NR$^{20}$C(O)substituted alkenyl, —NR$^{20}$C(O)alkynyl, —NR$^{20}$C(O)substituted alkynyl, —NR$^{20}$C(O)aryl, —NR$^{20}$C(O)substituted aryl, —NR$^{20}$C(O)heteroaryl, —NR$^{20}$C(O)substituted heteroaryl, —NR$^{20}$C(O)heterocyclic, and —NR$^{20}$C(O)substituted heterocyclic, wherein R$^{20}$ is hydrogen or alkyl and wherein alkyl, substituted alkyl, alkenyl, substituted alkenyl, alkynyl, substituted alkynyl, cycloalkyl, substituted cycloalkyl, cycloalkenyl, substituted cycloalkenyl, aryl, substituted aryl, heteroaryl, substituted heteroaryl, heterocyclic, and substituted heterocyclic are as defined herein.

"Aminocarbonyl" or the term "aminoacyl" refers to the group —C(O)NR$^{21}$R$^{22}$, wherein R$^{21}$ and R$^{22}$ independently are selected from the group consisting of hydrogen, alkyl, substituted alkyl, alkenyl, substituted alkenyl, alkynyl, substituted alkynyl, aryl, substituted aryl, cycloalkyl, substituted cycloalkyl, cycloalkenyl, substituted cycloalkenyl, heteroaryl, substituted heteroaryl, heterocyclic, and substituted heterocyclic and where R$^{21}$ and R$^{22}$ are optionally joined together with the nitrogen bound thereto to form a heterocyclic or substituted heterocyclic or substituted heterocyclic group, and wherein alkyl, substituted alkyl, alkenyl, substituted alkenyl, alkynyl, substituted alkynyl, cycloalkyl, substituted cycloalkyl, cycloalkenyl, substituted cycloalkenyl, aryl, substituted aryl, heteroaryl, substituted heteroaryl, heterocyclic, and substituted heterocyclic are as defined herein.

"Aminocarbonylamino" refers to the group —NR$^{21}$C(O) NR$^{22}$R$^{23}$ where R$^{21}$, R$^{22}$, and R$^{23}$ are independently selected from hydrogen, alkyl, aryl or cycloalkyl, or where two R groups are joined to form a heterocyclyl group.

The term "alkoxycarbonylamino" refers to the group —NRC(O)OR where each R is independently hydrogen, alkyl, substituted alkyl, aryl, heteroaryl, or heterocyclyl wherein alkyl, substituted alkyl, aryl, heteroaryl, and heterocyclyl are as defined herein.

The term "acyloxy" refers to the groups alkyl-C(O)O—, substituted alkyl-C(O)O—, cycloalkyl-C(O)O—, substituted cycloalkyl-C(O)O—, aryl-C(O)O—, heteroaryl-C(O)O—, and heterocyclyl-C(O)O— wherein alkyl, substituted alkyl, cycloalkyl, substituted cycloalkyl, aryl, heteroaryl, and heterocyclyl are as defined herein.

"Aminosulfonyl" refers to the group —SO$_2$NR$^{21}$R$^{22}$, wherein R$^{21}$ and R$^{22}$ independently are selected from the group consisting of hydrogen, alkyl, substituted alkyl, alkenyl, substituted alkenyl, alkynyl, substituted alkynyl, aryl, substituted aryl, cycloalkyl, substituted cycloalkyl, cycloalkenyl, substituted cycloalkenyl, heteroaryl, substituted heteroaryl, heterocyclic, substituted heterocyclic and where R$^{21}$ and R$^{22}$ are optionally joined together with the nitrogen bound thereto to form a heterocyclic or substituted heterocyclic group and alkyl, substituted alkyl, alkenyl, substituted alkenyl, alkynyl, substituted alkynyl, cycloalkyl, substituted cycloalkyl, cycloalkenyl, substituted cycloalkenyl, aryl, substituted aryl, heteroaryl, substituted heteroaryl, heterocyclic and substituted heterocyclic are as defined herein.

"Sulfonylamino" refers to the group —NR$^{21}$SO$_2$R$^{22}$, wherein R$^{21}$ and R$^{22}$ independently are selected from the group consisting of hydrogen, alkyl, substituted alkyl, alkenyl, substituted alkenyl, alkynyl, substituted alkynyl, aryl, substituted aryl, cycloalkyl, substituted cycloalkyl, cycloalkenyl, substituted cycloalkenyl, heteroaryl, substituted heteroaryl, heterocyclic, and substituted heterocyclic and where R$^{21}$ and R$^{22}$ are optionally joined together with the atoms bound thereto to form a heterocyclic or substituted heterocyclic group, and wherein alkyl, substituted alkyl, alkenyl, substituted alkenyl, alkynyl, substituted alkynyl, cycloalkyl, substituted cycloalkyl, cycloalkenyl, substituted cycloalkenyl, aryl, substituted aryl, heteroaryl, substituted heteroaryl, heterocyclic, and substituted heterocyclic are as defined herein.

"Aryl" or "Ar" refers to a monovalent aromatic carbocyclic group of from 6 to 18 carbon atoms having a single ring (such as is present in a phenyl group) or a ring system having multiple condensed rings (examples of such aromatic ring systems include naphthyl, anthryl and indanyl) which condensed rings may or may not be aromatic, provided that the point of attachment is through an atom of an aromatic ring. This term includes, by way of example, phenyl and naphthyl. Unless otherwise constrained by the definition for the aryl substituent, such aryl groups can optionally be substituted with from 1 to 5 substituents, or from 1 to 3 substituents, selected from acyloxy, hydroxy, thiol, acyl, alkyl, alkoxy, alkenyl, alkynyl, cycloalkyl, cycloalkenyl, substituted alkyl, substituted alkoxy, substituted alkenyl, substituted alkynyl, substituted cycloalkyl, substituted cycloalkenyl, amino, substituted amino, aminoacyl, acylamino, alkaryl, aryl, aryloxy, azido, carboxyl, carboxylalkyl, cyano, halogen, nitro, heteroaryl, heteroaryloxy, heterocyclyl, heterocyclooxy, aminoacyloxy, oxyacylamino, thioalkoxy, substituted thioalkoxy, thioaryloxy, thioheteroaryloxy, —SO-alkyl, —SO-substituted alkyl, —SO-aryl, —SO-heteroaryl, —SO$_2$-alkyl, —SO$_2$-substituted alkyl, —SO$_2$-aryl, —SO$_2$-heteroaryl and trihalomethyl.

"Aryloxy" refers to the group —O-aryl, wherein aryl is as defined herein, including, by way of example, phenoxy, naphthoxy, and the like, including optionally substituted aryl groups as also defined herein.

"Amino" refers to the group —NH$_2$.

The term "substituted amino" refers to the group —NRR where each R is independently selected from the group consisting of hydrogen, alkyl, substituted alkyl, cycloalkyl, substituted cycloalkyl, alkenyl, substituted alkenyl, cycloalkenyl, substituted cycloalkenyl, alkynyl, substituted alkynyl, aryl, heteroaryl, and heterocyclyl provided that at least one R is not hydrogen.

The term "azido" refers to the group —N$_3$.

"Carboxyl," "carboxy" or "carboxylate" refers to —CO$_2$H or salts thereof.

"Carboxyl ester" or "carboxy ester" or the terms "carboxyalkyl" or "carboxylalkyl" refers to the groups —C(O)O-alkyl, —C(O)O-substituted alkyl, —C(O)O-alkenyl, —C(O)O-substituted alkenyl, —C(O)O-alkynyl, —C(O)O-substituted alkynyl, —C(O)O-aryl, —C(O)O-substituted aryl, —C(O)β-cycloalkyl, —C(O)O-substituted cycloalkyl, —C(O)β-cycloalkenyl, —C(O)O-substituted cycloalkenyl, —C(O)O-heteroaryl, —C(O)O-substituted heteroaryl, —C(O)O-heterocyclic, and —C(O)O-substituted heterocyclic, wherein alkyl, substituted alkyl, alkenyl, substituted alkenyl, alkynyl, substituted alkynyl, cycloalkyl, substituted cycloalkyl, cycloalkenyl, substituted cycloalkenyl, aryl, substituted aryl, heteroaryl, substituted heteroaryl, heterocyclic, and substituted heterocyclic are as defined herein.

"(Carboxyl ester)oxy" or "carbonate" refers to the groups —O—C(O)O-alkyl, —O—C(O)O-substituted alkyl, —O—C(O)O-alkenyl, —O—C(O)O-substituted alkenyl, —O—C(O)O-alkynyl, —O—C(O)O-substituted alkynyl, —O—C(O)O-aryl, —O—C(O)O-substituted aryl, —O—C(O)β-cycloalkyl, —O—C(O)O-substituted cycloalkyl, —O—C(O)β-cycloalkenyl, —O—C(O)O-substituted cycloalkenyl, —O—C(O)O-heteroaryl, —O—C(O)O-substituted heteroaryl, —O—C(O)O-heterocyclic, and —O—C(O)O-substituted heterocyclic, wherein alkyl, substituted alkyl, alkenyl, substituted alkenyl, alkynyl, substituted alkynyl, cycloalkyl, substituted cycloalkyl, cycloalkenyl, substituted cycloalkenyl, aryl, substituted aryl, heteroaryl, substituted heteroaryl, heterocyclic, and substituted heterocyclic are as defined herein.

"Cyano" or "nitrile" refers to the group —CN.

"Cycloalkyl" refers to cyclic alkyl groups of from 3 to 10 carbon atoms having single or multiple cyclic rings including fused, bridged, and spiro ring systems. Examples of suitable cycloalkyl groups include, for instance, adamantyl, cyclopropyl, cyclobutyl, cyclopentyl, cyclooctyl and the like. Such cycloalkyl groups include, by way of example, single ring structures such as cyclopropyl, cyclobutyl, cyclopentyl, cyclooctyl, and the like, or multiple ring structures such as adamantanyl, and the like.

The term "substituted cycloalkyl" refers to cycloalkyl groups having from 1 to 5 substituents, or from 1 to 3 substituents, selected from alkyl, substituted alkyl, alkoxy, substituted alkoxy, cycloalkyl, substituted cycloalkyl, cycloalkenyl, substituted cycloalkenyl, acyl, acylamino, acyloxy, amino, substituted amino, aminoacyl, aminoacyloxy, oxyaminoacyl, azido, cyano, halogen, hydroxyl, oxo, thioketo, carboxyl, carboxylalkyl, thioaryloxy, thioheteroaryloxy, thioheterocyclooxy, thiol, thioalkoxy, substituted thioalkoxy, aryl, aryloxy, heteroaryl, heteroaryloxy, heterocyclyl, heterocyclooxy, hydroxyamino, alkoxyamino, nitro, —SO-alkyl, —SO-substituted alkyl, —SO-aryl, —SO-heteroaryl, —SO$_2$-alkyl, —SO$_2$-substituted alkyl, —SO$_2$-aryl and —SO$_2$-heteroaryl.

"Cycloalkenyl" refers to non-aromatic cyclic alkyl groups of from 3 to 10 carbon atoms having single or multiple rings and having at least one double bond and preferably from 1 to 2 double bonds.

The term "substituted cycloalkenyl" refers to cycloalkenyl groups having from 1 to 5 substituents, or from 1 to 3 substituents, selected from alkoxy, substituted alkoxy, cycloalkyl, substituted cycloalkyl, cycloalkenyl, substituted cycloalkenyl, acyl, acylamino, acyloxy, amino, substituted amino, aminoacyl, aminoacyloxy, oxyaminoacyl, azido, cyano, halogen, hydroxyl, keto, thioketo, carboxyl, carboxylalkyl, thioaryloxy, thioheteroaryloxy, thioheterocyclooxy, thiol, thioalkoxy, substituted thioalkoxy, aryl, aryloxy, heteroaryl, heteroaryloxy, heterocyclyl, heterocyclooxy, hydroxyamino, alkoxyamino, nitro, —SO-alkyl, —SO-substituted alkyl, —SO-aryl, —SO-heteroaryl, —SO$_2$-alkyl, —SO$_2$-substituted alkyl, —SO$_2$-aryl and —SO$_2$-heteroaryl.

"Cycloalkynyl" refers to non-aromatic cycloalkyl groups of from 5 to 10 carbon atoms having single or multiple rings and having at least one triple bond.

"Cycloalkoxy" refers to —O-cycloalkyl.

"Cycloalkenyloxy" refers to —O-cycloalkenyl.

"Halo" or "halogen" refers to fluoro, chloro, bromo, and iodo.

"Hydroxy" or "hydroxyl" refers to the group —OH.

"Heteroaryl" refers to an aromatic group of from 1 to 15 carbon atoms, such as from 1 to 10 carbon atoms and 1 to 10 heteroatoms selected from the group consisting of oxygen, nitrogen, and sulfur within the ring. Such heteroaryl groups can have a single ring (such as, pyridinyl, imidazolyl or furyl) or multiple condensed rings in a ring system (for example as in groups such as, indolizinyl, quinolinyl, benzofuran, benzimidazolyl or benzothienyl), wherein at least one ring within the ring system is aromatic and at least one ring within the ring system is aromatic, provided that the point of attachment is through an atom of an aromatic ring. In certain embodiments, the nitrogen and/or sulfur ring atom(s) of the heteroaryl group are optionally oxidized to provide for the N-oxide (N→O), sulfinyl, or sulfonyl moieties. This term includes, by way of example, pyridinyl, pyrrolyl, indolyl, thiophenyl, and furanyl. Unless otherwise constrained by the definition for the heteroaryl substituent, such heteroaryl groups can be optionally substituted with 1 to 5 substituents, or from 1 to 3 substituents, selected from acyloxy, hydroxy, thiol, acyl, alkyl, alkoxy, alkenyl, alkynyl, cycloalkyl, cycloalkenyl, substituted alkyl, substituted alkoxy, substituted alkenyl, substituted alkynyl, substituted cycloalkyl, substituted cycloalkenyl, amino, substituted amino, aminoacyl, acylamino, alkaryl, aryl, aryloxy, azido, carboxyl, carboxylalkyl, cyano, halogen, nitro, heteroaryl, heteroaryloxy, heterocyclyl, heterocyclooxy, aminoacyloxy, oxyacylamino, thioalkoxy, substituted thioalkoxy, thioaryloxy, thioheteroaryloxy, —SO-alkyl, —SO-substituted alkyl, —SO-aryl, —SO-heteroaryl, —SO$_2$-alkyl, —SO$_2$-substituted alkyl, —SO$_2$-aryl and —SO$_2$-heteroaryl, and trihalomethyl.

The term "heteroaralkyl" refers to the groups -alkylene-heteroaryl where alkylene and heteroaryl are defined herein. This term includes, by way of example, pyridylmethyl, pyridylethyl, indolylmethyl, and the like.

"Heteroaryloxy" refers to —O-heteroaryl.

"Heterocycle," "heterocyclic," "heterocycloalkyl," and "heterocyclyl" refer to a saturated or unsaturated group having a single ring or multiple condensed rings, including fused bridged and spiro ring systems, and having from 3 to 20 ring atoms, including 1 to 10 hetero atoms. These ring atoms are selected from the group consisting of nitrogen, sulfur, or oxygen, wherein, in fused ring systems, one or more of the rings can be cycloalkyl, aryl, or heteroaryl, provided that the point of attachment is through the non-aromatic ring. In certain embodiments, the nitrogen and/or sulfur atom(s) of the heterocyclic group are optionally oxidized to provide for the N-oxide, —S(O)—, or —SO$_2$— moieties.

Examples of heterocycles and heteroaryls include, but are not limited to, azetidine, pyrrole, imidazole, pyrazole, pyridine, pyrazine, pyrimidine, pyridazine, indolizine, isoindole, indole, dihydroindole, indazole, purine, quinolizine, isoquinoline, quinoline, phthalazine, naphthylpyridine, quinoxaline, quinazoline, cinnoline, pteridine, carbazole, carboline, phenanthridine, acridine, phenanthroline, isothiazole, phenazine, isoxazole, phenoxazine, phenothiazine, imidazolidine, imidazoline, piperidine, piperazine, indoline, phthalimide, 1,2,3,4-tetrahydroisoquinoline, 4,5,6,7-tetrahydrobenzo[b]thiophene, thiazole, thiazolidine, thiophene, benzo[b]thiophene, morpholinyl, thiomorpholinyl (also referred to as thiamorpholinyl), 1,1-dioxothiomorpholinyl, piperidinyl, pyrrolidine, tetrahydrofuranyl, and the like.

Unless otherwise constrained by the definition for the heterocyclic substituent, such heterocyclic groups can be optionally substituted with 1 to 5, or from 1 to 3 substituents, selected from alkoxy, substituted alkoxy, cycloalkyl, substituted cycloalkyl, cycloalkenyl, substituted cycloalkenyl, acyl, acylamino, acyloxy, amino, substituted amino, aminoacyl, aminoacyloxy, oxyaminoacyl, azido, cyano, halogen, hydroxyl, oxo, thioketo, carboxyl, carboxylalkyl, thioaryloxy, thioheteroaryloxy, thioheterocyclooxy, thiol, thioalkoxy, substituted thioalkoxy, aryl, aryloxy, heteroaryl, heteroaryloxy, heterocyclyl, heterocyclooxy, hydroxyamino, alkoxyamino, nitro, —SO-alkyl, —SO-substituted alkyl, —SO-aryl, —SO-heteroaryl, —SO$_2$-alkyl, —SO$_2$-substituted alkyl, —SO$_2$-aryl, —SO$_2$-heteroaryl, and fused heterocycle.

"Heterocyclyloxy" refers to the group —O-heterocyclyl.

The term "heterocyclylthio" refers to the group heterocyclic-S—.

The term "heterocyclene" refers to the diradical group formed from a heterocycle, as defined herein.

The term "hydroxyamino" refers to the group —NHOH.

"Nitro" refers to the group —NO$_2$.

"Oxo" refers to the atom (═O).

"Sulfonyl" refers to the group SO$_2$-alkyl, SO$_2$-substituted alkyl, SO$_2$-alkenyl, SO$_2$-substituted alkenyl, SO$_2$-cycloalkyl, SO$_2$-substituted cylcoalkyl, SO$_2$-cycloalkenyl, SO$_2$-substituted cylcoalkenyl, SO$_2$-aryl, SO$_2$-substituted aryl, SO$_2$-heteroaryl, SO$_2$-substituted heteroaryl, SO$_2$-heterocyclic, and SO$_2$-substituted heterocyclic, wherein alkyl, substituted alkyl, alkenyl, substituted alkenyl, alkynyl, substituted alkynyl, cycloalkyl, substituted cycloalkyl, cycloalkenyl, substituted cycloalkenyl, aryl, substituted aryl, heteroaryl, substituted heteroaryl, heterocyclic, and substituted heterocyclic are as defined herein. Sulfonyl includes, by way of example, methyl-SO$_2$—, phenyl-SO$_2$—, and 4-methylphenyl-SO$_2$—.

"Sulfonyloxy" refers to the group —OSO$_2$-alkyl, OSO$_2$-substituted alkyl, OSO$_2$-alkenyl, OSO$_2$-substituted alkenyl, OSO$_2$-cycloalkyl, OSO$_2$-substituted cylcoalkyl, OSO$_2$-cycloalkenyl, OSO$_2$-substituted cylcoalkenyl, OSO$_2$-aryl, OSO$_2$-substituted aryl, OSO$_2$-heteroaryl, OSO$_2$-substituted heteroaryl, OSO$_2$-heterocyclic, and OSO$_2$ substituted heterocyclic, wherein alkyl, substituted alkyl, alkenyl, substituted alkenyl, alkynyl, substituted alkynyl, cycloalkyl, substituted cycloalkyl, cycloalkenyl, substituted cycloalkenyl, aryl, substituted aryl, heteroaryl, substituted heteroaryl, heterocyclic, and substituted heterocyclic are as defined herein.

The term "aminocarbonyloxy" refers to the group —OC(O)NRR where each R is independently hydrogen, alkyl, substituted alkyl, aryl, heteroaryl, or heterocyclic wherein alkyl, substituted alkyl, aryl, heteroaryl and heterocyclic are as defined herein.

"Thiol" refers to the group —SH.

"Thioxo" or the term "thioketo" refers to the atom (═S).

"Alkylthio" or the term "thioalkoxy" refers to the group —S-alkyl, wherein alkyl is as defined herein. In certain embodiments, sulfur may be oxidized to —S(O)—. The sulfoxide may exist as one or more stereoisomers.

The term "substituted thioalkoxy" refers to the group —S-substituted alkyl.

The term "thioaryloxy" refers to the group aryl-S— wherein the aryl group is as defined herein including optionally substituted aryl groups also defined herein.

The term "thioheteroaryloxy" refers to the group heteroaryl-S— wherein the heteroaryl group is as defined herein including optionally substituted aryl groups as also defined herein.

The term "thioheterocyclooxy" refers to the group heterocyclyl-S— wherein the heterocyclyl group is as defined herein including optionally substituted heterocyclyl groups as also defined herein.

In addition to the disclosure herein, the term "substituted," when used to modify a specified group or radical, can also mean that one or more hydrogen atoms of the specified group or radical are each, independently of one another, replaced with the same or different substituent groups as defined below.

In addition to the groups disclosed with respect to the individual terms herein, substituent groups for substituting for one or more hydrogens (any two hydrogens on a single carbon can be replaced with ═O, ═NR$^{70}$, ═N—OR$^{70}$, ═N$_2$ or ═S) on saturated carbon atoms in the specified group or radical are, unless otherwise specified, —R$^{60}$, halo, ═O, —OR$^{70}$, —SR$^{70}$, —NR$^{80}$R$^{80}$, trihalomethyl, —CN, —OCN, —SCN, —NO, —NO$_2$, ═N$_2$, —N$_3$, —SO$_2$R$^{70}$, —SO$_2$O$^-$M$^+$, —SO$_2$OR$^{70}$, —OSO$_2$R$^{70}$, —OSO$_2$O$^-$M$^+$, —OSO$_2$OR$^{70}$, —P(O)(O$^-$)$_2$(M$^+$)$_2$, —P(O)(OR$^{70}$)O$^-$M$^+$, —P(O)(OR$^{70}$)$_2$, —C(O)R$^{70}$, —C(S)R$^{70}$, —C(NR$^{70}$)R$^{70}$, —C(O)O$^-$M$^+$, —C(O)OR$^{70}$, —C(S)OR$^{70}$, —C(O)NR$^{80}$R$^{80}$, —C(NR$^{70}$)NR$^{80}$R$^{80}$, —OC(O)R$^{70}$, —OC(S)R$^{70}$, —OC(O)O$^-$M$^+$, —OC(O)OR$^{70}$, —OC(S)OR$^{70}$, —NR$^{70}$C(O)R$^{70}$, —NR$^{70}$C(S)R$^{70}$, —NR$^{70}$CO$_2^-$M$^+$, —NR$^{70}$CO$_2$R$^{70}$, —NR$^{70}$C(S)OR$^{70}$, —NR$^{70}$C(O)NR$^{80}$R$^{80}$, —NR$^{70}$C(NR$^{70}$)R$^{70}$ and —NR$^{70}$C(NR$^{70}$)NR$^{80}$R$^{80}$, where R$^{60}$ is selected from the group consisting of optionally substituted alkyl, cycloalkyl, heteroalkyl, heterocycloalkylalkyl, cycloalkylalkyl, aryl, arylalkyl, heteroaryl and heteroarylalkyl, each R$^{70}$ is independently hydrogen or R$^{60}$; each R$^{80}$ is independently R$^{70}$ or alternatively, two R$^{80}$'s, taken together with the nitrogen atom to which they are bonded, form a 5-, 6- or 7-membered heterocycloalkyl which may optionally include from 1 to 4 of the same or different additional heteroatoms selected from the group consisting of O, N and S, of which N may have —H or C$_1$-C$_3$ alkyl substitution; and each M$^+$ is a counter ion with a net single positive charge. Each M$^+$ may independently be, for example, an alkali ion, such as K$^+$, Na$^+$, Li$^+$; an ammonium ion, such as $^+$N(R$^{60}$)$_4$; or an alkaline earth ion, such as [Ca$^{2+}$]$_{0.5}$, [Mg$^{2+}$]$_{0.5}$, or [Ba$^{2+}$]$_{0.5}$ ("subscript 0.5 means that one of the counter ions for such divalent alkali earth ions can be an ionized form of a compound of the invention and the other a typical counter ion such as chloride, or two ionized compounds disclosed herein can serve as counter ions for such divalent alkali earth ions, or a doubly ionized compound of the invention can serve as the counter ion for such divalent alkali earth ions). As specific examples, —NR$^{80}$R$^{80}$ is meant to include —NH$_2$, —NH-alkyl, N-pyrrolidinyl, N-piperazinyl, 4N-methyl-piperazin-1-yl and N-morpholinyl.

In addition to the disclosure herein, substituent groups for hydrogens on unsaturated carbon atoms in "substituted" alkene, alkyne, aryl and heteroaryl groups are, unless otherwise specified, —R$^{60}$, halo, —O$^-$M$^+$, —OR$^{70}$, —SR$^{70}$, —S$^-$M$^+$, —NR$^{80}$R$^{80}$, trihalomethyl, —CF$_3$, —CN, —OCN, —SCN, —NO, —NO$_2$, —N$_3$, —SO$_2$R$^{70}$, —SO$_3^-$M$^+$, —SO$_3$R$^{70}$, —OSO$_2$R$^{70}$, —OSO$_3^-$M$^+$, —OSO$_3$R$^{70}$, —PO$_3^{-2}$(M$^+$)$_2$, —P(O)(OR$^{70}$)O$^-$M$^+$, —P(O)(OR$^{70}$)$_2$, —C(O)R$^{70}$, —C(S) R$^{70}$, —C(NR$^{70}$)R$^{70}$, —CO$_2^-$M$^+$, —CO$_2$R$^{70}$, —C(S)OR$^{70}$, —C(O)NR$^{80}$R$^{80}$, —C(NR$^{70}$)NR$^{80}$R$^{80}$, —OC(O)R$^{70}$, —OC(S)R$^{70}$, —OCO$_2^-$M$^+$, —OCO$_2$R$^{70}$, —OC(S)OR$^{70}$, —NR$^{70}$C(O)R$^{70}$, —NR$^{70}$C(S)R$^{70}$, —NR$^{70}$CO$_2^-$M$^+$, —NR$^{70}$CO$_2$R$^{70}$, —NR$^{70}$C(S)OR$^{70}$, —NR$^{70}$C(O)NR$^{80}$R$^{80}$, —NR$^{70}$C(NR$^{70}$)R$^{70}$ and —NR$^{70}$C(NR$^{70}$)NR$^{80}$R$^{80}$, where R$^{60}$, R$^{70}$, R$^{80}$ and M$^+$ are as previously defined, provided that in case of substituted alkene or alkyne, the substituents are not —O$^-$M$^+$, —OR$^{70}$, —SR$^{70}$, or —S$^-$M$^+$.

In addition to the groups disclosed with respect to the individual terms herein, substituent groups for hydrogens on nitrogen atoms in "substituted" heteroalkyl and cycloheteroalkyl groups are, unless otherwise specified, —R$^{60}$, —OR$^{70}$, —NR trihalomethyl, —CF$_3$, —CN, —NO, —NO$_2$, —S(O)$_2$R$^{70}$, —S(O)$_2$O$^-$M$^+$, —S(O)$_2$OR$^{70}$, —OS(O)$_2$R$^{70}$, —OS(O)$_2$O$^-$M$^+$, —OS(O)$_2$OR$^{70}$, —P(O)(O$^-$)$_2$(M$^+$)$_2$, —P(O)(OR$^{70}$)O$^-$M$^+$, —P(O)(OR$^{70}$)(OR$^{70}$), —C(O)R$^{70}$, —C(S) R$^{70}$, —C(NR$^{70}$)R$^{70}$, —C(O)OR$^{70}$, —C(S)OR$^{70}$, —C(O)NR$^{80}$R$^{80}$, —C(NR$^{70}$)NR$^{80}$R$^{80}$, —OC(O)R$^{70}$, —OC(S) R$^{70}$, —OC(O)OR$^{70}$, —OC(S)OR$^{70}$, —NR$^{70}$C(O) R$^{70}$, —NR$^{70}$C(S)R$^{70}$, —NR$^{70}$C(O)OR$^{70}$, —NR$^{70}$C(S) OR$^{70}$, —NR$^{70}$C(O)NR$^{80}$R$^{80}$, —NR$^{70}$C(NR$^{70}$)R$^{70}$ and —NR$^{70}$C(NR$^{70}$)NR$^{80}$R$^{80}$, where R$^{60}$, R$^{70}$, R$^{80}$ and M$^+$ are as previously defined.

In addition to the disclosure herein, in a certain embodiment, a group that is substituted has 1, 2, 3, or 4 substituents, 1, 2, or 3 substituents, 1 or 2 substituents, or 1 substituent.

It is understood that in all substituted groups defined above, polymers arrived at by defining substituents with further substituents to themselves (e.g., substituted aryl having a substituted aryl group as a substituent which is itself substituted with a substituted aryl group, which is further substituted by a substituted aryl group, etc.) are not intended for inclusion herein. In such cases, the maximum number of such substitutions is three. For example, serial substitutions of substituted aryl groups specifically contemplated herein are limited to substituted aryl-(substituted aryl)-substituted aryl.

Unless indicated otherwise, the nomenclature of substituents that are not explicitly defined herein are arrived at by naming the terminal portion of the functionality followed by the adjacent functionality toward the point of attachment. For example, the substituent "arylalkyloxycarbonyl" refers to the group (aryl)-(alkyl)-O—C(O)—.

As to any of the groups disclosed herein which contain one or more substituents, it is understood, of course, that such groups do not contain any substitution or substitution patterns which are sterically impractical and/or synthetically nonfeasible. In addition, the subject compounds include all stereochemical isomers arising from the substitution of these compounds.

The term "pharmaceutically acceptable salt" means a salt which is acceptable for administration to a patient, such as a mammal (salts with counterions having acceptable mammalian safety for a given dosage regime). Such salts can be derived from pharmaceutically acceptable inorganic or organic bases and from pharmaceutically acceptable inorganic or organic acids. "Pharmaceutically acceptable salt" refers to pharmaceutically acceptable salts of a compound, which salts are derived from a variety of organic and inorganic counter ions well known in the art and include, by way of example only, sodium, potassium, calcium, magnesium, ammonium, tetraalkylammonium, and the like; and when the molecule contains a basic functionality, salts of organic or inorganic acids, such as hydrochloride, hydrobromide, formate, tartrate, besylate, mesylate, acetate, maleate, oxalate, and the like.

The term "salt thereof" means a compound formed when a proton of an acid is replaced by a cation, such as a metal cation or an organic cation and the like. Where applicable, the salt is a pharmaceutically acceptable salt, although this is not required for salts of intermediate compounds that are not intended for administration to a patient. By way of example, salts of the present compounds include those wherein the compound is protonated by an inorganic or organic acid to form a cation, with the conjugate base of the inorganic or organic acid as the anionic component of the salt.

"Solvate" refers to a complex formed by combination of solvent molecules with molecules or ions of the solute. The solvent can be an organic compound, an inorganic compound, or a mixture of both. Some examples of solvents include, but are not limited to, methanol, N,N-dimethylformamide, tetrahydrofuran, dimethylsulfoxide, and water. When the solvent is water, the solvate formed is a hydrate.

"Stereoisomer" and "stereoisomers" refer to compounds that have same atomic connectivity but different atomic arrangement in space. Stereoisomers include cis-trans isomers, E and Z isomers, enantiomers, and diastereomers.

"Tautomer" refers to alternate forms of a molecule that differ only in electronic bonding of atoms and/or in the position of a proton, such as enol-keto and imine-enamine tautomers, or the tautomeric forms of heteroaryl groups containing a —N═C(H)—NH— ring atom arrangement, such as pyrazoles, imidazoles, benzimidazoles, triazoles, and tetrazoles. A person of ordinary skill in the art would recognize that other tautomeric ring atom arrangements are possible.

It will be appreciated that the term "or a salt or solvate or stereoisomer thereof" is intended to include all permutations of salts, solvates and stereoisomers, such as a solvate of a pharmaceutically acceptable salt of a stereoisomer of subject compound.

"Pharmaceutically effective amount" and "therapeutically effective amount" refer to an amount of a compound sufficient to treat a specified disorder or disease or one or more of its symptoms and/or to prevent the occurrence of the disease or disorder. In reference to tumorigenic proliferative disorders, a pharmaceutically or therapeutically effective amount comprises an amount sufficient to, among other things, cause the tumor to shrink or decrease the growth rate of the tumor.

"Patient" refers to human and non-human subjects, especially mammalian subjects.

The term "treating" or "treatment" as used herein means the treating or treatment of a disease or medical condition in a patient, such as a mammal (particularly a human) that includes: (a) preventing the disease or medical condition from occurring, such as, prophylactic treatment of a subject; (b) ameliorating the disease or medical condition, such as, eliminating or causing regression of the disease or medical condition in a patient; (c) suppressing the disease or medical condition, for example by, slowing or arresting the development of the disease or medical condition in a patient; or (d) alleviating a symptom of the disease or medical condition in a patient.

Representative Embodiments

The following substituents and values are intended to provide representative examples of various aspects and embodiments. These representative values are intended to further define and illustrate such aspects and embodiments and are not intended to exclude other embodiments or to limit the scope of this invention. In this regard, the representation that a particular value or substituent is preferred is not intended in any way to exclude other values or substituents from this invention unless specifically indicated.

These compounds may contain one or more chiral centers and therefore, the embodiments are directed to racemic mixtures; pure stereoisomers (i.e., enantiomers or diastereomers); stereoisomer-enriched mixtures and the like unless otherwise indicated. When a particular stereoisomer is shown or named herein, it will be understood by those skilled in the art that minor amounts of other stereoisomers may be present in the compositions unless otherwise indicated, provided that the desired utility of the composition as a whole is not eliminated by the presence of such other isomers.

The compositions of the present disclosure include compounds of formulae I-V, shown below. Pharmaceutical compositions and methods of the present disclosure also contemplate compounds of formulae I-V.

Formula I

In one of its composition aspects, the present embodiments provide a compound of formula (I):

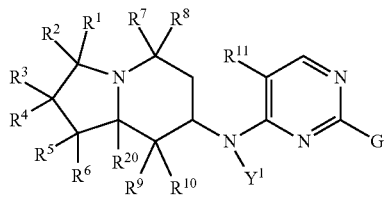

(I)

wherein $R^1$, $R^2$, $R^3$, $R^4$, $R^5$, and $R^6$ are independently selected from hydrogen, alkyl, substituted alkyl, alkoxy, substituted alkoxy, acyl, acylamino, acyloxy, amino, substituted amino, aminoacyl, aminoacyloxy, oxyaminoacyl, azido, cyano, halogen, hydroxyl, carboxyl, carboxylalkyl, thiol, thioalkoxy, substituted thioalkoxy, aryl, aryloxy, hydroxyamino, alkoxyamino, nitro, —SO-alkyl, —SO-substituted alkyl, —SO-aryl, —SO-heteroaryl, —SO$_2$-alkyl, —SO$_2$-substituted alkyl, —SO$_2$-aryl and —SO$_2$-heteroaryl; or $R^1$ and $R^2$ together form an oxo group; or $R^3$ and $R^4$ together form an oxo group; or $R^5$ and $R^6$ together form an oxo group;

$R^7$, $R^8$, $R^9$, and $R^{10}$ are independently selected from hydrogen, alkyl, substituted alkyl, alkoxy, substituted alkoxy, acyl, acylamino, acyloxy, amino, substituted amino, aminoacyl, aminoacyloxy, oxyaminoacyl, azido, cyano, halogen, hydroxyl, carboxyl, carboxylalkyl, thiol, thioalkoxy, substituted thioalkoxy, aryl, aryloxy, hydroxyamino, alkoxyamino, nitro, —SO-alkyl, —SO-substituted alkyl, —SO-aryl, —SO-heteroaryl, —SO$_2$-alkyl, —SO$_2$-substituted alkyl, —SO$_2$-aryl and —SO$_2$-heteroaryl; or $R^7$ and $R^8$ together form an oxo group; or $R^9$ and $R^{10}$ together form an oxo group;

$R^{11}$ is selected from alkyl, substituted alkyl, hydroxy, alkoxy, substituted alkoxy, amino, substituted amino, carboxyl, carboxyl ester, cyano, halogen, acyl, aminoacyl, nitro, alkenyl, substituted alkenyl, alkynyl, and substituted alkynyl;

$R^{20}$ is selected from hydrogen, alkyl, and substituted alkyl;

G is halogen or —NY$^2$Ar$^1$;

$Y^1$ and $Y^2$ are independently selected from hydrogen and alkyl; and

Ar$^1$ is selected from aryl, substituted aryl, heteroaryl, and substituted heteroaryl;

or a salt or stereoisomer thereof.

In formula (I), G is halogen or —NY$^2$Ar$^1$. In certain embodiments, G is halogen. In certain embodiments, G is —NY$^2$Ar$^1$.

In formula (I), Ar$^1$ is selected from aryl, substituted aryl, heteroaryl, and substituted heteroaryl. In certain embodiments, Ar$^1$ is aryl or substituted aryl. In certain embodiments, Ar$^1$ is aryl. In certain embodiments, Ar$^1$ is substituted aryl. In certain embodiments, Ar$^1$ is heteroaryl or substituted heteroaryl. In certain embodiments, Ar$^1$ is heteroaryl. In certain embodiments, Ar$^1$ is substituted heteroaryl.

In certain embodiments, a compound of formula (I) is of the formula:

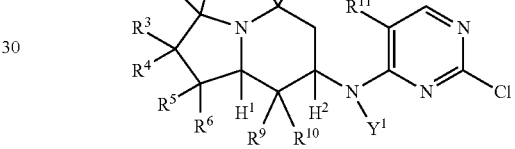

wherein $H^1$ and $H^2$ are hydrogen.

In certain embodiments, $H^1$ and $H^2$ are hydrogen with cis relative configuration. In certain embodiments, $H^1$ and $H^2$ are hydrogen with trans relative configuration.

Formula II

In one of its composition aspects, the present embodiments provide a compound of formula (II):

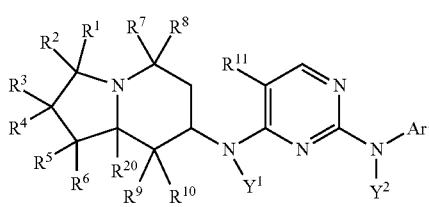

(II)

wherein $R^1$, $R^2$, $R^3$, $R^4$, $R^5$, and $R^6$ are independently selected from hydrogen, alkyl, substituted alkyl, alkoxy, substituted alkoxy, acyl, acylamino, acyloxy, amino, substituted amino, aminoacyl, aminoacyloxy, oxyaminoacyl, azido, cyano, halogen, hydroxyl, carboxyl, carboxylalkyl, thiol, thioalkoxy, substituted thioalkoxy, aryl, aryloxy, hydroxyamino, alkoxyamino, nitro, —SO-alkyl, —SO-substituted alkyl, —SO-aryl, —SO-heteroaryl, —SO$_2$-alkyl, —SO$_2$-substituted alkyl, —SO$_2$-aryl and —SO$_2$-heteroaryl; or $R^1$ and $R^2$ together form an oxo group; or $R^3$ and $R^4$ together form an oxo group; or $R^5$ and $R^6$ together form an oxo group;

$R^7$, $R^8$, $R^9$, and $R^{10}$ are independently selected from hydrogen, alkyl, substituted alkyl, alkoxy, substituted alkoxy, acyl, acylamino, acyloxy, amino, substituted amino, aminoacyl, aminoacyloxy, oxyaminoacyl, azido, cyano, halogen, hydroxyl, carboxyl, carboxylalkyl, thiol, thioalkoxy, substituted thioalkoxy, aryl, aryloxy, hydroxyamino, alkoxyamino, nitro, —SO-alkyl, —SO-substituted alkyl, —SO-aryl, —SO-heteroaryl, —SO$_2$-alkyl, —SO$_2$-substituted alkyl, —SO$_2$-aryl and —SO$_2$-heteroaryl; or $R^7$ and $R^8$ together form an oxo group; or $R^9$ and $R^{10}$ together form an oxo group;

$R^{11}$ is selected from alkyl, substituted alkyl, hydroxy, alkoxy, substituted alkoxy, amino, substituted amino, carboxyl, carboxyl ester, cyano, halogen, acyl, aminoacyl, nitro, alkenyl, substituted alkenyl, alkynyl, and substituted alkynyl;

$R^{20}$ is selected from hydrogen, alkyl, and substituted alkyl;

$Y^1$ and $Y^2$ are independently selected from hydrogen and alkyl; and $Ar^1$ is selected from aryl, substituted aryl, heteroaryl, and substituted heteroaryl;

or a salt or stereoisomer thereof.

In one of its composition aspects, the present embodiments provide a compound of formula (IIa):

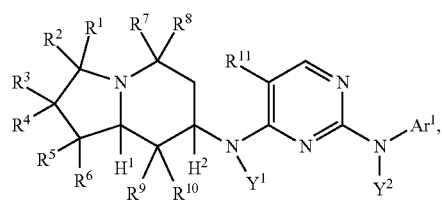

(IIa)

wherein $R^1$, $R^2$, $R^3$, $R^4$, $R^5$, and $R^6$ are independently selected from hydrogen, alkyl, substituted alkyl, alkoxy, substituted alkoxy, acyl, acylamino, acyloxy, amino, substituted amino, aminoacyl, aminoacyloxy, oxyaminoacyl, azido, cyano, halogen, hydroxyl, carboxyl, carboxylalkyl, thiol, thioalkoxy, substituted thioalkoxy, aryl, aryloxy, hydroxyamino, alkoxyamino, nitro, —SO-alkyl, —SO-substituted alkyl, —SO-aryl, —SO-heteroaryl, —SO$_2$-alkyl, —SO$_2$-substituted alkyl, —SO$_2$-aryl and —SO$_2$-heteroaryl; or $R^1$ and $R^2$ together form an oxo group; or $R^3$ and $R^4$ together form an oxo group; or $R^5$ and $R^6$ together form an oxo group;

$R^7$, $R^8$, $R^9$, and $R^{10}$ are independently selected from hydrogen, alkyl, substituted alkyl, alkoxy, substituted alkoxy, acyl, acylamino, acyloxy, amino, substituted amino, aminoacyl, aminoacyloxy, oxyaminoacyl, azido, cyano, halogen, hydroxyl, carboxyl, carboxylalkyl, thiol, thioalkoxy, substituted thioalkoxy, aryl, aryloxy, hydroxyamino, alkoxyamino, nitro, —SO-alkyl, —SO-substituted alkyl, —SO-aryl, —SO-heteroaryl, —SO$_2$-alkyl, —SO$_2$-substituted alkyl, —SO$_2$-aryl and —SO$_2$-heteroaryl; or $R^7$ and $R^8$ together form an oxo group; or $R^9$ and $R^{10}$ together form an oxo group;

$R^{11}$ is selected from alkyl, substituted alkyl, hydroxy, alkoxy, substituted alkoxy, amino, substituted amino, carboxyl, carboxyl ester, cyano, halogen, acyl, aminoacyl, nitro, alkenyl, substituted alkenyl, alkynyl, and substituted alkynyl;

$Y^1$ and $Y^2$ are independently selected from hydrogen and alkyl;

$Ar^1$ is selected from aryl, substituted aryl, heteroaryl, and substituted heteroaryl; and $H^1$ and $H^2$ are hydrogen with cis relative configuration;

or a salt or stereoisomer thereof.

In one of its composition aspects, the present embodiments provide a compound of formula (IIb):

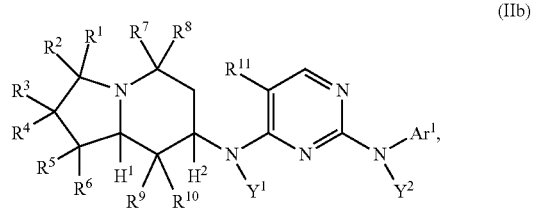

(IIb)

wherein $R^1$, $R^2$, $R^3$, $R^4$, $R^5$, and $R^6$ are independently selected from hydrogen, alkyl, substituted alkyl, alkoxy, substituted alkoxy, acyl, acylamino, acyloxy, amino, substituted amino, aminoacyl, aminoacyloxy, oxyaminoacyl, azido, cyano, halogen, hydroxyl, carboxyl, carboxylalkyl, thiol, thioalkoxy, substituted thioalkoxy, aryl, aryloxy, hydroxyamino, alkoxyamino, nitro, —SO-alkyl, —SO-substituted alkyl, —SO-aryl, —SO-heteroaryl, —SO$_2$-alkyl, —SO$_2$-substituted alkyl, —SO$_2$-aryl and —SO$_2$-heteroaryl; or $R^1$ and $R^2$ together form an oxo group; or $R^3$ and $R^4$ together form an oxo group; or $R^5$ and $R^6$ together form an oxo group;

$R^7$, $R^8$, $R^9$, and $R^{10}$ are independently selected from hydrogen, alkyl, substituted alkyl, alkoxy, substituted alkoxy, acyl, acylamino, acyloxy, amino, substituted amino, aminoacyl, aminoacyloxy, oxyaminoacyl, azido, cyano, halogen, hydroxyl, carboxyl, carboxylalkyl, thiol, thioalkoxy, substituted thioalkoxy, aryl, aryloxy, hydroxyamino, alkoxyamino, nitro, —SO-alkyl, —SO-substituted alkyl, —SO-aryl, —SO-heteroaryl, —SO$_2$-alkyl, —SO$_2$-substituted alkyl, —SO$_2$-aryl and —SO$_2$-heteroaryl; or $R^7$ and $R^8$ together form an oxo group; or $R^9$ and $R^{10}$ together form an oxo group;

$R^{11}$ is selected from alkyl, substituted alkyl, hydroxy, alkoxy, substituted alkoxy, amino, substituted amino, carboxyl, carboxyl ester, cyano, halogen, acyl, aminoacyl, nitro, alkenyl, substituted alkenyl, alkynyl, and substituted alkynyl;

$Y^1$ and $Y^2$ are independently selected from hydrogen and alkyl;

$Ar^1$ is selected from aryl, substituted aryl, heteroaryl, and substituted heteroaryl; and $H^1$ and $H^2$ are hydrogen with trans relative configuration.

or a salt or stereoisomer thereof.

Reference to formula (II) is meant to include compounds of formula (II) and (IIa)-(IIb).

In formulae (II), $Ar^1$ is selected from aryl, substituted aryl, heteroaryl, and substituted heteroaryl. In certain embodiments, $Ar^1$ is aryl or substituted aryl. In certain embodiments, $Ar^1$ is aryl. In certain embodiments, $Ar^1$ is substituted aryl. In certain embodiments, $Ar^1$ is heteroaryl or substituted heteroaryl. In certain embodiments, $Ar^1$ is heteroaryl. In certain embodiments, $Ar^1$ is substituted heteroaryl.

In formula (IIa) and (IIb), in certain embodiments, the compound is optically active. In certain embodiments, there is an enantiomeric excess of 90% or more. In certain embodiments, there is an enantiomeric excess of 95% or more. In certain embodiments, there is an enantiomeric excess of 99% or more.

Formula III

In one of its composition aspects, the present embodiments provide a compound of formula (III):

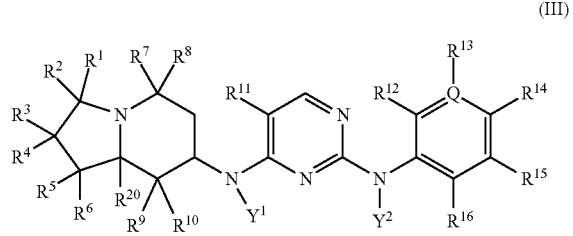

(III)

wherein $R^1$, $R^2$, $R^3$, $R^4$, $R^5$, and $R^6$ are independently selected from hydrogen, alkyl, substituted alkyl, alkoxy, substituted alkoxy, acyl, acylamino, acyloxy, amino, substituted amino, aminoacyl, aminoacyloxy, oxyaminoacyl, azido, cyano, halogen, hydroxyl, carboxyl, carboxylalkyl, thiol, thioalkoxy, substituted thioalkoxy, aryl, aryloxy, hydroxyamino, alkoxyamino, nitro, —SO-alkyl, —SO-substituted alkyl, —SO-aryl, —SO-heteroaryl, —SO$_2$-alkyl, —SO$_2$-substituted alkyl, —SO$_2$-aryl and —SO$_2$-heteroaryl; or $R^1$ and $R^2$ together form an oxo group; or $R^3$ and $R^4$ together form an oxo group; or $R^5$ and $R^6$ together form an oxo group;

$R^7$, $R^8$, $R^9$, and $R^{10}$ are independently selected from hydrogen, alkyl, substituted alkyl, alkoxy, substituted alkoxy, acyl, acylamino, acyloxy, amino, substituted amino, aminoacyl, aminoacyloxy, oxyaminoacyl, azido, cyano, halogen, hydroxyl, carboxyl, carboxylalkyl, thiol, thioalkoxy, substituted thioalkoxy, aryl, aryloxy, hydroxyamino, alkoxyamino, nitro, —SO-alkyl, —SO-substituted alkyl, —SO-aryl, —SO-heteroaryl, —SO$_2$-alkyl, —SO$_2$-substituted alkyl, —SO$_2$-aryl and —SO$_2$-heteroaryl; or $R^7$ and $R^8$ together form an oxo group; or $R^9$ and $R^{10}$ together form an oxo group;

$R^{11}$ is selected from alkyl, substituted alkyl, hydroxy, alkoxy, substituted alkoxy, amino, substituted amino, carboxyl, carboxyl ester, cyano, halogen, acyl, aminoacyl, nitro, alkenyl, substituted alkenyl, alkynyl, and substituted alkynyl;

$R^{20}$ is selected from hydrogen, alkyl, and substituted alkyl;

$Y^1$ and $Y^2$ are independently selected from hydrogen and alkyl;

Q is C or N; and $R^{12}$, $R^{13}$, $R^{14}$, $R^{15}$, and $R^{16}$ are independently selected from hydrogen, alkyl, substituted alkyl, alkenyl, substituted alkenyl, alkynyl, substituted alkynyl, halogen, cyano, hydroxyl, alkoxy, substituted alkoxy, amino, substituted amino, acylamino, aminocarbonylamino, alkoxycarbonylamino, acyl, carboxyl, carboxyl ester, aminoacyl, aminocarbonyloxy, nitro, sulfonyl, sulfonylamino, aminosulfonyl, sulfur pentafluoride, aryl, substituted aryl, cycloalkyl, substituted cycloalkyl, heteroaryl, substituted heteroaryl, heterocyclyl, substituted heterocyclyl, heterocyclyloxy, and substituted heterocyclyloxy, or $R^{14}$ and $R^{15}$ together with the carbon atoms to which they are attached form aryl, substituted aryl, heteroaryl, substituted heteroaryl, heterocyclyl, or substituted heterocyclyl;

or a salt or stereoisomer thereof.

In one of its composition aspects, the present embodiments provide a compound of formula (IIIa):

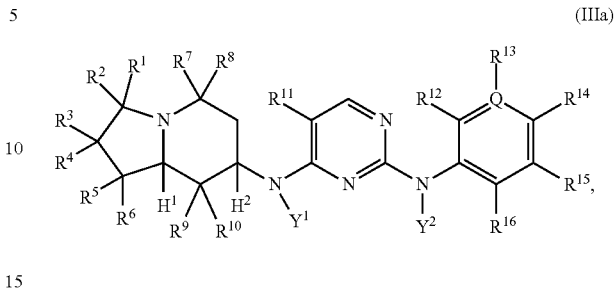

(IIIa)

wherein $R^1$, $R^2$, $R^3$, $R^4$, $R^5$, and $R^6$ are independently selected from hydrogen, alkyl, substituted alkyl, alkoxy, substituted alkoxy, acyl, acylamino, acyloxy, amino, substituted amino, aminoacyl, aminoacyloxy, oxyaminoacyl, azido, cyano, halogen, hydroxyl, carboxyl, carboxylalkyl, thiol, thioalkoxy, substituted thioalkoxy, aryl, aryloxy, hydroxyamino, alkoxyamino, nitro, —SO-alkyl, —SO-substituted alkyl, —SO-aryl, —SO-heteroaryl, —SO$_2$-alkyl, —SO$_2$-substituted alkyl, —SO$_2$-aryl and —SO$_2$-heteroaryl; or $R^1$ and $R^2$ together form an oxo group; or $R^3$ and $R^4$ together form an oxo group; or $R^5$ and $R^6$ together form an oxo group;

$R^7$, $R^8$, $R^9$, and $R^{10}$ are independently selected from hydrogen, alkyl, substituted alkyl, alkoxy, substituted alkoxy, acyl, acylamino, acyloxy, amino, substituted amino, aminoacyl, aminoacyloxy, oxyaminoacyl, azido, cyano, halogen, hydroxyl, carboxyl, carboxylalkyl, thiol, thioalkoxy, substituted thioalkoxy, aryl, aryloxy, hydroxyamino, alkoxyamino, nitro, —SO-alkyl, —SO-substituted alkyl, —SO-aryl, —SO-heteroaryl, —SO$_2$-alkyl, —SO$_2$-substituted alkyl, —SO$_2$-aryl and —SO$_2$-heteroaryl; or $R^7$ and $R^8$ together form an oxo group; or $R^9$ and $R^{10}$ together form an oxo group;

$R^{11}$ is selected from alkyl, substituted alkyl, hydroxy, alkoxy, substituted alkoxy, amino, substituted amino, carboxyl, carboxyl ester, cyano, halogen, acyl, aminoacyl, nitro, alkenyl, substituted alkenyl, alkynyl, and substituted alkynyl;

$Y^1$ and $Y^2$ are independently selected from hydrogen and alkyl;

Q is C or N;

$R^{12}$, $R^{13}$, $R^{14}$, $R^{15}$, and $R^{16}$ are independently selected from hydrogen, alkyl, substituted alkyl, alkenyl, substituted alkenyl, alkynyl, substituted alkynyl, halogen, cyano, hydroxyl, alkoxy, substituted alkoxy, amino, substituted amino, acylamino, aminocarbonylamino, alkoxycarbonylamino, acyl, carboxyl, carboxyl ester, aminoacyl, aminocarbonyloxy, nitro, sulfonyl, sulfonylamino, aminosulfonyl, sulfur pentafluoride, aryl, substituted aryl, cycloalkyl, substituted cycloalkyl, heteroaryl, substituted heteroaryl, heterocyclyl, substituted heterocyclyl, heterocyclyloxy, and substituted heterocyclyloxy, or $R^{14}$ and $R^{15}$ together with the carbon atoms to which they are attached form aryl, substituted aryl, heteroaryl, substituted heteroaryl, heterocyclyl, or substituted heterocyclyl; and $H^1$ and $H^2$ are hydrogen with cis relative configuration;

or a salt or stereoisomer thereof.

In one of its composition aspects, the present embodiments provide a compound of formula (IIIb):

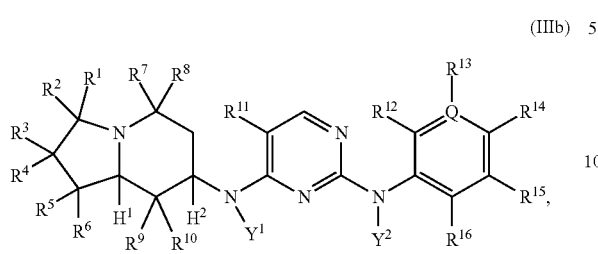

(IIIb)

wherein $R^1$, $R^2$, $R^3$, $R^4$, $R^5$, and $R^6$ are independently selected from hydrogen, alkyl, substituted alkyl, alkoxy, substituted alkoxy, acyl, acylamino, acyloxy, amino, substituted amino, aminoacyl, aminoacyloxy, oxyaminoacyl, azido, cyano, halogen, hydroxyl, carboxyl, carboxylalkyl, thiol, thioalkoxy, substituted thioalkoxy, aryl, aryloxy, hydroxyamino, alkoxyamino, nitro, —SO-alkyl, —SO-substituted alkyl, —SO-aryl, —SO-heteroaryl, —$SO_2$-alkyl, —$SO_2$-substituted alkyl, —$SO_2$-aryl and —$SO_2$-heteroaryl; or $R^1$ and $R^2$ together form an oxo group; or $R^3$ and $R^4$ together form an oxo group; or $R^5$ and $R^6$ together form an oxo group;

$R^7$, $R^8$, $R^9$, and $R^{10}$ are independently selected from hydrogen, alkyl, substituted alkyl, alkoxy, substituted alkoxy, acyl, acylamino, acyloxy, amino, substituted amino, aminoacyl, aminoacyloxy, oxyaminoacyl, azido, cyano, halogen, hydroxyl, carboxyl, carboxylalkyl, thiol, thioalkoxy, substituted thioalkoxy, aryl, aryloxy, hydroxyamino, alkoxyamino, nitro, —SO-alkyl, —SO-substituted alkyl, —SO-aryl, —SO-heteroaryl, —$SO_2$-alkyl, —$SO_2$-substituted alkyl, —$SO_2$-aryl and —$SO_2$-heteroaryl; or $R^7$ and $R^8$ together form an oxo group; or $R^9$ and $R^{10}$ together form an oxo group;

$R^{11}$ is selected from alkyl, substituted alkyl, hydroxy, alkoxy, substituted alkoxy, amino, substituted amino, carboxyl, carboxyl ester, cyano, halogen, acyl, aminoacyl, nitro, alkenyl, substituted alkenyl, alkynyl, and substituted alkynyl;

$Y^1$ and $Y^2$ are independently selected from hydrogen and alkyl;

Q is C or N;

$R^{12}$, $R^{13}$, $R^{14}$, $R^{15}$, and $R^{16}$ are independently selected from hydrogen, alkyl, substituted alkyl, alkenyl, substituted alkenyl, alkynyl, substituted alkynyl, halogen, cyano, hydroxyl, alkoxy, substituted alkoxy, amino, substituted amino, acylamino, aminocarbonylamino, alkoxycarbonylamino, acyl, carboxyl, carboxyl ester, aminoacyl, aminocarbonyloxy, nitro, sulfonyl, sulfonylamino, aminosulfonyl, sulfur pentafluoride, aryl, substituted aryl, cycloalkyl, substituted cycloalkyl, heteroaryl, substituted heteroaryl, heterocyclyl, substituted heterocyclyl, heterocyclyloxy, and substituted heterocyclyloxy, or $R^{14}$ and $R^{15}$ together with the carbon atoms to which they are attached form aryl, substituted aryl, heteroaryl, substituted heteroaryl, heterocyclyl, or substituted heterocyclyl; and $H^1$ and $H^2$ are hydrogen with trans relative configuration; or a salt or stereoisomer thereof.

Reference to formula (III) is meant to include compounds of formula (III) and (IIIa)-(IIIb).

In formula (III), Q is C or N. In certain embodiments, Q is C. In certain embodiments, Q is N.

In formula (IIIa) and (IIIb), in certain embodiments, the compound is optically active. In certain embodiments, there is an enantiomeric excess of 90% or more. In certain embodiments, there is an enantiomeric excess of 95% or more. In certain embodiments, there is an enantiomeric excess of 99% or more.

Formula IV

In one of its composition aspects, the present embodiments provide a compound of formula (IV):

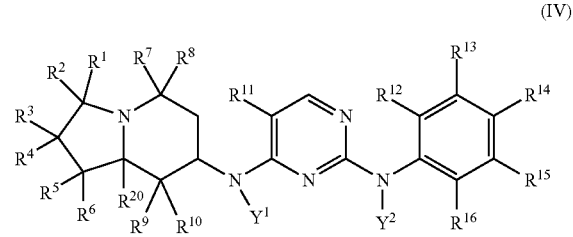

(IV)

wherein $R^1$, $R^2$, $R^3$, $R^4$, $R^5$, and $R^6$ are independently selected from hydrogen, alkyl, substituted alkyl, alkoxy, substituted alkoxy, acyl, acylamino, acyloxy, amino, substituted amino, aminoacyl, aminoacyloxy, oxyaminoacyl, azido, cyano, halogen, hydroxyl, carboxyl, carboxylalkyl, thiol, thioalkoxy, substituted thioalkoxy, aryl, aryloxy, hydroxyamino, alkoxyamino, nitro, —SO-alkyl, —SO-substituted alkyl, —SO-aryl, —SO-heteroaryl, —$SO_2$-alkyl, —$SO_2$-substituted alkyl, —$SO_2$-aryl and —$SO_2$-heteroaryl; or $R^1$ and $R^2$ together form an oxo group; or $R^3$ and $R^4$ together form an oxo group; or $R^5$ and $R^6$ together form an oxo group;

$R^7$, $R^8$, $R^9$, and $R^{10}$ are independently selected from hydrogen, alkyl, substituted alkyl, alkoxy, substituted alkoxy, acyl, acylamino, acyloxy, amino, substituted amino, aminoacyl, aminoacyloxy, oxyaminoacyl, azido, cyano, halogen, hydroxyl, carboxyl, carboxylalkyl, thiol, thioalkoxy, substituted thioalkoxy, aryl, aryloxy, hydroxyamino, alkoxyamino, nitro, —SO-alkyl, —SO-substituted alkyl, —SO-aryl, —SO-heteroaryl, —$SO_2$-alkyl, —$SO_2$-substituted alkyl, —$SO_2$-aryl and —$SO_2$-heteroaryl; or $R^7$ and $R^8$ together form an oxo group; or $R^9$ and $R^{10}$ together form an oxo group;

$R^{11}$ is selected from alkyl, substituted alkyl, hydroxy, alkoxy, substituted alkoxy, amino, substituted amino, carboxyl, carboxyl ester, cyano, halogen, acyl, aminoacyl, nitro, alkenyl, substituted alkenyl, alkynyl, and substituted alkynyl;

$R^{20}$ is selected from hydrogen, alkyl, and substituted alkyl;

$Y^1$ and $Y^2$ are independently selected from hydrogen and alkyl; and $R^{12}$, $R^{13}$, $R^{14}$, $R^{15}$, and $R^{16}$ are independently selected from hydrogen, alkyl, substituted alkyl, alkenyl, substituted alkenyl, alkynyl, substituted alkynyl, halogen, cyano, hydroxyl, alkoxy, substituted alkoxy, amino, substituted amino, acylamino, aminocarbonylamino, alkoxycarbonylamino, acyl, carboxyl, carboxyl ester, aminoacyl, aminocarbonyloxy, nitro, sulfonyl, sulfonylamino, aminosulfonyl, sulfur pentafluoride, aryl, substituted aryl, cycloalkyl, substituted cycloalkyl, heteroaryl, substituted heteroaryl, heterocyclyl, substituted heterocyclyl, heterocyclyloxy, and substituted heterocyclyloxy, or $R^{14}$ and $R^{15}$ together with the carbon atoms to which they are attached form aryl, substituted aryl, heteroaryl, substituted heteroaryl, heterocyclyl, or substituted heterocyclyl;

or a salt or stereoisomer thereof.

In one of its composition aspects, the present embodiments provide a compound of formula (IVa):

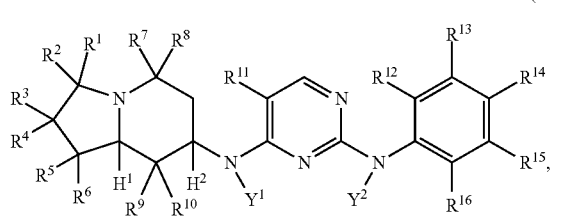

(IVa)

wherein $R^1$, $R^2$, $R^3$, $R^4$, $R^5$, and $R^6$ are independently selected from hydrogen, alkyl, substituted alkyl, alkoxy, substituted alkoxy, acyl, acylamino, acyloxy, amino, substituted amino, aminoacyl, aminoacyloxy, oxyaminoacyl, azido, cyano, halogen, hydroxyl, carboxyl, carboxylalkyl, thiol, thioalkoxy, substituted thioalkoxy, aryl, aryloxy, hydroxyamino, alkoxyamino, nitro, —SO-alkyl, —SO-substituted alkyl, —SO-aryl, —SO-heteroaryl, —$SO_2$-alkyl, —$SO_2$-substituted alkyl, —$SO_2$-aryl and —$SO_2$-heteroaryl; or $R^1$ and $R^2$ together form an oxo group; or $R^3$ and $R^4$ together form an oxo group; or $R^5$ and $R^6$ together form an oxo group;

$R^7$, $R^8$, $R^9$, and $R^{10}$ are independently selected from hydrogen, alkyl, substituted alkyl, alkoxy, substituted alkoxy, acyl, acylamino, acyloxy, amino, substituted amino, aminoacyl, aminoacyloxy, oxyaminoacyl, azido, cyano, halogen, hydroxyl, carboxyl, carboxylalkyl, thiol, thioalkoxy, substituted thioalkoxy, aryl, aryloxy, hydroxyamino, alkoxyamino, nitro, —SO-alkyl, —SO-substituted alkyl, —SO-aryl, —SO-heteroaryl, —$SO_2$-alkyl, —$SO_2$-substituted alkyl, —$SO_2$-aryl and —$SO_2$-heteroaryl; or $R^7$ and $R^8$ together form an oxo group; or $R^9$ and $R^{10}$ together form an oxo group;

$R^{11}$ is selected from alkyl, substituted alkyl, hydroxy, alkoxy, substituted alkoxy, amino, substituted amino, carboxyl, carboxyl ester, cyano, halogen, acyl, aminoacyl, nitro, alkenyl, substituted alkenyl, alkynyl, and substituted alkynyl;

$Y^1$ and $Y^2$ are independently selected from hydrogen and alkyl;

$R^{12}$, $R^{13}$, $R^{14}$, $R^{15}$, and $R^{16}$ are independently selected from hydrogen, alkyl, substituted alkyl, alkenyl, substituted alkenyl, alkynyl, substituted alkynyl, halogen, cyano, hydroxyl, alkoxy, substituted alkoxy, amino, substituted amino, acylamino, aminocarbonylamino, alkoxycarbonylamino, acyl, carboxyl, carboxyl ester, aminoacyl, aminocarbonyloxy, nitro, sulfonyl, sulfonylamino, aminosulfonyl, sulfur pentafluoride, aryl, substituted aryl, cycloalkyl, substituted cycloalkyl, heteroaryl, substituted heteroaryl, heterocyclyl, substituted heterocyclyl, heterocyclyloxy, and substituted heterocyclyloxy, or $R^{14}$ and $R^{15}$ together with the carbon atoms to which they are attached form aryl, substituted aryl, heteroaryl, substituted heteroaryl, heterocyclyl, or substituted heterocyclyl; and $H^1$ and $H^2$ are hydrogen with cis relative configuration; or a salt or stereoisomer thereof.

In one of its composition aspects, the present embodiments provide a compound of formula (IVb):

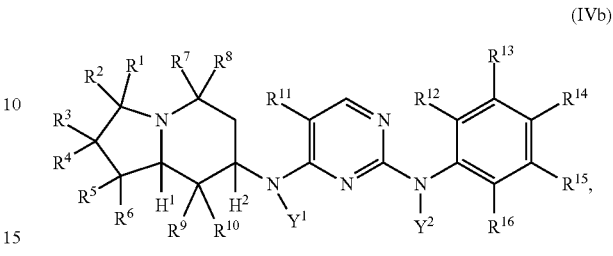

(IVb)

wherein $R^1$, $R^2$, $R^3$, $R^4$, $R^5$, and $R^6$ are independently selected from hydrogen, alkyl, substituted alkyl, alkoxy, substituted alkoxy, acyl, acylamino, acyloxy, amino, substituted amino, aminoacyl, aminoacyloxy, oxyaminoacyl, azido, cyano, halogen, hydroxyl, carboxyl, carboxylalkyl, thiol, thioalkoxy, substituted thioalkoxy, aryl, aryloxy, hydroxyamino, alkoxyamino, nitro, —SO-alkyl, —SO-substituted alkyl, —SO-aryl, —SO-heteroaryl, —$SO_2$-alkyl, —$SO_2$-substituted alkyl, —$SO_2$-aryl and —$SO_2$-heteroaryl; or $R^1$ and $R^2$ together form an oxo group; or $R^3$ and $R^4$ together form an oxo group; or $R^5$ and $R^6$ together form an oxo group;

$R^7$, $R^8$, $R^9$, and $R^{10}$ are independently selected from hydrogen, alkyl, substituted alkyl, alkoxy, substituted alkoxy, acyl, acylamino, acyloxy, amino, substituted amino, aminoacyl, aminoacyloxy, oxyaminoacyl, azido, cyano, halogen, hydroxyl, carboxyl, carboxylalkyl, thiol, thioalkoxy, substituted thioalkoxy, aryl, aryloxy, hydroxyamino, alkoxyamino, nitro, —SO-alkyl, —SO-substituted alkyl, —SO-aryl, —SO-heteroaryl, —$SO_2$-alkyl, —$SO_2$-substituted alkyl, —$SO_2$-aryl and —$SO_2$-heteroaryl; or $R^7$ and $R^8$ together form an oxo group; or $R^9$ and $R^{10}$ together form an oxo group;

$R^{11}$ is selected from alkyl, substituted alkyl, hydroxy, alkoxy, substituted alkoxy, amino, substituted amino, carboxyl, carboxyl ester, cyano, halogen, acyl, aminoacyl, nitro, alkenyl, substituted alkenyl, alkynyl, and substituted alkynyl;

$Y^1$ and $Y^2$ are independently selected from hydrogen and alkyl;

$R^{12}$, $R^{13}$, $R^{14}$, $R^{15}$, and $R^{16}$ are independently selected from hydrogen, alkyl, substituted alkyl, alkenyl, substituted alkenyl, alkynyl, substituted alkynyl, halogen, cyano, hydroxyl, alkoxy, substituted alkoxy, amino, substituted amino, acylamino, aminocarbonylamino, alkoxycarbonylamino, acyl, carboxyl, carboxyl ester, aminoacyl, aminocarbonyloxy, nitro, sulfonyl, sulfonylamino, aminosulfonyl, sulfur pentafluoride, aryl, substituted aryl, cycloalkyl, substituted cycloalkyl, heteroaryl, substituted heteroaryl, heterocyclyl, substituted heterocyclyl, heterocyclyloxy, and substituted heterocyclyloxy, or $R^{14}$ and $R^{15}$ together with the carbon atoms to which they are attached form aryl, substituted aryl, heteroaryl, substituted heteroaryl, heterocyclyl, or substituted heterocyclyl; and $H^1$ and $H^2$ are hydrogen with trans relative configuration; or a salt or stereoisomer thereof.

In one of its composition aspects, the present embodiments provide a compound of formula (IVc):

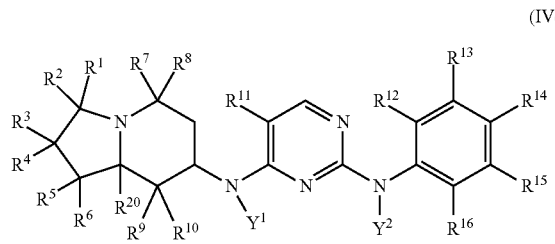

(IVc)

wherein $R^1$, $R^2$, $R^3$, $R^4$, $R^5$, and $R^6$ are independently selected from hydrogen, alkyl, substituted alkyl, alkoxy, substituted alkoxy, acyl, acylamino, acyloxy, amino, substituted amino, aminoacyl, aminoacyloxy, oxyaminoacyl, azido, cyano, halogen, hydroxyl, carboxyl, carboxylalkyl, thiol, thioalkoxy, substituted thioalkoxy, aryl, aryloxy, hydroxyamino, alkoxyamino, nitro, —SO-alkyl, —SO-substituted alkyl, —SO-aryl, —SO-heteroaryl, —$SO_2$-alkyl, —$SO_2$-substituted alkyl, —$SO_2$-aryl and —$SO_2$-heteroaryl; or $R^1$ and $R^2$ together form an oxo group; or $R^3$ and $R^4$ together form an oxo group; or $R^5$ and $R^6$ together form an oxo group;

$R^7$, $R^8$, $R^9$, and $R^{10}$ are independently selected from hydrogen, alkyl, substituted alkyl, alkoxy, substituted alkoxy, acyl, acylamino, acyloxy, amino, substituted amino, aminoacyl, aminoacyloxy, oxyaminoacyl, azido, cyano, halogen, hydroxyl, carboxyl, carboxylalkyl, thiol, thioalkoxy, substituted thioalkoxy, aryl, aryloxy, hydroxyamino, alkoxyamino, nitro, —SO-alkyl, —SO-substituted alkyl, —SO-aryl, —SO-heteroaryl, —$SO_2$-alkyl, —$SO_2$-substituted alkyl, —$SO_2$-aryl and —$SO_2$-heteroaryl; or $R^7$ and $R^8$ together form an oxo group; or $R^9$ and $R^{10}$ together form an oxo group;

$R^{11}$ is selected from alkyl, substituted alkyl, hydroxy, alkoxy, substituted alkoxy, amino, substituted amino, carboxyl, carboxyl ester, cyano, halogen, acyl, aminoacyl, nitro, alkenyl, substituted alkenyl, alkynyl, and substituted alkynyl;

$R^{20}$ is selected from hydrogen, alkyl, and substituted alkyl;

$Y^1$ and $Y^2$ are independently selected from hydrogen and alkyl; and $R^{12}$ is selected from hydrogen and halogen;

$R^{13}$ and $R^{16}$ are hydrogen;

$R^{14}$ is an alkoxy substituted with hydroxyl and optionally substituted with one or more alkyl groups;

$R^{15}$ is substituted heterocyclyl; or a salt or stereoisomer thereof.

In some embodiments of the present compounds, such as compounds of formula (IVc), $R^{14}$ has the formula —O-Alk-$OR^{25}$, where Alk is an optionally substituted alkylene group and $R^{25}$ is selected from H and an optionally substituted alkyl group. In some embodiments, Alk is an alkylene group. In some embodiments, Alk is a substituted alkylene group. In some embodiments of such compounds, Alk represents an optionally substituted ethylene or propylene moiety. In certain embodiments, Alk is an ethylene moiety. In certain embodiments, Alk is a propylene moiety. In certain embodiments, Alk is a substituted ethylene moiety. In certain embodiments, Alk is a substituted propylene moiety. In some embodiments, Alk is substituted with one, two or three $C_{1-6}$ alkyl groups, such as, by way of example, one or two methyl groups substituted on the same or different carbon atoms of the alkylene chain.

Reference to formula (IV) is meant to include compounds of formula (IV) and (IVa)-(IVc).

In formula (IVa) and (IVc), in certain embodiments, the compound is optically active. In certain embodiments, there is an enantiomeric excess of 90% or more. In certain embodiments, there is an enantiomeric excess of 95% or more. In certain embodiments, there is an enantiomeric excess of 99% or more.

Formula V

In one of its composition aspects, the present embodiments provide a compound of formula (V):

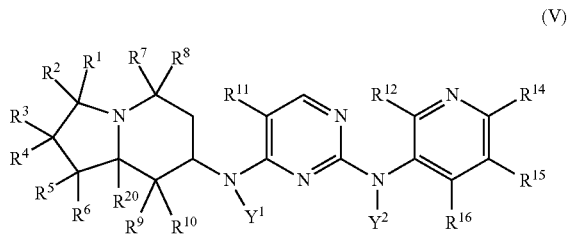

(V)

wherein $R^1$, $R^2$, $R^3$, $R^4$, $R^5$, and $R^6$ are independently selected from hydrogen, alkyl, substituted alkyl, alkoxy, substituted alkoxy, acyl, acylamino, acyloxy, amino, substituted amino, aminoacyl, aminoacyloxy, oxyaminoacyl, azido, cyano, halogen, hydroxyl, carboxyl, carboxylalkyl, thiol, thioalkoxy, substituted thioalkoxy, aryl, aryloxy, hydroxyamino, alkoxyamino, nitro, —SO-alkyl, —SO-substituted alkyl, —SO-aryl, —SO-heteroaryl, —$SO_2$-alkyl, —$SO_2$-substituted alkyl, —$SO_2$-aryl and —$SO_2$-heteroaryl; or $R^1$ and $R^2$ together form an oxo group; or $R^3$ and $R^4$ together form an oxo group; or $R^5$ and $R^6$ together form an oxo group;

$R^7$, $R^8$, $R^9$, and $R^{10}$ are independently selected from hydrogen, alkyl, substituted alkyl, alkoxy, substituted alkoxy, acyl, acylamino, acyloxy, amino, substituted amino, aminoacyl, aminoacyloxy, oxyaminoacyl, azido, cyano, halogen, hydroxyl, carboxyl, carboxylalkyl, thiol, thioalkoxy, substituted thioalkoxy, aryl, aryloxy, hydroxyamino, alkoxyamino, nitro, —SO-alkyl, —SO-substituted alkyl, —SO-aryl, —SO-heteroaryl, —$SO_2$-alkyl, —$SO_2$-substituted alkyl, —$SO_2$-aryl and —$SO_2$-heteroaryl; or $R^7$ and $R^8$ together form an oxo group; or $R^9$ and $R^{10}$ together form an oxo group;

$R^{11}$ is selected from alkyl, substituted alkyl, hydroxy, alkoxy, substituted alkoxy, amino, substituted amino, carboxyl, carboxyl ester, cyano, halogen, acyl, aminoacyl, nitro, alkenyl, substituted alkenyl, alkynyl, and substituted alkynyl;

$R^{20}$ is selected from hydrogen, alkyl, and substituted alkyl;

$Y^1$ and $Y^2$ are independently selected from hydrogen and alkyl; and $R^{12}$, $R^{14}$, $R^{15}$, and $R^{16}$ are independently selected from hydrogen, alkyl, substituted alkyl, alkenyl, substituted alkenyl, alkynyl, substituted alkynyl, halogen, cyano, hydroxyl, alkoxy, substituted alkoxy, amino, substituted amino, acylamino, aminocarbonylamino, alkoxycarbonylamino, acyl, carboxyl, carboxyl ester, aminoacyl, aminocarbonyloxy, nitro, sulfonyl, sulfonylamino, aminosulfonyl, sulfur pentafluoride, aryl, substituted aryl, cycloalkyl, substituted cycloalkyl, heteroaryl, substituted heteroaryl, heterocyclyl, substituted heterocyclyl, heterocyclyloxy, and substituted heterocyclyloxy, or $R^{14}$ and $R^{15}$ together with the carbon atoms to which they are attached form aryl, substituted aryl, heteroaryl, substituted heteroaryl, heterocyclyl, or substituted heterocyclyl;

or a salt or stereoisomer thereof.

In one of its composition aspects, the present embodiments provide a compound of formula (Va):

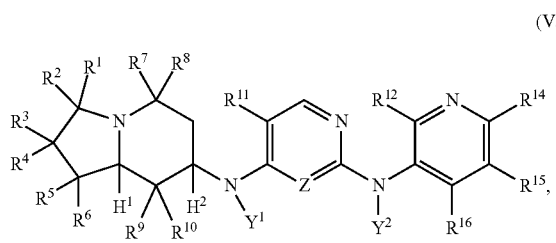

(Va)

wherein $R^1$, $R^2$, $R^3$, $R^4$, $R^5$, and $R^6$ are independently selected from hydrogen, alkyl, substituted alkyl, alkoxy, substituted alkoxy, acyl, acylamino, acyloxy, amino, substituted amino, aminoacyl, aminoacyloxy, oxyaminoacyl, azido, cyano, halogen, hydroxyl, carboxyl, carboxylalkyl, thiol, thioalkoxy, substituted thioalkoxy, aryl, aryloxy, hydroxyamino, alkoxyamino, nitro, —SO-alkyl, —SO-substituted alkyl, —SO-aryl, —SO-heteroaryl, —$SO_2$-alkyl, —$SO_2$-substituted alkyl, —$SO_2$-aryl and —$SO_2$-heteroaryl; or $R^1$ and $R^2$ together form an oxo group; or $R^3$ and $R^4$ together form an oxo group; or $R^5$ and $R^6$ together form an oxo group;

$R^7$, $R^8$, $R^9$, and $R^{10}$ are independently selected from hydrogen, alkyl, substituted alkyl, alkoxy, substituted alkoxy, acyl, acylamino, acyloxy, amino, substituted amino, aminoacyl, aminoacyloxy, oxyaminoacyl, azido, cyano, halogen, hydroxyl, carboxyl, carboxylalkyl, thiol, thioalkoxy, substituted thioalkoxy, aryl, aryloxy, hydroxyamino, alkoxyamino, nitro, —SO-alkyl, —SO-substituted alkyl, —SO-aryl, —SO-heteroaryl, —$SO_2$-alkyl, —$SO_2$-substituted alkyl, —$SO_2$-aryl and —$SO_2$-heteroaryl; or $R^7$ and $R^8$ together form an oxo group; or $R^9$ and $R^{10}$ together form an oxo group;

$R^{11}$ is selected from alkyl, substituted alkyl, hydroxy, alkoxy, substituted alkoxy, amino, substituted amino, carboxyl, carboxyl ester, cyano, halogen, acyl, aminoacyl, nitro, alkenyl, substituted alkenyl, alkynyl, and substituted alkynyl;

$Y^1$ and $Y^2$ are independently selected from hydrogen and alkyl;

$R^{12}$, $R^{14}$, $R^{15}$, and $R^{16}$ are independently selected from hydrogen, alkyl, substituted alkyl, alkenyl, substituted alkenyl, alkynyl, substituted alkynyl, halogen, cyano, hydroxyl, alkoxy, substituted alkoxy, amino, substituted amino, acylamino, aminocarbonylamino, alkoxycarbonylamino, acyl, carboxyl, carboxyl ester, aminoacyl, aminocarbonyloxy, nitro, sulfonyl, sulfonylamino, aminosulfonyl, sulfur pentafluoride, aryl, substituted aryl, cycloalkyl, substituted cycloalkyl, heteroaryl, substituted heteroaryl, heterocyclyl, substituted heterocyclyl, heterocyclyloxy, and substituted heterocyclyloxy, or $R^{14}$ and $R^{15}$ together with the carbon atoms to which they are attached form aryl, substituted aryl, heteroaryl, substituted heteroaryl, heterocyclyl, or substituted heterocyclyl; and $H^1$ and $H^2$ are hydrogen with cis relative configuration;

or a salt or stereoisomer thereof.

In one of its composition aspects, the present embodiments provide a compound of formula (Vb):

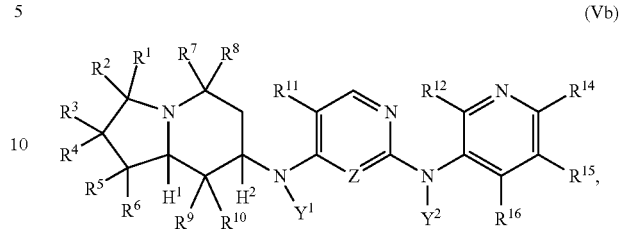

(Vb)

wherein $R^1$, $R^2$, $R^3$, $R^4$, $R^5$, and $R^6$ are independently selected from hydrogen, alkyl, substituted alkyl, alkoxy, substituted alkoxy, acyl, acylamino, acyloxy, amino, substituted amino, aminoacyl, aminoacyloxy, oxyaminoacyl, azido, cyano, halogen, hydroxyl, carboxyl, carboxylalkyl, thiol, thioalkoxy, substituted thioalkoxy, aryl, aryloxy, hydroxyamino, alkoxyamino, nitro, —SO-alkyl, —SO-substituted alkyl, —SO-aryl, —SO-heteroaryl, —$SO_2$-alkyl, —$SO_2$-substituted alkyl, —$SO_2$-aryl and —$SO_2$-heteroaryl; or $R^1$ and $R^2$ together form an oxo group; or $R^3$ and $R^4$ together form an oxo group; or $R^5$ and $R^6$ together form an oxo group;

$R^7$, $R^8$, $R^9$, and $R^{10}$ are independently selected from hydrogen, alkyl, substituted alkyl, alkoxy, substituted alkoxy, acyl, acylamino, acyloxy, amino, substituted amino, aminoacyl, aminoacyloxy, oxyaminoacyl, azido, cyano, halogen, hydroxyl, carboxyl, carboxylalkyl, thiol, thioalkoxy, substituted thioalkoxy, aryl, aryloxy, hydroxyamino, alkoxyamino, nitro, —SO-alkyl, —SO-substituted alkyl, —SO-aryl, —SO-heteroaryl, —$SO_2$-alkyl, —$SO_2$-substituted alkyl, —$SO_2$-aryl and —$SO_2$-heteroaryl; or $R^7$ and $R^8$ together form an oxo group; or $R^9$ and $R^{10}$ together form an oxo group;

$R^{11}$ is selected from alkyl, substituted alkyl, hydroxy, alkoxy, substituted alkoxy, amino, substituted amino, carboxyl, carboxyl ester, cyano, halogen, acyl, aminoacyl, nitro, alkenyl, substituted alkenyl, alkynyl, and substituted alkynyl;

$Y^1$ and $Y^2$ are independently selected from hydrogen and alkyl;

$R^{12}$, $R^{14}$, $R^{15}$, and $R^{16}$ are independently selected from hydrogen, alkyl, substituted alkyl, alkenyl, substituted alkenyl, alkynyl, substituted alkynyl, halogen, cyano, hydroxyl, alkoxy, substituted alkoxy, amino, substituted amino, acylamino, aminocarbonylamino, alkoxycarbonylamino, acyl, carboxyl, carboxyl ester, aminoacyl, aminocarbonyloxy, nitro, sulfonyl, sulfonylamino, aminosulfonyl, sulfur pentafluoride, aryl, substituted aryl, cycloalkyl, substituted cycloalkyl, heteroaryl, substituted heteroaryl, heterocyclyl, substituted heterocyclyl, heterocyclyloxy, and substituted heterocyclyloxy, or $R^{14}$ and $R^{15}$ together with the carbon atoms to which they are attached form aryl, substituted aryl, heteroaryl, substituted heteroaryl, heterocyclyl, or substituted heterocyclyl; and $H^1$ and $H^2$ are hydrogen with trans relative configuration; or a salt or stereoisomer thereof.

Reference to formula (V) is meant to include compounds of formula (V) and (Va)-(Vb)

In formula (Va) and (Vb), in certain embodiments, the compound is optically active. In certain embodiments, there is an enantiomeric excess of 90% or more. In certain embodiments, there is an enantiomeric excess of 95% or more. In certain embodiments, there is an enantiomeric excess of 99% or more.

Certain Embodiments of Formulae I-V

With reference to formulae I-V, the formula

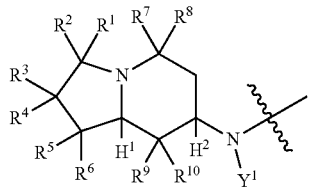

includes at least two chiral centers, and thus at least four stereoisomers. For clarity the numbering of the ring system is shown below with optional substituents omitted.

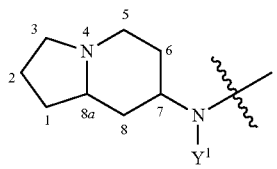

With continued reference to formulae I-V, (7,8a) cis diastereomer has the structure:

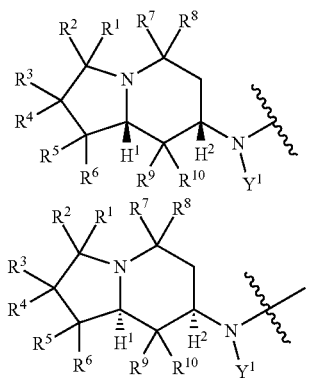

and the (7,8a) trans diastereomer:

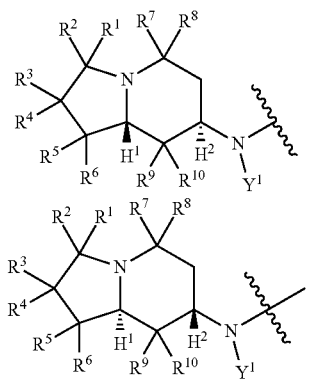

In formulae I-V, $R^1$, $R^2$, $R^3$, $R^4$, $R^5$, and $R^6$ are independently selected from hydrogen, alkyl, substituted alkyl, alkoxy, substituted alkoxy, acyl, acylamino, acyloxy, amino, substituted amino, aminoacyl, aminoacyloxy, oxyaminoacyl, azido, cyano, halogen, hydroxyl, carboxyl, carboxylalkyl, thiol, thioalkoxy, substituted thioalkoxy, aryl, aryloxy, hydroxyamino, alkoxyamino, nitro, —SO-alkyl, —SO-substituted alkyl, —SO-aryl, —SO-heteroaryl, —SO$_2$-alkyl, —SO$_2$-substituted alkyl, —SO$_2$-aryl and —SO$_2$-heteroaryl; or $R^1$ and $R^2$ together form an oxo group; or $R^3$ and $R^4$ together form an oxo group; or $R^5$ and $R^6$ together form an oxo group.

In certain embodiments, $R^1$, $R^2$, $R^3$, $R^4$, $R^5$, and $R^6$ are independently selected from hydrogen, alkyl, substituted alkyl, cyano, halogen, hydroxyl, acyl, aminoacyl, and nitro; or $R^1$ and $R^2$ together form an oxo group; or $R^3$ and $R^4$ together form an oxo group; or $R^5$ and $R^6$ together form an oxo group.

In certain embodiments, $R^1$, $R^2$, $R^3$, $R^4$, $R^5$, and $R^6$ are independently selected from hydrogen, alkyl, substituted alkyl, halogen, and hydroxyl; or $R^1$ and $R^2$ together form an oxo group; or $R^3$ and $R^4$ together form an oxo group; or $R^5$ and $R^6$ together form an oxo group.

In certain embodiments, $R^1$ and $R^2$ are each hydrogen. In certain embodiments, $R^1$ and $R^2$ are each alkyl, such as $C_1$-$C_6$ alkyl, or $C_1$-$C_3$ alkyl. In certain embodiments, $R^1$ and $R^2$ are each methyl.

In certain embodiments, at least one of $R^3$ and $R^4$ is hydrogen. In certain embodiments, $R^3$ and $R^4$ are each hydrogen. In certain embodiments, at least one of $R^3$ and $R^4$ is halogen or hydroxyl. In certain embodiments, at least one of $R^3$ and $R^4$ is halogen. In certain embodiments, one of $R^3$ and $R^4$ is halogen. In certain embodiments, at least one of $R^3$ and $R^4$ is F. In certain embodiments, one of $R^3$ and $R^4$ is F. In certain embodiments, $R^3$ and $R^4$ are each halogen. In certain embodiments, $R^3$ and $R^4$ are each F. In certain embodiments, at least one of $R^3$ and $R^4$ is hydroxyl. In certain embodiments, one of $R^3$ and $R^4$ is hydroxyl.

In certain embodiments, at least one of $R^5$ and $R^6$ is hydrogen. In certain embodiments, $R^5$ and $R^6$ are each hydrogen.

In certain embodiments, $R^1$ and $R^2$ together form an oxo group; or $R^3$ and $R^4$ together form an oxo group; or $R^5$ and $R^6$ together form an oxo group. In certain embodiments, $R^1$ and $R^2$ together form an oxo group. In certain embodiments, $R^3$ and $R^4$ together form an oxo group. In certain embodiments, $R^5$ and $R^6$ together form an oxo group.

In certain embodiments, $R^1$, $R^2$, $R^3$, $R^4$, $R^5$, and $R^6$ are each hydrogen.

In certain embodiments, $R^1$, $R^2$, $R^3$, $R^4$, $R^5$, and $R^6$ are independently selected from hydrogen, alkyl, and substituted alkyl. In certain embodiments, $R^1$, $R^2$, $R^3$, $R^4$, $R^5$, and $R^6$ are independently selected from hydrogen, alkoxy, substituted alkoxy, aryloxy, hydroxyamino, alkoxyamino, and nitro. In certain embodiments, $R^1$, $R^2$, $R^3$, $R^4$, $R^5$, and $R^6$ are independently selected from hydrogen, acyl, acylamino, acyloxy, amino, substituted amino, aminoacyl, aminoacyloxy, oxyaminoacyl, and azido. In certain embodiments, $R^1$, $R^2$, $R^3$, $R^4$, $R^5$, and $R^6$ are independently selected from hydrogen, cyano, halogen, and hydroxyl. In certain embodiments, $R^1$, $R^2$, $R^3$, $R^4$, $R^5$, and $R^6$ re independently selected from hydrogen, carboxyl, carboxylalkyl, thiol, thioalkoxy, and substituted thioalkoxy. In certain embodiments, $R^1$, $R^2$, $R^3$, $R^4$, $R^5$, and $R^6$ are independently selected from hydrogen and aryl. In certain embodiments, $R^1$, $R^2$, $R^3$, $R^4$, $R^5$, and $R^6$ are independently selected from hydrogen, —SO-alkyl, —SO-substituted alkyl, —SO-aryl, —SO-heteroaryl, —SO$_2$-alkyl, —SO$_2$-substituted alkyl, —SO$_2$-aryl and —SO$_2$-heteroaryl.

In certain embodiments, $R^1$ and $R^2$ together form an oxo group; or $R^3$ and $R^4$ together form an oxo group; or $R^5$ and $R^6$ together form an oxo group.

In formulae I-V, $R^7$, $R^8$, $R^9$, and $R^{10}$ are independently selected from hydrogen, alkyl, substituted alkyl, alkoxy, substituted alkoxy, acyl, acylamino, acyloxy, amino, substituted amino, aminoacyl, aminoacyloxy, oxyaminoacyl, azido, cyano, halogen, hydroxyl, carboxyl, carboxylalkyl, thiol, thioalkoxy, substituted thioalkoxy, aryl, aryloxy, hydroxyamino, alkoxyamino, nitro, —SO-alkyl, —SO-substituted alkyl, —SO-aryl, —SO-heteroaryl, —SO$_2$-alkyl, —SO$_2$-substituted alkyl, —SO$_2$-aryl and —SO$_2$-heteroaryl; or $R^7$ and $R^8$ together form an oxo group; or $R^9$ and $R^{10}$ together form an oxo group.

In certain embodiments, $R^7$, $R^8$, $R^9$, and $R^{10}$ are independently selected from hydrogen, alkyl, substituted alkyl, alkoxy, substituted alkoxy, cyano, halogen, acyl, aminoacyl, and nitro; or $R^7$ and $R^8$ together form an oxo group. In certain embodiments, $R^7$, $R^8$, $R^9$, and $R^{10}$ are independently selected from hydrogen, alkyl, substituted alkyl, and halogen; or $R^7$ and $R^8$ together form an oxo group.

In certain embodiments, $R^7$ and $R^8$ are each hydrogen. In certain embodiments, $R^7$ and $R^8$ are each alkyl, such as $C_1$-$C_6$ alkyl, or $C_1$-$C_3$ alkyl. In certain embodiments, $R^7$ and $R^8$ are each methyl. In certain embodiments, $R^7$ and $R^8$ together form an oxo group.

In certain embodiments, at least one of $R^9$ and $R^{10}$ is hydrogen. In certain embodiments, $R^9$ and $R^{10}$ are each hydrogen. In certain embodiments, at least one of $R^9$ and $R^{10}$ is alkyl, such as $C_1$-$C_6$ alkyl, or $C_1$-$C_3$ alkyl. In certain embodiments, at least one of $R^9$ and $R^{10}$ is methyl. In certain embodiments, one of $R^9$ and $R^{10}$ is methyl. In certain embodiments, $R^9$ and $R^{10}$ together form an oxo group.

In certain embodiments, $R^7$, $R^8$, $R^9$, and $R^{10}$ are independently selected from hydrogen, alkyl, and substituted alkyl. In certain embodiments, $R^7$, $R^8$, $R^9$, and $R^{10}$ are independently selected from hydrogen, alkoxy, substituted alkoxy, aryloxy, hydroxyamino, alkoxyamino, and nitro. In certain embodiments, $R^7$, $R^8$, $R^9$, and $R^{10}$ are independently selected from hydrogen, acyl, acylamino, acyloxy, amino, substituted amino, aminoacyl, aminoacyloxy, oxyaminoacyl, and azido. In certain embodiments, $R^7$, $R^8$, $R^9$, and $R^{10}$ are independently selected from hydrogen, cyano, halogen, and hydroxyl. In certain embodiments, $R^7$, $R^8$, $R^9$, and $R^{10}$ are independently selected from hydrogen, carboxyl, carboxylalkyl, thiol, thioalkoxy, and substituted thioalkoxy. In certain embodiments, $R^7$, $R^8$, $R^9$, and $R^{10}$ are independently selected from hydrogen and aryl. In certain embodiments, $R^7$, $R^8$, $R^9$, and $R^{10}$ are independently selected from hydrogen, —SO-alkyl, —SO-substituted alkyl, —SO-aryl, —SO-heteroaryl, —SO$_2$-alkyl, —SO$_2$-substituted alkyl, —SO$_2$-aryl and —SO$_2$-heteroaryl. In certain embodiments, $R^7$ and $R^8$ together form an oxo group; or $R^9$ and $R^{10}$ together form an oxo group.

In formulae I-V, $R^{11}$ is selected from alkyl, substituted alkyl, hydroxy, alkoxy, substituted alkoxy, amino, substituted amino, carboxyl, carboxyl ester, cyano, halogen, acyl, aminoacyl, nitro, alkenyl, substituted alkenyl, alkynyl, and substituted alkynyl.

In certain embodiments, $R^{11}$ is selected from alkoxy, substituted alkoxy, cyano, halogen, acyl, aminoacyl, and nitro. In certain embodiments, $R^{11}$ is cyano, halogen, acyl, aminoacyl, or nitro. In certain embodiments, $R^{11}$ is fluoro or cyano. In certain embodiments, $R^{11}$ is fluoro. In certain embodiments, $R^{11}$ is cyano. In certain embodiments, $R^{11}$ is acyl or aminoacyl. In certain embodiments, $R^{11}$ is nitro.

In formulae I-V, $R^{20}$ is selected from hydrogen, alkyl, and substituted alkyl. In certain embodiments, $R^{20}$ is hydrogen. In certain embodiments, $R^{20}$ is alkyl. In certain embodiments, $R^{20}$ is substituted alkyl.

In formulae I-V, $Y^1$ and $Y^2$ are independently selected from hydrogen and alkyl. In certain embodiments, $Y^1$ and $Y^2$ are hydrogen. In certain embodiments, $Y^1$ and $Y^2$ are alkyl.

In formulae III-V, $R^{12}$, $R^{13}$, $R^{14}$, $R^{15}$, and $R^{16}$ are independently selected from hydrogen, alkyl, substituted alkyl, alkenyl, substituted alkenyl, alkynyl, substituted alkynyl, halogen, cyano, hydroxyl, alkoxy, substituted alkoxy, amino, substituted amino, acylamino, aminocarbonylamino, alkoxycarbonylamino, acyl, carboxyl, carboxyl ester, aminoacyl, aminocarbonyloxy, nitro, sulfonyl, sulfonylamino, aminosulfonyl, sulfur pentafluoride, aryl, substituted aryl, cycloalkyl, substituted cycloalkyl, heteroaryl, substituted heteroaryl, heterocyclyl, substituted heterocyclyl, heterocyclyloxy, and substituted heterocyclyloxy, or $R^{14}$ and $R^{15}$ together with the carbon atoms to which they are attached form aryl, substituted aryl, heteroaryl, substituted heteroaryl, heterocyclyl, or substituted heterocyclyl.

In certain embodiments, $R^{12}$, $R^{13}$, $R^{14}$, $R^{15}$, and $R^{16}$ are independently selected from hydrogen, alkyl, substituted alkyl, halogen, cyano, hydroxyl, alkoxy, substituted alkoxy, amino, substituted amino, acylamino, aminocarbonylamino, acyl, aminoacyl, aminocarbonyloxy, sulfur pentafluoride, aryl, substituted aryl, cycloalkyl, substituted cycloalkyl, heteroaryl, substituted heteroaryl, heterocyclyl, substituted heterocyclyl, heterocyclyloxy, and substituted heterocyclyloxy, or $R^{14}$ and $R^{15}$ together with the carbon atoms to which they are attached form aryl, substituted aryl, heteroaryl, substituted heteroaryl, heterocyclyl, or substituted heterocyclyl.

In certain embodiments, $R^{12}$, $R^{13}$, $R^{14}$, $R^{15}$, and $R^{16}$ are independently selected from hydrogen, alkyl, halogen, cyano, hydroxyl, alkoxy, substituted alkoxy, acylamino, aminocarbonylamino, sulfur pentafluoride, cycloalkyl, substituted cycloalkyl, heteroaryl, substituted heteroaryl, heterocyclyl, substituted heterocyclyl, heterocyclyloxy, and substituted heterocyclyloxy, or $R^{14}$ and $R^{15}$ together with the carbon atoms to which they are attached form aryl, substituted aryl, heteroaryl, substituted heteroaryl, heterocyclyl, or substituted heterocyclyl.

In certain embodiments, $R^{12}$, $R^{13}$, $R^{14}$, $R^{15}$, and $R^{16}$ are independently selected from hydrogen, halogen, cycloalkyl, substituted cycloalkyl, heteroaryl, and substituted heteroaryl. In certain embodiments, $R^{12}$, $R^{13}$, $R^{14}$, $R^{15}$, and $R^{16}$ are independently selected from hydrogen, alkoxy, substituted alkoxy, heteroaryl, and substituted heteroaryl. In certain embodiments, $R^{12}$, $R^{13}$, $R^{14}$, $R^{15}$, and $R^{16}$ are independently selected from hydrogen, alkyl, alkoxy, substituted alkoxy, and cyano. In certain embodiments, $R^{12}$, $R^{13}$, $R^{14}$, $R^{15}$, and $R^{16}$ are independently selected from hydrogen, alkyl, heteroaryl, and substituted heteroaryl.

In certain embodiments, $R^{12}$, $R^{13}$, $R^{14}$, $R^{15}$, and $R^{16}$ are independently selected from hydrogen, alkyl, and substituted alkyl. In certain embodiments, at least one of $R^{12}$, $R^{13}$, $R^{14}$, $R^{15}$, and $R^{16}$ are hydrogen. In certain embodiments, one of $R^{12}$, $R^{13}$, $R^{14}$, $R^{15}$, and $R^{16}$ is hydrogen. In certain embodiments, two of $R^{12}$, $R^{13}$, $R^{14}$, $R^{15}$, and $R^{16}$ are hydrogen. In certain embodiments, three of $R^{12}$, $R^{13}$, $R^{14}$, $R^{15}$, and $R^{16}$ are hydrogen. In certain embodiments, $R^{12}$ and $R^{16}$ are hydrogen. In certain embodiments, $R^{12}$, $R^{13}$, and $R^{16}$ are hydrogen. In certain embodiments, $R^{12}$, $R^{13}$, $R^{14}$, $R^{15}$, and $R^{16}$ are independently selected from alkyl and substituted alkyl. In certain embodiments, $R^{12}$, $R^{13}$, $R^{14}$, $R^{15}$, and $R^{16}$ are independently selected from alkyl, such as $C_1$-$C_6$ alkyl, or $C_1$-$C_3$ alkyl. In certain embodiments, $R^{12}$, $R^{13}$, $R^{14}$, $R^{15}$, and $R^{16}$ are independently selected from methyl. In certain embodiments, $R^{12}$, $R^{13}$, $R^{14}$, $R^{15}$, and $R^{16}$ are independently selected from alkenyl, substituted alkenyl, alkynyl, and substituted alkynyl.

In certain embodiments, $R^{12}$, $R^{13}$, $R^{14}$, $R^{15}$, and $R^{16}$ are independently selected from halogen, cyano, hydroxyl, alkoxy, and substituted alkoxy. In certain embodiments, $R^{12}$, $R^{13}$, $R^{14}$, $R^{15}$, and $R^{16}$ are independently selected from halogen. In certain embodiments, $R^{12}$, $R^{13}$, $R^{14}$, $R^{15}$, and $R^{16}$ are independently selected from fluoro. In certain embodiments, $R^{12}$, $R^{13}$, $R^{14}$, $R^{15}$, and $R^{16}$ are independently selected from cyano. In certain embodiments, $R^{12}$, $R^{13}$, $R^{14}$, $R^{15}$, and $R^{16}$ are independently selected from hydroxyl. In certain embodiments, $R^{12}$, $R^{13}$, $R^{14}$, $R^{15}$, and $R^{16}$ are independently selected from alkoxy. In certain embodiments, $R^{12}$, $R^{13}$, $R^{14}$, $R^{15}$, and $R^{16}$ are independently selected from $C_1$-$C_6$ alkoxy. In certain embodiments, $R^{12}$, $R^{13}$, $R^{14}$, $R^{15}$, and $R^{16}$ are independently selected from $C_1$-$C_3$ alkoxy, such as methoxy, isopropoxy, and the like. In certain embodiments, $R^{12}$, $R^{13}$, $R^{14}$, $R^{15}$, and $R^{16}$ are independently selected from substituted alkoxy. In certain embodiments, $R^{12}$, $R^{13}$, $R^{14}$, $R^{15}$, and $R^{16}$ are independently selected from $C_1$-$C_6$ substituted alkoxy. In certain embodiments, $R^{12}$, $R^{13}$, $R^{14}$, $R^{15}$, and $R^{16}$ are independently selected from $C_1$-$C_3$ substituted alkoxy. In certain embodiments, the substituted alkoxy group is substituted with one or more groups selected from halogen, hydroxyl, alkyl (e.g., $C_1$-$C_6$ alkyl, such as $C_1$-$C_3$ alkyl, including methyl).

In certain embodiments, $R^{12}$, $R^{13}$, $R^{14}$, $R^{15}$, and $R^{16}$ are independently selected from amino and substituted amino. In certain embodiments, $R^{12}$, $R^{13}$, $R^{14}$, $R^{15}$, and $R^{16}$ are independently selected from acylamino, aminocarbonylamino, alkoxycarbonylamino, acyl, carboxyl, carboxyl ester, aminoacyl, and aminocarbonyloxy. In certain embodiments, $R^{12}$, $R^{13}$, $R^{14}$, $R^{15}$, and $R^{16}$ are independently selected from acylamino and aminocarbonylamino. In certain embodiments, $R^{12}$, $R^{13}$, $R^{14}$, $R^{15}$, and $R^{16}$ are independently selected from acylamino. In certain embodiments, $R^{12}$, $R^{13}$, $R^{14}$, $R^{15}$, and $R^{16}$ are independently selected from aminocarbonylamino.

In certain embodiments, $R^{12}$, $R^{13}$, $R^{14}$, $R^{15}$, and $R^{16}$ are independently selected from nitro, sulfonyl, sulfonylamino, aminosulfonyl, and sulfur pentafluoride. In certain embodiments, $R^{12}$, $R^{13}$, $R^{14}$, $R^{15}$, and $R^{16}$ are independently selected from sulfur pentafluoride.

In certain embodiments, $R^{12}$, $R^{13}$, $R^{14}$, $R^{15}$, and $R^{16}$ are independently selected from aryl, substituted aryl, cycloalkyl, substituted cycloalkyl, heteroaryl, substituted heteroaryl, heterocyclyl, substituted heterocyclyl, heterocyclyloxy, and substituted heterocyclyloxy. In certain embodiments, $R^{12}$, $R^{13}$, $R^{14}$, $R^{15}$, and $R^{16}$ are independently selected from aryl and substituted aryl. In certain embodiments, $R^{12}$, $R^{13}$, $R^{14}$, $R^{15}$, and $R^{16}$ are independently selected from cycloalkyl and substituted cycloalkyl. In certain embodiments, $R^{12}$, $R^{13}$, $R^{14}$, $R^{15}$, and $R^{16}$ are independently selected from cycloalkyl. For example, cycloalkyl groups may include, but are not limited to, $C_3$-$C_8$ cycloalkyl, including $C_3$-$C_6$ cycloalkyl, such as cyclohexyl, cyclopentyl, cyclobutyl, cyclopropyl. In certain embodiments, $R^{12}$, $R^{13}$, $R^{14}$, $R^{15}$, and $R^{16}$ are independently selected from cyclopropyl.

In certain embodiments, $R^{12}$, $R^{13}$, $R^{14}$, $R^{15}$, and $R^{16}$ are independently selected from heteroaryl, substituted heteroaryl, heterocyclyl and substituted heterocyclyl. In certain embodiments, $R^{12}$, $R^{13}$, $R^{14}$, $R^{15}$, and $R^{16}$ are independently selected from heteroaryl. In certain embodiments, $R^{12}$, $R^{13}$, $R^{14}$, $R^{15}$, and $R^{16}$ are independently selected from substituted heteroaryl. In certain embodiments, $R^{12}$, $R^{13}$, $R^{14}$, $R^{15}$, and $R^{16}$ are independently selected from heterocyclyl. In certain embodiments, $R^{12}$, $R^{13}$, $R^{14}$, $R^{15}$, and $R^{16}$ are independently selected from substituted heterocyclyl. Examples of heterocycles and heteroaryls include, but are not limited to, tetrazolyl and substituted tetrazolyl. For example, a tetrazolyl group may be substituted with one or more groups, such as an oxo, alkyl, e.g., $C_1$-$C_6$ alkyl, including $C_1$-$C_3$ alkyl, such as methyl, and the like.

In certain embodiments, $R^{12}$, $R^{13}$, $R^{14}$, $R^{15}$, and $R^{16}$ are independently selected from heterocyclyloxy and substituted heterocyclyloxy. In certain embodiments, $R^{12}$, $R^{13}$, $R^{14}$, $R^{15}$, and $R^{16}$ are independently selected from heterocyclyloxy. In certain embodiments, $R^{12}$, $R^{13}$, $R^{14}$, $R^{15}$, and $R^{16}$ are independently selected from substituted heterocyclyloxy. In certain embodiments, heterocyclyloxy and substituted heterocyclyloxy groups include a 3 to 8-membered ring, such as a 3 to 6-membered ring, that includes 1 to 5 heteroatoms, or 1 to 3 heteroatoms, such as 1 heteroatom (e.g., oxygen, nitrogen or sulfur). For example, heterocyclyloxy and substituted heterocyclyloxy groups may include rings such as, but not limited to, tetrahydropyran, tetrahydrofuran, oxetane, piperidine, and the like. Substituted heterocyclyloxy groups may be substituted with one or more groups, such as alkyl, e.g., $C_1$-$C_6$ alkyl, including $C_1$-$C_3$ alkyl, such as methyl, isopropyl, and the like.

In certain embodiments, $R^{14}$ and $R^{15}$ together with the carbon atoms to which they are attached form aryl, substituted aryl, heteroaryl, substituted heteroaryl, heterocyclyl, or substituted heterocyclyl. In certain embodiments, $R^{14}$ and $R^{15}$ together with the carbon atoms to which they are attached form an aryl or heteroaryl 5 to 10-membered ring. In certain embodiments, $R^{14}$ and $R^{15}$ together with the carbon atoms to which they are attached form a heterocyclyl or substituted heterocyclyl 5 to 10-membered ring. For example, $R^{14}$ and $R^{15}$ together with the carbon atoms to which they are attached may form a tetrazolooxazinyl group, which may be substituted with one or more groups, such as alkyl, e.g., $C_1$-$C_6$ alkyl, including $C_1$-$C_3$ alkyl, such as methyl.

In certain embodiments, $R^{12}$, $R^{13}$, $R^{14}$, $R^{15}$, and $R^{16}$ are independently selected from hydrogen, methyl, fluoro, hydroxyl, methoxy, isopropoxy, cyano, sulfur pentafluoride, —$OCHF_2$, $OCH_2CH_2OH$, —$OCH_2CH(OH)CH_3$, —$OCH_2C(CH_3)_2OH$, —$OCH_2CH(CH_3)OH$, —$OC(CH_3)_2CH_2OH$,

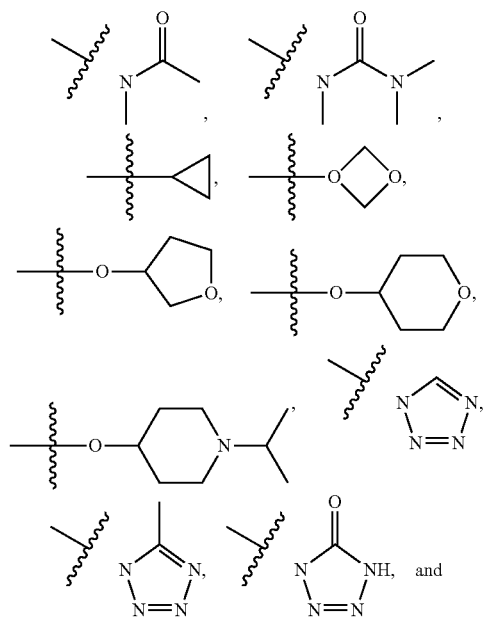

-continued

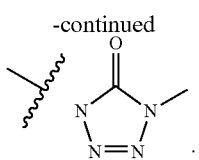

In certain embodiments, including those of formulae (I-V), $R^{12}$ is selected from hydrogen and halogen. In certain embodiments, $R^{12}$ is hydrogen. In certain embodiments, $R^{12}$ is halogen. In certain embodiments, $R^{12}$ is fluoro.

In certain embodiments, $R^{13}$ and $R^{16}$ are hydrogen.

In certain embodiments, $R^{14}$ is a substituted alkoxy. In certain embodiments, $R^{14}$ is a $C_1$-$C_6$ substituted alkoxy, such as a $C_1$-$C_3$ substituted alkoxy. In certain embodiments, $R^{14}$ is a substituted propoxy. In certain embodiments, $R^{14}$ is a substituted ethoxy. In certain embodiments, $R^{14}$ is an alkoxy substituted with hydroxyl and optionally substituted with one or more alkyl groups. In certain embodiments, $R^{14}$ is an alkoxy substituted with hydroxyl. In certain embodiments, $R^{14}$ is an alkoxy substituted with hydroxyl and an alkyl group, such as a $C_1$-$C_6$ alkyl group, such as a $C_1$-$C_3$ alkyl group, such as a methyl group. In certain embodiments, $R^{14}$ is an alkoxy substituted with hydroxyl and two alkyl groups. In certain embodiments, the alkyl substituents are each independently a $C_1$-$C_6$ alkyl group, such as a $C_1$-$C_3$ alkyl group, such as a methyl group. In certain embodiments, $R^{14}$ is an ethoxy group substituted with hydroxyl. In certain embodiments, $R^{14}$ is an ethoxy group substituted with hydroxyl and an alkyl group, such as a $C_1$-$C_6$ alkyl group, such as a $C_1$-$C_3$ alkyl group, such as a methyl group. In certain embodiments, $R^{14}$ is an ethoxy group substituted with hydroxyl and two alkyl groups. In certain embodiments, the alkyl substituents are each independently a $C_1$-$C_6$ alkyl group, such as a $C_1$-$C_3$ alkyl group, such as a methyl group.

In certain embodiments, $R^{15}$ is an optionally substituted heterocyclyl. In certain embodiments, $R^{15}$ is an optionally substituted tetrazolone of the formula

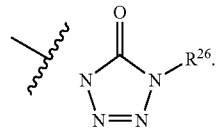

where $R^{26}$ is —H, a haloalkyl group or an alkyl group, such as a $C_1$-$C_6$ alkyl group, such as a $C_1$-$C_3$ alkyl group, such as a methyl group. In some embodiments, compounds of formula (IV), such as compounds of formula (IVc), have $R^{15}$ being tetrazolone. In certain embodiments, including those of formula (IV), such as formula (IVc), $R^{15}$ is a tetrazolone (e.g., an optionally substituted tetrazolone as described above) and $R^{12}$ is a halo group, such as fluoro.

Particular compounds of interest are shown illustrated the following table.

TABLE 1

| # | $R^1/R^2$ | $R^3/R^4$ | $R^5/R^6$ | $R^7/R^8$ | $R^9/R^{10}$ | $R^{11}$ | $Y^1$ | $Y^2$ | $Ar^1$ | $H^1/H^2$ |
|---|-----------|-----------|-----------|-----------|--------------|----------|-------|-------|--------|-----------|
| 1 | H/H | H/H | H/H | $CH_3/CH_3$ | H/H | F | H | H | benzoxazine-tetrazole | mixture of diastereomers |
| 2 | H/H | H/H | H/H | $CH_3/CH_3$ | H/H | F | H | H | benzoxazine-tetrazole | single enantiomer |
| 3 | H/H | H/H | H/H | $CH_3/CH_3$ | H/H | F | H | H | benzoxazine-tetrazole | single enantiomer |
| 4 | H/H | H/H | H/H | $CH_3/CH_3$ | H/H | F | H | H | benzoxazine-tetrazole | Racemic (single diastereomer) |

TABLE 1-continued

| | R¹/R² | R³/R⁴ | R⁵/R⁶ | R⁷/R⁸ | R⁹/R¹⁰ | R¹¹ | Y¹ | Y² | Ar¹ | H¹/H² |
|---|---|---|---|---|---|---|---|---|---|---|
| 5 | H/H | H/H | H/H | CH₃/CH₃ | H/H | F | H | H | | Racemic cis diastereomer |
| 6 | H/H | H/H | H/H | CH₃/CH₃ | H/H | F | H | H | | mixture of diastereomers |
| 7 | H/H | H/H | H/H | CH₃/CH₃ | H/H | F | H | H | | single enantiomer |
| 8 | H/H | H/H | H/H | CH₃/CH₃ | H/H | F | H | H | | single enantiomer |
| 9 | H/H | H/H | H/H | CH₃/CH₃ | H/H | F | H | H | | single enantiomer |

TABLE 1-continued

| | R¹/R² | R³/R⁴ | R⁵/R⁶ | R⁷/R⁸ | R⁹/R¹⁰ | R¹¹ | Y¹ | Y² | Ar¹ | H¹/H² |
|---|---|---|---|---|---|---|---|---|---|---|
| 10 | H/H | H/H | H/H | CH₃/CH₃ | H/H | F | H | H | 4-(1-isopropylpiperidin-4-yloxy)-3-(difluoromethoxy)phenyl | single enantiomer |
| 11 | H/H | H/H | H/H | CH₃/CH₃ | H/H | F | H | H | 3-methoxy-5-(5-methyltetrazol-1-yl)phenyl | single enantiomer |
| 12 | H/H | H/H | H/H | CH₃/CH₃ | H/H | F | H | H | 3-methoxy-5-(5-methyltetrazol-1-yl)phenyl | single enantiomer |
| 13 | H/H | H/H | H/H | CH₃/CH₃ | H/H | F | H | H | 3-methoxy-5-(5-methyltetrazol-1-yl)phenyl | single enantiomer |
| 14 | H/H | H/H | H/H | CH₃/CH₃ | H/H | F | H | H | 3-methoxy-5-(5-methyltetrazol-1-yl)phenyl | single enantiomer |
| 15 | H/H | H/H | H/H | CH₃/CH₃ | H/H | F | H | H | 2-methyl-3-(5-methyltetrazol-1-yl)pyridin-5-yl | single enantiomer |

TABLE 1-continued
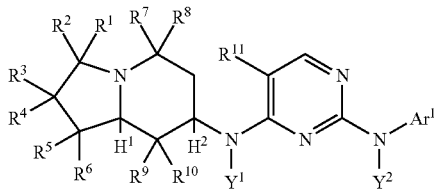
| | R¹/R² | R³/R⁴ | R⁵/R⁶ | R⁷/R⁸ | R⁹/R¹⁰ | R¹¹ | Y¹ | Y² | Ar¹ | H¹/H² |
|---|---|---|---|---|---|---|---|---|---|---|
| 16 | H/H | H/H | H/H | CH₃/CH₃ | H/H | F | H | H | 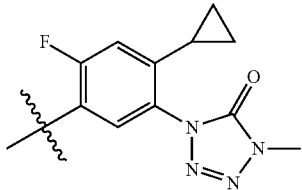 [SMILES: *c1cc(-n2nnn(C)c2=O)c(C2CC2)cc1F] | racemic |
| 17 | H/H | H/H | H/H | CH₃/CH₃ | H/H | F | H | H | 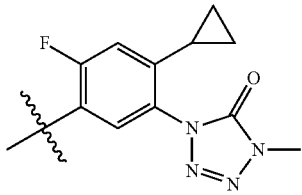 [SMILES: *c1cc(-n2nnn(C)c2=O)c(C2CC2)cc1F] | ◂■H/◂■H 7R,8aS |
| 18 | H/H | H/H | H/H | CH₃/CH₃ | H/H | F | H | H | 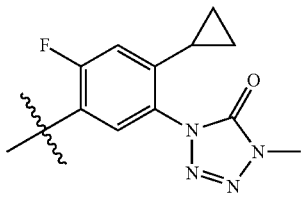 [SMILES: *c1cc(-n2nnn(C)c2=O)c(C2CC2)cc1F] | ⋯⋯H/⋯⋯H 7S,8aR |
| 19 | H/H | H/H | H/H | CH₃/CH₃ | H/H | F | H | H | 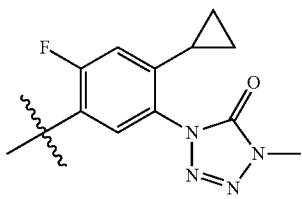 | trans |
| 20 | H/H | H/H | H/H | CH₃/CH₃ | H/H | F | H | H | 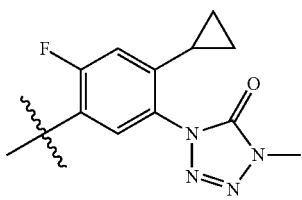 [SMILES: *c1cc(-n2nnn(C)c2=O)c(C2CC2)cc1F] | single enantiomer |
| 21 | H/H | H/H | H/H | CH₃/CH₃ | H/H | F | H | H | 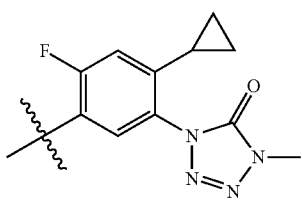 [SMILES: *c1cc(-n2nnn(C)c2=O)c(C2CC2)cc1F] | single enantiomer |

TABLE 1-continued

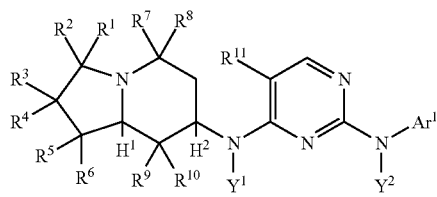

| | R¹/R² | R³/R⁴ | R⁵/R⁶ | R⁷/R⁸ | R⁹/R¹⁰ | R¹¹ | Y¹ | Y² | Ar¹ | H¹/H² |
|---|---|---|---|---|---|---|---|---|---|---|
| 22 (p-toluene-sulfonic salt) | H/H | H/H | H/H | CH₃/CH₃ | H/H | F | H | H | 4-F, 2-OMe, tetrazolinone-phenyl | 7R,8aS |
| 23 (p-toluene-sulfonic salt) | H/H | H/H | H/H | CH₃/CH₃ | H/H | F | H | H | 4-F, 2-OiPr, tetrazolinone-phenyl | 7R,8aS |
| 24 | H/H | H/H | H/H | H/H | H/H | F | H | H | 4-F, 2-cyclopropyl, tetrazole-phenyl | racemic (single diasteromer) |
| 25 | CH₃/CH₃ | H/H | H/H | H/H | H/H | F | H | H | 4-F, 2-cyclopropyl, tetrazolinone-phenyl | racemic (single diastereomer) |
| 26 | CH₃/CH₃ | H/H | H/H | H/H | H/H | F | H | H | 4-F, 2-cyclopropyl, tetrazolinone-phenyl | racemic (single diastereomer) |
| 27 | H/H | H/H | H/H | H/H | H/H | F | H | H | 4-F, 2-cyclopropyl, tetrazolinone-phenyl | racemic (single diastereomer) |

TABLE 1-continued

|  | R¹/R² | R³/R⁴ | R⁵/R⁶ | R⁷/R⁸ | R⁹/R¹⁰ | R¹¹ | Y¹ | Y² | Ar¹ | H¹/H² |
|---|---|---|---|---|---|---|---|---|---|---|
| 28 | H/H | H/H | H/H | H/H | H/H | F | H | H | | racemic (single diastereomer) |
| 29 | H/H | H/H | H/H | H/H | H/H | F | H | H | | racemic (single diastereomer) |
| 30 | CH₃/CH₃ | H/H | H/H | =O | H/H | F | H | H | | racemic (single diasteromer) |
| 31 | =O | H/H | H/H | CH₃/CH₃ | H/H | F | H | H | | racemic (7,8a cis) |
| 32 | =O | H/H | H/H | CH₃/CH₃ | H/H | F | H | H | | racemic (7,8a trans) |
| 33 (formic salt) | =O | H/H | H/H | CH₃/CH₃ | H/H | F | H | H | | racemic (7,8a trans) |

TABLE 1-continued
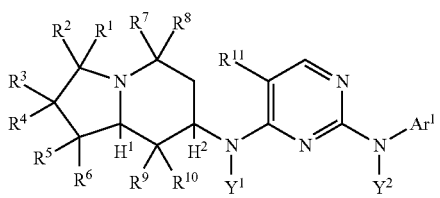
| | R¹/R² | R³/R⁴ | R⁵/R⁶ | R⁷/R⁸ | R⁹/R¹⁰ | R¹¹ | Y¹ | Y² | Ar¹ | H¹/H² |
|---|---|---|---|---|---|---|---|---|---|---|
| 34 | CH₃/CH₃ | H/H | H/H | H/H | H/H | F | H | H | 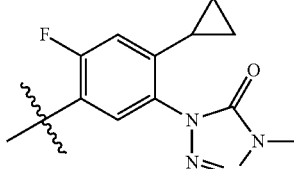 | single enantiomer |
| 35 | CH₃/CH₃ | H/H | H/H | H/H | H/H | F | H | H | 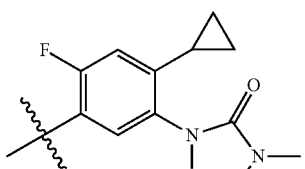 | single enantiomer |
| 36 | CH₃/CH₃ | H/H | H/H | H/H | H/H | F | H | H | 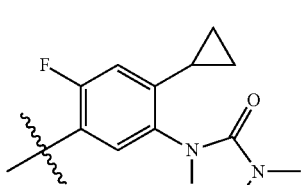 | single enantiomer |
| 37 | CH₃/CH₃ | H/H | H/H | H/H | H/H | F | H | H | 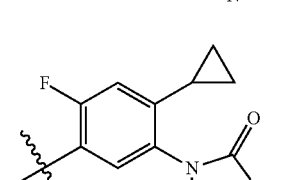 | single enantiomer |
| 38 | H/H | H/H | H/H | CH₃/CH₃ | H/H | F | H | H | 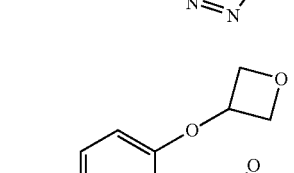 | racemic (single diastereomer) |
| 39 | H/H | H/H | H/H | CH₃/CH₃ | H/H | F | H | H | 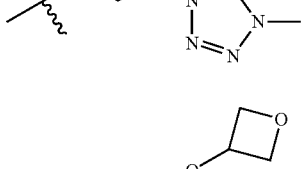 | single enantiomer |

TABLE 1-continued
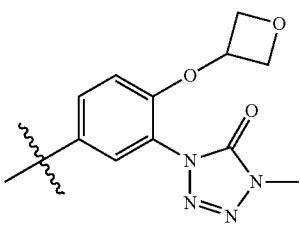 [SMILES: *c1ccc(OC2COC2)c(-n2nnn(C)c2=O)c1]
| | R¹/R² | R³/R⁴ | R⁵/R⁶ | R⁷/R⁸ | R⁹/R¹⁰ | R¹¹ | Y¹ | Y² | Ar¹ | H¹/H² |
|---|---|---|---|---|---|---|---|---|---|---|
| 40 | H/H | H/H | H/H | CH₃/CH₃ | H/H | F | H | H | 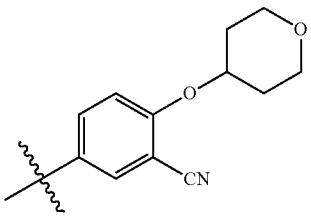 [SMILES: *c1ccc(OC2CCOCC2)c(C#N)c1] | single enantiomer |
| 41 | H/H | H/H | H/H | CH₃/CH₃ | H/H | F | H | H | 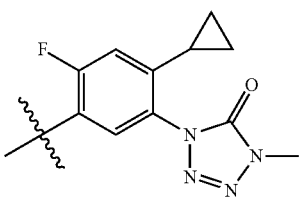 [SMILES: *c1cc(-n2nnn(C)c2=O)c(C2CC2)cc1F] | racemic (single diastereomer) |
| 42 | H/H | F/F | H/H | CH₃/CH₃ | H/H | F | H | H | 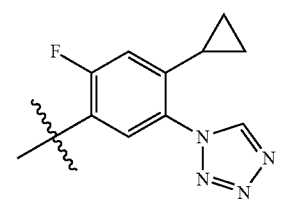 [SMILES: *c1cc(-n2cnnn2)c(C2CC2)cc1F] | trans (7S,8aR) |
| 43 | H/H | F/F | H/H | CH₃/CH₃ | H/H | F | H | H | 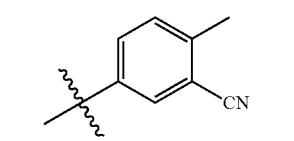 [SMILES: *c1ccc(C)c(C#N)c1] | trans (7S,8aR) |
| 44 | H/H | F/F | H/H | CH₃/CH₃ | H/H | F | H | H | 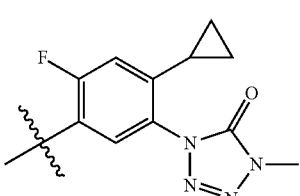 | trans |
| 45 | H/H | F/F | H/H | CH₃/CH₃ | H/H | F | H | H |  | cis |

TABLE 1-continued
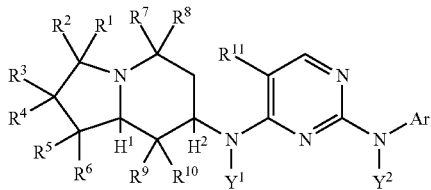
| | R¹/R² | R³/R⁴ | R⁵/R⁶ | R⁷/R⁸ | R⁹/R¹⁰ | R¹¹ | Y¹ | Y² | Ar¹ | H¹/H² |
|---|---|---|---|---|---|---|---|---|---|---|
| 46 | H/H | F/F | H/H | CH₃/CH₃ | H/H | F | H | H | 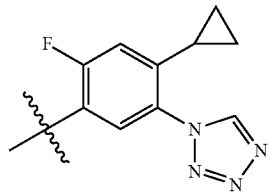 [SMILES: *c1cc(-n2cnnn2)c(C2CC2)cc1F] | cis |
| 47 | H/H | H/H | H/H | CH₃/CH₃ | H/H | F | H | H | 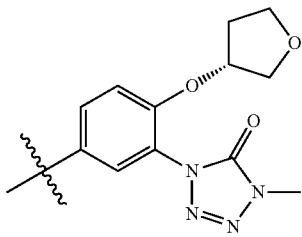 [SMILES: *c1ccc(O[C@@H]2CCOC2)c(-n2nnn(C)c2=O)c1] | mixture of two diastereomers |
| 48 | H/H | H/H | H/H | CH₃/CH₃ | H/H | F | H | H | 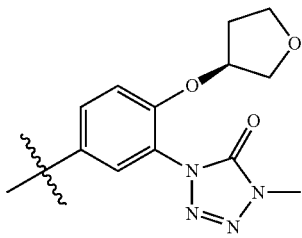 [SMILES: *c1ccc(O[C@H]2CCOC2)c(-n2nnn(C)c2=O)c1] | 7R,8aS |
| 49 | H/H | H/H | H/H | CH₃/CH₃ | H/H | F | H | H | 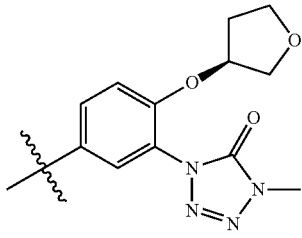 [SMILES: *c1ccc(O[C@H]2CCOC2)c(-n2nnn(C)c2=O)c1] | two diastereomers |
| 50 | H/H | H/H | H/H | CH₃/CH₃ | H/H | F | H | H | 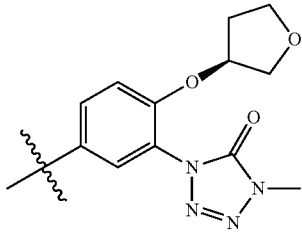 [SMILES: *c1ccc(O[C@H]2CCOC2)c(-n2nnn(C)c2=O)c1] | ◂▬H/◂▬H 7R,8aS |

TABLE 1-continued
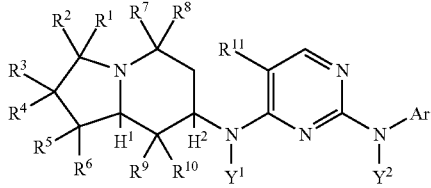
| | R¹/R² | R³/R⁴ | R⁵/R⁶ | R⁷/R⁸ | R⁹/R¹⁰ | R¹¹ | Y¹ | Y² | Ar¹ | H¹/H² |
|---|---|---|---|---|---|---|---|---|---|---|
| 51 | H/H | H/H | H/H | CH₃/CH₃ | H/H | F | H | H | 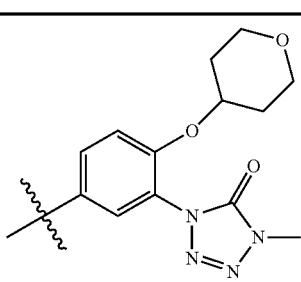 | racemic |
| 52 | H/H | H/H | H/H | CH₃/CH₃ | H/H | F | H | H | 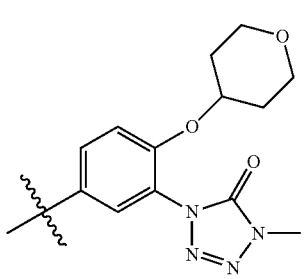 [SMILES: *c1ccc(OC2CCOCC2)c(-n2nnn(C)c2=O)c1] | ◂H/◂H 7R,8aS |
| 53 | H/H | H/H | H/H | CH₃/CH₃ | H/H | F | H | H | 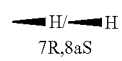 | cis racemic (single diasteromer) |
| 54 | H/H | H/H | H/H | CH₃/CH₃ | H/H | F | H | H | 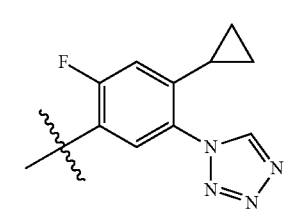 [SMILES: *c1cc(-n2cnnn2)c(C2CC2)cc1F] | single enantiomer |
| 55 | H/H | H/H | H/H | CH₃/CH₃ | H/H | F | H | H | 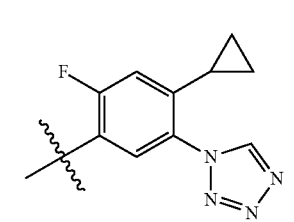 [SMILES: *c1cc(-n2cnnn2)c(C2CC2)cc1F] | single enantiomer |
| 56 | H/H | H/H | H/H | CH₃/CH₃ | H/H | CN | H | H | 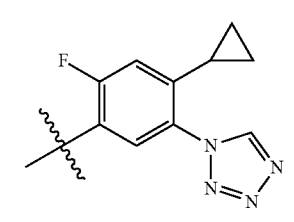 [SMILES: *c1cc(-n2cnnn2)c(C2CC2)cc1F] | cis racemic (single diastereomer) |

TABLE 1-continued
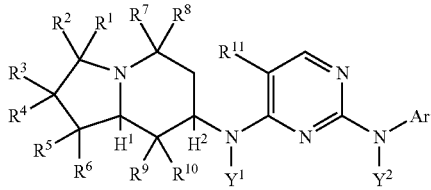
| | R¹/R² | R³/R⁴ | R⁵/R⁶ | R⁷/R⁸ | R⁹/R¹⁰ | R¹¹ | Y¹ | Y² | Ar¹ | H¹/H² |
|---|---|---|---|---|---|---|---|---|---|---|
| 57 | H/H | H/H | H/H | CH₃/CH₃ | H/H | F | H | H | 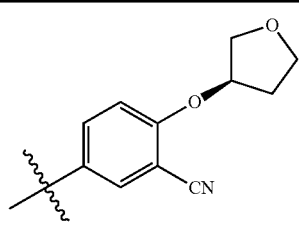 | two diastereomers (7,8a-cis) |
| 58 | H/H | H/H | H/H | CH₃/CH₃ | H/H | F | H | H | 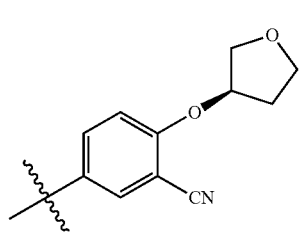 [SMILES: *c1ccc(O[C@@H]2CCOC2)c(C#N)c1] | single enantiomer (7,8a-cis) |
| 59 | H/H | H/H | H/H | CH₃/CH₃ | H/H | F | H | H | 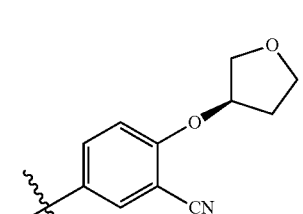 | single enantiomer |
| 60 | H/H | H/H | H/H | CH₃/CH₃ | H/H | F | H | H | 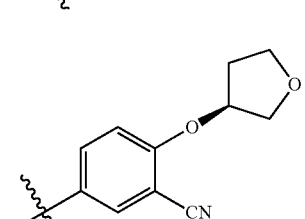 | two diasteromers (7,8a-cis) |
| 61 | H/H | H/H | H/H | CH₃/CH₃ | H/H | F | H | H | 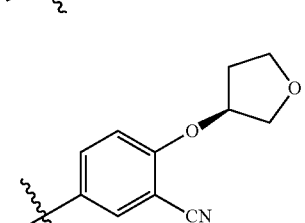 | single enantiomer |
| 62 | H/H | H/H | H/H | CH₃/CH₃ | H/H | F | H | H | 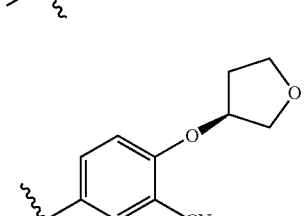 | single enantiomer |

TABLE 1-continued
| | R¹/R² | R³/R⁴ | R⁵/R⁶ | R⁷/R⁸ | R⁹/R¹⁰ | R¹¹ | Y¹ | Y² | Ar¹ | H¹/H² |
|---|---|---|---|---|---|---|---|---|---|---|
| 63 | H/H | H/H | H/H | CH₃/CH₃ | H/H | F | H | H | 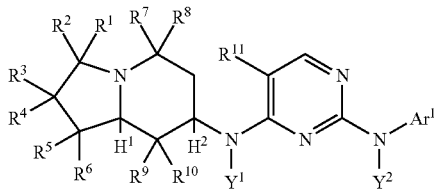 | racemic (single diastereomer) |
| 64 | H/H | H/▬F (R) | H/H | CH₃/CH₃ | H/H | F | H | H | 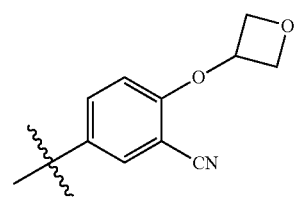 [SMILES: *c1ccc(OC2COC2)c(C#N)c1] | ▬H/▬H 7R,8aR |
| 65 | H/H | H/▬F (R) | H/H | CH₃/CH₃ | H/H | F | H | H | 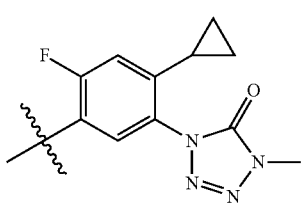 [SMILES: *c1cc(-n2nnn(C)c2=O)c(C2CC2)cc1F] | ▬H/⋯H 7S,8aR |
| 66 | H/H | H/H | H/H | CH₃/CH₃ | H/H | CN | H | H | 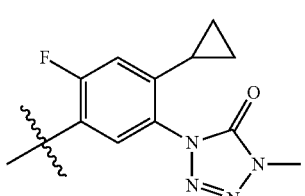 | (cis) racemic |
| 67 | H/H | H/⋯F (S) | H/H | CH₃/CH₃ | H/H | F | H | H | 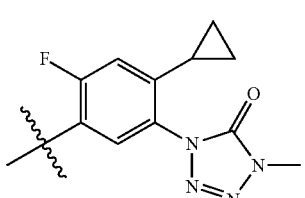 | ▬H/▬H 7R,8aR |
| 68 | H/H | H/▬OH (R) | H/H | CH₃/CH₃ | H/H | F | H | H | 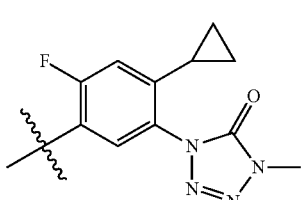 | ▬H/▬H 7R,8aR |

TABLE 1-continued

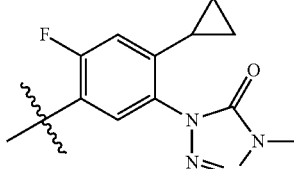

| | R¹/R² | R³/R⁴ | R⁵/R⁶ | R⁷/R⁸ | R⁹/R¹⁰ | R¹¹ | Y¹ | Y² | Ar¹ | H¹/H² |
|---|---|---|---|---|---|---|---|---|---|---|
| 69 (p-toluene-sulfonic salt) | H/H | H/H | H/H | CH₃/CH₃ | H/CH₃ | F | H | H | 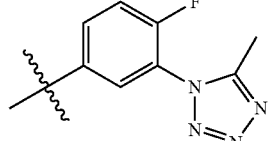 | racemic (single diastereomer) |
| 70 (formic acid) | H/H | H/H | H/H | CH₃/CH₃ | H/CH₃ | F | H | H | 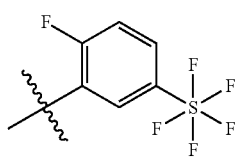 [SMILES: *c1cc(S(F)(F)(F)(F)F)ccc1F] | racemic (single diastereomer) |
| 71 | H/H | H/H | H/H | CH₃/CH₃ | H/H | F | H | H | 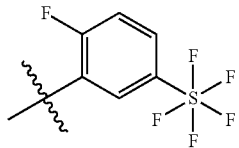 [SMILES: *c1cc(S(F)(F)(F)(F)F)ccc1F] | ◂H/◂H 7R,8aS |
| 72 | H/H | H/H | H/H | CH₃/CH₃ | H/H | F | H | H | 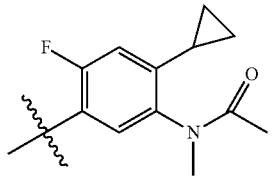 [SMILES: *c1cc(N(C)C(C)=O)c(C2CC2)cc1F] | ◂H/◂H 7R,8aS |
| 73 (formic acid) | H/H | H/H | H/H | CH₃/CH₃ | H/H | F | H | H | 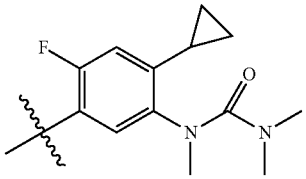 [SMILES: *c1cc(N(C)C(=O)N(C)C)c(C2CC2)cc1F] | ◂H/◂H 7R,8aS |
| 74 (formic acid) | H/H | H/H | H/H | CH₃/CH₃ | H/H | F | H | H | 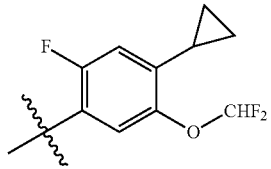 [SMILES: *c1cc(OC(F)F)c(C2CC2)cc1F] | ◂H/◂H 7R,8aS |
| 75 (formic acid) | H/H | H/H | H/H | CH₃/CH₃ | H/H | F | H | H |  | ◂H/◂H 7R,8aS |

TABLE 1-continued
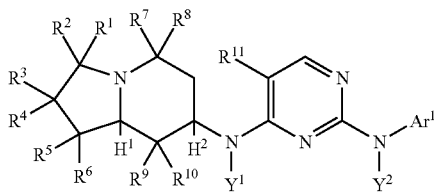
| | R¹/R² | R³/R⁴ | R⁵/R⁶ | R⁷/R⁸ | R⁹/R¹⁰ | R¹¹ | Y¹ | Y² | Ar¹ | H¹/H² |
|---|---|---|---|---|---|---|---|---|---|---|
| 76 | H/H | H/H | H/H | CH₃/CH₃ | H/H | CN | H | H | 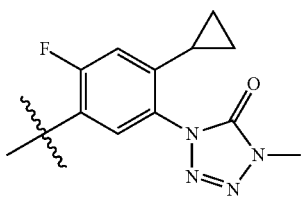 [SMILES: *c1cc(-n2nnn(C)c2=O)c(C2CC2)cc1F] | ◂H/◂H 7R,8aS |
| 77 | H/H | H/H | H/H | CH₃/CH₃ | H/H | F | H | H |  | ◂H/◂H 7R,8aS |
| 78 | H/H | H/H | H/H | CH₃/CH₃ | H/H | CN | H | H | 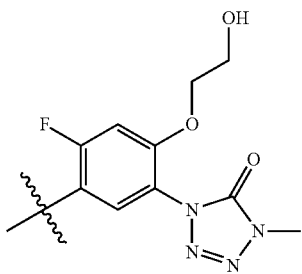 [SMILES: *c1cc(-n2nnn(C)c2=O)c(OCCO)cc1F] | ◂H/◂H 7R,8aS |
| 79 | H/H | H/H | H/H | CH₃/CH₃ | H/H | CN | H | H |  | ◂H/◂H 7R,8aS |
| 80 | H/H | H/H | H/H | CH₃/CH₃ | H/H | CN | H | H | 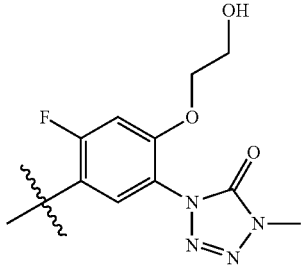 [SMILES: *c1cc(-n2nnn(C)c2=O)c(OCCO)cc1F] | ◂H/◂H 7R,8aS |

TABLE 1-continued
| | R¹/R² | R³/R⁴ | R⁵/R⁶ | R⁷/R⁸ | R⁹/R¹⁰ | R¹¹ | Y¹ | Y² | Ar¹ | H¹/H² |
|---|---|---|---|---|---|---|---|---|---|---|
| 81 | H/H | H/H | H/H | CH₃/CH₃ | H/H | F | H | H | 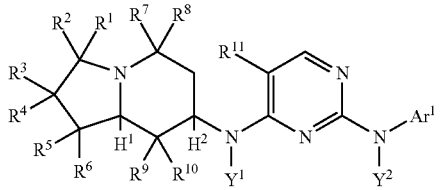 | ◄H/◄H 7R,8aS |
| 82 | H/H | H/H | H/H | CH₃/CH₃ | H/H | F | H | H | 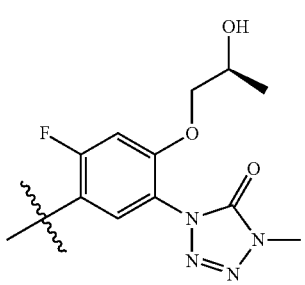 [SMILES: *c1cc(-n2nnn(C)c2=O)c(OC[C@H](C)O)cc1F] | ◄H/◄H 7R,8aS |
| 83 | H/H | H/H | H/H | CH₃/CH₃ | H/H | CN | H | H |  | ◄H/◄H 7R,8aS |
| 84 | H/H | H/H | H/H | CH₃/CH₃ | H/H | CN | H | H | 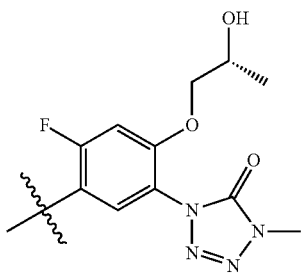 [SMILES: *c1cc(-n2nnn(C)c2=O)c(OC[C@@H](C)O)cc1F] | ◄H/◄H 7R,8aS |
| 85 | H/H | H/H | H/H | CH₃/CH₃ | H/H | F | H | H |  | ◄H/◄H 7R,8aS |

TABLE 1-continued
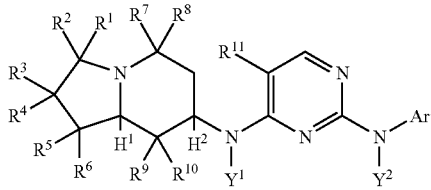
| | R¹/R² | R³/R⁴ | R⁵/R⁶ | R⁷/R⁸ | R⁹/R¹⁰ | R¹¹ | Y¹ | Y² | Ar¹ | H¹/H² |
|---|---|---|---|---|---|---|---|---|---|---|
| 86 (pamoic acid) | H/H | H/H | H/H | CH₃/CH₃ | H/H | F | H | H | 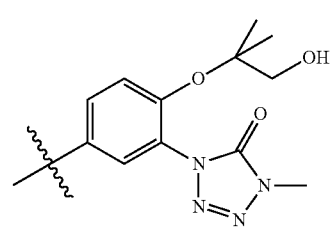 [SMILES: *c1ccc(OC(C)(C)CO)c(-n2nnn(C)c2=O)c1] | ◂H/◂H 7R,8aS |
| 87 | H/H | H/H | H/H | CH₃/CH₃ | H/H | F | H | H |  | ◂H/◂H 7R,8aS |
| 88 | H/H | H/H | H/H | CH₃/CH₃ | H/H | F | H | H | 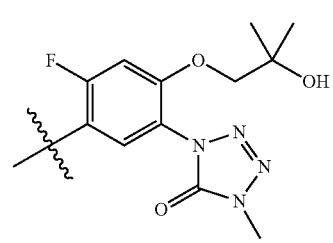 [SMILES: *c1cc(-n2nnn(C)c2=O)c(OCC(C)(C)O)cc1F] | ◂H/◂H 7R,8aS |
| 89 | H/H | H/H | H/H | CH₃/CH₃ | H/H | F | H | H |  | ◂H/◂H 7R,8aS |
| 90 | H/H | H/H | H/H | CH₃/CH₃ | H/H | CN | H | H | 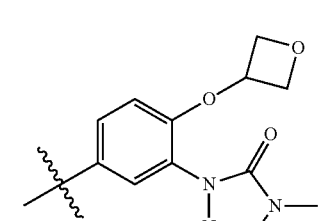 | ◂H/◂H 7R,8aS |

Particular compounds of interest, and salts or solvates or stereoisomers thereof, include:

Compounds 1-4: N2-(4,4-dimethyl-4H-benzo[b]tetrazolo[1,5-d][1,4]oxazin-8-yl)-5-fluoro-N4-(octahydro-5,5-dimethylindolizin-7-amine)pyrimidine-2,4-diamine;

Compound 5: N2-(4,4-dimethyl-4H-benzo[b]tetrazolo[1,5-d][1,4]oxazin-8-yl)-5-fluoro-N4-(octahydro-5,5-dimethylindolizin-7-yl)pyrimidine-2,4-diamine;

Compounds 6-10: (R/S,S/R,R/R,S/S)—$N^2$-(4-(1-isopropylpiperidin-4-yloxy)-3-(difluoromethoxy)phenyl)-5-fluoro-$N^4$-(octahydro-5,5-dimethylindolizin-7-yl)pyrimidine-2,4-diamine;

Compounds 11-14: (R/S,S/R,R/R,S/S)-5-fluoro-N4-(octahydro-5,5-dimethylindolizin-7-yl)N2-(3-methoxy-5-(5-methyl-1H-tetrazol-1-yl)phenyl)pyrimidine-2,4-diamine;

Compounds 16-21: octahydro-5,5-dimethylindolizin-7-ylamino)-5-fluoropyrimidin-2-yl-amino)-2-cyclopropyl-4-fluorophenyl)-4-methyl-1H-tetrazol-5(4H)-one;

Compound 17: 1-(5-(4-((7R,8a5)-octahydro-5,5-dimethylindolizin-7-ylamino)-5-fluoropyrimidin-2-yl-amino)-2-cyclopropyl-4-fluorophenyl)-4-methyl-1H-tetrazol-5(4H)-one;

Compound 18: 1-(5-(4-(((7S,8aR)-octahydro-5,5-dimethylindolizin-7-ylamino)-5-fluoropyrimidin-2-yl amino)-2-cyclopropyl-4-fluorophenyl)-4-methyl-1H-tetrazol-5(4H)-one;

Compound 22: 1-(5-(4-((7R,8aS)-5,5-dimethyl-octahydroindolizin-7-ylamino)-5-fluoropyrimidin-2-ylamino)-4-fluoro-2-methoxyphenyl)-4-methyl-1H-tetrazol-5(4H)-one;

Compound 23: 1-(5-(4-((7R,8aS)-5,5-dimethyl-octahydroindolizin-7-ylamino)-5-fluoropyrimidin-2-ylamino)-4-fluoro-2-isopropoxyphenyl)-4-methyl-1H-tetrazol-5(4H)-one;

Compound 24: (±)-$N^2$-(4-cyclopropyl-2-fluoro-S-(1H-tetrazol-1-yl)phenyl)-5-fluoro-$n^4$-(octahydroindolizin-7-yl)pyrimidine-2,4-diamine;

Compound 26: N2-(4-cyclopropyl-2-fluoro-5-(4,5-dihydro-4-methyl-5-oxotetrazol-yl)phenylamino)-5-fluoro-N4-(octahydro-5,5-dimethylindolizin-7-ylamino)pyrimidine-2,4-diamine;

Compound 27: (±)-1-(5-(5-fluoro-4-(octahydroindolizin-7-ylamino)pyrimidin-2-ylamino)-2-cyclopropyl-4-fluorophenyl)-4-methyl-1H-tetrazol-5(4H)one;

Compound 28: (±)-$N^2$-(4-cyclopropyl-2-fluoro-5-(5-methyl-1H-tetrazol-1-yl)phenyl)-5-fluoro-$n^4$-(octahydroindolizin-7-yl)pyrimidine-2,4-diamine;

Compound 30: N2-{4-cyclopropyl-6-fluoro-[3-(4-methyl)-1,2,3,4-tetrazol-5-one-1-yl]}phenyl-5-fluoro-N4(7-amino-hexahydro-3,3-dimethylindolizin-5(1H)-one))2,4-pyrimidinediamine;

Compounds 31-33: 1-(5-(5-fluoro-4-(hexahydro-5,5-dimethylindolizin-3(5H)-one-7-ylamino)pyrimidin-2-ylamino)-2-cyclopropyl-4-fluorophenyl)-4-methyl-1H-tetrazol-5(4H)-one;

Compound 31: 1-(5-(5-fluoro-4-(hexahydro-5,5-dimethylindolizin-3(5H)-one-7-ylamino)pyrimidin-2-ylamino)-2-cyclopropyl-4-fluorophenyl)-4-methyl-1H-tetrazol-5(4H)-one;

Compound 32: 1-(5-(5-fluoro-4-(hexahydro-5,5-dimethylindolizin-3(5H)-one-7-ylamino)pyrimidin-2-ylamino)-2-cyclopropyl-4-fluorophenyl)-4-methyl-1H-tetrazol-5(4H)-one;

Compound 33: 1-(5-(5-fluoro-4-(hexahydro-5,5-dimethylindolizin-3(5H)-one-7-ylamino)pyrimidin-2-ylamino)-2-cyclopropyl-4-fluorophenyl)-4-methyl-1H-tetrazol-5(4H)-one formate;

Compounds 34 and 35: 1-(5-(5-fluoro-4-(octahydro-3,3-dimethylindolizin-7-ylamino)pyrimidin-2-ylamino)-2-cyclopropyl-4-fluorophenyl)-4-methyl-1H-tetrazol-5(4H)-one;

Compound 38: 1-(5-(5-fluoro-4-(octahydro-5,5-dimethylindolizin-7-ylamino)pyrimidin-2-ylamino)-2-(oxetan-3-yloxy)phenyl)-4-methyl-1H-tetrazol-5(4H)-one;

Compounds 39-40: 1-(5-(5-fluoro-4-(octahydro-5,5-dimethylindolizin-7-ylamino)pyrimidin-2-ylamino)-2-(oxetan-3-yloxy)phenyl)-4-methyl-1H-tetrazol-5(4H)-one;

Compound 41: 5-(5-fluoro-4-(octahydro-5,5-dimethylindolizin-7-ylamino)pyrimidin-2-ylamino)-2-(tetrahydro-2H-pyran-4-yloxy)benzonitrile;

Compound 42: 1-(5-(4-((7S,8aR)-2,2-difluoro-octahydro-5,5-dimethylindolizin-7-ylamino)-5-fluoropyrimidin-2-ylamino)-2-cyclopropyl-4-fluorophenyl)-4-methyl-1H-tetrazol-5(4H)-one;

Compound 43: $N^2$-(4-cyclopropyl-2-fluoro-5-(1H-tetrazol-1-yl)phenyl)-5-fluoro-$N^4$-((7S,8aR)-2,2-difluoro-octahydro-5,5-dimethylindolizin-7-yl)pyrimidine-2,4-diamine;

Compound 44: (4-((7S,8aR)-2,2-difluoro-octahydro-5,5-dimethylindolizin-7-ylamino)-5-fluoropyrimidin-2-ylamino)-2-methylbenzonitrile;

Compound 45: 1-(5-(4-((7R,8aR)-2,2-difluoro-octahydro-5,5-dimethylindolizin-7-ylamino)-5-fluoropyrimidin-2-ylamino)-2-cyclopropyl-4-fluorophenyl)-4-methyl-1H-tetrazol-5(4H)-one;

Compound 46: $N^2$-(4-cyclopropyl-2-fluoro-5-(1H-tetrazol-1-yl)phenyl)-5-fluoro-$N^4$-((7R,8aR)-2,2-difluoro-octahydro-5,5-dimethylindolizin-7-yl)pyrimidine-2,4-diamine;

Compound 47: 1-(2-((R)-tetrahydrofuran-3-yloxy)-5-(5-fluoro-4-(octahydro-5,5-dimethylindolizin-7-ylamino)pyrimidin-2-ylamino)phenyl)-4-methyl-1H-tetrazol-5(4H)-one;

Compound 48: 1-(2-((R)-tetrahydrofuran-3-yloxy)-5-(5-fluoro-4-(octahydro-5,5-dimethylindolizin-7-ylamino)pyrimidin-2-ylamino)phenyl)-4-methyl-1H-tetrazol-5(4H)-one;

Compound 49: 1-(2-((S)-tetrahydrofuran-3-yloxy)-5-(5-fluoro-4-(octahydro-5,5-dimethylindolizin-7-ylamino)pyrimidin-2-ylamino)phenyl)-4-methyl-1H-tetrazol-5(4H)-one;

Compound 50: 1-(2-((S)-tetrahydrofuran-3-yloxy)-5-(5-fluoro-4-(octahydro-5,5-dimethylindolizin-7-ylamino)pyrimidin-2-ylamino)phenyl)-4-methyl-1H-tetrazol-5(4H)-one;

Compound 51: 1-(5-(5-fluoro-4-(octahydro-5,5-dimethylindolizin-7-ylamino)pyrimidin-2-ylamino)-2-(tetrahydro-2H-pyran-4-oxy)phenyl)-4-methyl-1H-tetrazol-5(4H)-one;

Compound 52: 1-(5-(5-fluoro-4-(octahydro-5,5-dimethylindolizin-7-ylamino)pyrimidin-2-ylamino)-2-(tetrahydro-2H-pyran-4-yloxy)phenyl)-4-methyl-1H-tetrazol-5(4H)-one;

Compound 53: (±)-$N^2$-(4-cyclopropyl-2-fluoro-5-(1H-tetrazol-1-yl)phenyl)-5-fluoro-$n^4$-(octahydro-5,5-dimethylindolizin-7-yl)pyrimidine-2,4-diamine;

Compounds 54 and 55: (±)-$N^2$-(4-cyclopropyl-2-fluoro-5-(1H-tetrazol-1-yl)phenyl)-5-fluoro-$n^4$-(octahydro-5,5-dimethylindolizin-7-yl)pyrimidine-2,4-diamine;

Compound 56: (±)-2-(4-cyclopropyl-2-fluoro-5-(1H-tetrazol-1-yl)phenylamino)-4-(octahydro-5,5-dimethylindolizin-7-ylamino)pyrimidine-5-carbonitrile;

Compound 57: 2-((R)-tetrahydrofuran-3-yloxy)-5-(5-fluoro-4-(octahydro-5,5-dimethylindolizin-7-ylamino)pyrimidin-2-ylamino)benzonitrile;

Compounds 58-59: 2-((R)-tetrahydrofuran-3-yloxy)-5-(5-fluoro-4-(octahydro-5,5-dimethylindolizin-7-ylamino)pyrimidin-2-ylamino)benzonitrile;

Compound 60: 2-((S)-tetrahydrofuran-3-yloxy)-5-(5-fluoro-4-(octahydro-5,5-dimethylindolizin-7-ylamino)pyrimidin-2-ylamino)benzonitrile;

Compounds 61-62: 2-((S)-tetrahydrofuran-3-yloxy)-5-(5-fluoro-4-(octahydro-5,5-dimethylindolizin-7-ylamino)pyrimidin-2-ylamino)benzonitrile;

Compound 63: 5-(5-fluoro-4-(octahydro-5,5-dimethylindolizin-7-ylamino)pyrimidin-2-ylamino)-2-(oxetan-3-yloxy)benzonitrile;

Compound 64: 1-(5-(4-((2R,7R,8aR)-2-fluoro-octahydro-5,5-dimethylindolizin-7-ylamino)-5-fluoropyrimidin-2-ylamino)-2-cyclopropyl-4-fluorophenyl)-4-methyl-1H-tetrazol-5(4H)-one;

Compound 65: 1-(5-(4-((2R,7S,8aR)-2-fluoro-octahydro-5,5-dimethylindolizin-7-ylamino)-5-fluoropyrimidin-2-ylamino)-2-cyclopropyl-4-fluorophenyl)-4-methyl-1H-tetrazol-5(4H)-one;

Compound 66: 4-((R/S,S/R)-Octahydro-5,5-dimethylindolizin-7-ylamino)-2-(4-cyclopropyl-2-fluoro-5-(4,5-dihydro-4-methyl-5-oxotetrazol-yl)phenylamino)pyrimidine-5-carbonitrile;

Compound 67: 1-(5-(4-((2S,7R,8aR)-2-fluoro-octahydro-5,5-dimethylindolizin-7-ylamino)-5-fluoropyrimidin-2-ylamino)-2-cyclopropyl-4-fluorophenyl)-4-methyl-1H-tetrazol-5(4H)-one;

Compound 68: 1-(5-(4-((2R,7R,8aR)-2-hydroxy-octahydro-5,5-dimethylindolizin-7-ylamino)-5-fluoropyrimidin-2-ylamino)-2-cyclopropyl-4-fluorophenyl)-4-methyl-1H-tetrazol-5(4H)-one;

Compounds 69-70: 5-Fluoro-N2-(4-fluoro-3-(5-methyl-1H-tetrazol-1-yl)phenyl)-N4-(octahydro-5,5,8-trimethylindolizin-7-yl)pyrimidine-2,4-diamine;

Compound 69: 1-(5-(5-Fluoro-4-(octahydro-5,5,8-trimethylindolizin-7-ylamino)pyrimidin-2-ylamino)-2-cyclopropyl-4-fluorophenyl)-4-methyl-1H-tetrazol-5(4H)-one;

Compound 70: 5-Fluoro-N2-(4-fluoro-3-(5-methyl-1H-tetrazol-1-yl)phenyl)-N4-(octahydro-5,5,8-trimethylindolizin-7-yl)pyrimidine-2,4-diamine;

Compound 76: 4-(R,S)-Octahydro-5,5-dimethylindolizin-7-ylamino)-2-(4-cyclopropyl-2-fluoro-5-(4,5-dihydro-4-methyl-5-oxotetrazol-yl)phenylamino)pyrimidine-5-carbonitrile;

Compound 77: 1-(2-(2-hydroxyethoxy)-5-(4-((7R,8aS)-octahydro-5,5-dimethylindolizin-7-ylamino)-5-fluoropyrimidin-2-ylamino)-4-fluorophenyl)-4-methyl-1H-tetrazol-5(4H)-one;

Compound 78: 4-((7R,8aS)-octahydro-5,5-dimethylindolizin-7-ylamino)-2-(4-(2-hydroxyethoxy)-2-fluoro-5-(4,5-dihydro-4-methyl-5-oxotetrazol-1-yl)phenylamino)pyrimidine-5-carbonitrile;

Compound 79: 4-((7R,8aS)-octahydro-5,5-dimethylindolizin-7-ylamino)-2-(4-((S)-2-hydroxypropoxy)-2-fluoro-5-(4,5-dihydro-4-methyl-5-oxotetrazol-1-yl)phenylamino)pyrimidine-5-carbonitrile;

Compound 80: 4-((7R,8aS)-octahydro-5,5-dimethylindolizin-7-ylamino)-2-(4-(2-hydroxy-2-methylpropoxy)-2-fluoro-5-(4,5-dihydro-4-methyl-5-oxotetrazol-1-yl)phenylamino)pyrimidine-5-carbonitrile;

Compound 81: 1-(2-((S)-2-hydroxypropoxy)-5-(4-((7R,8aS)-octahydro-5,5-dimethylindolizin-7-ylamino)-5-fluoropyrimidin-2-ylamino)-4-fluorophenyl)-4-methyl-1H-tetrazol-5(4H)-one;

Compound 82: 1-(5-(4-((7R,8aS)-5,5-dimethyloctahydroindolizin-7-ylamino)-5-fluoropyrimidin-2-ylamino)-4-fluoro-2-((R)-2-hydroxypropoxy)phenyl)-4-methyl-1H-tetrazol-5(4H)-one;

Compound 83: 4-((7R,8aS)-octahydro-5,5-dimethylindolizin-7-ylamino)-2-(4-(1-hydroxy-2-methylpropan-2-yloxy)-3-(4,5-dihydro-4-methyl-5-oxotetrazol-1-yl)phenylamino)pyrimidine-5-carbonitrile;

Compound 84: 4-((7R,8aS)-5,5-dimethyloctahydroindolizin-7-ylamino)-2-(2-fluoro-4-(1-hydroxy-2-methylpropan-2-yloxy)-5-(4-methyl-5-oxo-4,5-dihydro-1H-tetrazol-1-yl)phenylamino)pyrimidine-5-carbonitrile;

Compound 85: 1-(5-(4-((7R,8aS)-5,5-dimethyloctahydroindolizin-7-ylamino)-5-fluoropyrimidin-2-ylamino)-4-fluoro-2-(1-hydroxy-2-methylpropan-2-yloxy)phenyl)-4-methyl-1H-tetrazol-5(4H)-one;

Compound 86: 1-(5-(4-((7R,8aS)-5,5-dimethyloctahydroindolizin-7-ylamino)-5-fluoropyrimidin-2-ylamino)-2-(1-hydroxy-2-methylpropan-2-yloxy)phenyl)-4-methyl-1H-tetrazol-5(4H)-one;

Compound 87: 1-(5-(4-((7R,8aS)-5,5-dimethyloctahydroindolizin-7-ylamino)-5-fluoropyrimidin-2-ylamino)-4-fluoro-2-(2-hydroxy-2-methylpropoxy)phenyl)-4-methyl-1H-tetrazol-5(4H)-one;

Compound 88: 1-(5-(4-((7R,8aS)-octahydro-5,5-dimethylindolizin-7-ylamino)-5-fluoropyrimidin-2-ylamino)-4-fluoro-2-(oxetan-3-yloxy)phenyl)-4-methyl-1H-tetrazol-5(4H)-one;

Compound 89: 1-(5-(4-((7R,8aS)-5,5-dimethyloctahydroindolizin-7-ylamino)-5-fluoropyrimidin-2-ylamino)-4-fluoro-2-hydroxyphenyl)-4-methyl-1H-tetrazol-5(4H)-one; and Compound 90: 4-((7R,8aS)-octahydro-5,5-dimethylindolizin-7-ylamino)-2-(4-((R)-2-hydroxypropoxy)-2-fluoro-5-(4,5-dihydro-4-methyl-5-oxotetrazol-1-yl)phenylamino)pyrimindine-5-carbonitrile.

The present disclosure provides a compound according to the formula:

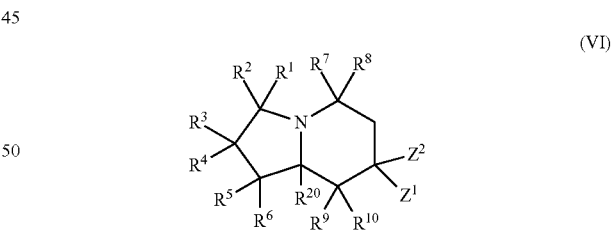

(VI)

wherein $R^1$, $R^2$, $R^3$, $R^4$, $R^5$, and $R^6$ are independently selected from hydrogen, alkyl, substituted alkyl, alkoxy, substituted alkoxy, acyl, acylamino, acyloxy, amino, substituted amino, aminoacyl, aminoacyloxy, oxyaminoacyl, azido, cyano, halogen, hydroxyl, carboxyl, carboxylalkyl, thiol, thioalkoxy, substituted thioalkoxy, aryl, aryloxy, hydroxyamino, alkoxyamino, nitro, —SO-alkyl, —SO-substituted alkyl, —SO-aryl, —SO-heteroaryl, —SO$_2$-alkyl, —SO$_2$-substituted alkyl, —SO$_2$-aryl and —SO$_2$-heteroaryl; or $R^1$ and $R^2$ together form an oxo group; or $R^3$ and $R^4$ together form an oxo group; or $R^5$ and $R^6$ together form an oxo group;

$R^7$, $R^8$, $R^9$, and $R^{10}$ are independently selected from hydrogen, alkyl, substituted alkyl, alkoxy, substituted alkoxy, acyl, acylamino, acyloxy, amino, substituted amino, aminoacyl, aminoacyloxy, oxyaminoacyl, azido, cyano, halogen, hydroxyl, carboxyl, carboxylalkyl, thiol, thioalkoxy, substituted thioalkoxy, aryl, aryloxy, hydroxyamino, alkoxyamino, nitro, —SO-alkyl, —SO-substituted alkyl, —SO-aryl, —SO-heteroaryl, —SO$_2$-alkyl, —SO$_2$-substituted alkyl, —SO$_2$-aryl and —SO$_2$-heteroaryl; or $R^7$ and $R^8$ together form an oxo group; or $R^9$ and $R^{10}$ together form an oxo group;

$R^{20}$ is selected from hydrogen, alkyl, and substituted alkyl;

$Z^1$ is $OR^{17}$, —$NR^{17}R^{18}$ or X;

$Z^2$ is H, or $Z^1$ and $Z^2$ together form an oxo, =$NR^{19}$ or =$NNR^{20}R^{21}$;

$R^{17}$ is H, alkyl, substituted alkyl, acyl, acylamino, —SO$_2$-alkyl or —SO$_2$-aryl;

$R^{18}$ is H, alkyl, substituted alkyl, acyl, acylamino, —SO$_2$-alkyl, —SO$_2$-aryl, aryl or heteroaryl;

X is halo or azido;

$R^{19}$, $R^{20}$ and $R^{21}$ each independently are selected from alkyl, substituted alkyl, aryl substituted aryl, heteroaryl and substituted heteroaryl; and the compound is optically active.

In certain embodiments, for formula (VI), there is an enantiomeric excess of 90% or more. In certain embodiments, for formula (VI), there is an enantiomeric excess of 95% or more.

In certain embodiments, in formula (VI), $R^{18}$ comprises the formula

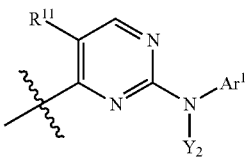

wherein $R^{11}$ is selected from alkyl, substituted alkyl, hydroxy, alkoxy, substituted alkoxy, amino, substituted amino, carboxyl, carboxyl ester, cyano, halogen, acyl, aminoacyl, nitro, alkenyl, substituted alkenyl, alkynyl, and substituted alkynyl; $Y^1$ and $Y^2$ are independently selected from hydrogen and alkyl; and $Ar^1$ is selected from aryl, substituted aryl, heteroaryl, and substituted heteroaryl.

In certain embodiments, the compound of formula (VI) comprises the formula

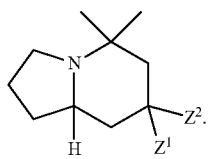

In certain embodiments, the compound of formula (VI) comprises the formula

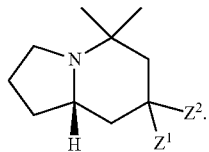

In certain embodiments, the compound of formula (VI) comprises the formula

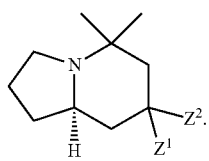

In certain embodiments, the compound of formula (VI) comprises the formula

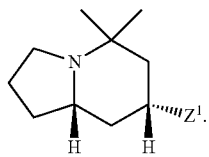

In certain embodiments, the compound of formula (VI) comprises the formula

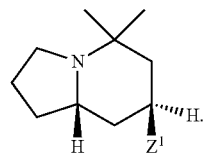

The compounds described also include isotopically labeled compounds where one or more atoms have an atomic mass different from the atomic mass conventionally found in nature. Examples of isotopes that may be incorporated into the compounds disclosed herein include, but are not limited to, $^2$H, $^3$H, $^{11}$C, $^{13}$C, $^{14}$C, $^{15}$N, $^{18}$O, $^{17}$O, etc. Thus, the disclosed compounds may be enriched in one or more of these isotopes relative to the natural abundance of such isotope. By way of example, deuterium ($^2$H) has a natural abundance of about 0.015%. Accordingly, for approximately every 6,500 hydrogen atoms occurring in nature, there is one deuterium atom. Specifically contemplated herein are compounds enriched in deuterium at one or more positions. Thus, deuterium containing compounds of the disclosure have deuterium at one or more positions (as the case may be) in an abundance of greater than 0.015%.

The present disclosure also provides pharmaceutical compositions comprising a pharmaceutically acceptable carrier and a therapeutically effective amount of a compound of formula I-V or a pharmaceutically acceptable salt or solvate or stereoisomer thereof.

A disclosed compound can be administered alone, as the sole active pharmaceutical agent, or in combination with one or more additional compounds of formula I-V or in conjunction with other agents. When administered as a combination, the therapeutic agents can be formulated as separate compositions that are administered simultaneously or at different times, or the therapeutic agents can be administered together as a single composition combining two or more therapeutic agents. Thus, the pharmaceutical compositions disclosed herein containing a compound of formula I-V optionally contain other therapeutic agents. Accordingly, certain embodiments are directed to such pharmaceutical compositions, wherein the composition further comprises a therapeutically effective amount of an agent selected as is known to those of skill in the art.

Since subject compounds possess PKC inhibitory properties, such compounds are also useful as research tools. Accordingly, the disclosure also provides for a method for using a compound of formula I-V or a salt or solvate or stereoisomer thereof as a research tool for studying a biological system or sample, or for discovering new chemical compounds having PKC inhibitory properties.

The embodiments are also directed to a compound of formula I-V or a salt or solvate or stereoisomer thereof, for use in therapy or as a medicament.

Additionally, the embodiments are directed to the use of a compound of formula I-V or a salt or solvate or stereoisomer thereof, for the manufacture of a medicament; especially for the manufacture of a medicament for the inhibition of protein kinase C (PKC) activity. The embodiments are also directed to the use of a compound of formula I-V or a salt or solvate or stereoisomer thereof for the manufacture of a medicament for the treatment of a disease or disorder mediated or sustained through the activity of PKC activity. The embodiments are also directed to the use of a compound of formula I-V or a salt or solvate or stereoisomer thereof for the manufacture of a medicament for the treatment of a disease or disorder associated with the activation of T-cells, including, inflammatory, autoimmune and allergic disorders.

General Synthetic Procedures

Many general references providing commonly known chemical synthetic schemes and conditions useful for synthesizing the disclosed compounds are available (see, e.g., Smith and March, March's Advanced Organic Chemistry: Reactions, Mechanisms, and Structure, Fifth Edition, Wiley-Interscience, 2001; or Vogel, A Textbook of Practical Organic Chemistry, Including Qualitative Organic Analysis, Fourth Edition, New York: Longman, 1978).

Compounds as described herein can be purified by any of the means known in the art, including chromatographic means, such as HPLC, preparative thin layer chromatography, flash column chromatography and ion exchange chromatography. Any suitable stationary phase can be used, including normal and reversed phases as well as ionic resins. Most typically the disclosed compounds are purified via silica gel and/or alumina chromatography. See, e.g., Introduction to Modern Liquid Chromatography, 2nd Edition, ed. L. R. Snyder and J. J. Kirkland, John Wiley and Sons, 1979; and Thin Layer Chromatography, ed E. Stahl, Springer-Verlag, New York, 1969.

During any of the processes for preparation of the subject compounds, it may be necessary and/or desirable to protect sensitive or reactive groups on any of the molecules concerned. This may be achieved by means of conventional protecting groups as described in standard works, such as J. F. W. McOmie, "Protective Groups in Organic Chemistry", Plenum Press, London and New York 1973, in T. W. Greene and P. G. M. Wuts, "Protective Groups in Organic Synthesis", Third edition, Wiley, New York 1999, in "The Peptides"; Volume 3 (editors: E. Gross and J. Meienhofer), Academic Press, London and New York 1981, in "Methoden der organischen Chemie", Houben-Weyl, $4^{th}$ edition, Vol. 15/1, Georg Thieme Verlag, Stuttgart 1974, in H.-D. Jakubke and H. Jescheit, "Aminosauren, Peptide, Proteine", Verlag Chemie, Weinheim, Deerfield Beach, and Basel 1982, and/or in Jochen Lehmann, "Chemie der Kohlenhydrate: Monosaccharide and Derivate", Georg Thieme Verlag, Stuttgart 1974. The protecting groups may be removed at a convenient subsequent stage using methods known from the art.

The subject compounds can be synthesized via a variety of different synthetic routes using commercially available starting materials and/or starting materials prepared by conventional synthetic methods. Suitable exemplary methods that can be routinely adapted to synthesize the 2,4-pyrimidinediamine compounds and prodrugs of the invention are found in U.S. Pat. No. 5,958,935, the disclosure of which is incorporated herein by reference. Specific examples describing the synthesis of numerous 2,4-pyrimidinediamine compounds and prodrugs, as well as intermediates therefore, are described in the U.S. publication No. US2004/0029902A1, the contents of which are incorporated herein by reference. Suitable exemplary methods that can be routinely used and/or adapted to synthesize active 2,4-pyrimidinediamine compounds can also be found in WO 03/063794, U.S. application Ser. No. 10/631,029 filed Jul. 29, 2003, WO2004/014382, U.S. publication No. 2005-0234049 A1, and WO005/016893, the disclosures of which are incorporated herein by reference. All of the compounds described herein (including prodrugs) can be prepared by routine adaptation of these methods.

Exemplary synthetic methods for the 2,4-substituted pyrimidinediamines described herein are described below. Those of skill in the art will also be able to readily adapt these methods for the synthesis of specific 2,4-substituted pyrimidinediamines as described herein.

A variety of exemplary synthetic routes that can be used to synthesize the 2,4-pyrimidinediamine compounds of the invention are described in scheme below. These methods can be routinely adapted to synthesize the 2,4-pyrimidinediamine compounds and prodrugs described herein.

Synthesis of Compounds

In a certain embodiment, the compounds can be synthesized from substituted or unsubstituted uracils as illustrated in Scheme 1, below:

Scheme 1

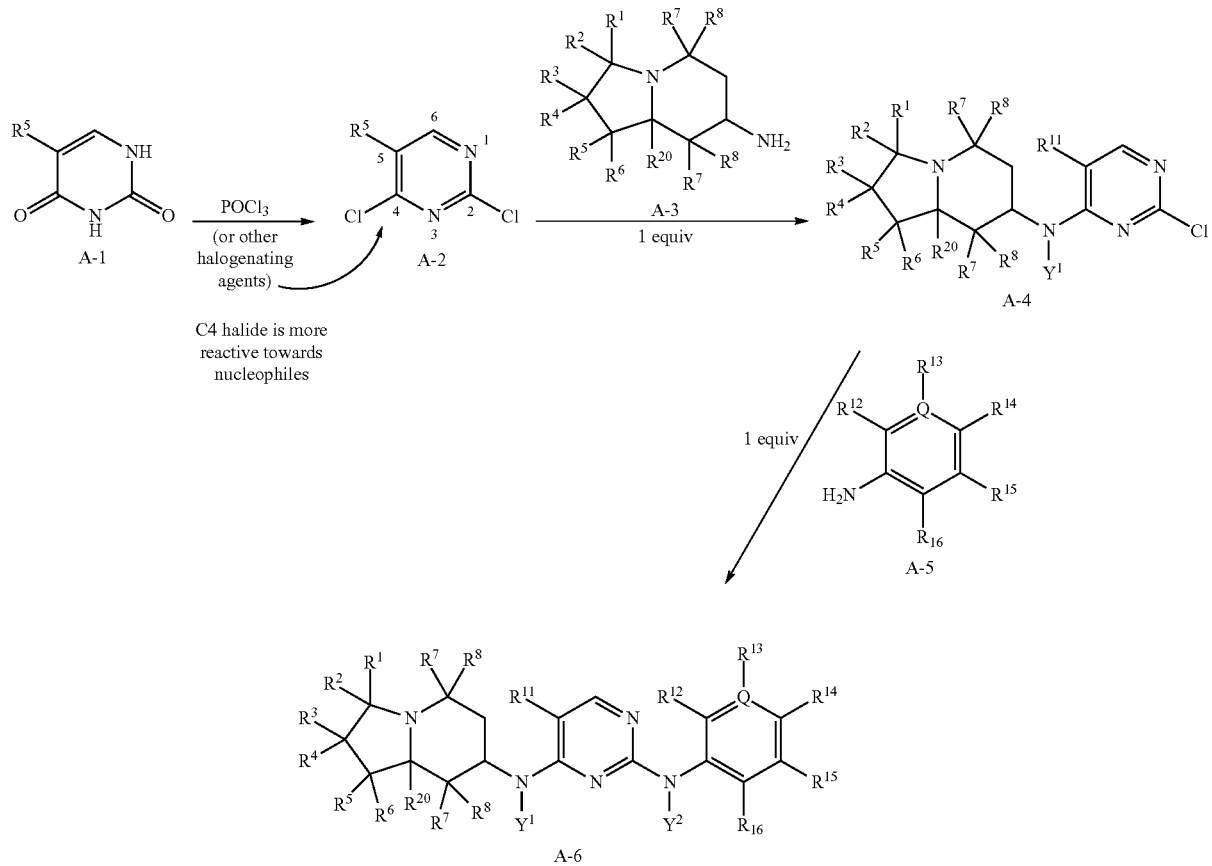

In Scheme 1, $R^1$, $R^2$, $R^3$, $R^4$, $R^5$, $R^6$, $R^7$, $R^8$, $R^9$, $R^{10}$, $R^{11}$, $R^{20}$, $Y^1$, $Y^2$, Q, $R^{12}$, $R^{13}$, $R^{14}$, $R^{15}$, and $R^{16}$ are as set forth hereinbefore.

According to Scheme 1, uracil A-1 is dihalogenated at the 2- and 4-positions using a standard dehydrating-halogenating agent such as $POCl_3$ (phosphorus oxychloride) (or other standard halogenating agent) under standard conditions to yield 2,4 dichloropyrimidine A-2. Depending upon the substituents in pyrimidinediamine A-2, the chloride at the C4 position is more reactive towards nucleophiles than the chloride at the C2 position. This differential reactivity can be exploited by first reacting 2,4 dichloropyrimidine A-2 with one equivalent of amine A-3, yielding 4N-substituted-2-chloro-4-pyrimidineamine A-4, followed by amine A-5 to yield a 2,4-pyrimidinediamine derivative A-6.

Typically, the C4 halide is more reactive towards nucleophiles, as illustrated in the scheme. However, as will be recognized by skilled artisans, the identity of the substituent may alter this reactivity. For example, when the substituent is trifluoromethyl, a 50:50 mixture of 4N-substituted-4-pyrimidineamine A-4 and the corresponding 2N-substituted-2-pyrimidineamine is obtained. The regioselectivity of the reaction can also be controlled by adjusting the solvent and other synthetic conditions (such as temperature), as is well-known in the art.

In a certain embodiment, to couple compounds with an electrophilic leaving group, such as halides or pseudohalides, and compounds with an amino group, nucleophilic aromatic substitution can be used. For example, a halogen substituent on Compound A-2 and the amino group on Compound A-3 can react. Also for example, a halogen substituent on Compound A-4 and the amino group on Compound A-5 can react. Conditions for nucleophilic aromatic substitution include the compounds reacting in a polar aprotic solvent or polar protic solvent. Suitable solvents include alcohols (such as isopropanol, methanol, ethanol), formic acid, dimethylsulfoxide, dimethylformamide, dioxane, and tetrahydrofuran. The reaction can be run at room temperature or can be heated.

In a certain embodiment, to couple compounds with an electrophilic leaving group, such as halides or pseudohalides, and aryl compounds with an amino group, a coupling reaction, such as a Buchwald coupling reaction, can be used. The Buchwald coupling reaction involves palladium-catalyzed synthesis of aryl amines. Starting materials are aryl halides or pseudohalides (for example, triflates) and primary or secondary amines. Such reaction can be performed using a variety of methods well known in the art and specific examples can be had by reference to the Examples hereunder described.

The reactions depicted in Scheme 1 may proceed more quickly when the reaction mixtures are heated via microwave. When heating in this fashion, the following conditions can be used: heat to 175° C. in ethanol for 5-20 minutes in a Smith Reactor (Personal Chemistry, Uppsala, Sweden) in a sealed tube (at 20 bar pressure).

A specific embodiment of Scheme 1 utilizing 5-fluorouracil (Aldrich #32, 937-1) as a starting material is illustrated in Scheme 2, below.

Scheme 2

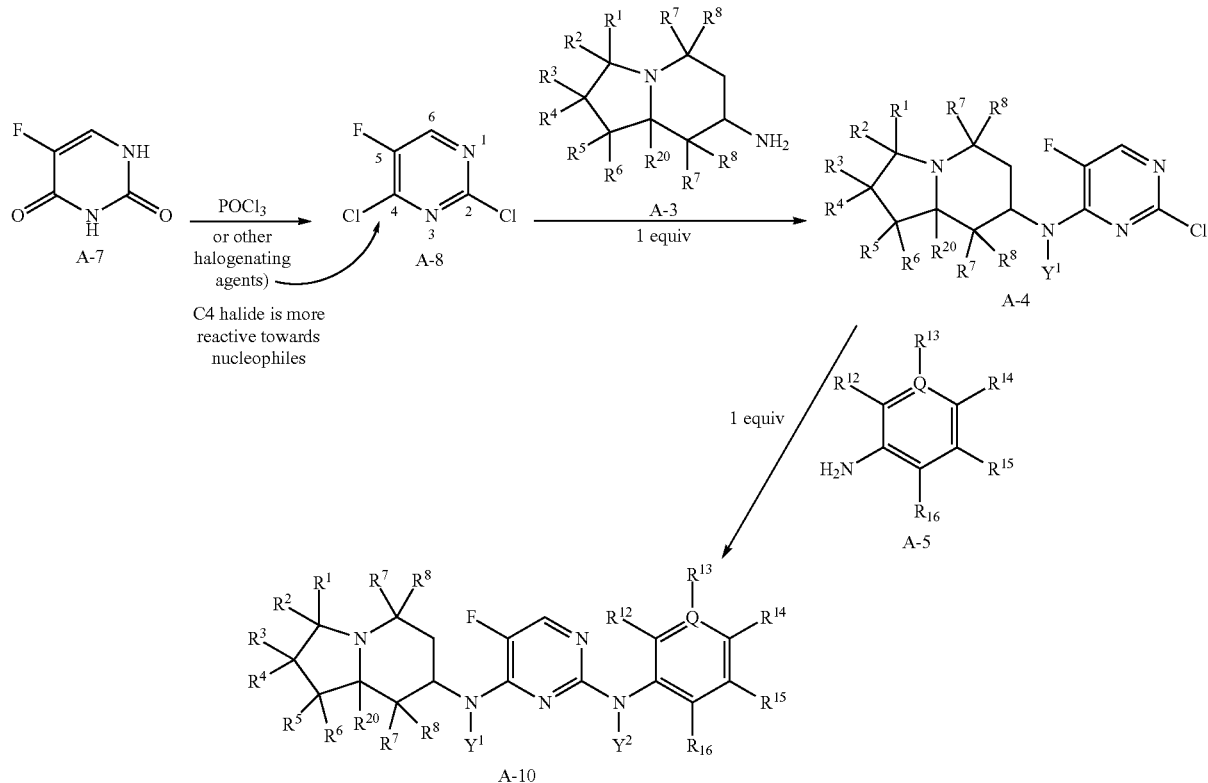

In Scheme 2, $R^1$, $R^2$, $R^3$, $R^4$, $R^5$, $R^6$, $R^7$, $R^8$, $R^9$, $R^{10}$, $R^{11}$, $R^{20}$, $Y^1$, $Y^2$, Q, $R^{12}$, $R^{13}$, $R^{14}$, $R^{15}$, and $R^{16}$ are as set forth hereinbefore.

Asymmetric 2N,4N-disubstituted-5-fluoro-2,4-pyrimidinediamine A-10 can be obtained by reacting 2,4-dichloro-5-fluoropyrimidine A-8 with one equivalent of amine A-3 (to yield 2-chloro-N4-substituted-5-fluoro-4-pyrimidineamine A-9) followed by one or more equivalents of amine A-5.

A specific embodiment of Scheme 1 to form cyano derivatives is illustrated in Scheme 3, below.

Scheme 3

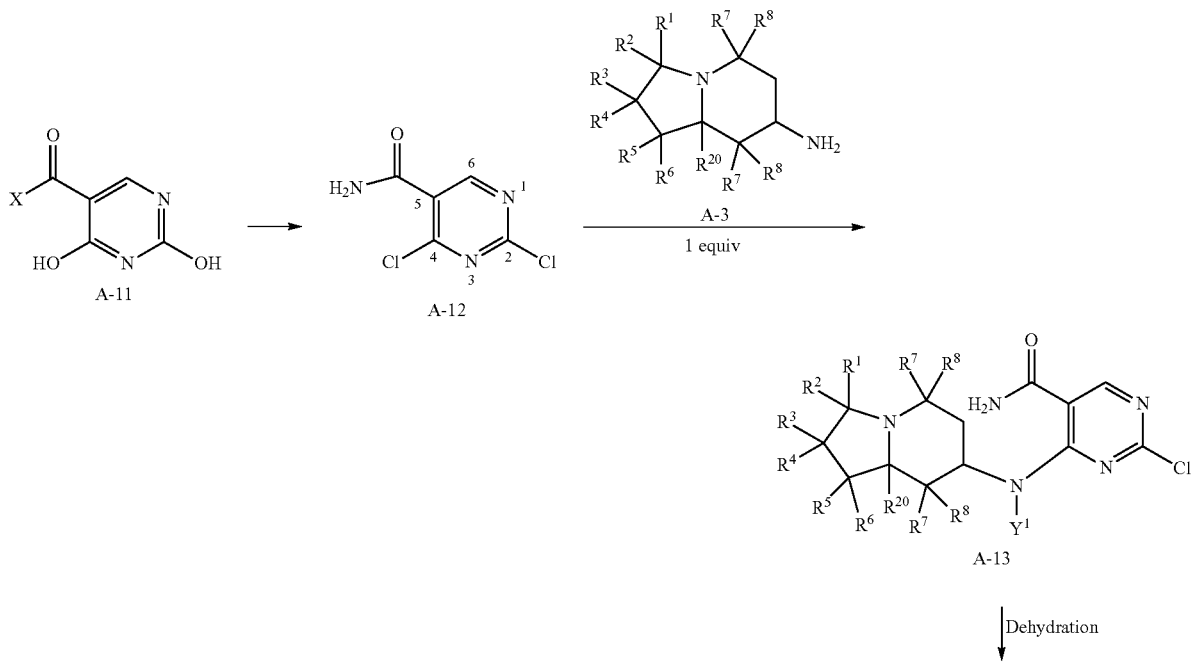

Dehydration

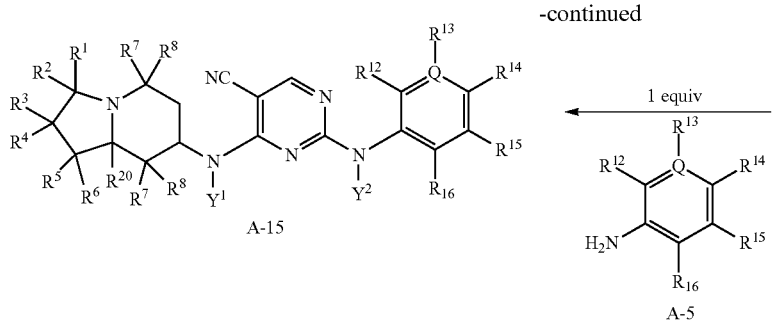

A-15

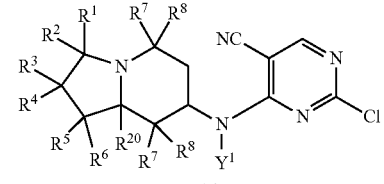

A-14

In Scheme 3, $R^1$, $R^2$, $R^3$, $R^4$, $R^5$, $R^6$, $R^7$, $R^8$, $R^9$, $R^{10}$, $R^{11}$, $R^{20}$, $Y^1$, $Y^2$, Q, $R^{12}$, $R^{13}$, $R^{14}$, $R^{15}$, and $R^{16}$ are as set forth hereinbefore.

Asymmetric 2N,4N-disubstituted-5-cyano-2,4-pyrimidinediamine A-15 can be obtained by reacting 2,4-dichloro-5-carbamoylpyrimidine A-12 with one equivalent of amine A-3 (to yield 2-chloro-N4-substituted-5-carbamoyl-4-pyrimidineamine A-13). The amide group of Compound A-13 is converted to a cyano group to yield Compound A-14, followed by reaction with one or more equivalents of amine A-5. Conversion of the amide group to the cyano group can be accomplished with dehydration, such as with use of Burgess reagent or trifluoroacetic anhydride. As will be recognized by those of skill in the art and exemplified herein, aniline A-5 may also be reacted with intermediate A-13, and the resultant N2,N4-disubstituted diaminopyrimidine-5-carbamoylpyrimidine can be dehydrated to yield the corresponding 5-cyano compound A-15.

Uracil Starting Materials and Intermediates

The uracil A-1, A-7, and A-11 starting materials can be purchased from commercial sources or prepared using standard techniques of organic chemistry. Commercially available uracils that can be used as starting materials in the schemes disclosed herein include, by way of example and not limitation, uracil (Aldrich #13, 078-8; CAS Registry 66-22-8); 5 bromouracil (Aldrich #85, 247-3; CAS Registry 51-20-7; 5 fluorouracil (Aldrich #85, 847-1; CAS Registry 51-21-8); 5 iodouracil (Aldrich #85, 785-8; CAS Registry 696-07-1); 5 nitrouracil (Aldrich #85, 276-7; CAS Registry 611-08-5); 5 (trifluoromethyl)-uracil (Aldrich #22, 327-1; CAS Registry 54-20-6). Additional 5-substituted uracils are available from General Intermediates of Canada, Inc., Edmonton, Calif. and/or Interchim, Cedex, France, or can be prepared using standard techniques. Myriad textbook references teaching suitable synthetic methods are provided infra.

Amino Starting Materials and Intermediates

Amines, such as A-3 and A-5 can be purchased from commercial sources or, alternatively, can be synthesized utilizing standard techniques. For example, suitable amines can be synthesized from nitro precursors using standard chemistry. See also Vogel, 1989, Practical Organic Chemistry, Addison Wesley Longman, Ltd. and John Wiley & Sons, Inc. By way of example amines A-5 can be prepared as described in WO 2010/090875, WO 2010-083207, WO 2011/068898 and WO 2012/012619, each of which are incorporated herein by reference.

In a certain embodiment, Compound A-3 can be synthesized as illustrated in Scheme 4, below:

Scheme 4

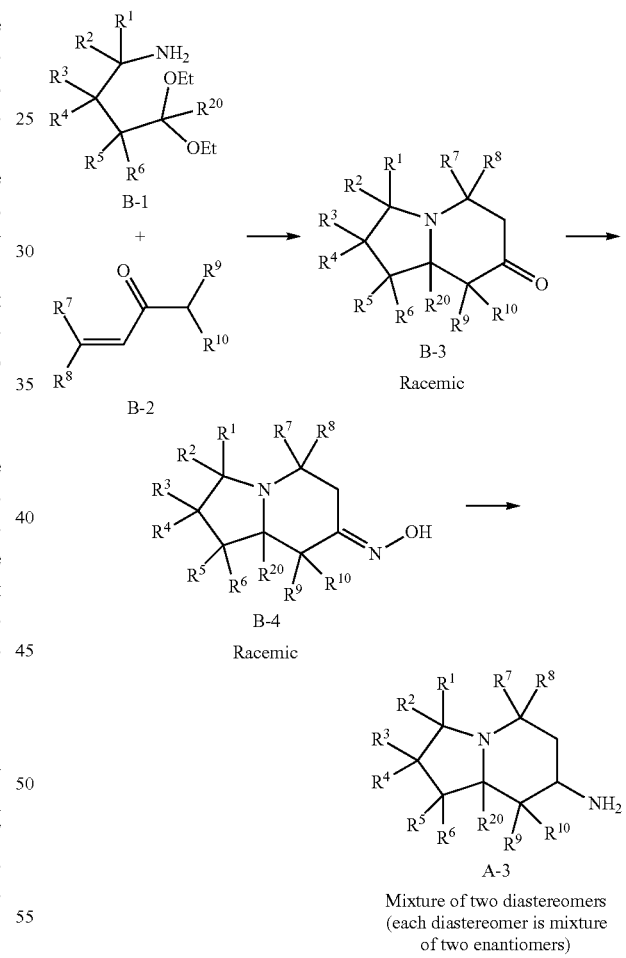

Mixture of two diastereomers (each diastereomer is mixture of two enantiomers)

Referring to Scheme 4, amine Compound B-1 reacts with enone Compound B-2 to form Compound B-3. First, the condensation reaction between Compound B-1 and Compound B-2 occurs by mixing the compounds neat or in a solvent. Then, the intermediate from the reaction between Compound B-1 and Compound B-2 is formed. The protecting groups are removed from intermediate. For example and not meant to be limiting, Scheme 4 shows a diethyl acetal as a protecting group. Conditions to remove the diethyl acetal protecting group include refluxing the intermediate in aqueous acid. After the protecting group is removed, further reaction affords Compound B-3.

With continued reference to Scheme 4, the carbonyl group of Compound B-3 reacts with hydroxylamine to form Compound B-4. Then, reduction of the oxime group of Compound B-4 affords Compound A-3. Suitable conditions for reduction of the oxime group include hydrogenation or reaction with sodium amalgam, borane, or sodium cyanoborohydride. In certain embodiments, the oxime group is hydrogenated with a catalyst. Suitable hydrogenation catalysts include $PtO_2$ and Raney Ni.

The isomers of Compound A-3 can be isolated by procedures known to those skilled in the art. The individual isomers may be obtained, for instance, by a resolution technique or by chiral chromatography techniques.

In a certain embodiment, Compound A-3 can be synthesized as illustrated in Scheme 5, below:

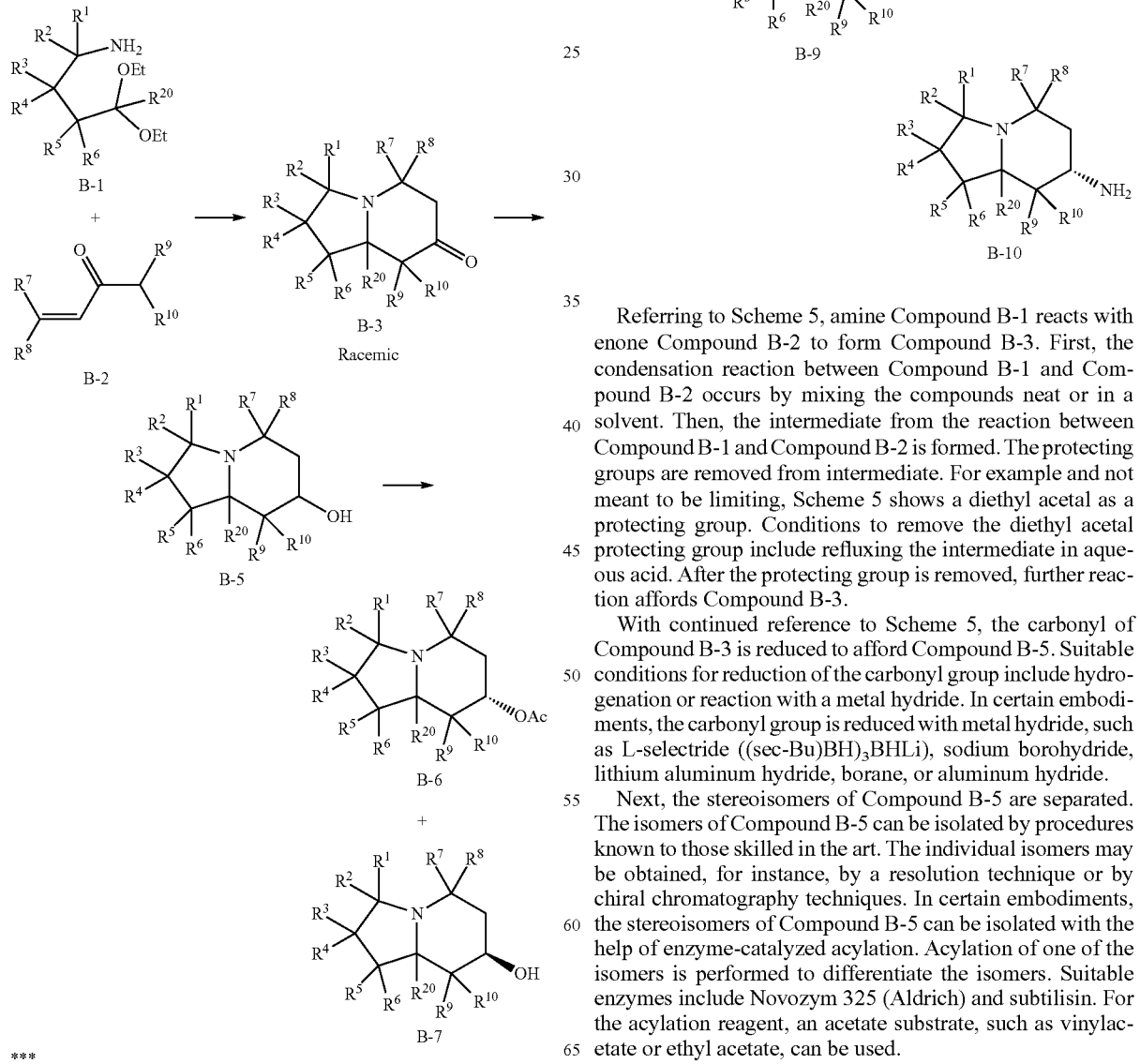

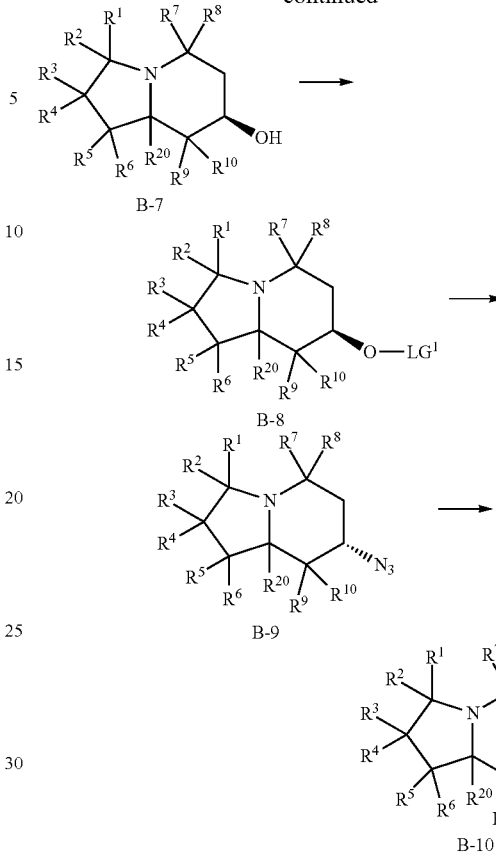

Referring to Scheme 5, amine Compound B-1 reacts with enone Compound B-2 to form Compound B-3. First, the condensation reaction between Compound B-1 and Compound B-2 occurs by mixing the compounds neat or in a solvent. Then, the intermediate from the reaction between Compound B-1 and Compound B-2 is formed. The protecting groups are removed from intermediate. For example and not meant to be limiting, Scheme 5 shows a diethyl acetal as a protecting group. Conditions to remove the diethyl acetal protecting group include refluxing the intermediate in aqueous acid. After the protecting group is removed, further reaction affords Compound B-3.

With continued reference to Scheme 5, the carbonyl of Compound B-3 is reduced to afford Compound B-5. Suitable conditions for reduction of the carbonyl group include hydrogenation or reaction with a metal hydride. In certain embodiments, the carbonyl group is reduced with metal hydride, such as L-selectride ((sec-Bu)BH)$_3$BHLi), sodium borohydride, lithium aluminum hydride, borane, or aluminum hydride.

Next, the stereoisomers of Compound B-5 are separated. The isomers of Compound B-5 can be isolated by procedures known to those skilled in the art. The individual isomers may be obtained, for instance, by a resolution technique or by chiral chromatography techniques. In certain embodiments, the stereoisomers of Compound B-5 can be isolated with the help of enzyme-catalyzed acylation. Acylation of one of the isomers is performed to differentiate the isomers. Suitable enzymes include Novozym 325 (Aldrich) and subtilisin. For the acylation reagent, an acetate substrate, such as vinylacetate or ethyl acetate, can be used.

Next, for example and not meant to be limiting, Compound B-7 is obtained for further reaction. Alternatively, Compound B-6 can also be obtained for further reaction, depending on which stereoisomer is desired. However, Compound B-7 is shown in the above scheme for further reaction for the purposes of being an example. With continued reference to Scheme 5, the hydroxyl group of Compound B-7 is converted to a leaving group (—O-LG$^1$) to form Compound B-8. Examples of leaving groups include nonaflates, triflates, fluorosulfonates, tosylates, and mesylates. In certain embodiments, the hydroxyl group of Compound B-7 is converted to a tosylate or mesylate. Alternatively the transformation of B-7 to B-9 can be accomplished as is known to those of skill in the art via in situ activation of the B-7 hydroxyl group, such as via a Mitsonobu reaction.

Then, the leaving group of Compound B-8 is displaced with an azide (—N$_3$) to form Compound B-9. Reaction of Compound B-8 with sodium azide can form Compound B-9. Then, conversion of the azide of Compound B-9 to form an amine of Compound B-10 can be performed with reduction. Azides may be reduced to amines by hydrogenolysis or with a phosphine, e.g. triphenylphosphine, in the Staudinger reaction. Hydrogenolysis conditions include reaction with hydrogen and a catalyst, such as Pd(OH)$_2$ or Pd/C.

Although many of the synthetic schemes discussed above do not illustrate the use of protecting groups, skilled artisans will recognize that in some instances certain substituents may include functional groups requiring protection. The exact identity of the protecting group used will depend upon, among other things, the identity of the functional group being protected and the reaction conditions used in the particular synthetic scheme, and will be apparent to those of skill in the art. Guidance for selecting protecting groups, their attachment and removal suitable for a particular application can be found, for example, in Greene & Wuts, supra.

Prodrugs as described herein can be prepared by routine modification of the above-described methods. Alternatively, such prodrugs can be prepared by reacting a suitably protected 2,4-pyrimidinediamine with a suitable progroup. Conditions for carrying out such reactions and for deprotecting the product to yield prodrugs as described herein are well-known.

Myriad references teaching methods useful for synthesizing pyrimidines generally, as well as starting materials described in Schemes (I)-(VII), are known in the art. For specific guidance, the reader is referred to Brown, D. J., "The Pyrimidines", in The Chemistry of Heterocyclic Compounds, Volume 16 (Weissberger, A., Ed.), 1962, Interscience Publishers, (A Division of John Wiley & Sons), New York ("Brown I"); Brown, D. J., "The Pyrimidines", in The Chemistry of Heterocyclic Compounds, Volume 16, Supplement I (Weissberger, A. and Taylor, E. C., Ed.), 1970, Wiley-Interscience, (A Division of John Wiley & Sons), New York (Brown II"); Brown, D. J., "The Pyrimidines", in The Chemistry of Heterocyclic Compounds, Volume 16, Supplement II (Weissberger, A. and Taylor, E. C., Ed.), 1985, An Interscience Publication (John Wiley & Sons), New York ("Brown III"); Brown, D. J., "The Pyrimidines" in The Chemistry of Heterocyclic Compounds, Volume 52 (Weissberger, A. and Taylor, E. C., Ed.), 1994, John Wiley & Sons, Inc., New York, pp. 1-1509 (Brown IV"); Kenner, G. W. and Todd, A., in Heterocyclic Compounds, Volume 6, (Elderfield, R. C., Ed.), 1957, John Wiley, New York, Chapter 7 (pyrimidines); Paquette, L. A., Principles of Modern Heterocyclic Chemistry, 1968, W. A. Benjamin, Inc., New York, pp. 1-401 (uracil synthesis pp. 313, 315; pyrimidinediamine synthesis pp. 313-316; amino pyrimidinediamine synthesis pp. 315); Joule, J. A., Mills, K. and Smith, G. F., Heterocyclic Chemistry, 3rd Edition, 1995, Chapman and Hall, London, UK, pp. 1-516; Vorbrüggen, H. and Ruh-Pohlenz, C., Handbook of Nucleoside Synthesis, John Wiley & Sons, New York, 2001, pp. 1-631 (protection of pyrimidines by acylation pp. 90-91; silylation of pyrimidines pp. 91-93); Joule, J. A., Mills, K. and Smith, G. F., Heterocyclic Chemistry, 4th Edition, 2000, Blackwell Science, Ltd, Oxford, UK, pp. 1-589; and Comprehensive Organic Synthesis, Volumes 1-9 (Trost, B. M. and Fleming, I., Ed.), 1991, Pergamon Press, Oxford, UK.

The embodiments are also directed to processes and novel intermediates useful for preparing compounds of formula I-V or a salt or solvate or stereoisomer thereof.

Accordingly, the present disclosure provides a method for making a compound according to the formula

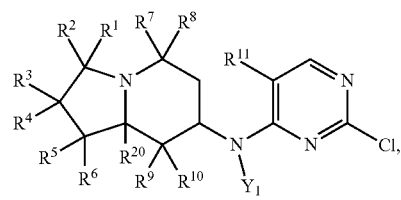

wherein $R^1$, $R^2$, $R^3$, $R^4$, $R^5$, and $R^6$ are independently selected from hydrogen, alkyl, substituted alkyl, alkoxy, substituted alkoxy, acyl, acylamino, acyloxy, amino, substituted amino, aminoacyl, aminoacyloxy, oxyaminoacyl, azido, cyano, halogen, hydroxyl, carboxyl, carboxylalkyl, thiol, thioalkoxy, substituted thioalkoxy, aryl, aryloxy, hydroxyamino, alkoxyamino, nitro, —SO-alkyl, —SO-substituted alkyl, —SO-aryl, —SO-heteroaryl, —SO$_2$-alkyl, —SO$_2$-substituted alkyl, —SO$_2$-aryl and —SO$_2$-heteroaryl; or $R^1$ and $R^2$ together form an oxo group; or $R^3$ and $R^4$ together form an oxo group; or $R^5$ and $R^6$ together form an oxo group;

$R^7$, $R^8$, $R^9$, and $R^{10}$ are independently selected from hydrogen, alkyl, substituted alkyl, alkoxy, substituted alkoxy, acyl, acylamino, acyloxy, amino, substituted amino, aminoacyl, aminoacyloxy, oxyaminoacyl, azido, cyano, halogen, hydroxyl, carboxyl, carboxylalkyl, thiol, thioalkoxy, substituted thioalkoxy, aryl, aryloxy, hydroxyamino, alkoxyamino, nitro, —SO-alkyl, —SO-substituted alkyl, —SO-aryl, —SO-heteroaryl, —SO$_2$-alkyl, —SO$_2$-substituted alkyl, —SO$_2$-aryl and —SO$_2$-heteroaryl; or $R^7$ and $R^8$ together form an oxo group; or $R^9$ and $R^{10}$ together form an oxo group;

$R^{11}$ is selected from alkyl, substituted alkyl, hydroxy, alkoxy, substituted alkoxy, amino, substituted amino, carboxyl, carboxyl ester, cyano, halogen, acyl, aminoacyl, nitro, alkenyl, substituted alkenyl, alkynyl, and substituted alkynyl;

$R^{20}$ is selected from hydrogen, alkyl, and substituted alkyl, and $Y^1$ is selected from hydrogen and alkyl;

the method comprising contacting a compound of the formula

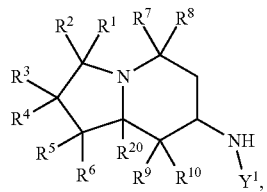

with a compound of the formula:

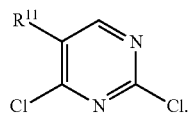

The present disclosure provides a method for making a compound according to the formula

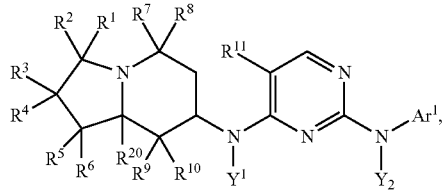

wherein $R^1$, $R^2$, $R^3$, $R^4$, $R^5$, and $R^6$ are independently selected from hydrogen, alkyl, substituted alkyl, alkoxy, substituted alkoxy, acyl, acylamino, acyloxy, amino, substituted amino, aminoacyl, aminoacyloxy, oxyaminoacyl, azido, cyano, halogen, hydroxyl, carboxyl, carboxylalkyl, thiol, thioalkoxy, substituted thioalkoxy, aryl, aryloxy, hydroxyamino, alkoxyamino, nitro, —SO-alkyl, —SO-substituted alkyl, —SO-aryl, —SO-heteroaryl, —SO$_2$-alkyl, —SO$_2$-substituted alkyl, —SO$_2$-aryl and —SO$_2$-heteroaryl; or $R^1$ and $R^2$ together form an oxo group; or $R^3$ and $R^4$ together form an oxo group; or $R^5$ and $R^6$ together form an oxo group;

$R^7$, $R^8$, $R^9$, and $R^{10}$ are independently selected from hydrogen, alkyl, substituted alkyl, alkoxy, substituted alkoxy, acyl, acylamino, acyloxy, amino, substituted amino, aminoacyl, aminoacyloxy, oxyaminoacyl, azido, cyano, halogen, hydroxyl, carboxyl, carboxylalkyl, thiol, thioalkoxy, substituted thioalkoxy, aryl, aryloxy, hydroxyamino, alkoxyamino, nitro, —SO-alkyl, —SO-substituted alkyl, —SO-aryl, —SO-heteroaryl, —SO$_2$-alkyl, —SO$_2$-substituted alkyl, —SO$_2$-aryl and —SO$_2$-heteroaryl; or $R^7$ and $R^8$ together form an oxo group; or $R^9$ and $R^{10}$ together form an oxo group;

$R^{11}$ is selected from alkyl, substituted alkyl, hydroxy, alkoxy, substituted alkoxy, amino, substituted amino, carboxyl, carboxyl ester, cyano, halogen, acyl, aminoacyl, nitro, alkenyl, substituted alkenyl, alkynyl, and substituted alkynyl;

$R^{20}$ is selected from hydrogen, alkyl, and substituted alkyl;

$Y^1$ and $Y^2$ are independently selected from hydrogen and alkyl; and $Ar^1$ is selected from aryl, substituted aryl, heteroaryl, and substituted heteroaryl;

the method comprising contacting a compound of the formula

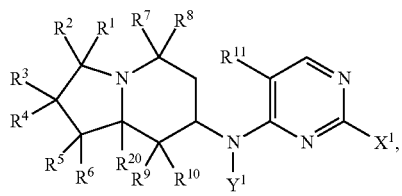

wherein $X^1$ is a halogen;
with a compound of the formula $HNY^2Ar^1$.

In certain embodiments, in the above methods, the method further comprises performing separation of isomers with chiral chromatography. In certain embodiments, in the above methods, the method further comprises performing separation of isomers with a resolution technique.

The present disclosure provides a method for preparing an optically active compound comprising contacting a racemic mixture of compounds of the formula

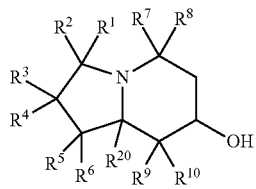

with a lipase; wherein $R^1$, $R^2$, $R^3$, $R^4$, $R^5$, and $R^6$ are independently selected from hydrogen, alkyl, substituted alkyl, alkoxy, substituted alkoxy, acyl, acylamino, acyloxy, amino, substituted amino, aminoacyl, aminoacyloxy, oxyaminoacyl, azido, cyano, halogen, hydroxyl, carboxyl, carboxylalkyl, thiol, thioalkoxy, substituted thioalkoxy, aryl, aryloxy, hydroxyamino, alkoxyamino, nitro, —SO-alkyl, —SO-substituted alkyl, —SO-aryl, —SO-heteroaryl, —SO$_2$-alkyl, —SO$_2$-substituted alkyl, —SO$_2$-aryl and —SO$_2$-heteroaryl; or $R^1$ and $R^2$ together form an oxo group; or $R^3$ and $R^4$ together form an oxo group; or $R^5$ and $R^6$ together form an oxo group;

$R^7$, $R^8$, $R^9$, and $R^{10}$ are independently selected from hydrogen, alkyl, substituted alkyl, alkoxy, substituted alkoxy, acyl, acylamino, acyloxy, amino, substituted amino, aminoacyl, aminoacyloxy, oxyaminoacyl, azido, cyano, halogen, hydroxyl, carboxyl, carboxylalkyl, thiol, thioalkoxy, substituted thioalkoxy, aryl, aryloxy, hydroxyamino, alkoxyamino, nitro, —SO-alkyl, —SO-substituted alkyl, —SO-aryl, —SO-heteroaryl, —SO$_2$-alkyl, —SO$_2$-substituted alkyl, —SO$_2$-aryl and —SO$_2$-heteroaryl; or $R^7$ and $R^8$ together form an oxo group; or $R^9$ and $R^{10}$ together form an oxo group; and $R^{20}$ is selected from hydrogen, alkyl, and substituted alkyl.

In one embodiment, the above process further comprises the step of forming a salt of a compound of formula I-V. Embodiments are directed to the other processes described herein; and to the product prepared by any of the processes described herein.

Pharmaceutical Compositions

The disclosed compounds are useful, at least, for the inhibition of PKC activity and the treatment of a disease or disorder that is mediated through the activity of a PKC activity. Accordingly, pharmaceutical compositions comprising at least one disclosed compound are also described herein.

A pharmaceutical composition comprising a subject compound may be administered to a patient alone, or in combination with other supplementary active agents. The pharmaceutical compositions may be manufactured using any of a variety of processes, including, without limitation, conventional mixing, dissolving, granulating, dragee-making, levigating, emulsifying, encapsulating, entrapping, and lyophilizing. The pharmaceutical composition can take any of a variety of forms including, without limitation, a sterile solution, suspension, emulsion, lyophilisate, tablet, pill, pellet, capsule, powder, syrup, elixir or any other dosage form suitable for administration.

A subject compound may be administered to the host using any convenient means capable of resulting in the desired reduction in disease condition or symptom. Thus, a subject compound can be incorporated into a variety of formulations for therapeutic administration. More particularly, a subject compound can be formulated into pharmaceutical compositions by combination with appropriate pharmaceutically acceptable carriers or diluents, and may be formulated into preparations in solid, semi-solid, liquid or gaseous forms, such as tablets, capsules, powders, granules, ointments, solutions, suppositories, injections, inhalants and aerosols.

Formulations for pharmaceutical compositions are well known in the art. For example, Remington's Pharmaceutical Sciences, by E. W. Martin, Mack Publishing Co., Easton, Pa., 19th Edition, 1995, describes exemplary formulations (and components thereof) suitable for pharmaceutical delivery of disclosed compounds. Pharmaceutical compositions comprising at least one of the subject compounds can be formulated for use in human or veterinary medicine. Particular formulations of a disclosed pharmaceutical composition may depend, for example, on the mode of administration and/or on the location of the infection to be treated. In some embodiments, formulations include a pharmaceutically acceptable carrier in addition to at least one active ingredient, such as a subject compound. In other embodiments, other medicinal or pharmaceutical agents, for example, with similar, related or complementary effects on the affliction being treated can also be included as active ingredients in a pharmaceutical composition.

Pharmaceutically acceptable carriers useful for the disclosed methods and compositions are conventional in the art. The nature of a pharmaceutical carrier will depend on the particular mode of administration being employed. For example, parenteral formulations usually comprise injectable fluids that include pharmaceutically and physiologically acceptable fluids such as water, physiological saline, balanced salt solutions, aqueous dextrose, glycerol or the like as a vehicle. For solid compositions (e.g., powder, pill, tablet, or capsule forms), conventional non-toxic solid carriers can include, for example, pharmaceutical grades of mannitol, lactose, starch, or magnesium stearate. In addition to biologically neutral carriers, pharmaceutical compositions to be administered can optionally contain minor amounts of non-toxic auxiliary substances (e.g., excipients), such as wetting or emulsifying agents, preservatives, and pH buffering agents and the like; for example, sodium acetate or sorbitan monolaurate. Other non-limiting excipients include, nonionic solubilizers, such as cremophor, or proteins, such as human serum albumin or plasma preparations.

Some examples of materials which can serve as pharmaceutically-acceptable carriers include: (1) sugars, such as lactose, glucose and sucrose; (2) starches, such as corn starch and potato starch; (3) cellulose, and its derivatives, such as sodium carboxymethyl cellulose, ethyl cellulose and cellulose acetate; (4) powdered tragacanth; (5) malt; (6) gelatin; (7) talc; (8) excipients, such as cocoa butter and suppository waxes; (9) oils, such as peanut oil, cottonseed oil, safflower oil, sesame oil, olive oil, corn oil and soybean oil; (10) glycols, such as propylene glycol; (11) polyols, such as glycerin, sorbitol, mannitol, and polyethylene glycol; (12) esters, such as ethyl oleate and ethyl laurate; (13) agar; (14) buffering agents, such as magnesium hydroxide and aluminum hydroxide; (15) alginic acid; (16) pyrogen-free water; (17) isotonic saline; (18) Ringer's solution; (19) ethyl alcohol; (20) pH buffered solutions; (21) polyesters, polycarbonates and/or polyanhydrides; and (22) other non-toxic compatible substances employed in pharmaceutical formulations.

The disclosed pharmaceutical compositions may be formulated as a pharmaceutically acceptable salt of a disclosed compound. Pharmaceutically acceptable salts are non-toxic salts of a free base form of a compound that possesses the desired pharmacological activity of the free base. These salts may be derived from inorganic or organic acids. Non-limiting examples of inorganic acids suitable for forming salts with the present compounds are hydrochloric acid, nitric acid, hydrobromic acid, sulfuric acid, hydroiodic acid, and phosphoric acid. Non-limiting examples of suitable organic acids for forming salts with the present compounds are acetic acid, propionic acid, glycolic acid, lactic acid, pyruvic acid, malonic acid, succinic acid, malic acid, maleic acid, fumaric acid, tartaric acid, citric acid, benzoic acid, cinnamic acid, mandelic acid, methanesulfonic acid, ethanesulfonic acid, methyl sulfonic acid, salicylic acid, formic acid, trichloroacetic acid, trifluoroacetic acid, gluconic acid, asparagic acid, aspartic acid, benzenesulfonic acid, para-toluenesulfonic acid, naphthalenesulfonic acid, 1-hydroxy-2-napthoic acid, and the like. Lists of other suitable pharmaceutically acceptable salts are found in Remington's Pharmaceutical Sciences, 19th Edition, Mack Publishing Company, Easton, Pa., 1995. A pharmaceutically acceptable salt may also serve to adjust the osmotic pressure of the composition.

A subject compound can be used alone or in combination with appropriate additives to make tablets, powders, granules or capsules, for example, with conventional additives, such as lactose, mannitol, corn starch or potato starch; with binders, such as crystalline cellulose, cellulose derivatives, acacia, corn starch or gelatins; with disintegrators, such as corn starch, potato starch or sodium carboxymethylcellulose; with lubricants, such as talc or magnesium stearate; and if desired, with diluents, buffering agents, moistening agents, preservatives and flavoring agents. Such preparations can be used for oral administration.

A subject compound can be formulated into preparations for injection by dissolving, suspending or emulsifying them in an aqueous or nonaqueous solvent, such as vegetable or other similar oils, synthetic aliphatic acid glycerides, esters of higher aliphatic acids or propylene glycol; and if desired, with conventional additives such as solubilizers, isotonic agents, suspending agents, emulsifying agents, stabilizers and preservatives. The preparation may also be emulsified or the active ingredient encapsulated in liposome vehicles. Formulations suitable for injection can be administered by an intravitreal, intraocular, intramuscular, subcutaneous, sublingual, or other route of administration, e.g., injection into the gum tissue or other oral tissue. Such formulations are also suitable for topical administration.

In some embodiments, a subject compound can be delivered by a continuous delivery system. The term "continuous delivery system" is used interchangeably herein with "controlled delivery system" and encompasses continuous (e.g., controlled) delivery devices (e.g., pumps) in combination with catheters, injection devices, and the like, a wide variety of which are known in the art.

A subject compound can be utilized in aerosol formulation to be administered via inhalation. A subject compound can be formulated into pressurized acceptable propellants such as dichlorodifluoromethane, propane, nitrogen and the like.

Furthermore, a subject compound can be made into suppositories by mixing with a variety of bases such as emulsifying bases or water-soluble bases. A subject compound can be administered rectally via a suppository. The suppository can include vehicles such as cocoa butter, carbowaxes and polyethylene glycols, which melt at body temperature, yet are solidified at room temperature.

The term "unit dosage form," as used herein, refers to physically discrete units suitable as unitary dosages for human and animal subjects, each unit containing a predetermined quantity of a subject compound calculated in an amount sufficient to produce the desired effect in association with a pharmaceutically acceptable diluent, carrier or vehicle. The specifications for a subject compound depend on the particular compound employed and the effect to be achieved, and the pharmacodynamics associated with each compound in the host.

The dosage form of a disclosed pharmaceutical composition will be determined by the mode of administration chosen. For example, in addition to injectable fluids, topical or oral dosage forms may be employed. Topical preparations may include eye drops, ointments, sprays and the like. Oral formulations may be liquid (e.g., syrups, solutions or suspensions), or solid (e.g., powders, pills, tablets, or capsules). Methods of preparing such dosage forms are known, or will be apparent, to those skilled in the art.

Certain embodiments of the pharmaceutical compositions comprising a subject compound may be formulated in unit dosage form suitable for individual administration of precise dosages. The amount of active ingredient administered will depend on the subject being treated, the severity of the affliction, and the manner of administration, and is known to those skilled in the art. Within these bounds, the formulation to be administered will contain a quantity of the extracts or compounds disclosed herein in an amount effective to achieve the desired effect in the subject being treated.

Each therapeutic compound can independently be in any dosage form, such as those described herein, and can also be administered in various ways, as described herein. For example, the compounds may be formulated together, in a single dosage unit (that is, combined together in one form such as capsule, tablet, powder, or liquid, etc.) as a combination product. Alternatively, when not formulated together in a single dosage unit, an individual subject compound may be administered at the same time as another therapeutic compound or sequentially, in any order thereof.

Methods of Administration

The subject compounds can inhibit a protein kinase C activity. Accordingly, the subject compounds are useful for treating a disease or disorder that is mediated through the activity of a PKC activity in a subject. Accordingly, the subject compounds are useful for treating a disease or disorder that is associated with the activation of T-cells in a subject.

The route of administration will be selected according to a variety of factors including, but not necessarily limited to, the condition to be treated, the formulation and/or device used, the patient to be treated, and the like. Routes of administration useful in the disclosed methods include but are not limited to oral and parenteral routes, such as intravenous (iv), intraperitoneal (ip), rectal, topical, ophthalmic, nasal, and transdermal. Formulations for these dosage forms are described herein.

An effective amount of a subject compound will depend, at least, on the particular method of use, the subject being treated, the severity of the affliction, and the manner of administration of the therapeutic composition. A "therapeutically effective amount" of a composition is a quantity of a specified compound sufficient to achieve a desired effect in a subject (host) being treated. For example, this may be the amount of a subject compound necessary to prevent, inhibit, reduce or relieve a disease or disorder that is mediated through the activity of a PKC activity in a subject. Ideally, a therapeutically effective amount of a compound is an amount sufficient to prevent, inhibit, reduce or relieve a disease or disorder that is mediated through the activity of a PKC activity in a subject without causing a substantial cytotoxic effect on host cells.

Therapeutically effective doses (or growth inhibitory amounts) of a subject compound or pharmaceutical composition can be determined by one of skill in the art, with a goal of achieving local (e.g., tissue) concentrations that are at least as high as the $IC_{50}$ of an applicable compound disclosed herein.

An example of a dosage range is from about 0.1 to about 200 mg/kg body weight orally in single or divided doses. In particular examples, a dosage range is from about 1.0 to about 100 mg/kg body weight orally in single or divided doses, including from about 1.0 to about 50 mg/kg body weight, from about 1.0 to about 25 mg/kg body weight, from about 1.0 to about 10 mg/kg body weight (assuming an average body weight of approximately 70 kg; values adjusted accordingly for persons weighing more or less than average). For oral administration, the compositions are, for example, provided in the form of a tablet containing from about 50 to about 1000 mg of the active ingredient, particularly about 75 mg, about 100 mg, about 200 mg, about 400 mg, about 500 mg, about 600 mg, about 750 mg, or about 1000 mg of the active ingredient for the symptomatic adjustment of the dosage to the subject being treated. In one exemplary oral dosage regimen, a tablet containing from about 500 mg to about 1000 mg active ingredient is administered once (e.g., a loading dose) followed by administration of ½ dosage tablets (e.g., from about 250 to about 500 mg) each 6 to 24 hours for at least 3 days.

The specific dose level and frequency of dosage for any particular subject may be varied and will depend upon a variety of factors, including the activity of the subject compound, the metabolic stability and length of action of that compound, the age, body weight, general health, sex and diet of the subject, mode and time of administration, rate of excretion, drug combination, and severity of the condition of the host undergoing therapy.

The present disclosure also contemplates combinations of one or more disclosed compounds with one or more other agents or therapies useful in the treatment of a disease or disorder. In certain instances, the disease or disorder is mediated through the activity of a PKC activity in a subject. In certain instances, the disease or disorder is cell proliferative disorder. For example, one or more disclosed compounds may be administered in combination with effective doses of other medicinal and pharmaceutical agents, or in combination other non-medicinal therapies, such as hormone or radiation therapy. The term "administration in combination with" refers to both concurrent and sequential administration of the active agents.

Protein Kinase C

Protein Kinase C

PKC is a family of enzymes that function as serine/threonine kinases. The isoenzymes of PKC differ in their tissue distribution, enzymatic selectivity, requirement for $Ca^{2+}$, and regulation. PKCs play an important role in cell-cell signaling, gene expression and in the control of cell differentiation and growth.

The subject compound can be a selective inhibitor of PKC, e.g. an inhibitor selective for PKC over one or more other protein kinases, e.g. over one or more tyrosine kinases, for instance, over one or more non-receptor or receptor tyrosine kinases, e.g. over one or more of PKA, PKB, Abl Met, Src, Ins-R, Flt-3, JAK-2, KDR and/or Ret proteins. The selective PKC inhibitors may optionally be selective over one or more serine/threonine kinases, e.g. one or more serine/threonine kinases which do not belong to the CDK family. The subject compounds can exhibit a selectivity of at least 10 fold, or 20 fold, or 100 fold for the PKC over one or more other protein kinases, e.g. over one or more tyrosine kinases, e.g. over Flt-3, JAK-2, KDR and/or Ret proteins, or over one or more serine/threonine kinases which do not belong to the CDK family.

The selectivity of a selective inhibitor of PKC over other protein kinases may be calculated as the ratio of the $IC_{50}$ measured for PKC in an assay described herein over the $IC_{50}$ determined for another kinase. In a certain instance, there is provided a PKC inhibitor for which the ratio of the $IC_{50}$ value as determined in an Allogeneic Mixed Lymphocyte Reaction (MLR) assay to the $IC_{50}$ value as determined in a BM assay is higher than 5, 10, 20, or 30. MLR and BM assays can be done according to known methods, e.g. mouse or human MLR and BM assays, such as disclosed herein.

The disclosure provides an inhibitor of PKC, which can be an isozyme-selective PKC inhibitor, wherein the subject compound possesses selectivity for the isoforms θ and α of PKC over one or more of the other PKC isoforms. In a certain instance, the subject compound possesses selectivity for the isoform θ of PKC over one or more of the other PKC isoforms. In a certain instance, the subject compound possesses selectivity for the isoform α of PKC over one or more of the other PKC isoforms. In one embodiment, the disclosed compounds exhibit selectivity for PKC θ and PKC α over at least one PKC isoform.

A subject compound can show a selectivity of at least 10 fold, or 20 fold, or 100 fold for the isoforms θ or α of PKC over one or more of the other PKC isoforms. Selectivity for the isoforms θ or α of PKC over one or more of the other PKC isoforms can be measured by comparing the $IC_{50}$ of the subject compound for the isoforms θ or α of PKC to the $IC_{50}$ of the subject compound for the other PKC isoforms. In a certain instance, the selectivity can be determined by calculating the ratio of $IC_{50}$ of the subject compound for the other isoforms of PKC to the $IC_{50}$ of the subject compound for θ or α isoforms of PKC. In certain examples subject compounds exhibit a selectivity for PKC θ, α or both over another PKC isoform of at least about 2-fold, such as from about 3-fold to about 300-fold, from about 10-fold to about 100-fold or from about 5-fold to 50-fold. $IC_{50}$ values are obtained, for example, according to PKC assays described herein. The subject compounds can show an $IC_{50}$ value for the isoforms θ or α of PKC of 1 μM or less, such as less than about 300 nM, such as from about 1 nM to about 250 nM, less than 100 nM or even less than 10 nM in the assays disclosed herein.

The subject compounds can show a selectivity of the isoforms θ or μ of PKC over other isoforms of PKC, as well as a selectivity over one or more of the other protein kinases, e.g. over one or more tyrosine kinases, or over one or more serine/threonine kinases which do not belong to the CDK-family, e.g. over one or more of PKA, PKB, Abl, Met, Src, Ins-it, Flt-3, JAK-2, KDR and Ret proteins, e.g. over one or more of Flt-3, JAK-2, KDR and Ret proteins.

Certain isozymes of PKC have been implicated in the mechanisms of various disease states, including, but not necessarily limited to, the following: cancer (PKC α, βI, βII, and δ); cardiac hypertrophy and heart failure (PKC βI and PKC βII) nociception (PKC γ and ε); ischemia including myocardial infarction (PKC ε and δ); immune response, particularly T-cell mediated (PKC θ and α); and fibroblast growth and memory (PKC δ and ζ). The role of PKC ε is also implicated in pain perception. PKC inhibitors can also be used for treating an ocular disease or disorder involving inflammatory and/or neovascular events.

The subject compounds can be used in the treatment of mammalian (especially human) disease states characterized by aberrant, elevated activity of a PKC isozyme in a tissue as compared to non-disease tissue of the same origin. PKC isozymes and disease states and/or biological functions amenable to therapy by inhibition of activity of the PKC isozyme include, but are not necessarily limited to: PKC α (hyperproliferative cellular diseases, such as cancer); PKC βI and PKC βII (cardiac hypertrophy and heart failure); PKC γ (pain management); PKC δ (ischemia, hypoxia (e.g., such as in myocardial infarction and in stroke); apoptosis induced by UV irradiation; and aberrant fibroblast growth (e.g., as may occur in wound healing)); PKC ε (pain management, myocardial dysfunction); PKC θ (immune system diseases, particularly those involving T-cell mediated responses); and PKC ζ (memory and fibroblast growth).

PKC Theta

PKC θ is expressed predominantly in lymphoid tissue and skeletal muscle. PKC θ is selectively expressed in T-cells and plays a role in mature T-cell activation. It has been shown that PKC θ is involved in T-cell receptor (TCR)-mediated T-cell activation but inessential during TCR-dependent thymocyte development. PKC θ, but not other PKC isoforms, translocates to the site of cell contact between antigen-specific T-cells and antigen presenting cells (APC), where it localizes with the TCR in the central core of the T-cell activation. PKC θ, but not the α, ε, or ζ isoenzymes, can selectively activate a FasL promoter-reporter gene and upregulate the mRNA or cell surface expression of endogenous FasL. On the other hand, PKC θ and ε can promote T-cell survival by protecting the cells from Fas-induced apoptosis, and this protective effect was mediated by promoting p90Rsk-dependent phosphorylation of BCL-2 family member BAD. Thus, PKC θ appears to play a dual regulatory role in T-cell apoptosis.

PKC θ inhibitors can find use in the treatment or prevention of disorders or diseases mediated by T lymphocytes, for example, autoimmune disease such as rheumatoid arthritis, psoriasis and lupus erythematosus, and inflammatory and/or allergic diseases such as asthma and inflammatory bowel diseases.

PKC θ is a drug target for immunosuppression in transplantation and autoimmune diseases (Isakov et al. (2002) Annual Review of Immunology, 20, 761-794). PCT Publication WO2004/043386 identifies PKC θ as a target for treatment of transplant rejection and multiple sclerosis. PKC θ also plays a role in inflammatory bowel disease (The Journal of Pharmacology and Experimental Therapeutics (2005), 313 (3), 962-982), asthma (WO 2005062918), and lupus (Current Drug Targets: Inflammation & Allergy (2005), 4 (3), 295-298).

In addition, PKC θ is highly expressed in gastrointestinal stromal tumors (Blay, P. et al. (2004) Clinical Cancer Research, 10, 12, Pt. 1), it has been suggested that PKC θ is a molecular target for treatment of gastrointestinal cancer (Wiedmann, M. et al. (2005) Current Cancer Drug Targets 5(3), 171).

Experiments induced in PKC θ knock-out mice led to the conclusion that PKC θ inactivation prevented fat-induced defects in insulin signalling and glucose transport in skeletal muscle (Kim J. et al, 2004, The J. of Clinical Investigation 114 (6), 823). This data indicates PKC θ is a therapeutic target for the treatment of type 2 diabetes, and hence PKC θ inhibitors can be useful for treating such disease.

Therapeutic Applications

The subject compounds are useful for treating a disease or disorder that is mediated through, or exacerbated by, the activity of a PKC in a subject in need of treatment. Also, the compounds are useful for treating a disease or disorder that is associated with aberrant or otherwise undesirable T cell activation in a subject.

Accordingly, the present disclosure provides methods of treating an inflammatory disease in a subject by administering an effective amount of a subject compound, including a salt or solvate or stereoisomer thereof, so as to treat inflammation. Inflammatory diseases contemplated for therapy include those characterized by acute inflammation, chronic inflammation or both.

The present disclosure also provides methods of treating an autoimmune disease in a subject by administering to the subject an effective amount of a subject compound, including a salt or solvate or stereoisomer thereof, so as to treat the autoimmune disease.

The present disclosure also provides methods of treating an ocular disease or disorder involving inflammatory and/or neovascular events by administration of a subject compound, including a salt or solvate or stereoisomer thereof, in an effective amount.

Diseases or conditions of interest for treatment according to the present disclosure include, but are not limited to, atherosclerosis, cardiac arrhythmia, vascular occlusion due to vascular injury such as angioplasty, restenosis, obesity, syndrome X, impaired glucose tolerance, polycystic ovary syndrome, hypertension, heart failure, chronic obstructive pulmonary disease, CNS diseases such as Alzheimer disease or amyotrophic lateral sclerosis, Parkinson's disease, bipolar disorder, and can be used to induce axon regeneration. Further the compounds can be used to treat cancer, infectious diseases such as: AIDS, malaria, such as by blocking the development of cerebral malaria, septic shock or adult respiratory distress syndrome, ischemia/reperfusion injury, myocardial infarction, stroke, gut ischemia, renal failure, hemorrhagic shock, and traumatic shock, for example traumatic brain injury. In one aspect, the present compounds are useful in treating muscle diseases or disorders, including inflammatory muscle disease and dystrophic disorders, such as Duchenne muscular dystrophy and myotonic muscular dystrophy.

Further diseases or conditions that can be treated with the disclosed compounds according to the present disclosure include, but are not limited to, T-cell mediated acute or chronic inflammatory, allergic, autoimmune diseases or disorders, including, without limitation rheumatoid arthritis, osteoarthritis, systemic lupus erythematosus, Hashimoto's thyroiditis, multiple sclerosis, myasthenia gravis, diabetes type I or II and the disorders associated therewith, transplant rejection, graft versus host disease, respiratory diseases, asthma, allergic rhinitis, inflammatory lung injury, inflammatory liver injury, inflammatory glomerular injury, cutaneous manifestations of immunologically-mediated disorders or illnesses, such as cutaneous lupus, including discoid lupus, inflammatory and hyperproliferative skin diseases (such as psoriasis, atopic dermatitis, allergic contact dermatitis, irritant contact dermatitis and further eczematous dermatitises, seborrhoeic dermatitis), inflammatory eye diseases (such as Sjoegren's syndrome, keratoconjunctivitis, uveitis) inflammatory bowel disease, Crohn's disease or ulcerative colitis, Guillain-Barre syndrome, and allergies. The disclosed compounds can be used to treat symptoms associated with the disorders described above. In particular the presently disclosed compounds can be used to treat complications of diabetes or insulin resistance and conditions associated therewith, including diabetic cardiomyopathy, glucose intolerance, fatty liver disease, hepatic steatosis, particularly non-alcoholic hepatic steatosis, and can be used to improve insulin sensitivity. Moreover, the present compounds also may be used to improve metabolic efficiency, for example, they can be used to treat exercise intolerance and intermittent claudication caused by, for example, peripheral artery disease.

The subject compounds can also be used for preventing or treating or delaying ocular diseases and disorders involving autoimmune or allergic inflammation and/or neovascularization. Ocular diseases or disorders involving inflammatory and/or neovascular events include, but are not limited to, macular degeneration (AMD), allergic conjunctivitis, diabetic ocular diseases or disorders, including diabetic retinopathy, uveitis, optic neuritis, ocular edema, ocular angiogenesis, ischemic retinopathy, anterior ischemic optic neuropathy, optic neuropathy and neuritis, macular edema, cystoid macular edema (CME), retinal disease or disorder, such as retinal detachment, retinitis pigmentosa (RP), Stargart's disease, Best's vitelliform retinal degeneration, Leber's congenital amaurosis and other hereditary retinal degenerations, Sorsby's fundus dystrophy, pathologic myopia, retinopathy of prematurity (ROP), Leber's hereditary optic neuropathy, corneal transplantation or refractive corneal surgery, keratoconjunctivitis, or dry eye.

Generally, cell proliferative disorders treatable with the subject compound disclosed herein relate to any disorder characterized by aberrant cell proliferation. These include various tumors and cancers, benign or malignant, metastatic or non-metastatic. Specific properties of cancers, such as tissue invasiveness or metastasis, can be targeted using the methods described herein. Cell proliferative disorders that can be treated using the present compounds include a variety of cancers, including, among others, breast cancer, ovarian cancer, renal cancer, gastrointestinal cancer, including gastrointestinal stromal tumors, Ewing's sarcoma, kidney cancer, bladder cancer, pancreatic cancer, lung cancer, including non-small cell lung cancer, including lung squamous carcinoma, adenocarcinoma and large cell carcinomas.

In some embodiments, the cell proliferative disorder treated is a hematopoietic neoplasm, which is aberrant growth of cells of the hematopoietic system. Hematopoietic malignancies can have its origins in pluripotent stem cells, multipotent progenitor cells, oligopotent committed progenitor cells, precursor cells, and terminally differentiated cells involved in hematopoiesis. Some hematological malignancies are believed to arise from hematopoietic stem cells, which have the ability for self renewal. For instance, cells capable of developing specific subtypes of acute myeloid leukemia (AML) upon transplantation display the cell surface markers of hematopoietic stem cells, implicating hematopoietic stem cells as the source of leukemic cells. Blast cells that do not have a cell marker characteristic of hematopoietic stem cells appear to be incapable of establishing tumors upon transplantation (Blaire et al., 1997, Blood 89:3104-3112). The stem cell origin of certain hematological malignancies also finds support in the observation that specific chromosomal abnormalities associated with particular types of leukemia can be found in normal cells of hematopoietic lineage as well as leukemic blast cells. For instance, the reciprocal translocation t(9q34;22q11) associated with approximately 95% of chronic myelogenous leukemia appears to be present in cells of the myeloid, erythroid, and lymphoid lineage, suggesting that the chromosomal aberration originates in hematopoietic stem cells. A subgroup of cells in certain types of CML displays the cell marker phenotype of hematopoietic stem cells.

Although hematopoietic neoplasms often originate from stem cells, committed progenitor cells or more terminally differentiated cells of a developmental lineage can also be the source of some leukemias. For example, forced expression of the fusion protein Bcr/Abl (associated with chronic myelogenous leukemia) in common myeloid progenitor or granulocyte/macrophage progenitor cells produces a leukemic-like condition. Moreover, some chromosomal aberrations associated with subtypes of leukemia are not found in the cell population with a marker phenotype of hematopoietic stem cells, but are found in a cell population displaying markers of a more differentiated state of the hematopoietic pathway (Turhan et al., 1995, Blood 85:2154-2161). Thus, while committed progenitor cells and other differentiated cells may have only a limited potential for cell division, leukemic cells may have acquired the ability to grow unregulated, in some instances mimicking the self-renewal characteristics of hematopoietic stem cells (Passegue et al., Proc. Natl. Acad. Sci. USA, 2003, 100:11842-9).

In some embodiments, the hematopoietic neoplasm treated is a lymphoid neoplasm, where the abnormal cells are derived from and/or display the characteristic phenotype of cells of the lymphoid lineage. Lymphoid neoplasms can be subdivided into B-cell neoplasms, T and NK-cell neoplasms, and Hodgkin's lymphoma. B-cell neoplasms can be further subdivided into precursor B-cell neoplasm and mature/peripheral B-cell neoplasm. Exemplary B-cell neoplasms are precursor B-lymphoblastic leukemia/lymphoma (precursor B-cell acute lymphoblastic leukemia) while exemplary mature/peripheral B-cell neoplasms are B-cell chronic lymphocytic leukemia/small lymphocytic lymphoma, B-cell prolymphocytic leukemia, lymphoplasmacytic lymphoma, splenic marginal zone B-cell lymphoma, hairy cell leukemia, plasma cell myeloma/plasmacytoma, extranodal marginal zone B-cell lymphoma of MALT type, nodal marginal zone B-cell lymphoma, follicular lymphoma, mantle-cell lymphoma, diffuse large B-cell lymphoma, mediastinal large B-cell lymphoma, primary effusion lymphoma, and Burkitt's lymphoma/Burkitt cell leukemia. T-cell and Nk-cell neoplasms are further subdivided into precursor T-cell neoplasm and mature (peripheral) T-cell neoplasms. Exemplary precursor T-cell neoplasm is precursor T-lymphoblastic lymphoma/leukemia (precursor T-cell acute lymphoblastic leukemia) while exemplary mature (peripheral) T-cell neoplasms are T-cell prolymphocytic leukemia T-cell granular lymphocytic leukemia, aggressive NK-cell leukemia, adult T-cell lymphoma/leukemia (HTLV-1), extranodal NK/T-cell lymphoma, nasal type, enteropathy-type T-cell lymphoma, hepatosplenic gamma-delta T-cell lymphoma, subcutaneous panniculitis-like T-cell lymphoma, Mycosis fungoides/Sezary syndrome, Anaplastic large-cell lymphoma, T/null cell, primary cutaneous type, Peripheral T-cell lymphoma, not otherwise characterized, Angioimmunoblastic T-cell lymphoma, Anaplastic large-cell lymphoma, T/null cell, primary systemic type. The third member of lymphoid neoplasms is Hodgkin's lymphoma, also referred to as Hodgkin's disease. Exemplary diagnosis of this class that can be treated with the compounds include, among others, nodular lymphocyte-predominant Hodgkin's lymphoma, and various classical forms of Hodgkin's disease, exemplary members of which are Nodular sclerosis Hodgkin's lymphoma (grades 1 and 2), Lymphocyte-rich classical Hodgkin's lymphoma, Mixed cellularity Hodgkin's lymphoma, and Lymphocyte depletion Hodgkin's lymphoma.

In some embodiments, the hematopoietic neoplasm treated is a myeloid neoplasm. This group comprises a large class of cell proliferative disorders involving or displaying the characteristic phenotype of the cells of the myeloid lineage. Myeloid neoplasms can be subdivided into myeloproliferative diseases, myelodysplastic/myeloproliferative diseases, myelodysplastic syndromes, and acute myeloid leukemias. Exemplary myeloproliferative diseases are chronic myelogenous leukemia (e.g., Philadelphia chromosome positive (t(9;22)(qq34;q11)), chronic neutrophilic leukemia, chronic eosinophilic leukemialhypereosinophilic syndrome, chronic idiopathic myelofibrosis, polycythemia vera, and essential thrombocythemia. Exemplary myelodysplastic/myeloproliferative diseases are chronic myelomonocytic leukemia, atypical chronic myelogenous leukemia, and juvenile myelomonocytic leukemia. Exemplary myelodysplastic syndromes are refractory anemia, with ringed sideroblasts and without ringed sideroblasts, refractory cytopenia (myelodysplastic syndrome) with multilineage dysplasia, refractory anemia (myelodysplastic syndrome) with excess blasts, 5q-syndrome, and myelodysplastic syndrome with t(9;12) (q22;p12) (TEL-Syk fusion; see, e.g., Kuno et al., 2001, Blood 97:1050).

In some embodiments, the composition can be used to treat acute myeloid leukemias (AML), which represent a large class of myeloid neoplasms having its own subdivision of disorders. These subdivisions include, among others, AMLs with recurrent cytogenetic translocations, AML with multilineage dysplasia, and other AML not otherwise categorized. Exemplary AMLs with recurrent cytogenetic translocations include, among others, AML with t(8;21)(q22;q22), AML1 (CBF-alpha)/ETO, Acute promyelocytic leukemia (AML with t(15;17)(q22;q11-12) and variants, PML/RAR-alpha), AML with abnormal bone marrow eosinophils (inv(16) (p13q22) or t(16;16)(p13;q11), CBFb/MYH11X), and AML with 11q23 (MLL) abnormalities. Exemplary AML with multilineage dysplasia are those that are associated with or without prior myelodysplastic syndrome. Other acute myeloid leukemias not classified within any definable group include, AML minimally differentiated, AML without maturation, AML with maturation, Acute myelomonocytic leukemia, Acute monocytic leukemia, Acute erythroid leukemia, Acute megakaryocytic leukemia, Acute basophilic leukemia, and Acute panmyelosis with myelofibrosis.

In other aspects, cell proliferative disorders comprise virally mediated tumors. These can arise from infection of cells by an oncogenic virus that has the capability of transforming a normal cell into a tumor cell. Because rates of viral infection far exceed the number of actual incidence of cell transformation, viral mediated transformation generally act together with other cellular factors to generate a transformed tumor cell. Thus, a virally mediated tumor does not require the virus to be the sole causative agent of the cell proliferative disorder, but rather that the viral infection or persistent presence of virus is associated with the generation of the tumor. Generally, tumors where the causative agent is a virus typically has continual expression of a limited number of viral genes and that viral these oncogenes, expressed as part of the viral infection or through persistence of the virus, disrupts the normal cellular gene expression and signal transduction pathways. Without being bound by theory, viral oncogenes involved in cell transformation appear to disrupt four main cellular processes: cell surface receptors that interact with growth factors and extracellular matrix, transmembrane signaling networks, cytosolic elements such as soluble proteins and second messengers, and nuclear proteins including DNA binding proteins and factors which function directly and indirectly in gene regulation and replication.

Characterization of Functional Properties

The following are exemplary assays useful in characterizing activities of a compound of interest.

A. In Vitro

1. Protein Kinase C assay

The inhibition of PKC activity is measured by monitoring the production of phosphorylated peptide by fluorescence polarization at different concentrations of the inhibitor. Reactions are carried out in 96-well plate format with a total volume of 20 μL containing 20 mM HEPES, pH 7.4, 5 mM $MgCl_2$, 0.2 mM $CaCl_2$, 1 mM DTT, 0.02% Brij-35, 0.1 mg/ml phosphatidylserine, 0.02 mg/ml dioleoyl-sn-glycerol and 5 μM each of ATP and the peptide substrate. Compounds are first diluted serially in DMSO and then transferred to a solution containing the above concentrations of HEPES, $MgCl_2$, $CaCl_2$, DTT, and Brij-35 to yield 5× compound solutions in 2% DMSO, which is then added to the reaction solution. Reactions are initiated by the addition of PKC at a typical concentration as described in the table below, and then allowed to incubate at room temperature for 20 minutes. At the end of this time, a combination of quench (EDTA) and detection (peptide tracer and antibody) reagents is added using the protocol of Invitrogen P2748 (Carlsbad, Calif.), a Protein Kinase C Fluorescence polarization Assay Kit. After a 30 minute period of incubation, the amount of phosphorylated peptide generated is measured by fluorescence polarization (Ex=485 nm, Em=535 nm) using a Tecan Polarian instrument (Switzerland).

TABLE 2

| | Peptide substrate | SEQ ID | Enzyme source | enzyme concentration |
|---|---|---|---|---|
| PKC theta | RFARKGSLRQ KNV | Seq ID No. 1 | Upstate Biotechnologies, Temecula, CA, cat. #14-444 | 40 ng/ml |
| PKC epsilon | RFARKGSLRQ KNV | Seq ID No. 1 | Upstate Biotechnologies, Temecula, CA, cat. #14-518 | 50 ng/ml |

2. IL-2 ELISA, Human Primary T Cell, Anti-CD3+CD28+ Assays

Human Primary T Cell Isolation and Culture:

Human primary T cells were prepared as follows. Fresh PBMC's from All Cells (Cat #PB002) were re-suspended in RPMI (RPMI-1640 with L-Glutamine; Mediatech, Inc., Herndon Va., cat. #10-040-CM) with 10% FBS and seeded into flasks and incubated at 37° C. for 2 hours to allow the monocytes to adhere. The non-adherent cells were then centrifuged and re-suspended in RPMI medium containing 40 U/ml IL2 and seeded into a flask pre-coated with 1 μg/ml aCD3 and 5 ug/ml aCD28 (Anti-Human CD3, BD Pharmingen Catalog #555336, Anti-Human CD28, Beckman Coulter Catalog #IM1376). The cells were stimulated for 3-4 days, then transferred to a fresh flask and maintained in RPMI (RPMI-1640 with L-Glutamine; Mediatech, Inc., Herndon Va., cat. #10-040-CM) with 10% FBS and 40 U/ml IL-2.

Primary T Cell Stimulation and IL2 ELISA:

Human primary T cells (100,000 cells per well) were pre-incubated with or without test compound in RPMI-1640 with L-Glutamine and 10% FBS for 1 hour at 37° C. Cells were then stimulated by transferring them to round-bottom 96-well plates pre-coated with 1 μg/ml αCD3 and 5 μg/ml αCD28. For counter assay, cells were instead stimulated by adding 8× stock solutions of PMA and ionomycin in RPMI-1640 with L-Glutamine and 10% FBS (for final concentrations of 0.5 ng/ml PMA and 0.1 μM ionomycin, both from Calbiochem). Cells were incubated at 37° C. for 24 hours before 100 μL supernatants were harvested for quantification of IL-2 by ELISA using Human IL-2 Duoset ELISA Kit from R and D Systems, Cat. #DY202E.

3. Protein Kinase C assay

The subject compounds can be tested for activity on different PKC isoforms according to the following method. Assay is performed in a white with clear bottom 384-well microtiterplate with non-binding surface. The reaction mixture (25 μl) contains 1.5 μM of a tridecapeptide acceptor substrate that mimics the pseudo substrate sequence of PKC α with the Ala→Ser replacement, 10 μM $^{33}$P-ATP, 10 mM $Mg(NO_3)_2$, 0.2 mM $CaCl_2$, PKG at a protein concentration varying from 25 to 400 ng/ml (depending on the isotype used), lipid vesicles (containing 30 mol % phosphatidylserine, 5 mol % DAG and 65 mol % phosphatidylcholine) at a final lipid concentration of 0.5 mM, in 20 mM Tris-HCl buffer pH 7.4+0.1% BSA. Incubation is performed for 60 minutes at room temperature. Reaction is stopped by adding 50 μl of stop mix (100 mM EDTA, 200 μM ATP, 0.1% Triton X-100, 0.375 mg/well streptavidin-coated SPA beads in phosphate buffered saline w/o Ca, Mg. After 10 minutes incubation at room temperature, the suspension is spun down for 10 minutes at 300 g. Incorporated radioactivity is measured in a Trilux counter for 1 minute. $IC_{50}$ measurement is performed on a routine basis by incubating a serial dilution of inhibitor at concentrations ranging between 1-1000 μM. $IC_{50}$ values are calculated from the graph by curve fitting with XL Fit® software.

4. Protein Kinase C α Assay

Human recombinant PKC α is obtained from Oxford Biomedical Research and is used under the assay conditions as described under Section A.1 above.

5. Protein Kinase C β1 Assay

Human recombinant PKC β1 is obtained from Oxford Biomedical Research and is used under the assay conditions as described under Section A.1 above.

6. Protein Kinase C δ Assay

Human recombinant PKC δ is obtained from Oxford Biomedical Research and is used under the assay conditions as described under Section A.1 above.

7. Protein Kinase C & Assay

Human recombinant PKC c is obtained from Oxford Biomedical Research and is used under the assay conditions as described under Section A.1 above.

8. Protein Kinase C η Assay

Human recombinant PKC η is obtained from PanVera and is used under the assay conditions as described under Section A.1 above.

9. Protein Kinase C θ Assay

Human recombinant PKC θ is used under the assay conditions as described above.

10. CD28 Costimulation Assay

The assay is performed with Jurkat cells transfected with a human interleukin-2 promoter/reporter gene construct as described by Baumann G et al. in Transplant. Proc. 1992; 24:43-8, the β-galactosidase reporter gene being replaced by the luciferase gene (de Wet J., et al., Mol. Cell. Biol. 1987, 7(2), 725-737). Cells are stimulated by solid phase-coupled antibodies or phorbol myristate acetate (PMA) and the $Ca^{++}$ ionophore ionomycin as follows. For antibody-mediated stimulation Microlite TM1 microtiter plates (Dynatech) are coated with 3 µg/ml goat anti-mouse IgG Fc antibodies (Jackson) in 55 µl phosphate-buffered saline (PBS) per well for three hours at room temperature. Plates are blocked after removing the antibodies by incubation with 2% bovine serum albumin (BSA) in PBS (300 µl per well) for 2 hours at room temperature. After washing three times with 300 µl PBS per well, 10 ng/ml anti-T cell receptor antibodies (WT31, Becton & Dickinson) and 300 ng/ml anti-CD28 antibodies (15E8) in 50 µl 2% BSA/PBS are added as stimulating antibodies and incubated overnight at 4° C. Finally the plates are washed three times with 300 µl PBS per well. Seven three-fold serial dilutions of test compounds in duplicates in assay medium (RPMI 1640/10% fetal calf serum (FCS) containing 50 µM 2-mercaptoethanol, 100 units/ml penicillin and 100 µg/ml streptomycin) are prepared in separate plates, mixed with transfected Jurkat cells (clone K22 290_H23) and incubated for 30 minutes at 37° C. in 5% $CO_2$ 100 µl of this mixture containing $1 \times 10^5$ cells are then transferred to the antibody-coated assay plates. In parallel 100 µl are incubated with 40 ng/ml PMA and 2 µM ionomycin. After incubation for 5.5 hours at 37° C. in 5% $CO_2$, the level of luciferase is determined by bioluminescence measurement. The plates are centrifuged for 10 minutes at 500 g and the supernatant is removed by flicking. Lysis buffer containing 25 mM Tris-phosphate, pH 7.8, 2 mM DTT, 2 mM 1,2-diaminocyclohexane-N,N,N',N-tetraacetic acid, 10% (v/v) glycerol and 1% (v/v) Triton X-100 is added (20 µl per well). The plates are incubated at room temperature for 10 minutes under constant shaking. Luciferase activity is assessed with a bioluminescence reader (Labsystem, Helsinki, Finland) after automatic addition of 50 µl per well luciferase reaction buffer containing 20 mM Tricine, 1.07 mM $(MgCO_3)_4Mg(OH)_2 \times 5H_2O$, 2.67 mM $MgSO_4$, 0.1 mM EDTA, 33.3 mM DTT, 270 µM coenzyme A, 470 µM luciferin (Chemie Brunschwig AG), 530 µM ATP, pH 7.8. Lag time is 0.5 seconds, total measuring time is 1 or 2 seconds. Low control values are light units from anti-T cell receptor- or PMA-stimulated cells, high controls are from anti-T cell receptor/anti-CD28- or PMA/ionomycin-stimulated cells without any test sample. Low controls are subtracted from all values. The inhibition obtained in the presence of a test compound is calculated as percent inhibition of the high control. The concentration of test compounds resulting in 50% inhibition ($IC_{50}$) is determined from the dose-response curves.

11. Bone Marrow Proliferation (BM) Assay

Bone marrow cells from CBA mice ($2.5 \times 10^4$ cells per well in flat bottom tissue culture microtiter plates) are incubated in 100 µl RPMI medium containing 10% FCS, 100 U/ml penicillin, 100 µg/ml streptomycin (Gibco BRL, Basel, Switzerland), 50 tJM 2-mercaptoethanol (Fluke, Buchs, Switzerland), WEHI-3 conditioned medium (7.5% v/v) and L929 conditioned medium (3% v/v) as a source of growth factors and serially diluted compounds. Seven three-fold dilution steps in duplicates per test compound are performed. After four days of incubation 1 µCi$^3$H-thymidine is added. Cells are harvested after an additional five-hour incubation period, and incorporated $^3$H-thymidine is determined according to standard procedures. Conditioned media are prepared as follows. WEHI-3 cells 1 (ATCC TIB68) and L929 cells (ATCC CCL 1) are grown in RPMI medium until confluence for 4 days and one week, respectively. Cells are harvested, resuspended in the same culture flasks in medium C containing 1% FCS (Schreier and Tees 1981) for WEHI-3 cells and RPMI medium for L929 cells and incubated for 2 days (WEHI-3) or one week (L929). The supernatant is collected, filtered through 0.2 µm and stored in aliquots at −80° C. Cultures without test compounds and without WEHI-3 and L929 supernatants are used as low control values. Low control values are subtracted from all values. High controls without any sample are taken as 100% proliferation. Percent inhibition by the samples is calculated and the concentrations required for 50% inhibition ($IC_{50}$ values) are determined.

12. Allogeneic Mixed Lymphocyte Reaction (MLR)

The two-way MLR is performed according to standard procedures (J. Immunol. Methods, 1973, 2, 279 and Meo T. et al., Immunological Methods, New York, Academic Press, 1979, 227-39). Briefly, spleen cells from CBA and BALB/c mice ($1.6 \times 10^5$ cells from each strain per well in flat bottom tissue culture microtiter plates, $3.2 \times 10^5$ in total) are incubated in RPMI medium containing 10% FCS, 100 U/ml penicillin, 100 µg/ml streptomycin (Gibco BRL, Basel, Switzerland), 50 µM 2-mercaptoethanol (Fluka, Buchs, Switzerland) and serially diluted compounds. Seven three-fold dilution steps in duplicates per test compound are performed. After four days of incubation 1 µCi$^3$H-thymidine is added. Cells are harvested after an additional five-hour incubation period, and incorporated $^3$H-thymidine is determined according to standard procedures. Background values (low control) of the MLR are the proliferation of BALB/c cells alone. Low controls are subtracted from all values. High controls without any sample are taken as 100% proliferation. Percent inhibition by the samples is calculated, and the concentrations required for 50% inhibition ($IC_{50}$ values) are determined.

B. In Vivo

Heart Transplantation Model

The strain combination used: Male Lewis (RT$^1$ haplotype) and BN (RT$^1$ haplotype). The animals are anaesthetised using inhalational isofluorane. Following heparinisation of the donor rat through the abdominal inferior vena cava with simultaneous exsanguination via the aorta, the chest is opened and the heart rapidly cooled. The aorta is ligated and divided distal to the first branch and the brachiocephalic trunk is divided at the first bifurcation. The left pulmonary artery is ligated and divided and the right side divided but left open. All other vessels are dissected free, ligated and divided and the donor heart is removed into iced saline.

The recipient is prepared by dissection and cross-clamping of the infra-renal abdominal aorta and vena cava. The graft is implanted with end-to-side anastomoses, using 1010 monofilament suture, between the donor brachiocephalic trunk and the recipient aorta and the donor right pulmonary artery to the recipient vena cava. The clamps are removed, the graft tethered retroabdominally, the abdominal contents washed with warm saline and the animal is closed and allowed to recover under a heating lamp. Graft survival is monitored by daily palpation of the beating donor heart through the abdominal wall. Rejection is considered to be complete when-heart beat stops. Graft survival is monitored in animals treated with compounds.

Graft v. Host Model

Spleen cells ($2 \times 10^7$) from Wistar/F rats are injected subcutaneously into the right hind footpad of (Wistar/F×Fischer 344)$F_1$ hybrid rats. The left footpad is left untreated. The animals are treated with the test compounds on 4 consecutive days (0-3). The popliteal lymph nodes are removed on day 7, and the weight differences between two corresponding lymph nodes are determined. The results are expressed as the inhibition of lymph node enlargement (given in percent) comparing the lymph node weight differences in the experimental groups to the weight difference between the corresponding lymph nodes from a group of animals left untreated with a test compound. In certain instances the test compound is a selective PKC inhibitor. For example, disclosed compounds that are particularly useful for treating graft versus host disease and related disorders are selective PKC α and θ inhibitors.

Rat Collagen-Induced Arthritis Model

Rheumatoid arthritis (RA) is characterized by chronic joint inflammation eventually leading to irreversible cartilage destruction. IgG-containing IC are abundant in the synovial tissue of patients with RA. While it is still debated what role these complexes play in the etiology and pathology of the disease, IC communicate with the hematopoetic cells via the FcγR.

CIA is a widely accepted animal model of RA that results in chronic inflammatory synovitis characterized by pannus formation and joint degradation. In this model, intradermal immunization with native type II collagen, emulsified with incomplete Freund's adjuvant, results in an inflammatory polyarthritis within 10 or 11 days and subsequent joint destruction in 3 to 4 weeks.

Study Protocol

Syngeneic LOU rats are immunized with native type II collagen on Day 0, and efficacy of a test compound is evaluated in a prevention regimen and a treatment regimen. In the prevention protocol, either vehicle or various doses of a test compound are administered via oral gavage starting on day of immunization (Day 0). In the treatment protocol, after clinical signs of arthritis develop on Day 10, treatment with a test compound is initiated (e.g., 300 mg/kg by oral gavage, qd) and continued until sacrifice on Day 28. In both protocols, clinical scores are obtained daily, and body weights are measured twice weekly. At Day 28, radiographic scores are obtained, and serum levels of collagen II antibody are measured by ELISA.

Determination of Results

By 10 days after immunization, rats can develop clinical CIA, as determined by an increase in their arthritis scores. The mean arthritic score gradually increases in the rats treated with vehicle alone after Day 10, and by Day 28 the mean clinical score can reach about 6.75. Mean clinical scores in animals treated from the day of immunization (Day 0) with a test compound can be significantly reduced on Days 10-28 compared with vehicle controls. In the rats treated with a test compound at disease onset, there can be a significantly lower arthritis score beginning around Day 16, and this difference can be observed until the end of the study on Day 28.

Blinded radiographic scores (scale 0-6) can be obtained on Day 28 of CIA and compared between the animals in the vehicle group, animals in the prevention group, and animals in the treatment group.

The groups administered with a test compound, either prophylactically (at immunization) or after disease onset can preclude the development of erosions and reduced soft tissue swelling. Similarly, the groups administered with a test compound can result in reduction of serum anti-collagen II antibody.

Mouse Experimental Autoimmune Encephalomyelitis

The in vivo efficacy of a test compound towards autoimmune diseases can be demonstrated in a mouse model of experimental autoimmune encephalomyelitis (EAE).

Model Description

EAE is a useful model for multiple sclerosis (MS), an autoimmune disease of the CNS that is caused by immune-cell infiltration of the CNS white matter. Inflammation and subsequent destruction of myelin cause progressive paralysis. Like the human disease, EAE is associated with peripheral activation of T cells autoreactive with myelin proteins, such as myelin basic protein (MBP), proteolipid protein (PLP), or myelin oligodendrocyte protein (MOG). Activated neuroantigen-specific T cells pass the blood-brain barrier, leading to focal mononuclear cell infiltration and demyelination. EAE can be induced in susceptible mouse strains by immunization with myelin-specific proteins in combination with adjuvant. In the SJL mouse model used in these studies, hind limb and tail paralysis is apparent by Day 10 after immunization, the peak of disease severity can be observed between Days 10 and 14, and a cycle of partial spontaneous remission followed by relapse can be observed up to Day 35. The results can demonstrate the potential of the test compound to suppress disease severity and prevent relapse of disease symptoms that may be the result of FcγR-mediated cytokine release from immune cells.

Study Protocol

In the SJL murine model of EAE, each mouse is sensitized with PLP/CFA. (150 µg PLP139-151 with 200 µg CFA in 0.05 ml of homogenate on four sites of hind flank for a total of 0.2 ml emulsion is used to induce EAE). In a suppression protocol, either vehicle or various doses of a test compound are administered via oral gavage starting on the day of immunization (Day 0). In a treatment protocol, at onset of disease, animals are separated to achieve groups with a similar mean clinical score at onset and administered vehicle or various dose frequencies of test compounds via oral gavage. In both protocols, clinical scores are monitored daily, and body weights are measured twice weekly.

Determination of Results

By 10 days after PLP immunization, SJL mice can develop clinical EAE, as evidenced by an increase in their mean clinical scores. The paralytic score can gradually increase in the animals treated with vehicle only from the day of immunization (Day 0), and by Day 14 the mean score can reach a peak of about 5.1. At disease peak (e.g., Day 14), the mean clinical score in animals treated with either daily or twice daily can be significantly reduced. By Day 16, animals can exhibit a partial remission of mean clinical severity, which is a characteristic of the SJL model. The lower clinical scores in animals treated twice daily with a test compound can remain significant throughout the experiment until the animals are sacrificed on Day 30. These lower scores throughout the treatment period are reflected in the significantly lower cumulative disease index (CDI) and increase in cumulative weight index (CWI).

SJL mice treated with a test compound at disease onset (e.g., Day 11) can show a significant decrease in CDI. Further, there can be a decrease in the number of relapses in animals treated with a test compound compared with the number of relapses in animals treated with vehicle.

Research Applications

Since subject compounds can inhibit a PKC activity, such compounds are also useful as research tools. The present disclosure also provides a method for using subject compounds as a research tool for studying a biological system or sample, or for discovering new chemical compounds that can inhibit a PKC activity.

The disclosure provides for a method of studying a biological system or sample known to comprise PKC, the method comprising: (a) contacting the biological sample with a compound of formula I-V or a salt or solvate or stereoisomer thereof; and (b) determining the inhibiting effects caused by the compound on the biological sample.

Any suitable biological sample having PKC can be employed in such studies which can be conducted either in vitro or in vivo. Representative biological samples suitable for such studies include, but are not limited to, cells, cellular extracts, plasma membranes, tissue samples, isolated organs, mammals (such as mice, rats, guinea pigs, rabbits, dogs, pigs, humans, and so forth), and the like, with mammals being of particular interest.

When used as a research tool, a biological sample comprising PKC is typically contacted with a PKC activity-inhibiting amount of a subject compound. After the biological sample is exposed to the compound, the effects of inhibition of a PKC activity are determined using conventional procedures and equipment, such as the assays disclosed herein. Exposure encompasses contacting the biological sample with the compound or administering the compound to a subject. The determining step can involve measuring a response (a quantitative analysis) or can involve making an observation (a qualitative analysis). Measuring a response involves, for example, determining the effects of the compound on the biological sample using conventional procedures and equipment, such as radioligand binding assays and measuring ligand-mediated changes in functional assays. The assay results can be used to determine the activity level as well as the amount of compound necessary to achieve the desired result, that is, a PKC activity-inhibiting amount.

Additionally, subject compounds can be used as research tools for evaluating other chemical compounds, and thus are also useful in screening assays to discover, for example, new compounds having a PKC inhibiting activity. In this manner, a subject compound can be used as a standard in an assay to allow comparison of the results obtained with a test compound and with the subject compounds to identify those test compounds that have about equal or superior activity, if any. For example, $IC_{50}$ data for a test compound or a group of test compounds is compared to the $IC_{50}$ data for a subject compound to identify those test compounds that have the desired properties, for example, test compounds having an $IC_{50}$ about equal or superior to a subject compound, if any.

This aspect includes, as separate embodiments, both the generation of comparison data (using the appropriate assays) and the analysis of test data to identify test compounds of interest. Thus, a test compound can be evaluated in a biological assay, by a method comprising the steps of: (a) conducting a biological assay with a test compound to provide a first assay value; (b) conducting the biological assay with a subject compound to provide a second assay value; wherein step (a) is conducted either before, after or concurrently with step (b); and (c) comparing the first assay value from step (a) with the second assay value from step (b). The assays that can be used for generation of comparison data are disclosed herein, such as the PKC assays.

EXAMPLES

The following examples are put forth so as to provide those of ordinary skill in the art with a complete disclosure and description of how to make and use the embodiments, and are not intended to limit the scope of what the inventors regard as their invention nor are they intended to represent that the experiments below are all or the only experiments performed. Efforts have been made to ensure accuracy with respect to numbers used (e.g. amounts, temperature, etc.) but some experimental errors and deviations should be accounted for. As will be understood, by those of skill in the art of organic synthesis and medicinal chemistry the specific conditions set forth below are exemplary and can be varied or adapted to other reagents and products in routine fashion. Unless indicated otherwise, parts are parts by weight, molecular weight is weight average molecular weight, temperature is in degrees Celsius, and pressure is at or near atmospheric. Standard abbreviations may be used.

As referred to in the Examples, HPLC and LCMS protocols are as follows:
Protocol-1:
HPLC: Waters 2690 Alliance
Diode array detector (210-400 nm)
Column: Phenomenex Gemini 4.6×100 mm, 5 µm, 110 Å
Column temperature 30° C.
Sample temperature 15° C.
Solvent A—0.05% Formic acid in Water
Solvent B—0.05% Formic acid in Acetonitrile
Flow rate—1.5 ml/min
Gradient:

| Time | A % | B % |
|------|-----|-----|
| 0 | 95 | 5 |
| 10 | 0 | 100 (curve = 6) |
| 11.1 | 0 | 100 |
| 11.2 | 95 | 5 |
| 12.1 | 95 | 5 |

Protocol-2:
HPLC: Waters 2690 Alliance
Diode array detector (210-400 nm)
Column: Phenomenex Gemini 4.6×100 mm, 5 µm, 110 Å
Column temperature 30° C.
Sample temperature 15° C.
Solvent A—0.05% Formic acid in Water
Solvent B—0.05% Formic acid in Acetonitrile
Flow rate—1.5 ml/min
Gradient:

| Time | A % | B % |
|------|-----|-----|
| 0 | 95 | 5 |
| 10 | 0 | 100 (curve = 8) |
| 11.1 | 0 | 100 |
| 11.2 | 95 | 5 |
| 12.1 | 95 | 5 |

Protocol-3:
HPLC: Waters 2695 Alliance
Diode array detector (210-400 nm)
Column: Phenomenex Gemini 4.6×100 mm, 5 µm, 110 Å
Column temperature 30° C.
Sample temperature 15° C.
Solvent A—0.05% Formic acid in Water
Solvent B—0.05% Formic acid in Acetonitrile
Flow rate—1.5 ml/min
Gradient:

| Time | A % | B % |
|------|-----|-----|
| 0 | 95 | 5 |
| 10 | 0 | 100 (curve = 6) |
| 11.1 | 0 | 100 |
| 11.2 | 95 | 5 |
| 12.1 | 95 | 5 |

Chiral HPLC methods:
Protocol-4:
HPLC: Waters 2695 Alliance
Diode array detector (210-400 nm)
Column: Chiralcel-OJ, 4.6×250 mm, with guard
Mobil phase (isocratic): 40% methanol, 40% ethanol, 19.9% Hexane, 0.1% triethylamine
Flow rate: 0.5 ml/min Injection volume: 3 μL Concentration: approx 5 mg/ml Detection: UV at 254 nm Run Time: 30 minutes Protocol-5:

HPLC: Waters 2695 Alliance

Diode array detector (210-400 nm)

Column: Chiralcel-OJ, 4.6×250 mm, with guard

Mobil phase (isocratic): 89.9% Hexane, 5% methanol, 5% ethanol 0.1% triethylamine Flow rate: 0.5 ml/min Injection volume: 3 μL Concentration: approx 5 mg/ml Detection: UV at 254 nm Run Time: 45 minutes Synthesis of Octahydroindolizine Portions Example 1

Synthesis of (RS,SR,RR,SS)—N-(2-chloro-5-fluoro-pyrimidin-4-yl)-octahydro-5,5-dimethylindolizin-7-amine

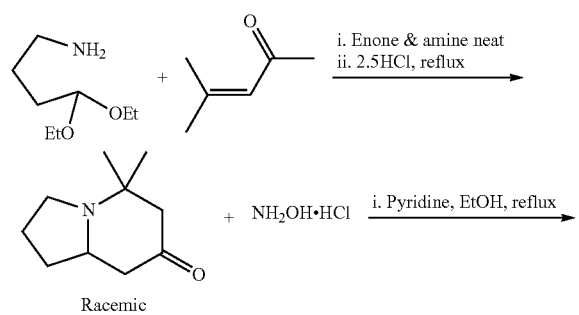
Racemic

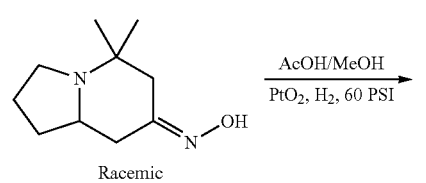
Racemic

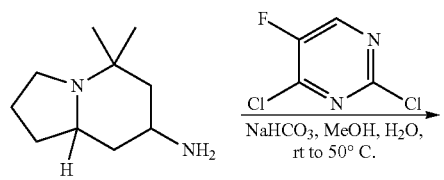
Mixture of two diastereomers
(each diastereomer is mixture
of two enantiomers)

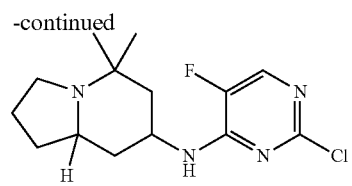
Mixture of two diastereomers (D1:D2 = 1:3)
(each diastereomer is mixture of
two enantiomers)

Preparation of
(R/S)-Hexahydro-5,5-dimethylindolizin-7(1H)-one

The compound was prepared as described in *J. Chem. Soc., Perkin Trans.* 1 1986, 447-453, which is hereby incorporated by reference in its entirety.

4-Aminobutyraldehyde diethyl acetal (6.4 g, 39.7 mmol) and mesityl oxide (20 ml, 175.2 mmol) were mixed neat and stirred at room temperature for 1 hour. After this time, the reaction mixture was extracted with 2.5 M HCl and the extract washed with ether. The aqueous layer was heated at reflux for 3 hours. The reaction mixture was concentrated in vacuo to reduce the volume by ~50%. The concentrated aqueous layer was cooled on ice and diluted with methylene chloride (~100 ml). The mixture was basified with aqueous potassium hydroxide and the layers separated. The aqueous layer was further extracted with methylene chloride (100 ml) and the combined organic extracts were washed with aqueous potassium carbonate. The organic layer was dried over potassium carbonate, filtered and concentrated. Purification by flash column chromatography, on silica gel, eluting with neat EtOAc provided the product as pale yellow oil, 3.2 g (48% yield). The mixture can also be purified by distillation from $K_2CO_3$ (instead of column chromatography) to afford the ketone in a similar yield.

$^1$H NMR (CDCl$_3$, 300 MHz) δ: 3.02 (dt, J=8.8, 3.6 Hz, 1H), 2.74-2.84 (m, 1H), 2.38-2.54 (m, 3H), 2.09-2.24 (m, 2H), 1.86-2.02 (m, 2H), 1.72-1.82 (m, 1H), 1.45-1.57 (m, 1H), 1.24 (s, 3H), 0.92 (s, 3H).

Preparation of (R/S)-Hexahydro-5,5-dimethylindolizin-7(1H)-one-oxime

The compound was prepared as described in *J. Chem. Soc., Perkin Trans.* 1 1986, 447-453, which is hereby incorporated by reference in its entirety.

Mixture of (R,S)-hexahydro-5,5-dimethylindolizin-7(1H)-one-oxime (2.9 g, 17.3 mmol) and hydroxylamine hydrochloride (1.2 g, 17.3 mmol) in EtOH (10 ml) and pyridine (10 ml) were heated to reflux and the mixture stirred for 2 hours. A thick precipitate develops. After allowing the reaction mixture to cool to room temperature, the mixture was placed in a −18° C. freezer where it was left for 1 hour. The mixture was then filtered, and the filter cake washed with cold EtOH (2×5 ml) to afford the oxime (3.00 g, 95%) as a solid.

LCMS (m/z): 183 (MH$^+$), RT=0.89 min. (Protocol-1)

Preparation of (R/S,S/R,R/R,S/S)-Octahydro-5,5-dimethylindolizin-7-amine (R,S)-Hexahydro-5,5-dimethylindolizin-7(1H)-one-oxime (3.2 g, 17.6 mmol) was dissolved in AcOH (30 ml). The clear solution is transferred to a Pan hydrogenation flask and placed under nitrogen. $PtO_2$ (0.5 g) is added to the Parr flask under nitrogen. The mixture was then transferred to a Parr hydrogenation apparatus, evacuated and filled with hydrogen (×3). The mixture was hydrogenated at 55-60 psi (optionally topping-up hydrogen) until LC/MS and TLC indicated complete reaction to the amine. After complete reaction, the mixture was placed under nitrogen and filtered through a small pad of Celite. The filter cake was washed with MeOH (×3) and the filtrate was concentrated under vacuum to leave the octahydro-5,5-dimethylindolizin-7-amine as a salt—yield assumed quantitative, and amine was used directly in a displacement reaction after drying under high vacuum.

Preparation of (R/S,S/R,R/R,S/S)—N-(2-chloro-5-fluoropyrimidin-4-yl)-octahydro-5,5-dimethylindolizin-7-amine A mixture of octahydro-5,5-dimethylindolizin-7-amine acetic acid salt (4.1 g, 14.1 mmol) and dichloro-5-fluoropyrimidine (2.83 g, 17 mmol) and $NaHCO_3$ (3.6 g, 42.4 mmol) in $MeOH/H_2O$ (50:10) was stirred at 45° C. for 12 hours. Both the diastereomers were detected by LC/MS and TLC. Volatiles were removed and 100 ml of 4 N HCl in dioxane was added to the crude reaction mixture. Volatiles were removed and the crude mixture was adsorbed on silica gel. Combiflash column chromatography was performed to separate the diastereomers using $DCM/2N\ NH_3$ in MeOH (90:10) as eluent. Column purification gave the product as a mixture of two diastereomers [each diastereomer is mixture of two enantiomers] in 74% yield (3.1 g).

A note should be made that the desired isomer can be prepared in a ca. 6:1 ratio by use of the Na/pentanol reduction used in *J. Chem. Soc., Perkin Trans.* 1 1986, 447-453, which is hereby incorporated by reference in its entirety.

Example 2

Chromatography of N-(2-chloro-5-fluoropyrimidin-4-yl)-octahydro-5,5-dimethylindolizin-7-amine

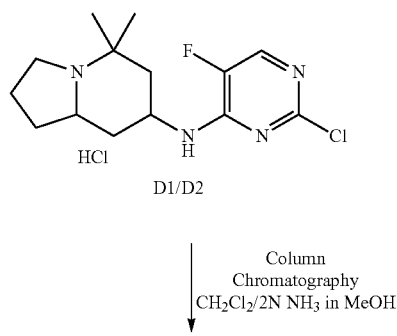

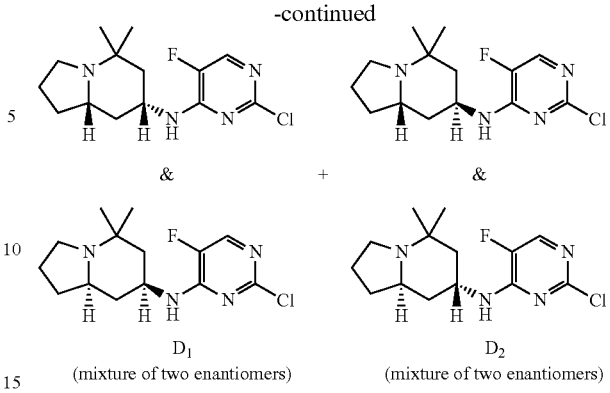

Preparation of (R/S,S/R)—N-(2-chloro-5-fluoropyrimidin-4-yl)-octahydro-5,5-dimethylindolizin-7-amine and (S/S & R/R)—N-(2-chloro-5-fluoropyrimidin-4-yl)-octahydro-5,5-dimethylindolizin-7-amine A mixture of octahydro-5,5-dimethylindolizin-7-amine acetic acid salt (4.1 g, 14.1 mmol) and dichloro-5-fluoropyrimidine (2.8 g, 17 mmol) and $NaHCO_3$ (3.6 g, 42.4 mmol) in $MeOH/H_2O$ (50:10) was stirred at 45° C. for 12 hours. Both the diastereomers were detected by LC/MS and TLC. Volatiles were removed and 100 ml of 4 N HCl in dioxane was added to the crude reaction mixture. Volatiles were removed and the crude mixture was adsorbed on silica gel. Combiflash column chromatography was performed to separate the diastereomers using $DCM/2N\ NH_3$ in MeOH (95:5) as eluent. Column purification gave separated diastereomers D1 & D2 in 12% yield (0.5 g) and 62% yield (2.6 g) respectively as HCl salts.

A small quantity of each diastereomer was neutralized with aq. 1N NaOH and analyzed. Aqueous 1N NaOH was added to diastereomeric HCl salt (50 mg) in EtOAc (10 ml) and the layers were separated. Aqueous layer was worked up twice with EtOAc (10 ml) and the combined organic layers were dried over $Na_2SO_4$. Removal of the volatiles in vacuo gave the product.

Data for (R/S,S/R)—N-(2-chloro-5-fluoropyrimidin-4-yl)-octahydro-5,5-dimethylindolizin-7-amine (D1)

[Single Diastereomer, Mix of Enantiomers]
$^1$H NMR ($CDCl_3$, 300 MHz) δ: 7.84 (dd, J=2.8, 1.4 Hz, 1H), 5.02 (br. s, 1H), 4.17-4.27 (m, 1H), 2.97 (dt, J=8.5, 2.8 Hz, 1H), 2.57-2.51 (m, 1H), 2.38 (q, J=8.5 Hz, 1H), 2.26 (dd, J=11.8, 1.6 Hz, 1H), 1.79-1.90 (m, 2H), 1.64-1.78 (m, 2H), 1.33-1.47 (m, 2H), 1.23-1.26 (m, 1H), 1.19 (s, 3H), 1.06 (s, 3H).
$^{19}$F NMR (DMSO) δ: −159.91.
LCMS (m/z): 299 ($MH^+$) (D1 retention time: 4.75 min. see Protocol-2 in general methods).

Data for (S/S, R/R)—N-(2-chloro-5-fluoropyrimidin-4-yl)-octahydro-5,5-dimethylindolizin-7-amine (D2)

[Single Diastereomer, Mix of Enantiomers]
$^1$H NMR ($CDCl_3$, 300 MHz) δ: 7.86 (d, J=2.8 Hz, 1H), 5.35 (br. d, J=3.6 Hz, 1H), 4.37-4.40 (m, 1H), 3.02 (dt, J=8.5, 2.75 Hz, 1H), 2.58-2.50 (m, 1H), 2.42 (q, J=8.8 Hz, 1H), 2.05 (dd, J=13.8, 2.2 Hz, 1H), 1.86-1.96 (m, 2H), 1.61-1.82 (m, 2H), 1.37-1.61 (m, 3H), 1.18 (s, 3H), 1.08 (s, 3H).
LCMS (m/z): 299 ($MH^+$) (D2 retention time: 3.99 min. (see Protocol-2 in general methods).

Example 3

Synthesis of (7R,8aS)—N-(2-chloro-5-fluoropyrimidin-4-yl)-octahydro-5,5-dimethylindolizin-7-amine

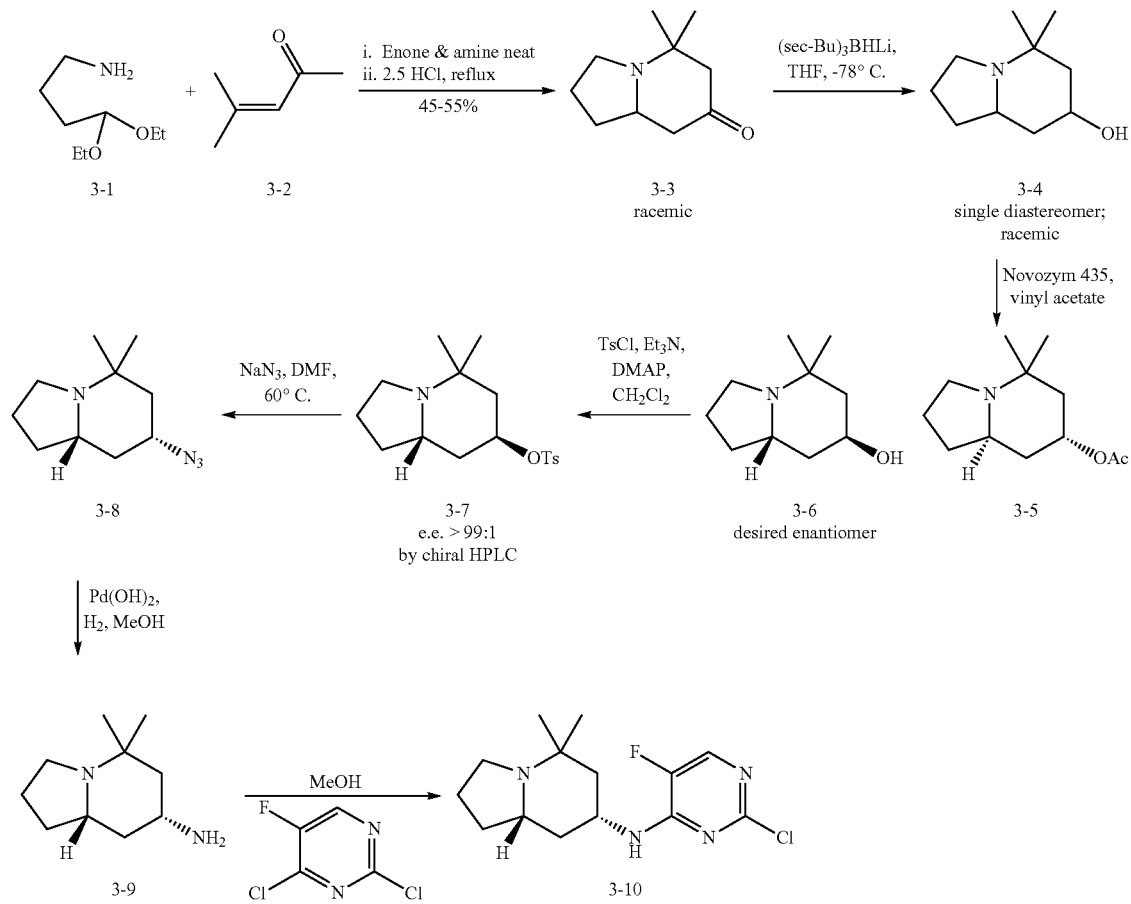

Preparation of Preparation of (±)-hexahydro-5,5-dimethylindolizin-7-(1H)-one (Compound 3-3

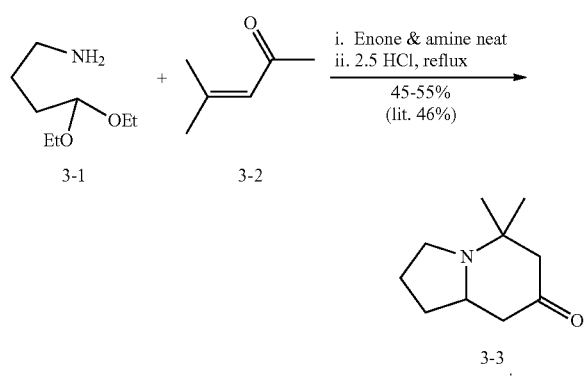

This is based on a literature procedure—see F. D. King *J. Chem. Soc., Perkin Trans.* 1 1986, 447-453, which is hereby incorporated by reference in its entirety.

4-Aminobutyraldehyde diethyl acetal (Compound 3-1) (94 g, 0.58 mol) and mesityl oxide (Compound 3-2) (290 g, 2.95 mol) were mixed neat and stirred at room temperature for 1 hour. After this time, the reaction mixture was extracted with 2.5 M HCl and the extract washed with ether. The aqueous layer was heated at reflux for 3 hours. The reaction mixture was concentrated under vacuum to reduce the volume by ~50%. The concentrated aqueous layer was cooled on ice and diluted with methylene chloride (~300 mL). The mixture was basified with aqueous KOH and the layers separated. The aqueous layer was further extracted with $CH_2Cl_2$ (200 mL) and the combined organic extracts were washed with aqueous $K_2CO_3$. The organic layer was dried over $K_2CO_3$, filtered and concentrated in vacuo to leave a crude residue. The residue was purified by flash column chromatography, on silica gel, eluting with neat methylene chloride to provide the product (45.5 g, 47%) as a pale yellow oil.

$^1$H NMR (CDCl$_3$, 300 MHz): δ 2.96 (dt, J=9.0, 3.0 Hz, 1H), 2.79-2.69 (m, 1H), 2.48-2.32 (m, 3H), 2.18-2.04 (m, 2H), 1.97-1.63 (m, 3H), 1.51-1.41 (m, 1H), 1.18 (s, 3H), 0.87 (s, 3H).

$^{13}$C NMR (CDCl$_3$, 75 MHz): δ 210.1, 56.8, 54.7, 54.1, 47.3, 44.3, 31.5, 30.2, 21.2, 16.6.

It should be noted that, after workup, the reaction mixture can also be purified by distillation from K₂CO₃ (instead of column chromatography), to afford the ketone product in a similar yield.

Preparation of
(±)-octahydro-5,5-dimethylindolizin-7-ol
(Compound 3-4)

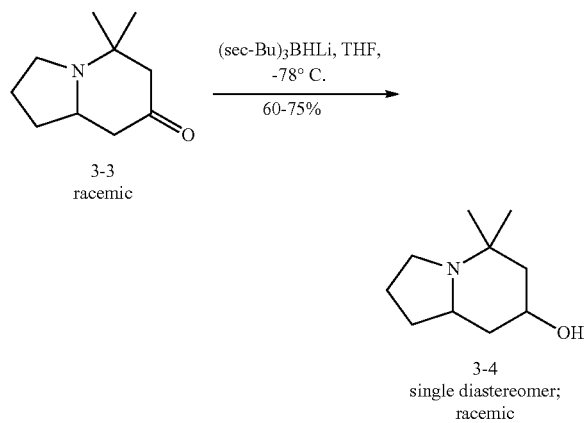

A solution of 1.0 M L-selectride in THF (419.5 mL, 419.5 mmol) was added dropwise over ca. 120 minutes to a mixture of (±)-hexahydro-5,5-dimethylindolizin-7-(1H)-one (Compound 3-3) (50.0 g, 299 mmol) in anhydrous THF (200 mL) at −78° C. The reaction mixture was stirred at −78° C. for a further 4 hours. The mixture was lifted from the bath and allowed to warm to −15° C. over 1 hour. Analysis of the crude reaction by TLC indicated complete conversion to alcohol (Compound 3-4). The reaction mixture was cooled to −78° C. and quenched by the dropwise addition of MeOH (150 mL). The reaction mixture was then allowed to warm to room temperature and stirred overnight. The solvent was then removed in vacuo to leave a crude residue. The residue was dissolved in 3N HCl (200 mL) and extracted with EtOAc (250 mL then 100 mL). The aqueous layer was then basified using 12N NaOH to pH 14, and extracted with CH₂Cl₂ (4×500 mL). The combined organic layers were dried (Na₂SO₄), filtered and the solvent removed in vacuo to leave a light brown solid. The solid was titurated with Et₂O to give the product (29.2 g). The filtrate was concentrated in vacuo and triturated with Et₂O/hexane (1:1) to give a further crop of product (5.8 g). The combined yield of the alcohol product (Compound 3-4) was 35.0 g (70%).

¹H NMR (CDCl₃, 300 MHz): δ 4.17 (m, 1H), 2.98 (dt, J=8.7, 3.0 Hz, 1H), 2.78-2.68 (m, 1H), 2.43 (q, J=8.7 Hz, 1H), 1.93-1.83 (m, 2H), 1.80-1.54 (m, 5H), 1.46-1.34 (m, 2H), 1.16 (s, 3H), 1.14 (s, 3H).

¹³C NMR (CDCl₃, 75 MHz): δ 66.9, 52.5, 50.9, 45.8, 45.1, 39.4, 31.6, 31.0, 20.6, 17.1.

An alternative workup using hydrogen peroxide and NaOH is also possible. (±)-Hexahydro-5,5-dimethylindolizin-7-(1H)-one (Compound 3-3) (30.6 g, 0.18 mol) was dissolved in anhydrous THF and cooled to −78° C. L-Selectride, 1.0 M in THF (260 mL, 0.26 mol) was added dropwise over 90 minutes. The resulting mixture was allowed to stir at −78° C. for 4 hours. The reaction was quenched by dropwise addition of hydrogen peroxide, 30% wt in H₂O (150 mL), followed by dropwise addition of 3N sodium hydroxide solution (150 mL). The cold bath was removed and replaced with a lukewarm water bath—the resulting mixture was allowed to stir for 1 hour after reaching room temperature. A white precipitate formed and was removed by vacuum filtration through a pad of Celite, and the filter cake was rinsed with EtOAc (×3). The filtrate was diluted further with EtOAc and H₂O and the layers were separated. The organic layer was washed with brine, dried (Na₂SO₄), filtered and concentrated in vacuo to provide the product (27.6 g) as a solid. Trituration with an Et₂O/hexane solution (1:1) provided the product (21.5 g, 71% yield) as an off-white solid.

Preparation of
(7S,8aS)-octahydro-5,5-dimethylindolizin-7-ol
(Compound 3-6)

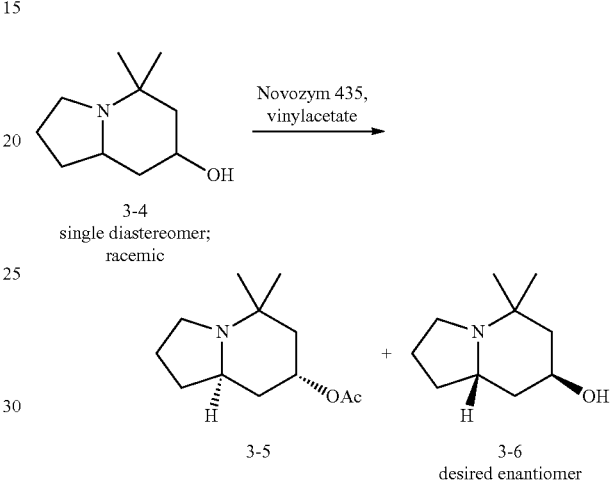

A mixture of (±)-octahydro-5,5-dimethylindolizin-7-ol (Compound 3-4) (20.4 g, 118.3 mmol) and Novozym 435 (20.4 g) in vinyl acetate (400 mL) was slowly stirred (150 revolutions per minute) at room temperature for 16 hours. The reaction mixture was then filtered and the filter cake washed with EtOAc (400 mL). The filtrate was concentrated in vacuo to leave a crude residue that was separated by column chromatography on silica gel using CH₂Cl₂/2N NH₃ in MeOH (95:5) as eluent to give the desired chiral alcohol (Compound 3-6) (9.0 g, 44%)

[α]_D=−25.1° (c=0.34 in MeOH).

¹H NMR (CDCl₃, 300 MHz): δ 4.19-4.17 (m, 1H), 2.98 (td, J=8.7, 3.0 Hz, 1H), 2.78-2.68 (m, 1H), 2.44 (q, J=8.7 Hz, 1H), 1.93-1.82 (m, 2H), 1.80-1.57 (m, 5H), 1.47-1.34 (m, 2H), 1.16 (s, 3H), 1.14 (s, 3H).

¹³C NMR (CDCl₃, 75 MHz): δ 66.8, 52.4, 50.8, 45.6, 45.0, 39.2, 31.5, 30.8, 20.5, 16.9.

m/z=170.17 (M+H)⁺.

Alternatively, the product can be purified by column chromatography on basic alumina using EtOAc/hexane (0:1 to 2:3) or CH₂Cl₂/MeOH (1:0 to 95:5) as eluent.

The effect of time on the yield and enantiomeric excess from this resolution is shown below.

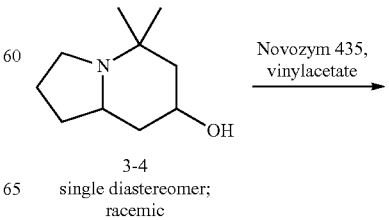

-continued

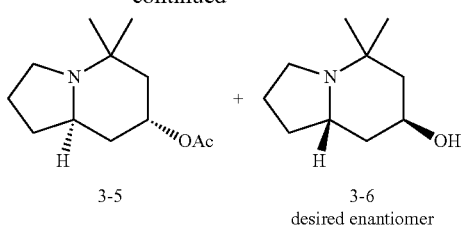

3-5

3-6
desired enantiomer

Effect Upon Yield and Enantiomeric Excess with Variation in Time for Kinetic Resolution of (±)-octahydro-5,5-dimethylindolizin-7-ol (Compound 3-4)

| Time (hours) | Absolute yield of recovered alcohol (Compound 3-6) (theoretical yield) | Enantiomer excess of recovered alcohol (Compound 3-6) |
|---|---|---|
| 8 | 62% | 48% |
| 16 | 44% (88% theoretical) | >99% |
| 24 | 40% (80% theoretical) | >99% |
| 60 | 35% (70% theoretical) | >99% |
| >72 | 21% (42% theoretical) | >99% |

Reactions were undertaken with alcohol 4 (1 equivalent) and Novozym 435 (same weight as alcohol) in vinyl acetate at room temperature while stirring at ca. 150 revolutions per minute.

Enantiomer excess ascertained by measuring enantiomeric excess of tosylate derivative 3-7 by chiral HPLC, after reaction of the alcohol 3-6 with p-TsCl, Et$_3$N and DMAP in CH$_2$Cl$_2$.

Other Procedures for Resolution of Racemic Mixture 3-4

Enzymatic Resolution Using Amano Lipase a, from *Aspergilus Niger*

Amano Lipase A, from *Aspergilus niger* (100 mg; Aldrich catalogue number 534781) was added in one portion to a mixture of racemic alcohol (1.0 g, 5.9 mmol) in vinyl acetate (20 mL). The mixture was sealed, then stirred at room temperature overnight. TLC analysis indicated no substantial formation of acetate product.

Attempted enzymatic resolution using Amano Lipase A, from *Aspergilus niger* at 40° C.:

Amano Lipase A, from *Aspergilus niger* (100 mg; Aldrich catalogue number 534781) was added in one portion to a mixture of racemic alcohol (0.5 g, 3.0 mmol) in vinyl acetate (10 mL). The mixture was sealed, then heated to 40° C. and stirred at overnight. TLC analysis indicated no formation of acetate product.

Attempted Enzymatic Resolution Using Amano Lipase M, from *Mucor javanicus*

Amano Lipase M, from *Mucor javanicus* (100 mg; Aldrich catalogue number 534803) was added in one portion to a mixture of racemic alcohol (0.5 g, 3.0 mmol) in vinyl acetate (10 mL) under nitrogen. The mixture was stirred at room temperature overnight. TLC analysis indicated no formation of acetate product.

Preparation of (7S,8aS)-octahydro-5,5-dimethylindolizin-7-yl-4-methylbenzenesulfonate (Compound 3-7)

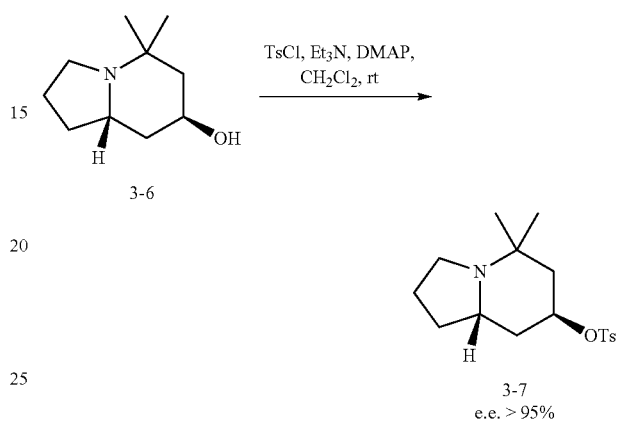

para-Toluenesulfonyl chloride (13.2 g, 69.2 mmol) was added in portions to a mixture of (7S,8aS)-octahydro-5,5-dimethylindolizin-7-ol (Compound 3-6) (9.0 g, 53.25 mmol, 1.0 equiv), 4-N,N-dimethylaminopyridine (9.8 g, 79.9 mmol) and Et$_3$N (11.1 mL, 79.9 mmol) in CH$_2$Cl$_2$ (180 mL) at 0° C. The mixture was allowed to warm to room termperature and then stirred for 4 days. EtOAc (600 mL) was added, and the resulting solid was filtered and washed with EtOAc (ca. 150 mL). The filtrate was washed with water (600 mL) and concentrated in vacuo to leave a crude residue. The residue was purified by column chromatography on silica gel using EtOAc/MeOH (9:1) as eluent to give the product (14.5 g, 84%) as a solid.

$[\alpha]_D = -6.1°$ (c=0.43 in MeOH).

$^1$H NMR (CDCl$_3$, 300 MHz): δ 7.75 (d, J=8.4 Hz, 2H), 7.30 (d, J=8.1 Hz, 2H), 4.80-4.78 (m, 1H), 2.92 (td, J=9.0, 3.3 Hz, 1H), 2.69-2.60 (m, 1H), 2.41 (s, 3H), 2.39 (q, J=8.7 Hz, 1H), 2.01-1.96 (m, 1H), 1.88-1.78 (m, 1H), 1.74-1.68 (m, 2H), 1.65-1.56 (m, 1H), 1.55-1.49 (m, 1H), 1.40-1.26 (m, 2H), 1.07 (s, 3H), 1.05 (s, 3H).

$^{13}$C NMR (CDCl$_3$, 75 MHz): δ 144.5, 134.3, 129.8, 127.6, 78.7, 52.5, 50.9, 44.9, 42.9, 36.7, 31.0, 30.6, 21.6, 20.4, 16.6.

m/z=324.42 (M+H)$^+$.

Chiral HPLC Conditions:

Column: Daicel Chemical Industries, Chiralcel OJ, 4.6× 250 mm

Mobile phase: 1:1 Methanol/Ethanol 0.1% diaethylamine (isocratic)

Flow rate: 0.5 ml/min

Run time: 15 minutes

Temperature: room temperature

Detection: Water 996 PDA HPLC: Waters 2690 Separations Module

Preparation of (7R,8aS)-7-azido-octahydro-5,5-dimethylindolizine (Compound 3-8)

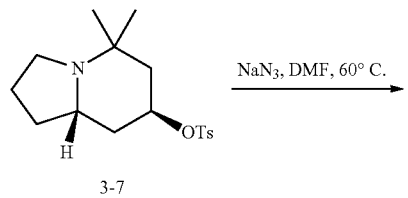

A mixture of (7S,8aS)-octahydro-5,5-dimethylindolizin-7-yl-4-methylbenzenesulfonate (Compound 3-7) (14.5 g, 44.9 mmol) and NaN$_3$ (8.8 g, 134.7 mmol) in DMF (120 mL) was heated at 80° C. overnight. After cooling, the reaction mixture was diluted with EtOAc (400 mL) and H$_2$O (300 mL). The aqueous and organic layers were separated and the aqueous layer extracted with EtOAc (200 mL). The combined organic layers were washed with H$_2$O (200 mL), dried (MgSO$_4$) and concentrated in vacuo to leave the product which was directly used in the next step—yield assumed quantitative (8.7 g).

$^1$H NMR (CDCl$_3$, 300 MHz): δ 3.48-3.40 (m, 1H), 3.00-2.92 (m, 1H), 2.46-2.40 (m, 1H), 2.35 (q, J=8.7 Hz, 1H), 2.01-1.96 (m, 1H), 1.89-1.64 (m, 4H), 1.50-1.40 (m, 2H), 1.20 (s, 3H), 0.96 (s, 3H).

m/z=195.08 (M+H)$^+$.

Preparation of (7R,8aS)-octahydro-5,5-dimethylindolizin-7-amine (Compound 3-9)

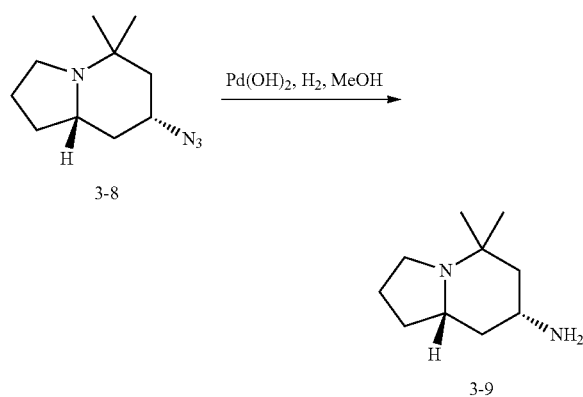

A solution of crude (7R,8aS)-7-azido-octahydro-5,5-dimethylindolizine (Compound 3-8) (assumed 8.7 g) and Pd(OH)$_2$ (20% weight on carbon; 1.7 g) in MeOH (150 mL) was hydrogenated at 30 psi at room temperature for 6 hours. The reaction mixture was filtered through a pad of Celite and the filter cake was washed with MeOH (200 mL). The filtrate was concentrated under vacuum to give the product, which was used directly in the next step—yield assumed quantitative (7.5 g).

$^1$H NMR (CDCl$_3$, 300 MHz): δ 3.03-2.96 (m, 1H), 2.55-2.47 (m, 1H), 2.41 (q, J=8.7 Hz, 1H), 2.08-2.03 (m, 1H), 1.93-1.80 (m, 2H), 1.77-1.65 (m, 2H), 1.37-1.20 (m, 2H), 1.21 (s, 3H), 1.10-1.06 (m, 1H), 0.99 (s, 3H).

m/z=169.10 (M+H)$^+$.

Preparation of (7R,8aS)—N-(2-chloro-5-fluoropyrimidin-4-yl)-octahydro-5,5-dimethylindolizin-7-amine (Compound 3-10)

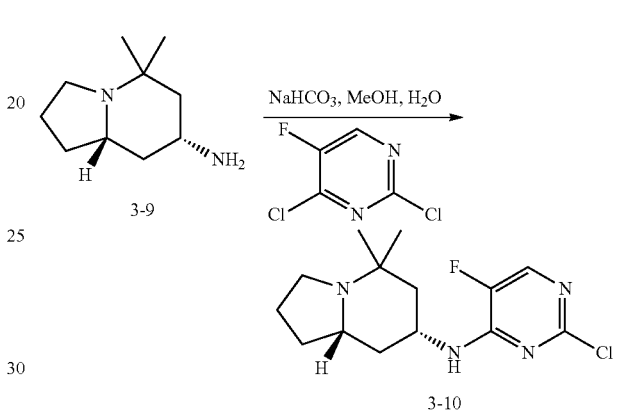

A mixture of crude (7R,8aS)-octahydro-5,5-dimethylindolizin-7-amine (Compound 3-9) (assumed 7.5 g, 44.9 mmol) and dichlorofluoropyrimidine (7.5 g, 44.9 mmol) in MeOH (120 mL) was stirred at room temperature for 20 hours. The solvent was removed in vacuo and the residue was purified by column chromatography on silica gel using CH$_2$Cl$_2$/2N NH$_3$ in MeOH (95:5) as eluent to give the product (10.8 g, 80% over 3 steps).

[α]$_D$=-1.7° (c=0.35 in MeOH).

$^1$H NMR (CDCl$_3$, 300 MHz): δ 7.89 (d, J=2.7 Hz, 1H), 5.83 (d, J=5.7 Hz, 1H), 4.55-4.38 (m, 1H), 3.55-3.45 (m, 1H), 3.25-3.10 (m, 1H), 2.82 (q, J=8.1 Hz, 1H), 2.42-2.38 (m, 1H), 2.32-1.92 (m, 7H), 1.55 (s, 3H), 1.36 (s, 3H).

$^{13}$C NMR (CDCl$_3$, 300 MHz): δ 154.3 (d, J=3.3 Hz), 152.9 (d, J=12.6 Hz), 145.1 (d, J=256.1 Hz), 139.7 (d, J=20.3 Hz), 59.0, 58.2, 44.8, 44.0, 41.6, 33.9, 28.8, 27.7, 20.0, 17.9.

$^{19}$F NMR (CDCl$_3$, 282 MHz): δ -158.0 (s).

m/z=299.03 (M+H)$^+$.

Example 4

Synthesis of 7-Amino-hexahydro-3,3-dimethylindolizin-5(1H)-one

Synthesis of 7-amino-hexahydro-3,3-dimethylindolizin-5(1H)-one is illustrated in scheme below. Although the absolute stereochemistry was not established for any of the intermediates, from the analysis of $^1$H NMR spectral pattern indicates that the final product and the intermediates were single diastereomers (racemic). Absolute stereochemistry of individual enantiomers was not established.

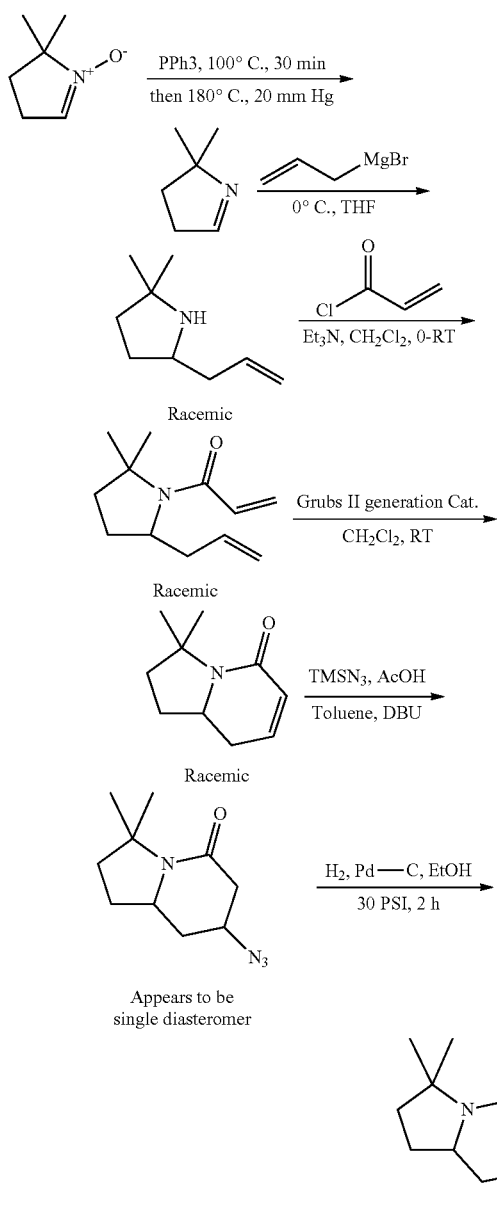

Preparation of 5,5-Dimethyl-1-pyrroline 5,5-Dimethyl-1-pyrroline was prepared with reference to Can. J. Chem. 1962, 40, 181, which is hereby incorporated by reference in its entirety.

A suspension of 5,5-dimethyl-1-pyrroline N-oxide (20 g, 177 mmol) and triphenylphosphine (52.38 g, 200 mmol) were heated at 100° C. for 30 minutes, under a short Vigreux column under argon. The liquid which formed was further heated up to 180° C. under vacuum (20 torr), and the distillate was collected. The boiling point varied from 46° C. to 58° C. at 20 torr (lit. 104° C. 760 torr) to give 5,5-dimethyl-1-pyrroline (8.60 g, 50%) as a colorless liquid which becomes yellowish upon standing, even when kept in the refrigerator.

$^1$H NMR (DMSO d$_6$, 300 MHz) δ 7.31 (s, 1H), 2.48-2.55 (m, 2H), 1.50-1.55 (m, 2H), 1.11-1.15 (m, 6H); m/z=98 (M+H)$^+$.

Preparation of 5-Allyl-2,2-dimethylpyrrolidine

To a solution of 5,5-dimethyl-1-pyrroline (2.3 g, 23.7 mmol) in anhydrous THF (50 ml) 1.0 M solution of allylmagnesium bromide in diethyl ether (43.3 ml, 47.3 mmol) was added dropwise at 0° C. The reaction mixture was allowed to stir at 0° C. for 1 hour and brought to room temperature and stirred for 3 hours. Analysis of the reaction mixture by LC-MS indicated the completion of the reaction. The reaction mixture was cooled to 0° C. and quenched with 5 ml of 1N aqueous HCl and partitioned with 50 ml of EtOAc. Organic layer was separated and the aqueous layer was worked up with 2×50 ml of EtOAc. Combined organic layers were dried over MgSO$_4$ and concentrated under vacuum gave the product as light yellow oil in 44% yield (1.5 g). The crude product was taken to the next step without further purification.

LCMS (m/z)=140 (M+H)$^+$.

Preparation of 1-(5-Allyl-2,2-dimethylpyrrolidine-1-yl)prop-2-en-1-one

To a solution of 5-allyl-2,2-dimethylpyrrolidine (1.5 g, 10.5 mmol) in 50 ml of anhydrous CH$_2$Cl$_2$, triethylamine (3 ml, 21 mmol) and acryloyl chloride (0.94 ml, 11.6 mmol) were added at 0° C. The reaction mixture was stirred at 0° C. for 1 hour and allowed to warm to room temperature and stirred for overnight. Analysis of the reaction mixture by LCMS indicated the completion of the reaction. Saturated aqueous NaHCO$_3$ was added to the reaction mixture and the layers were separated. Aqueous layer was worked up twice with CH$_2$Cl$_2$ and the combined organic layers were dried over Na$_2$SO$_4$. Removal of the volatiles and purification of the crude by column chromatography gave the product in 80% yield (1.60 g) as colorless oil.

$^1$H NMR (CDCl$_3$, 300 MHz) δ 6.33-6.52 (m, 2H), 5.68-5.75 (m, 1H), 5.62 (dd, J=7.0, 2.6 Hz, 1H), 5.09 (s, 1H), 5.06-5.07 (m, 1H), 3.97-4.00 (m, 1H), 2.15-2.33 (m, 2H), 1.88-1.95 (m, 2H), 1.66-1.83 (m, 2H), 1.60 (s, 3H), 1.45 (s, 3H); LCMS (m/z)=194 (M+H)$^+$.

Preparation of 2,3,8,8a-Tetrahydro-3,3-dimethylindolizin-5-(1H)-one

5-Allyl-2,2-dimethylpyrrolidine (0.5 g, 2.6 mmol) was taken in a 250 ml RB flask and flushed with nitrogen for three times. To the above flask 100 ml of anhydrous CH$_2$Cl$_2$ and Grubbs 2$^{nd}$ generation catalyst (0.27 g, 0.3 mmol) were added at room temperature. The reaction mixture was stirred for overnight at room temperature. LCMS analysis indicated completion of the reaction. Volatiles were removed in vacuo and the crude was purified by column chromatography to give 0.32 g (yield=74%) of the product as colorless oil.

$^1$H NMR (CDCl$_3$, 300 MHz) δ 6.38-6.46 (m, appears to be dt, 1H), 5.84 (dd, J=9.7, 3.2 Hz, 1H), 3.69-3.80 (m, 1H), 2.40 (td, J=17.3, 6.2 Hz, 1H), 2.07-2.14 (m, 1H), 1.97-2.02 (m, 1H), 1.61-1.84 (m, 3H), 1.56 (s, 3H), 1.44 (s, 3H); LCMS (m/z)=166 (M+H)$^+$.

Preparation of 7-Azido-3,3-dimethylindolizin-5-(1H)-one

A solution of 2,3,8,8a-tetrahydro-3,3-dimethylindolizin-5 (1H)-one (0.3 g, 1.8 mmol) in 10 ml of toluene was taken a 25 ml RB flask. To the above flask azido-trimethylsilane (2.42 ml, 18.2 mmol), AcOH (1.2 ml, 20 mmol) and DBU (0.27 ml, 1.8 mmol) were added. The reaction mixture was stirred at room temperature for overnight. Volatiles were removed under vacuum and the crude reaction mixture was purified by column chromatography. The product was obtained as colorless oil in 85% yield (0.32 g).

$^1$H NMR (CDCl$_3$, 300 MHz) δ 4.10-4.13 (m, 1H), 3.68-3.78 (m, 1H), 2.58 (dd, J=17.9, 5.6 Hz, 1H), 2.42-2.49 (m, 1H), 2.14-2.20 (m, 1H), 1.90-1.96 (m, 1H), 1.72-1.80 (m, 2H), 1.55 (s, 3H), 1.47-1.49 (m, 2H), 1.42 (s, 3H); LCMS (m/z)=209 (M+H)$^+$.

The product from the above reaction appears to be a single diastereomer—see *Journal of Organic Chemistry*, 71, 6630-6633; 2006, which is hereby incorporated by reference in its entirety, for a similar addition of TMS-N$_3$ to a tetrahydroindolizin-5(1H)-one system to give a single diastereomeric product.

Preparation of 7-amino-hexahydro-3,3-dimethylindolizin-5(1H)-one

7-Azido-3,3-dimethylindolizin-5(1H)-one (0.3 g, 1.5 mmol) is dissolved in EtOH (20 ml). The clear solution is transferred to a Parr hydrogenation flask and placed under nitrogen. 10% Pd—C (0.25 g) was added to the Parr flask under nitrogen. The mixture was then transferred to a Pan hydrogenation apparatus, evacuated and filled with hydrogen (×3). The mixture was hydrogenated at 30 psi (optionally topping-up hydrogen) until LC/MS and TLC indicated complete reaction to the amine. After complete reaction, the mixture was placed under nitrogen and filtered through a small pad of Celite. The filter cake was washed with MeOH (×3) and the filtrate was concentrated under vacuum to leave the 7-amino-hexahydro-3,3-dimethylindolizin-5-(1H)-one in 89% yield (0.25 g).

$^1$H NMR (CDCl$_3$, 300 MHz) δ 3.75-3.92 (m, 1H), 3.50-3.54 (m, 1H), 2.54 (dd, J=16.9, 5.9 Hz, 1H), 2.13 (dd, J=17.6, 1.8 Hz, 1H), 1.87-1.95 (m, 2H), 1.67-1.76 (m, 2H), 1.56 (s, 3H), 1.44-1.53 (m, 2H), 1.42 (s, 3H); LCMS (m/z)=183 (M+H)$^+$.

Example 5

Synthesis of (R/R,S/S)—N-(2-chloro-5-fluoropyrimidin-4-yl)octahydroindolizin-7-amine and (R,S/S,R)—N-(2-chloro-5-fluoropyrimidin-4-yl)octahydroindolizin-7-amine

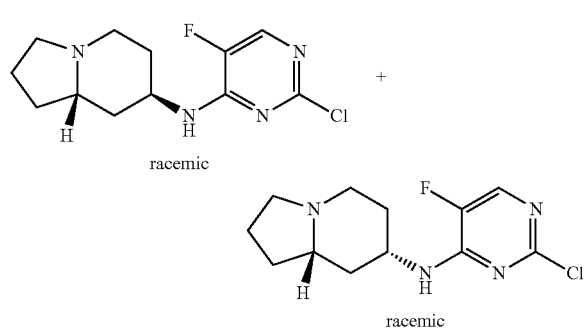

Preparation of (R/S)-octahydroindolizin-7-one

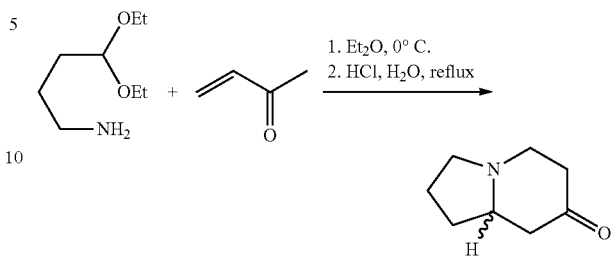

The compound was prepared according to *J. Chem. Soc., Perkin Trans.* 1 1986, 447-453, which is hereby incorporated by reference in its entirety.

A mixture of but-3-en-2-one (5.4 g, 75 mmol) was added dropwise over ca. 10 minutes to a solution of 4,4-diethoxybutan-1-amine (9.6 g, 60 mmol) in Et$_2$O (30 ml) at 0° C. under nitrogen. The mixture was stirred at 0° C. for a further 60 minutes then extracted with 2.5 M HCl (150 ml). The aqueous acid layer was then heated to reflux and stirred for 150 minutes. After allowing to cool to room temperature, the mixture was concentrated in vacuo to about one third of the original volume. The mixture was cooled to 0° C. and CH$_2$Cl$_2$ (200 ml) was added, followed by 3N NaOH until pH>10. The aqueous and organic layers were partitioned and the organic layer was washed with a K$_2$CO$_3$ solution (×1). The combined aqueous layers were extracted with CH$_2$Cl$_2$ (2×150 ml) and then the combined organic layers were dried (K$_2$CO$_3$), filtered and concentrated in vacuo. The residue was dry-loaded on to silica gel and purified by column chromatography on silica gel using CH$_2$Cl$_2$/MeOH (100:0 to 94:6 in increments of 2% MeOH) to give the desired product (2.0 g, 24%) as an oil.

$^1$H NMR (300 MHz; CDCl$_3$) δ 3.37-3.30 (m, 1H), 3.20-3.14 (m, 1H), 2.68-2.51 (m, 2H), 2.40-2.19 (m, 5H), 2.03-1.93 (m, 2H), 1.91-1.80 (m, 1H), 1.60-1.48 (m, 1H).

$^{13}$C NMR (75 MHz; CDCl$_3$) δ 209.3, 64.2, 53.3, 50.3, 47.4, 40.7, 31.5, 22.6.

Preparation of (R/S)-octahydroindolizin-7-one oxime

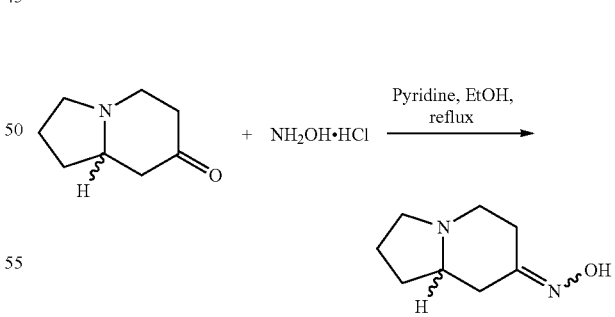

The compound was prepared according to *J. Chem. Soc., Perkin Trans.* 1 1986, 447-453, which is hereby incorporated by reference in its entirety.

A mixture of octahydroindolizin-7-one (1.8 g, 12.9 mmol) and hydroxylamine hydrochloride (0.8 g, 12.9 mmol) in EtOH (10 ml) and pyridine (10 ml) was heated to reflux and stirred for 90 minutes. After allowing to cool, the mixture was concentrated in vacuo to leave a crude solid (a bath temperature of 50° C. was used to remove solvent). The solid was triturated with cold (~18° C.) EtOH and filtered and the filter cake was washed with a further small portion of cold (~18° C.) EtOH. The solid was used directly in the next step and the yield was assumed quantitative=2.0 g. m/z=155.01 (M+H)+; rt=0.90 min (HPLC protocol-1).

Preparation of (R/R,R/S,S/R,S/S)-octahydroindolizin-7-amine

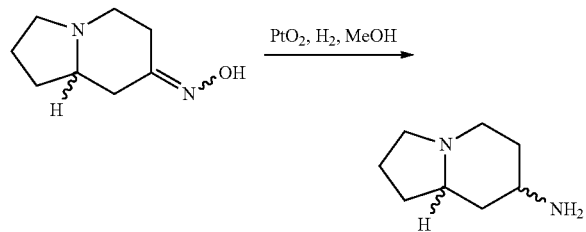

A mixture of octahydroindolizin-7-one oxime (2.0 g, 12.9 mmol) and platinum(IV) oxide (0.5 g) in AcOH (30 ml) was hydrogenated at 60 psi overnight. The mixture was filtered through Celite and the filter cake washed with EtOH (3×30 ml). The filtrate was concentrated in vacuo to give the product as an acetate salt. The yield was assumed to be quantitative=1.81 g of the free amine.

Synthesis of (R/R,S/S)—N-(2-chloro-5-fluoropyrimidin-4-yl)octahydroindolizin-7-amine and (R,S/S,R)—N-(2-chloro-5-fluoropyrimidin-4-yl)octahydroindolizin-7-amine

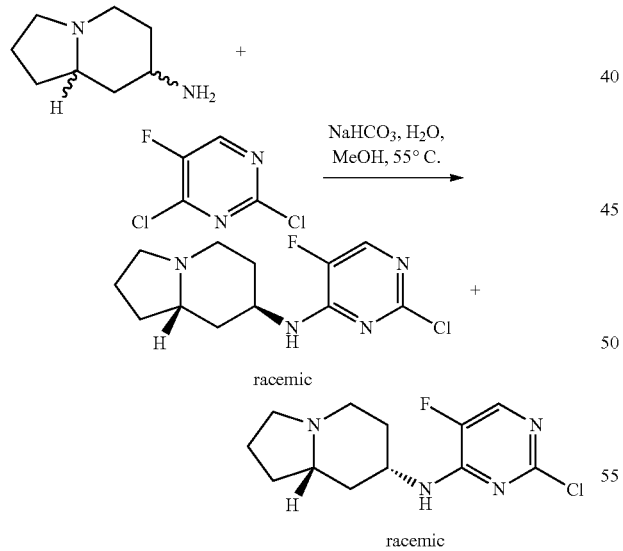

A mixture of 2,4-dichloro-5-fluoropyrimidine (3.45 g, 20.7 mmol), (R/R,R/S,S/R,S/S)-octahydroindolizin-7-amine (1.81 g, 12.9 mmol) and NaHCO$_3$ (2.71 g, 32.3 mmol) in MeOH (66 ml) and H$_2$O (22 ml) was heated at 55° C. and stirred for 5 hours. After cooling, the MeOH was removed in vacuo. CH$_2$Cl$_2$ (100 ml) and H$_2$O (100 ml) was added to the residue and the organic and aqueous layers were partitioned. The aqueous layer was extracted with CH$_2$Cl$_2$ (2×50 ml) and the combined organic layers were dried (MgSO$_4$), filtered and the solvent removed in vacuo to leave a crude oil. The crude residue was dry-loaded on to silica gel and purified by column chromatography on silica gel (ISCO Redisep Rf Gold column) using a 2M NH$_3$ in MeOH/CH$_2$Cl$_2$ gradient system to give a pure first-eluting diastereomer (small quantity), mixed fractions, a second-eluting pure diastereomer and mixed fractions.

Data for second-eluting pure diastereomer: $^1$H NMR (300 MHz; CDCl$_3$) δ 7.86 (t, J=2.6 Hz, 1H), 5.33 (br. d, J=7.4 Hz, 1H), 4.20-4.07 (m, 1H), 3.25-3.12 (m, 2H), 2.32-2.10 (m, 5H), 1.99-1.46 (m, 5H), 1.30 (q, J=11.5 Hz, 1H); $^{13}$C NMR (75 MHz; CDCl$_3$) δ 154.6 (d, J=4.4 Hz), 153.1 (d, J=12.0 Hz), 143.4 (d, J=254.8 Hz), 139.5 (d, J=20.1 Hz), 63.3, 53.4, 50.4, 48.4, 37.0, 31.6, 30.1, 21.5; $^{19}$F NMR (282 MHz; CDCl$_3$) δ −159.4; m/z=271.08 (M+H)+ for $^{35}$Cl; rt=1.91 min (HPLC protocol-1).

The mixed fractions from the first column were combined and re-columned using the same silica gel and gradient system to give a pure first-eluting diastereomer, a pure second-eluting diastereomer and mixed fractions.

Data for pure first-eluting diastereomer from the above column: m/z=271.04 (M+H)+ for $^{35}$Cl; rt=2.35 min (HPLC protocol-1).

Data for pure second-eluting diastereomer from the above column: m/z=269.05 (M−H)+ for $^{35}$Cl; rt=1.97 min (HPLC protocol-1).

Example 6

Synthesis of (±)-2-chloro-4-(octahydro-5,5-dimethylindolizin-7-ylamino)pyrimidine-5-carboxamide

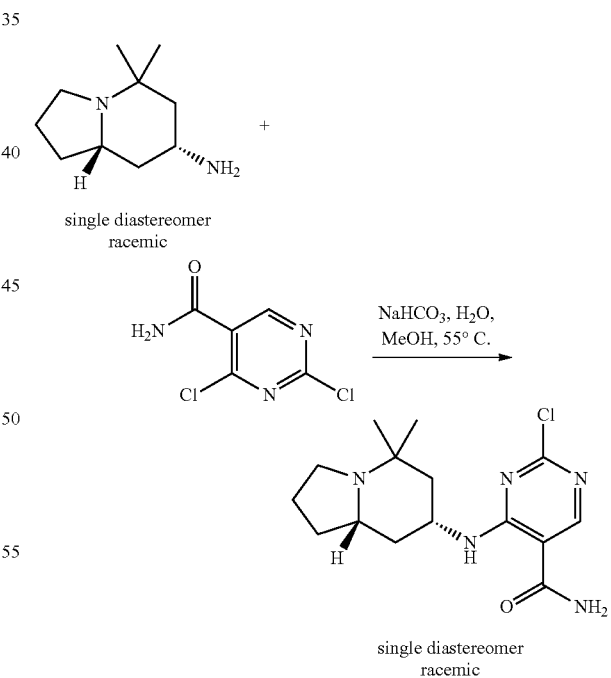

A mixture of (±)-octahydro-5,5-dimethylindolizin-7-amine (0.65 g, 3.9 mmol) in MeOH (10 ml) was added to a stirred solution of 2,4-dichloropyrimidine-5-carboxamide (0.75 g, 3.9 mmol; prepared according to the procedure set forth in US patent application publication US20110130415, page 41) in MeOH (30 ml) and H$_2$O (4 ml) at 0° C. under nitrogen. After complete addition, the mixture was slowly warmed to room temperature and stirred at room temperature overnight. The mixture was then concentrated in vacuo and the residue partitioned between EtOAc (150 ml) and 1N NaOH (100 ml). The aqueous layer was extracted with EtOAc (1×100 ml) and the combined organic extracts were dried (Na$_2$SO$_4$), filtered and the solvent removed in vacuo. The residue was dry-loaded on to basic alumina (Brockmann grade IV) and then purified by column chromatography on basic alumina (Brockmann grade IV) using CH$_2$Cl$_2$/MeOH (1:0 to 95:5) as eluent to give the product (550 mg).

Note: the product eluted very quickly from the basic alumina column, and a by-product also co-eluted with the desired compound. This by-product is believed to be (±)-2-methoxy-4-(octahydro-5,5-dimethylindolizin-7-ylamino)pyrimidine-5-carboxamide. However, the mixture (550 mg) was used directly in the next step without further purification.

Example 7

Synthesis of (±)-2-chloro-4-(octahydro-5,5-dimethylindolizin-7-ylamino)pyrimidine-5-carbonitrile

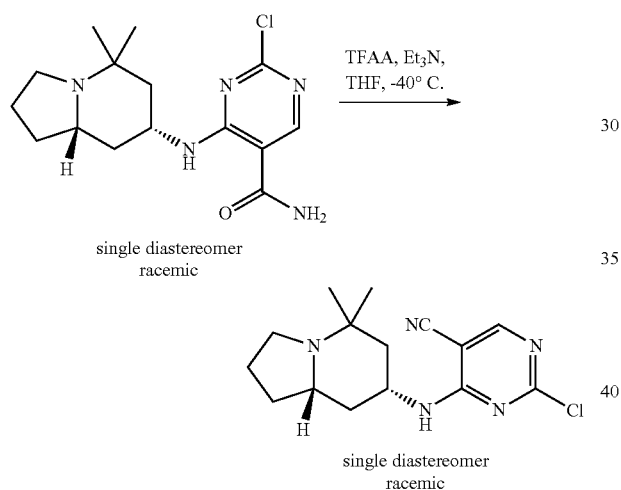

Trifluoroacetic anhydride (460 µL, 3.24 mmol) was added dropwise over 5-10 minutes to a stirred mixture of (±)-2-chloro-4-(octahydro-5,5-dimethylindolizin-7-ylamino)pyrimidine-5-carboxamide (500 mg; contaminated with (±)-2-methoxy-4-(octahydro-5,5-dimethylindolizin-7-ylamino)pyrimidine-5-carboxamide) and Et$_3$N (970 µL, 7.0 mmol) in THF (15 ml) at −40° C. (internal temperature) under nitrogen. The mixture was stirred at −40 to −50° C. (internal temperature) for 30 minutes, then allowed to warm to −30° C. (internal temperature) and the mixture stirred for 15 minutes. TLC analysis indicated completion of the reaction, so the mixture was worked-up by pouring in to an ice-H$_2$O mixture (50 ml) and EtOAc (50 ml). The aqueous and organic layers were partitioned and the aqueous layer was extracted with EtOAc (1×50 ml). The combined organic extracts were dried (MgSO$_4$), filtered and the solvent removed in vacuo to leave a crude residue. The residue was dry-loaded on to basic alumina (Brockmann grade IV) and purified by column chromatography on basic alumina (Redisep 24 g basic alumina column) using CH$_2$Cl$_2$/MeOH (gradient from 1:0 to 93:7) as eluent to give the product (128 mg). LC/MS indicated product to be of about 70% purity and it was used directly in the next step (the contaminant was N-(5-cyano-2-methoxypyrimidin-4-yl)-octahydro-5,5-dimethylindolizin-7-amine). m/z=306.13 (M+H)$^+$ for $^{35}$Cl; rt=2.64 min (HPLC protocol-1).

Also obtained from the column was a sample containing mostly N-(5-cyano-2-methoxypyrimidin-4-yl)-octahydro-5,5-dimethylindolizin-7-amine (100 mg). This was purified by high-performance liquid chromatography in order to confirm identity. m/z=302.17 (M+H)$^+$; rt=2.87 min (HPLC protocol-1).

Example 8

Synthesis of 7-(2-Chloro-5-fluoropyrimidin-4-ylamino)-hexahydro-5,5-dimethylindolizin-3(5H)-one

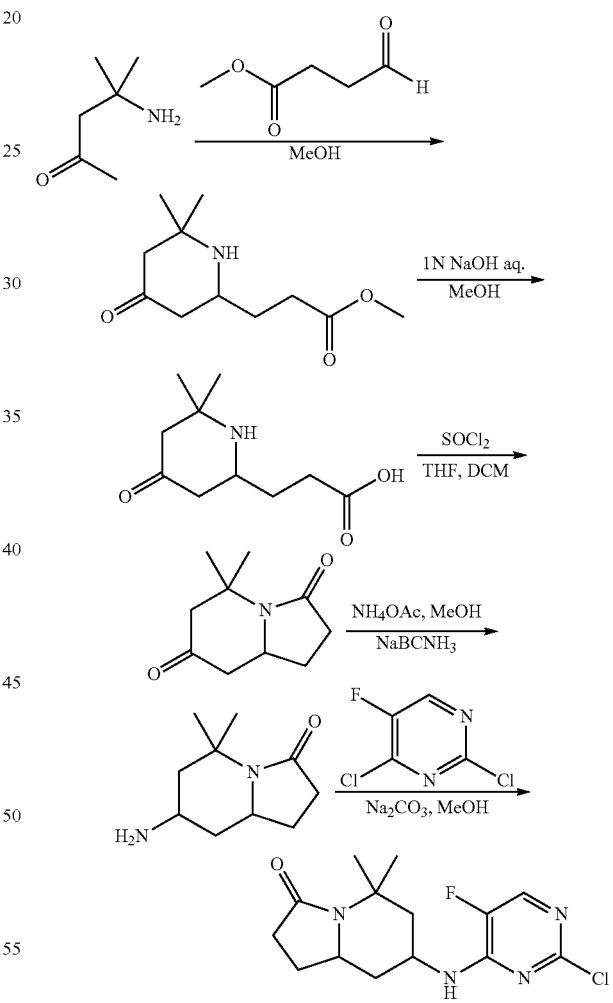

Preparation of Methyl 3-(6,6-dimethyl-4-oxopiperidin-2-yl)propanoate

Diacetoneamine hydrogen oxalate (4.25 g) and methyl 4-oxobutanoate (2 g) were suspended in methanol (20 ml). The reaction mixture were stirred at 100° C. for three hours and then at room temperature overnight. It was then evaporated and the residue was purified by Combiflash chromatography (2.0 M ammonia methanol in dichloromethane=0-30%) to give methyl 3-(6,6-dimethyl-4-oxopiperidin-2-yl)propanoate (1.35 g, 37%).

¹H NMR (300 MHz; CDCl₃) δ 3.62 (s, 3H), 3.21-3.16 (m, 1H), 2.41-2.32 (m, 4H), 2.20 (dd, J=1.8, 13.8 Hz, 2H), 1.85 (p, J=6.6 Hz, 2H), 1.28 (s, 3H), 1.09 (s, 3H).

Preparation of Hexahydro-5,5-dimethylindolizine-3,7-dione

Methyl 3-(6,6-dimethyl-4-oxopiperidin-2-yl)propanoate (1.35 g) was dissolved in methanol (25 ml) and 1.0 N sodium hydroxide aqueous solution was added (7.6 ml, 1.2 eq.). The reaction mixture was stirred at room temperature overnight. It was then evaporated and pumped to dryness to give the acid.

The acid was dissolved in THF (20 ml) and dichloromethane (100 ml). To this solution, was added thionyl chloride (0.69 ml, 1.5 eq.) dropwise. It was then stirred at 40° C. for three hours and evaporated. The residue was purified by Combiflash chromatography (2.0 M ammonia methanol in dichloromethane=0-30%) to give hexahydro-5,5-dimethylindolizine-3,7-dione.

¹H NMR (300 MHz; d₆-DMSO) δ 3.24 (m, 1H), 2.59 (dd, J=3.6, 18.0 Hz, 1H), 2.34-2.10 (m, 5H), 1.54-1.47 (m, 2H), 1.41 (s, 3H), 1.32 (s, 3H).

Preparation of 7-(2-Chloro-5-fluoropyrimidin-4-ylamino)-hexahydro-5,5-dimethylindolizin-3(5H)-one Hexahydro-5,5-dimethylindolizine-3,7-dione (230 mg) and ammonium acetate (990 mg, 10 eq.) were dissolved in methanol (5 ml). To the reaction mixture, was added sodium cyanoborohydride (56 mg, 0.7 eq.). The reaction mixture was stirred at room temperature overnight. LC-MS showed the formation of the amine. The reaction mixture was quenched with 10 N. HCl aqueous solution to pH 2. Then it was stirred for two hours.

To the reaction mixture, was added sodium carbonate to pH 7. Then 2,4-dichloro-5-fluoropyrimidine (500 mg) was added. It was then stirred at room temperature for three days and evaporated. The residue was purified by Combiflash chromatography (2.0 M ammonia methanol in dichloromethane=0-30%) to give two isomers of 7-(2-chloro-5-fluoropyrimidin-4-ylamino)-hexahydro-5,5-dimethylindolizin-3(5H)-one (a: 55 mg; b. 110 mg).

Example 9

Synthesis of N-(2-Chloro-5-fluoropyrimidin-4-yl)-2,2-difluoro-5,5-dimethyloctahydroindolizin-7-amine

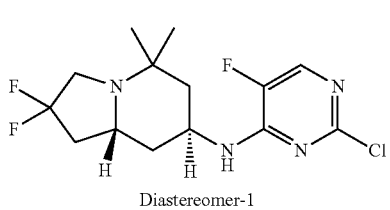

Diastereomer-1

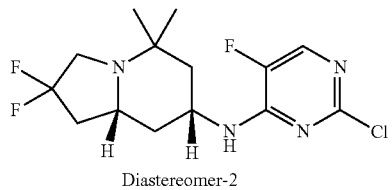

Diastereomer-2

Preparation of (S)-tert-butyl 4,4-difluoro-2-(hydroxymethyl)pyrrolidine-1-carboxylate

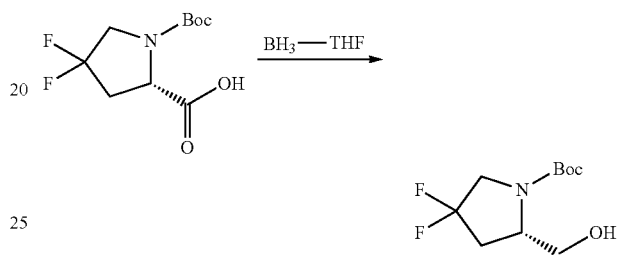

To a THF (30 ml) solution of (S)-1-(tert-butoxycarbonyl)-4,4-difluoropyrrolidine-2-carboxylic acid (3.77 g, 15 mmol) at 0° C., BH₃.THF solution (1.0 M in THF, 45 ml) was added dropwise over 20 minutes. The reaction mixture was allowed to warm to room temperature and stirring was continued for a total of 16 hours. Reaction went to completion as monitored by LC-MS. The reaction mixture was quenched by the addition of saturated aqueous solution of NaHCO₃ (60 ml) at room temperature and the stirring was continued at room temperature for 4 hours. Most THF was removed in vacuo and the mixture was extracted with EtOAc (~60 ml), two layers were separated, organic layer was washed with brine (~50 ml), repeat the extraction/wash cycle one more time. Organic layers were combined, dried (Na₂SO₄), filtered, solvent was removed in vacuo. Crude product was purified by silica gel chromatography (Hexane/EtOAc, gradient from 100:0 to 50:50). Compound (S)-tert-butyl 4,4-difluoro-2-(hydroxymethyl)pyrrolidine-1-carboxylate was obtained as a colorless oil: 2.6473 g (74% yield).

¹H NMR (300 MHz, CDCl₃) δ 4.18 (br s, 1H), 3.88-3.58 (m, 4H), 2.58-2.41 (m, 1H), 2.15 (br s, 1H), 1.59-1.33 (m, 9H, overlapped with water peak); LRMS (M+H-"Boc") m/z 137.96.

Preparation of (R)-tert-Butyl 2-(cyanomethyl)-4,4-difluoropyrrolidine-1-carboxylate

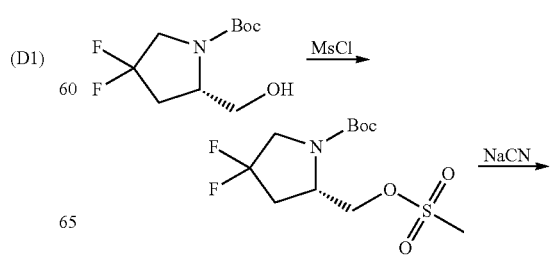

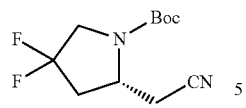

To a CH$_2$Cl$_2$ (22 ml) solution of (S)-tert-butyl 4,4-difluoro-2-(hydroxymethyl)pyrrolidine-1-carboxylate (2.65 g, 11.2 mmol) and Et$_3$N (2.3 ml, 16.8 mmol), at 0° C., methylsulfonyl chloride (0.95 ml, 12.3 mmol) was added dropwise over ~2 minutes, ice bath was removed after 15 minutes, and stirring was continued at room temperature for another 30 minutes. Reaction went to completion as monitored by LC-MS. The reaction mixture was cooled to 0° C. and was quenched by addition of saturated aqueous solution of NaHCO$_3$ (~30 ml), stifling was continued at 0° C. for 5 minutes and at room temperature for 15 minutes. Two layers were separated, aqueous layer was extracted with CH$_2$Cl$_2$ (~30 ml). Organic layers were combined, washed with brine (~25 ml), dried (Na$_2$SO$_4$), filtered, solvent was removed in vacuo. Compound ((S)-1-(tert-butoxycarbonyl)-4,4-difluoropyrrolidin-2-yl)methyl methanesulfonate was obtained as a very light yellow oil: 3.40 g (96% crude yield).

$^1$H NMR (300 MHz, CDCl$_3$) δ 4.42-4.23 (m, 3H), 3.84 (br s, 1H), 3.64 (dddd, J=12.6, 12.6, 12.6, 0.9 Hz, 1H), 3.04 (s, 3H), 2.59-2.43 (m, 2H), 1.49 (s, 9H); LRMS (M+H-"Boc") m/z 215.97. Crude product was used directly in next reaction without further purification.

A DMSO (40 ml) solution of ((S)-1-(tert-butoxycarbonyl)-4,4-difluoropyrrolidin-2-yl)methyl methanesulfonate and NaCN (1.59 g, 3.24 mmol) was stirred at 45° C. for 4 hours and at 50° C. for 2 days, the progress of the reaction was monitored by LC-MS. After cooling to room temperature, the reaction was quenched by the addition of water (~60 ml). Reaction mixture was extracted with EtOAc (~40 ml), two layers were separated, organic layer was washed with brine (~25 ml), the extraction and wash sequence was repeated for two more times. Organic layers were combined, dried (Na$_2$SO$_4$), filtered, solvent was removed in vacuo. Product was purified by silica gel chromatography (Hexane/EtOAc, gradient from 100:0 to 80:20). Compound (R)-tert-butyl 2-(cyanomethyl)-4,4-difluoropyrrolidine-1-carboxylate was obtained as a colorless oil: 2.10 g (76% yield over 2 steps).

$^1$H NMR (300 MHz, CDCl$_3$) δ 4.31-4.22 (m, 1H), 3.86-3.63 (m, 2H), 2.88-2.56 (m, 3H), 2.49-2.34 (m, 1H), 1.48 (s, 9H); LRMS (M+H-"Boc") m/z 146.94.

Preparation of (R)-tert-Butyl 2-((N-methoxy-N-methylcarbamoyl)methyl)-4,4-difluoropyrrolidine-1-carboxylate

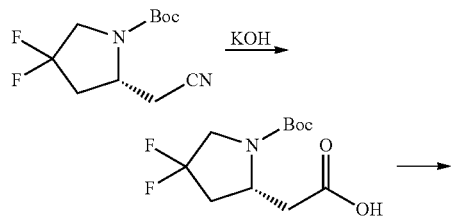

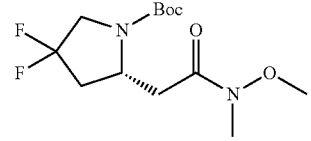

A MeOH (20 ml) solution of (R)-tert-butyl 2-(cyanomethyl)-4,4-difluoropyrrolidine-1-carboxylate (2.10 g, 8.5 mmol) and 0.5 N NaOH aqueous solution (34 ml, 17.0 mmol) was heated at 70° C. for 6 days until desired product became major, as monitored by LC-MS. Significant amount of de-Boc product was also observed. After cooling to room temperature, MeOH was removed in vacuo, aqueous mixture was extracted with Et$_2$O (~30 ml) which was discarded (note: mainly carboxamide intermediate). Aqueous layer was acidified with 6N HCl (aq.) until pH≤2 and was extracted with EtOAc (~25 ml×3). Organic layers were combined, dried (Na$_2$SO$_4$), filtered, solvent was removed in vacuo. A light brown oil was obtained: 1.62 g; LRMS (M+H-"Boc") m/z 166.89.

Additional product was recovered from aqueous layer by adding Boc group onto de-Boc by-product as follows: aqueous layer was basified to pH 8 by the addition of solid NaHCO$_3$, and was concentrated to ~15 ml in volume; to this aqueous mixture, THF (20 ml) was added, followed by Boc$_2$O (1.2 g, 5 mmol). The mixture was stirred at room temperature for 1 hour, LC-MS indicated the complete formation of the product. The reaction mixture was worked-up as above described and 0.4 g of product was obtained.

To a CH$_2$Cl$_2$ (10 ml) solution of 2-((R)-1-(tert-butoxycarbonyl)-4,4-difluoropyrrolidin-2-yl)acetic acid and hydroxylamine hydrogen chloride (713.8 mg, 7.32 mmol), EDCI.HCl (1.64 g, 8.54 mmol) and NMM (1.5 ml, 13.4 mmol) were added, the reaction mixture was stirred at room temperature for 15 hours. The reaction went to completion monitored by LC-MS and was quenched by addition of saturated aqueous NaHCO$_3$ solution (~25 ml). Two layers were separated, aqueous layer was extracted with CH$_2$Cl$_2$ (~20 ml). Organic layers were combined, dried (Na$_2$SO$_4$), filtered, solvent was removed in vacuo. Crude product was purified by silica gel chromatography (Hexane/EtOAc, gradient from 100:0 to 70:30). Compound (R)-tert-butyl 2-((N-methoxy-N-methylcarbamoyl)methyl)-4,4-difluoropyrrolidine-1-carboxylate was obtained as a light yellow oil: 1.20 g; additional product was obtained from recovered carboxylic acid: 0.2 g (53% combined overall yield over 2 steps).

$^1$H NMR (300 MHz, CDCl$_3$) δ 4.46-4.40 (m, 1H), 3.80-3.58 (m, 1H, overlapped), 3.69 (s, 3H, overlapped), 3.17 (s, 3H), 3.10-2.93 (m, 2H), 2.73-2.53 (m, 2H), 2.38-2.26 (m, 1H), 1.47 (s, 9H); LRMS (M+H-"Boc") m/z 208.98.

Preparation of (R)-tert-Butyl 4,4-difluoro-2-(4-methyl-2-oxopent-3-enyl)pyrrolidine-1-carboxylate

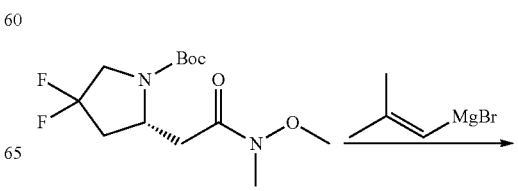

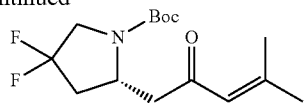

To a THF (23 ml) solution of (R)-tert-butyl 2-((N-methoxy-N-methylcarbamoyl)methyl)-4,4-difluoropyrrolidine-1-carboxylate (1.4 g, 4.54 mmol) over ice bath, 2-methyl-1-propenylmagnesium bromide solution (0.5 M in THF, 45 ml, 22.7 mmol) was added dropwise over 1 hour. Remove ice bath, stifling was continued for another 3 hours. The reaction was quenched with 1N HCl (aq., 30 ml) at 0° C., and was stirred at room temperature for 30 minutes. Two layers were separated, aqueous layer was extracted with EtOAc (25 ml×2), organic layers were combined, dried (Na₂SO₄), filtered, solvent was removed in vacuo. Product was purified by silica gel chromatography (Hexane/EtOAc, linear gradient from 100:0 to 80:20). Compound (R)-tert-butyl 4,4-difluoro-2-(4-methyl-2-oxopent-3-enyl)pyrrolidine-1-carboxylate was obtained as a light yellow oil: 1.10 g (79.5% yield).

¹H NMR (300 MHz, CDCl₃) δ 6.04 (s, 1H), 4.41-4.35 (m, 1H), 3.75-3.58 (m, 2H), 2.69-2.51 (m, 2H), 2.27-2.14 (m, 1H), 2.14 (s, 3H), 1.89 (s, 3H), 1.74 (dt, J=19.4, 10.4 Hz, 1H), 1.46 (s, 9H); LRMS (M+H-"Boc") m/z 204.07.

Preparation of (R)-2,2-Difluoro-hexahydro-5,5-dimethylindolizin-7(1H)-one

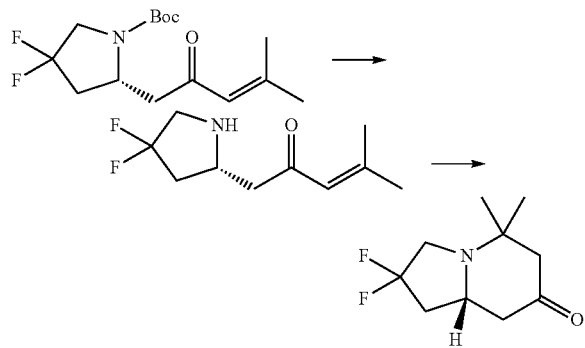

A HCO₂H (20 ml) solution of (R)-tert-butyl 4,4-difluoro-2-(4-methyl-2-oxopent-3-enyl)pyrrolidine-1-carboxylate (1.10 g, 3.6 mmol) was stirred at room temperature for 6 hours until only trace amount of SM was detected by LC-MS. Solvent was removed in vacuo with bath temperature ≤23° C. Compound 1-((R)-4,4-difluoropyrrolidin-2-yl)-4-methylpent-3-en-2-one was obtained as a light brown oil and was used directly in next reaction.

¹H NMR (300 MHz, CDCl₃) δ 8.08 (s, >1H, HCO₂H), 7.39 (br s, >2H, h⁺), 6.06-6.05 (m, 1H), 4.14-4.04 (m, 1H), 3.68 (dd, J=24.5, 13.2 Hz, 1H), 3.54 (td, J=13.9, 10.4 Hz, 1H), 3.09 (dd, J=18.2, 7.4 Hz, 1H), 2.91 (dd, J=18.2, 5.2 Hz, 1H), 2.68-2.55 (m, 1H), 2.42-2.23 (m, 1H), 2.16 (d, J=1.0 Hz, 3H), 1.93 (d, J=1.0 Hz, 3H); LRMS (M+H) m/z 204.08.

A MeOH (350 ml) solution of 1-((R)-4,4-difluoropyrrolidin-2-yl)-4-methylpent-3-en-2-one and K₂CO₃ (2.5 g, 18 mmol) was stirred at 40° C. for 15 hours, the reaction went to completion as monitored by LC-MS. Solvent was removed in vacuo, remaining material was suspended in CH₂Cl₂, solid was filtered off, filtrate was collected and solvent was removed in vacuo. Product was purified by silica gel chromatography (Hexane/EtOAc, linear gradient from 100:0 to 80:20). Compound (R)-2,2-difluoro-hexahydro-5,5-dimethylindolizin-7(1H)-one was obtained as a light yellow solid: 637.4 mg (69% yield over 3 steps).

¹H NMR (300 MHz, CDCl₃) δ 3.39 (ddd, J=14.2, 10.8, 7.6 Hz, 1H), 3.16-3.06 (m, 1H), 2.87 (ddd, J=19.1, 14.5, 10.8 Hz, 1H), 2.51-2.39 (m, 3H), 2.32 (dd, J=22.4, 11.0 Hz, 1H), 2.20 (dd, J=13.6, 2.1 Hz, 1H), 2.15-1.96 (m, 1H), 1.23 (s, 3H), 0.95 (s, 3H); LRMS (M+H) m/z 204.33.

Preparation of (8aR)-2,2-Difluoro-octahydro-5,5-dimethylindolizin-7-amine

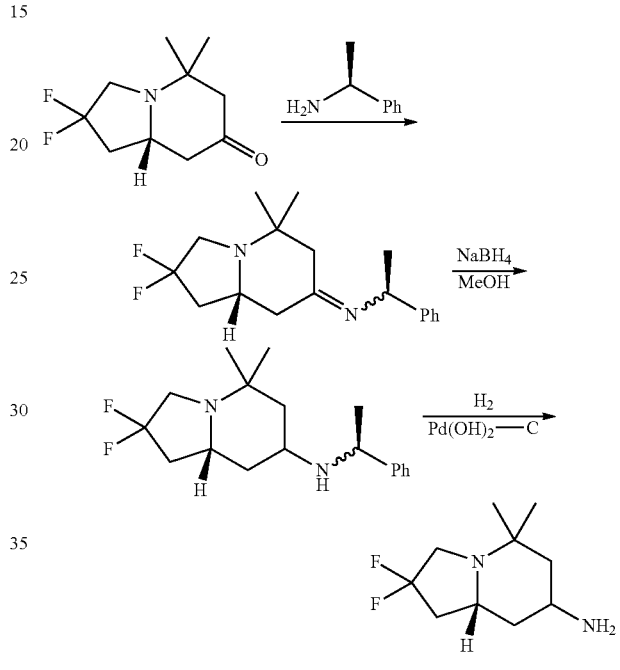

A toluene (12 ml) solution of (R)-2,2-difluoro-hexahydro-5,5-dimethylindolizin-7(1H)-one (487.8 mg, 2.4 mmol) and (S)-1-phenylethylamine (306 μL, 2.4 mmol) was heated under reflux in a flask equipped with a Dean-Stark distillation receiver. After 22 hours, most solvent was distilled off through Dean-Stark distillation receiver, and remaining solvent was removed in vacuo. Compound (1S)—N—((R)-2,2-difluoro-hexahydro-5,5-dimethylindolizin-7(1H)-ylidene)-1-phenylethanamine was obtained as a brown oil and was used directly in next reaction.

Over an ice bath, to a MeOH (10 ml) solution of (1S)—N—((R)-2,2-difluoro-hexahydro-5,5-dimethylindolizin-7(1H)-ylidene)-1-phenylethanamine, NaBH₄ (136 mg, 3.6 mmol) was added. After 30 minutes, reaction went to completion monitored by LC-MS. The reaction was quenched by the addition of saturated aqueous NaHCO₃ (10 ml), and most MeOH was removed in vacuo. More water (~10 ml) was added and aqueous solution was extracted with EtOAc (15 ml×3). Organic layers were combined, dried (Na₂SO₄), filtered, solvent was removed in vacuo. A light brown oil was obtained (690 mg: LRMS (M+H) ink 309.22) and was dissolved in MeOH (5 ml). This MeOH solution was cooled with ice bath, and concentrated HCl aqueous solution (0.3 ml) was added and mixed well. Volatiles was removed in vacuo and provided a brownish-green oil: 869 mg as HCl salt and was used directly in next reaction.

A MeOH (20 ml) solution of (8aR)-2,2-difluoro-octahydro-5,5-dimethyl-N—((S)-1-phenylethyl)indolizin-7-amine hydrogen chloride and Pd(OH)₂—C (20% on activated carbon, 50% wet, 0.2 g) was hydrogenated in a Parr flask under 45 psi of hydrogen. Additional Pd(OH)₂—C was added (~0.2 g) was added at 16 hours and 24 hours, and the reaction went to completion at 39 hours monitored by LC-MS. Solid was removed by filtration through a short Celite column, washing with MeOH. Filtrate was collected, solvent was removed in vacuo. Compound (8aR)-2,2-difluoro-octahydro-5,5-dimethylindolizin-7-amine hydrogen chloride was obtained as an off-white solid and was used directly in next reaction: 0.56 g; LRMS] (M+H) m/z 204.99.

Preparation of N-(2-Chloro-5-fluoropyrimidin-4-yl)-2,2-difluoro-5,5-dimethyloctahydroindolizin-7-amine

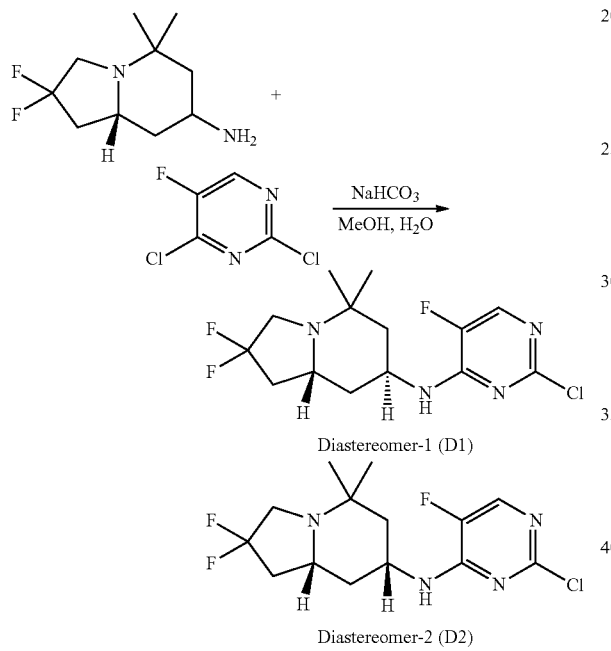

Diastereomer-1 (D1)

Diastereomer-2 (D2)

To a MeOH—H₂O (4:1, 10 ml) solution of (8aR)-2,2-difluoro-octahydro-5,5-dimethylindolizin-7-amine hydrogen chloride (crude product from above reaction, ~2.4 mmol) and 5-fluoro-2,4-dicholopyrimidine (480.9 mg, 2.88 mmol) was stirred at 30° C. for 25 hours until only trace amount of amine starting material was detected by LC-MS. MeOH was removed in vacuo. Additional H₂O (~10 ml) was added and the mixture was extracted with EtOAc (10 ml×3). Organic layers were combined, dried (Na₂SO₄), filtered, solvent was removed in vacuo. Two sets of diastereomers were observed with ratio of 3.1:1 (retention time of 5.6 min and 6.7 min under analytical HPLC conditions used: C18 column, solvents H₂O with 0.05% HCOOH and Acetonitrile with 0.05% HCOOH, a linear gradient from 90:10 to 0:100 over 9 minutes with a flow rate of 1.2 ml/min). Some level of diastereomer separation was achieved by prep-TLC (CH₂Cl₂:7N NH₃ in MeOH=97:3) and silica gel chromatography (CH₂Cl₂/2N NH₃ in MeOH, linear gradient from 100:0 to 95:5), pure Diastereomer 1 (7S,8aR)—N-(2-chloro-5-fluoropyrimidin-4-yl)-2,2-difluoro-octahydro-5,5-dimethylindolizin-7-amine was obtained as an off-white solid: ~300 mg; $[\alpha]_D^{20}$ −59.4, c=0.96 in MeOH.

¹H NMR (300 MHz, CDCl₃) δ 7.90 (d, J=2.7 Hz, 1H), 5.30 (br s, 1H), 4.48-4.36 (m, 1H), 3.35 (ddd, J=13.8, 10.7, 7.4 Hz, 1H), 3.00-2.90 (m, 1H), 2.82 (ddd, J=19.5, 15.1, 10.7 Hz, 1H), 2.43-2.29 (m, 1H), 2.10 (ddd, J=13.7, 4.5, 2.4 Hz, 1H), 2.02-1.77 (m, 3H), 1.66 (ddd, J=13.8, 11.8, 4.3 Hz, 1H), 1.15 (s, 3H), 1.12 (s, 3H); LRMS] (M+H) m/z 335.13.

Diastereomer 2 (7R,8aR)—N-(2-chloro-5-fluoropyrimidin-4-yl)-2,2-difluoro-octahydro-5,5-dimethylindolizin-7-amine was obtained as an off-white solid: 100 mg; ¹H NMR (300 MHz, CDCl₃) δ 7.88 (d, J=2.8 Hz, 1H), 4.93 (br d, J=8.0 Hz, 1H), 4.31-4.18 (m, 1H), 3.30 (ddd, J=14.4, 10.7, 6.6 Hz, 1H), 2.98-2.89 (m, 1H), 2.77 (ddd, J=19.2, 15.3, 10.7 Hz, 1H), 2.43-2.27 (m, 2H), 2.05-1.82 (m, 2H), 1.42 (dd, J=12.2, 12.2 Hz, 1H), 1.22-1.14 (m, 1H, overlapped), 1.16 (s, 3H, overlapped), 1.08 (s, 3H]; LRMS (M+H) ink 335.13.

Relative stereochemistry of Diastereomer-1 and Diastereomer-2 was assigned by using 1D-NOE technique after the assignment of relevant protons via COSY experiment: for Diastereomer-2, positive NOE was observed between H7 and H8a, H7 and CH₃ which was absent in Diastereomer-1.

Example 10

Synthesis of N-(2-Chloro-5-fluoropyrimidin-4-yl)-octahydro-5,5,8-trimethylindolizin-7-amine

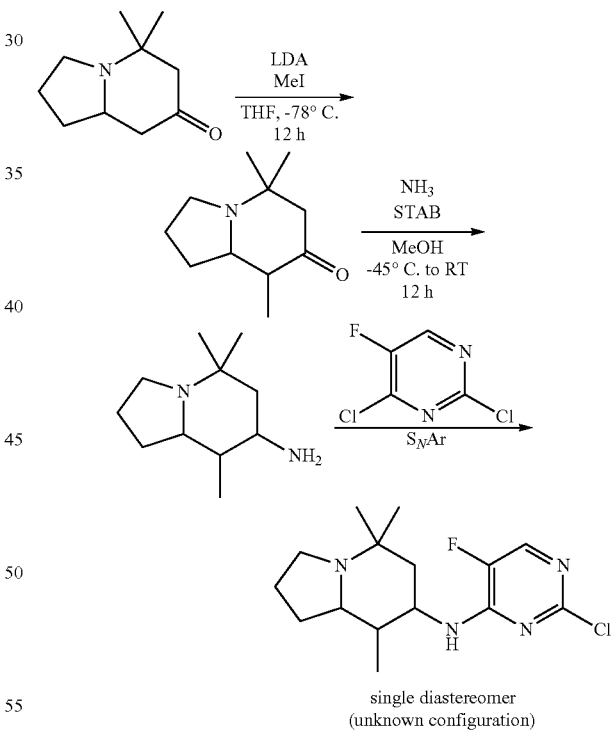

single diastereomer
(unknown configuration)

Preparation of Hexahydro-5,5,8-trimethylindolizin-7(1H)-one

Hexahydro-5,5-dimethylindolizin-7(1H)-one (racemic) (1.41 g, 8.43 mmol) was dissolved in dry THF (50 ml); the flask was flushed with nitrogen and cooled to −78° C. LDA (5.9 ml, 11.8 mmol) was added via syringe and stirred for 30 minutes. Subsequently, neat methyl iodide (1.30 ml, 21.1 mmol) was added via syringe. The clear, pale yellow solution was stirred overnight and allowed to warm to room temperature. The reaction was then quenched with a saturated NH$_4$Cl solution and extracted with ethyl acetate (3×40 ml). The organic phases were passed through a plug of MgSO$_4$ and solvents were evaporated in vacuo. The crude product (849 mg) was obtained in form of a yellow-brown oil and used without further purification in the next step.

Preparation of Octahydro-5,5,8-trimethylindolizin-7-amine

The crude product from the above reaction was dissolved in a 7M methanolic NH$_3$ (20 ml) solution and stirred for 6 hours at room temperature. NaBH$_4$ (849 mg, 12.6 mmol) was suspended in dry THF in a separate flask and cooled to −45° C. using a dry-ice/MeCN bath. The solution containing the imine was then transferred by cannulation into the flask with the reducing agent. The reaction mixture was stirred for 1 hour at −45° C. and then allowed to warm to room temperature overnight. Water (1 ml) was added to quench remaining hydride then solvents were removed in vacuo. The reaction mixture was passed through a plug of MgSO$_4$ to remove water and salts. After evaporation of solvents the remaining crude product (829 mg) was used without further purification in the next reaction.

Preparation of N-(2-Chloro-5-fluoropyrimidin-4-yl)-octahydro-5,5,8-trimethylindolizin-7-amine The product from the above reaction (829 mg, 4.55 mmol) was combined with 2,4-dichloro-5-fluoro-pyrimidine (911 mg, 5.45 mmol) and NaHCO$_3$ (457 mg, 5.45 mmol). A 4:1 mixture of MeOH:H$_2$O (50 ml) was added and the ensuing suspension was stirred for 2 days at room temperature. Analysis by HPLC showed that two diastereomers in a ratio of 3:1 had formed. Silica gel was added to the reaction mixture and solvents were evaporated in vacuo. The resulting solid was loaded onto a column and further purified by flash chromatography eluting with DCM/MeOH—NH$_3$ (2M) (gradient 0->5%). Combining the clean product fractions yielded 210 mg of the diastereomerically enriched mono-S$_N$Ar product. MS (ES) 313 (M+H), 311 (M−H).

Example 11

Synthesis of N-(2-Chloro-5-fluoropyrimidin-4-yl)-octahydro-3,3-dimethylindolizin-7(1H)-amine

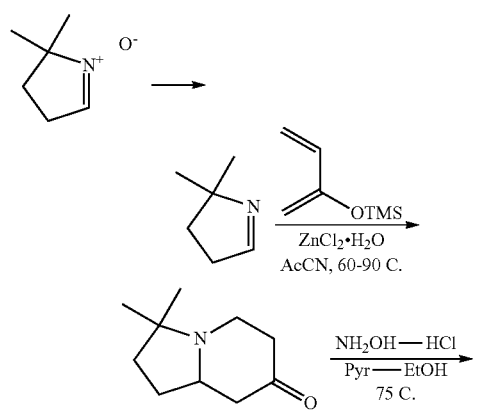

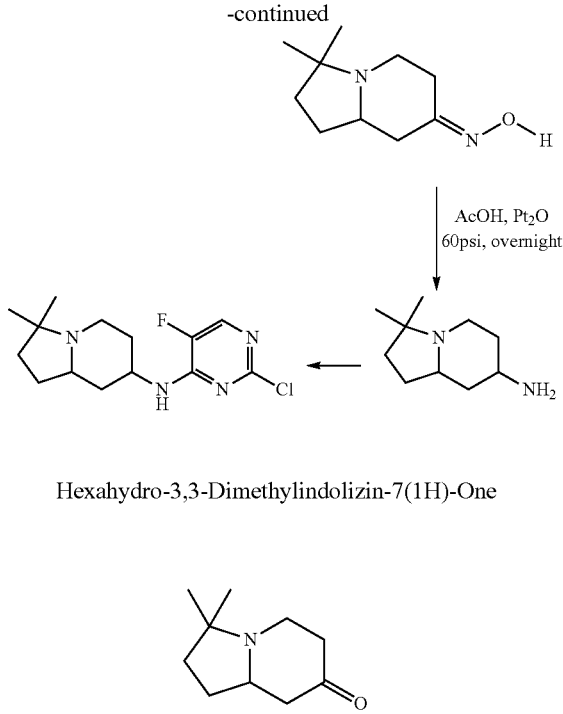

Hexahydro-3,3-Dimethylindolizin-7(1H)-One 3,4-Dihydro-2,2-diemthyl-2H-pyrrole (900 mg, 9.3 mmol) was added to acetonitrile (90 ml) in a 250 ml round bottom flask, fitted with water condenser. ZnCl$_2$ (0.5M) in THF (23 ml, 11.6 mmol) was added to the solution and warmed to 60° C. 2-(Trimethylsiloxy)-1,3-butadiene (2.6 g, mmol, 18.4 mmol) was added to the mixture and heated at 90° C. overnight. The solution was cooled to room temperature and diluted with dichloromethane (90 ml) and 1N HCl (90 ml). The two layers were separated, the aqueous layer was basified with NH$_3$ (28%) in H$_2$O, and extracted with dichloromethane. The organic layer was washed with brine and dried with Na$_2$SO$_4$. Solid was removed by filtration and mother liquor was concentrated in vacuo to give 250 mg brown color oil. This oil was further purified by column chromatography (100% ethyl acetate to 95% ethyl acetate: 5% methanol) to give a light yellow oil (170 mg, 11% yield).

$^1$H NMR (300 MHz; d$_6$-DMSO) δ 3.05-2.99 (m, 1H), 2.69-2.63 (m, 1H), 2.44-2.11 (m, 5H), 1.87-1.78 (m, 1H), 1.69-1.54 (m, 2H), 1.41-1.31 (m, 1H), 1.13 (s, 3H), 0.87 (s, 3H);

$^{13}$C NMR (300 MHz; d$_6$-DMSO) δ 209.7, 60.44, 48.69, 42.63, 41.17, 39.67, 38.60, 28.83, 28.10, 19.87; m/z=168.08 (M+H)$^+$.

Hexahydro-3,3-Dimethylindolizin-7(1H)-Ketoxime

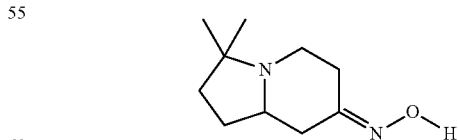

Hexahydro-3,3-dimethylindolizin-7(1H)-one (825 mg, 4.9 mmol) was added to a mixture of pyridine (8 ml) and ethanol (8 ml). Hydroxylamine-HCl salt (412 mg, 5.9 mmol) was added to the solution and the mixture was heated at 75° C. over weekend. The mixture was cooled to room temperature and concentrated under reduced pressure. N-heptane (20 ml)

was added to the residue and concentrated in vacuo, this was repeated twice to remove most of the pyridine. Ethanol (10 ml) was added to the residue to form a milky mixture, this was sonicated, filtered and the white color solid collected was dried under reduced pressure to give the product (613 mg, 68% yield).

$^1$H NMR (300 MHz; d$_6$-DMSO) δ 10.85 (s, 1H), 3.46-3.42 (m, 1H), 3.35-3.31 (m, 1H), 2.88-2.78 (m, 2H), 2.67-2.61 (m, 1H), 2.44-2.35 (m, 2H), 2.17-2.1 (m, 1H), 1.99-1.85 (m, 2H), 1.8-1.7 (m, 1H), 1.51 (s, 3H), 1.16 (s, 3H); m/z=184.04 (M+H)$^+$.

Octahydro-3,3-Dimethylindolizin-7(1H)-Amine

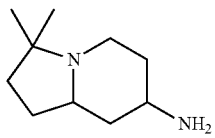

Hexahydro-3,3-diemthylindolizin-7(1H)-ketoxime (613 mg, 3.4 mmol) was added to acetic acid (30 ml) and followed by Pt$_2$O (76 mg) and was shook under 60 psi of H$_2$ overnight. Addition 34 mg of Pt$_2$O was added to ensure the completion of the reaction. Methanol (30 ml) was added to the mixture and the catalyst was filtered off through a bed of Celite. The mother liquor was concentrated in vacuo to give a dark brown oil. Ethyl acetate (50 ml) was added to the oil and it was passed through a bed of Celite to remove the residual catalyst. The mother liquor was concentrated in vacuo to give 720 mg of product as an acetate salt and was used for the next step without further purification.

$^1$H NMR (300 MHz; d$_6$-DMSO) δ 2.70-2.67 (m, 1H), 2.34-2.25 (m, 1H), 2.05-1.98 (m, 1H), 1.82-1.66 (m, 2H), 1.53-1.45 (m, 3H), 1.22-1.1 (m, 2H), 1.02 (s, 3H), 0.81 (s, 3H), m/z=169.09 (M+H)$^+$.

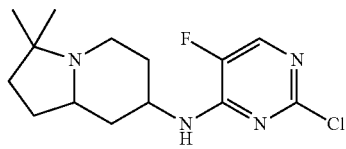 [SMILES: CC1(C)CCC2CC(Nc3nc(Cl)ncc3F)CCN21]

$^1$H NMR (300 MHz; d$_6$-DMSO) δ 8.19 (s, 1H), 8.07 (d, J=7.57 Hz, 1H), 7.68 (bd, J=5.4 Hz, 1H), 4.14 (s, 1H), 2.75-2.72 (m, 1H), 2.61-2.57 (m, 1H), 2.02-1.97 (m, 1H), 1.87-1.82 (m, 1H), 1.71-1.66 (m, 2H), 1.53-1.48 (m, 2H), 1.43-1.33 (m, 1H), 1.22-1.17 (m, 1H), 1.06 (s, 3H), 0.88 (s, 3H); m/z=299.09 (M+H)$^+$; m/z=297.09 (M−H)$^+$.

Example 12

Synthesis of N2-(4,4-dimethyl-4H-benzo[b]tetrazolo [1,5-d][1,4]oxazin-8-yl)-5-fluoro-N4-(octahydro-5, 5-dimethylindolizin-7-amine)pyrimidine-2,4-di-amine (Compounds 1-4)

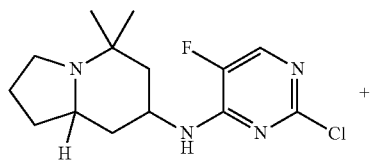

Mixture of both diastereomers (D1:D2 = 1:3)
Each diastereomers is a mixture of two enantiomers

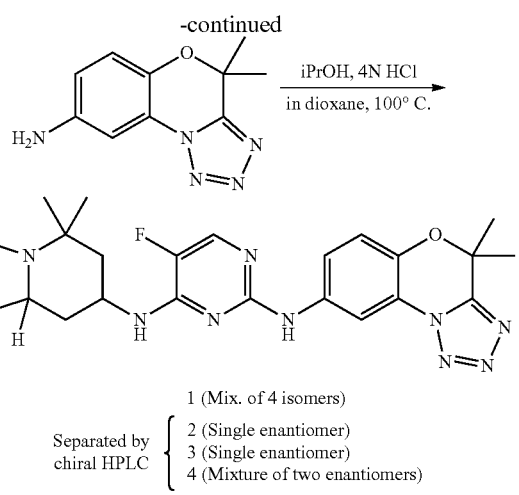

1 (Mix. of 4 isomers)
Separated by chiral HPLC
{ 2 (Single enantiomer)
3 (Single enantiomer)
4 (Mixture of two enantiomers) }

Compound 1 is a mixture of four isomers. Compound 2 is a single enantiomer separated by chiral HPLC. Compound 3 is a single enantiomer separated by chiral HPLC. Compound 4 is a mixture of two enantiomers (no separation).

The preparation of Compound 1, Compound 2, Compound 3, and Compound 4 is illustrated in accompanying scheme. In the second SNAr reaction the diastereomeric mixture (D1:D2=1:3) of (RS,SR,RR,SS)—N-(2-chloro-5-fluoropyrimi-din-4-yl)-octahydro-5,5-dimethylindolizin-7-amine was used and chiral HPLC was performed on the final product. Absolute stereochemistry of the individual isomers was not established in this series.

A solution of (R/S,S/R,R/R,S/S)—N-(2-chloro-5-fluoro-pyrimidin-4-yl)-octahydro-5,5-dimethylindolizin-7-amine (0.12 g, 0.4 mmol, mixture of both diastereomers 1:3) in 3 ml of iPrOH, 4,4-dimethyl-4H-benzo[b]tetrazolo[1,5-d][1,4] oxazin-8-amine (0.19 g, 0.5 mmol; prepared according to WO2010/083207 pages 73-74, which is hereby incorporated by reference in its entirety) and 4N HCl in dioxane (0.1 ml) were added. The reaction mixture was heated to 100° C. in a sealed vial for 4 hours. LCMS analysis of the crude reaction mixture indicated the completion of the reaction. The crude product was purified by column chromatography to give 0.18 g (95% yield) of the product as a mixture of four stereoisomers. Two enantiomers (Compounds 2 and 3) were obtained as single enantiomers after chiral HPLC purification. Compound 4 was obtained as a pure diastereomer (mixture of two enantiomers). Absolute stereochemistry of individual isomers was not determined.

Compound 2: (Single Enantiomer)

$^1$H NMR (DMSO d$_6$, 300 MHz) δ: 9.40 (s, 1H), 8.43 (s, 1H), 7.92 (d, J=8.9 Hz, 1H), 7.55-7.7.63 (m, 2H), 7.19 (d, J=8.9 Hz, 1H), 4.38 (br. m, 1H), 3.08 (m, 1H), 2.18-2.30 (m, 2H), 1.92-1.98 (m, 1H), 1.80-1.90 (m, 3H), 1.74 (s, 6H), 1.38-1.70 (m, 4H), 1.20 (s, 3H), 1.32 (s, 3H); LCMS (m/z): 480 (MH$^+$). Chiral HPLC Pk1 RT=14.91 min. (see protocol-5 in general methods).

Compound 3: (Single Enantiomer)

$^1$H NMR (DMSO d$_6$, 300 MHz) δ: 9.40 (s, 1H), 8.43 (s, 1H), 7.92 (d, J=8.9 Hz, 1H), 7.55-7.63 (m, 2H), 7.19 (d, J=8.9 Hz, 1H), 4.38 (br. m, 1H), 3.08 (m, 1H), 2.18-2.30 (m, 2H), 1.92-1.98 (m, 1H), 1.80-1.90 (m, 3H), 1.74 (s, 6H), 1.38-1.70 (m, 4H), 1.20 (s, 3H), 1.32 (s, 3H); LCMS (m/z): 480 (MH$^+$) (see protocol-1 in general methods). Chiral HPLC Pk1 RT=17.64 min. (see protocol-4 in general methods)

Compound 4: (Mixture of Two Enantiomers)

$^1$H NMR (DMSO $d_6$, 300 MHz) δ: 9.51 (s, 1H), 8.72 (s, 1H), 7.99 (d, J=8.7 Hz, 1H), 7.50-7.65 (m, 2H), 7.15 (d, J=8.7 Hz, 1H), 4.35 (br. s, 1H), 3.18 (m, 1H), 1.92-2.35 (m, 6H), 1.75 (s, 3H), 1.72 (s, 3H), 1.50-1.68 (m, 4H), 1.37 (s, 3H), 1.28 (s, 3H); LCMS (m/z): 480 (MH$^+$) (see protocol-1 in general methods). Chiral HPLC Pk1 RT=19.19 min. (see protocol-4 in general methods).

Example 13

Synthesis of (R/S,S/R,R/R,S/S)—N$^2$-(4-(1-isopropylpiperidin-4-yloxy)-3-(difluoromethoxy)phenyl)-5-fluoro-N$^4$-(octahydro-5,5-dimethylindolizin-7-yl)pyrimidine-2,4-diamine (Compounds 6-10)

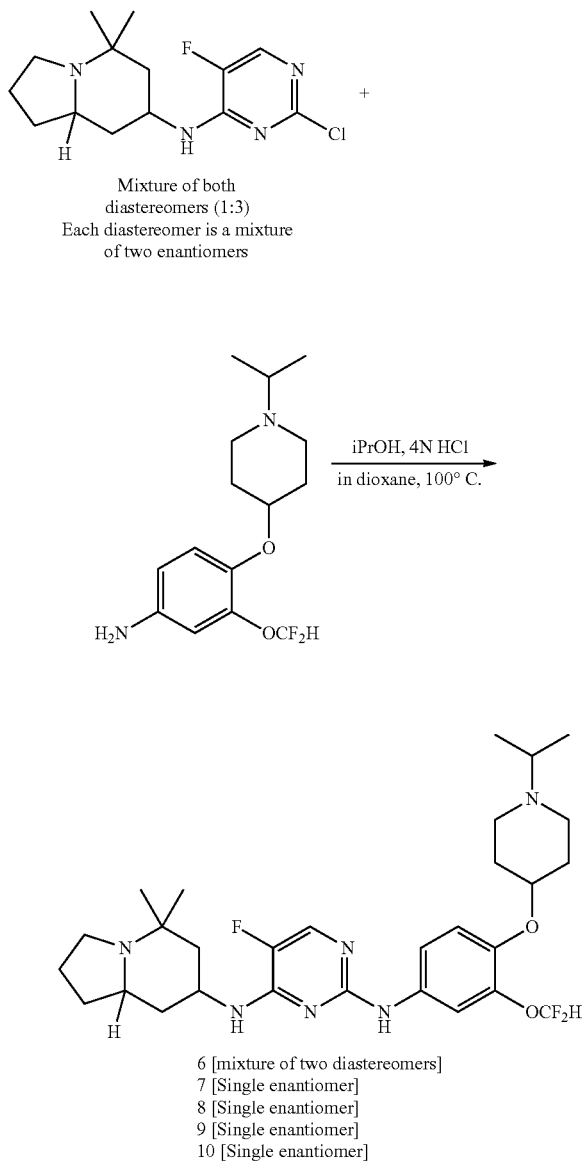

6 [mixture of two diastereomers]
7 [Single enantiomer]
8 [Single enantiomer]
9 [Single enantiomer]
10 [Single enantiomer]

Synthesis of Compound 6, Compound 7, Compound 8, Compound 9, and Compound 10 is illustrated in the accompanying scheme. In the 2$^{nd}$ SNAr reaction the diastereomeric mixture (D1:D2=1:3) of (R/S,S/R,R/R,S/S)—N-(2-chloro-5-fluoropyrimidin-4-yl)-octahydro-5,5-dimethylindolizin-7-amine was used and chiral HPLC was performed on the final product. Absolute stereochemistry of the individual isomers was not established in this series.

A solution of (R/S,S/R,R/R,S/S)—N-(2-chloro-5-fluoropyrimidin-4-yl)-octahydro-5,5-dimethylindolizin-7-amine (0.12 g, 0.40 mmol, mixture of both diastereomers 1:3) in 3 ml of iPrOH, 4-(1-isopropylpiperidin-4-yloxy)-3-(difluoromethoxy)benzeneamine (0.144 g, 0.48 mmol;) and 4N HCl in dioxane (0.1 ml) were added. The reaction mixture was heated to 100° C. in a sealed vial for overnight. LCMS analysis of the crude reaction mixture indicated the completion of the reaction. The crude product was purified by column chromatography to give 0.15 g (63% yield) of the product as a mixture of four isomers (Compound 6, (two diastereomers and each diastereomer is a mixture of 2 enantiomers). Chiral HPLC purification of the mixture gave all four isomers (Compound 7, Compound 8, Compound 9 and Compound 10). Absolute stereochemistry of the individual isomers was not determined.

Compound 7: (Single Enantiomer)

$^1$H NMR (DMSO $d_6$, 300 MHz): δ 9.39 (s, 1H), 8.47 (s, 1H), 8.11 (s, 1H), 7.94 (d, J=2.8 Hz, 1H), 7.56-7.70 (m, 3H), 7.14 (d, J=8.8 Hz, 1H), 5.74 (s, 1H), 4.32-4.40 (br. m, 1H), 4.11-4.13 (m, 1H), 3.08-3.15 (m, 4H), 2.70-2.81 (m, 2H), 2.44 (s, 3H), 2.21-2.27 (m, 1H), 1.90-1.97 (m, 2H), 1.69-1.75 (m, 1H), 1.51-1.55 (m, 2H), 1.32 (d, J=6.60 Hz, 6H), 1.26-1.41 (m, 2H), 1.13-1.18 (m, 1H), 0.95 (s, 3H), 0.90 (s, 3H); LCMS (m/z): 563 (MH$^+$). Chiral HPLC Pk1 RT=16.22 min. (see protocol-5 in general methods).

Compound 8: (Single Enantiomer)

$^1$H NMR (DMSO $d_6$, 300 MHz): δ 9.42 (s, 1H), 8.66 (s, 1H), 8.11 (s, 1H), 7.92 (d, J=2.9 Hz, 1H), 7.35-7.61 (m, 3H), 7.09 (d, J=8.9 Hz, 1H), 5.68 (s, 1H), 4.32-4.40 (br. s, 1H), 4.05-4.06 (m, 1H), 3.02-3.09 (m, 4H), 2.65-2.78 (m, 2H), 2.35 (s, 3H), 2.19-2.25 (m, 1H), 1.88-1.37 (m, 2H), 1.65-1.70 (m, 1H), 1.50-1.54 (m, 2H), 1.31 (d, J=6.6 Hz, 6H), 1.20-1.35 (m, 2H), 1.10-1.16 (m, 1H), 0.93 (s, 3H), 0.87 (s, 3H); LCMS (m/z): 563 (MH$^+$). Chiral HPLC Pk2 RT=21.28 min. (see protocol-5 in general methods).

Compound 9: (Single Enantiomer)

$^1$H NMR (DMSO $d_6$, 300 MHz): δ 9.45 (s, 1H), 8.40 (s, 1H), 8.25 (s, 1H), 7.90 (d, J=2.7 Hz, 1H), 7.55-7.70 (m, 3H), 7.18 (d, J=8.5 Hz, 1H), 5.72 (s, 1H), 4.30-4.40 (m, 1H), 4.01-4.10 (m, 1H), 3.05-3.16 (m, 4H), 2.75-2.82 (m, 2H), 2.46 (s, 3H), 2.20-2.23 (m, 1H), 1.95-2.15 (m, 2H), 1.69-1.75 (m, 1H), 1.50-1.65 (m, 2H), 1.42 (d, J=6.5 Hz, 6H), 1.26-1.41 (m, 2H), 1.14-1.17 (m, 1H), 1.10 (s, 3H), 0.85 (s, 3H); LCMS (m/z): 563 (MH$^+$). Chiral HPLC Pk3 RT=27.28 min. (see protocol-5 in general methods).

Compound 10: (Single Enantiomer)

$^1$H NMR (DMSO $d_6$, 300 MHz): δ 9.43 (s, 1H), 8.39 (s, 1H), 8.24 (s, 1H), 7.85 (d, J=2.5 Hz, 1H), 7.54-7.64 (m, 3H), 7.20 (d, J=8.5 Hz, 1H), 5.71 (s, 1H), 4.29-4.35 (m, 1H), 4.10-4.15 (m, 1H), 3.05-3.16 (m, 4H), 2.73-2.80 (m, 2H), 2.43 (s, 3H), 2.20-2.23 (m, 1H), 1.95-2.15 (m, 2H), 1.70-1.75 (m, 1H), 1.61-1.65 (m, 2H), 1.45 (d, J=6.50 Hz, 6H), 1.25-1.40 (m, 2H), 1.15-1.18 (m, 1H), 1.09 (s, 3H), 0.89 (s, 3H); LCMS (m/z): 563 (MH$^+$). Chiral HPLC Pk 4 RT=32.53 min. (see protocol-5 in general methods).

Example 14

Synthesis of (R/S,S/R,R/R,S/S)-5-fluoro-N4-(octahydro-5,5-dimethylindolizin-7-yl)N2-(3-methoxy-5-(5-methyl-1H-tetrazol-1-yl)phenyl)pyrimidine-2,4-diamine (Compounds 11-14)

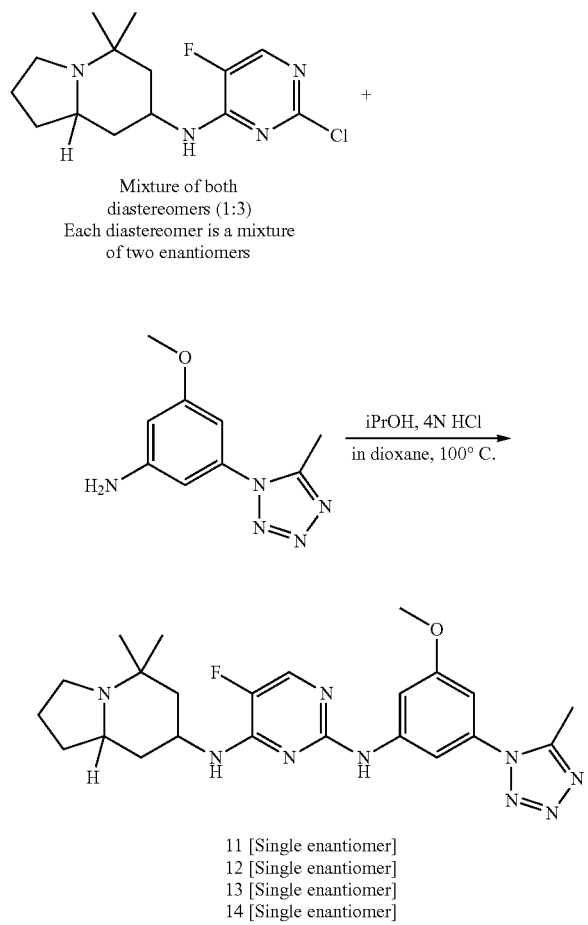

Synthesis of Compound 11, Compound 12, Compound 13 and Compound 14 was described in the accompanying scheme. In the 2$^{nd}$ SNAr reaction the diastereomeric mixture (D1:D2=1:3) of (R/S,S/R,R/R,S/S)—N-(2-chloro-5-fluoropyrimidin-4-yl)-octahydro-5,5-dimethylindolizin-7-amine was used and chiral HPLC was performed on the final product. Absolute stereochemistry of the individual isomers was not established.

A solution of (R/S,S/R,R/R,SS)—N-(2-chloro-5-fluoropyrimidin-4-yl)-octahydro-5,5-dimethylindolizin-7-amine (0.100 g, 0.34 mmol, mixture of two diastereomer (1:3)) in 3 ml of iPrOH, 3-methoxy-5-(5-methyl-1H-tetrazol-1-yl) aniline (0.077 g, 0.4 mmol; ChemBridge Building Blocks) and 4N HCl in dioxane (0.1 ml) were added. The reaction mixture was heated to 100° C. in a sealed vial for 12 hours. LCMS analysis of the crude reaction mixture indicated the completion of the reaction. The crude product was purified by column chromatography to give 0.14 g (Yield=88%) of the product as a mixture of four isomers (two diastereomers and each diastereomer is a mixture of 2 enantiomers). Chiral HPLC purification of the mixture gave all four isomers (Compound 11, Compound 12, Compound 13 and Compound 14). Absolute stereochemistry of the individual isomers was not established.

Compound 11: Single Diastereomer; Single Enantiomer $^1$H NMR (DMSO d$_6$, 300 MHz) δ: 9.98 (s, 1H), 9.42 (s, 1H), 8.11 (s, 1H), 7.88 (d, J=3.9 Hz, 1H), 7.33 (s, 1H), 6.98 (d, J=5.5 Hz, 1H), 6.94 (s, 1H), 4.19 (br. s, 1H), 3.75 (s, 3H), 2.72-2.82 (m, 2H), 2.45 (s, 3H), 2.21-2.25 (m, 1H), 1.92-1.98 (m, 2H), 1.71-1.75 (m, 1H), 1.49-1.56 (m, 2H), 1.28-1.39 (m, 2H), 1.15-1.20 (m, 1H), 0.92 (s, 3H), 0.90 (s, 3H); LCMS (m/z): 468 (MH$^+$); Chiral HPLC Pk1 RT=17.92 min. (see protocol-5 in general methods).

Compound 12: Single Diastereomer; Single Enantiomer $^1$H NMR (DMSO d$_6$, 300 MHz) δ: 9.98 (s, 1H), 9.42 (s, 1H), 8.11 (m, 1H), 7.87 (d, J=3.9 Hz, 1H), 7.33 (m, 1H), 6.94 (m, 2H), 4.12 (br. m, 1H), 3.75 (s, 3H), 2.70-2.81 (m, 2H), 2.44 (s, 3H), 2.21-2.27 (m, 1H), 1.90-1.97 (m, 2H), 1.70-1.76 (m, 1H), 1.50-1.57 (m, 2H), 1.26-1.41 (m, 2H), 1.13-1.18 (m, 1H), 0.91 (s, 3H), 0.88 (s, 3H); LCMS (m/z): 468 (MH$^+$); Chiral HPLC Pk2 RT=23.56 min. (see protocol-5 in general methods).

Compound 13: Single Diastereomer; Single Enantiomer $^1$H NMR (DMSO d$_6$, 300 MHz) δ: 9.99 (s, 1H), 9.32 (s, 1H), 7.91 (s, 1H), 7.83 (d, J=3.9 Hz, 1H), 7.40 (s, 1H), 7.25 (d, J=8.5 Hz, 1H), 6.91 (s, 1H), 4.01-4.16 (br. m, 1H), 2.73 (m, 1H), 3.74 (s, 3H), 2.44 (s, 3H), 2.16-2.20 (m, 2H), 1.91-2.03 (m, 1H), 1.49-1.70 (m, 4H), 1.30-1.40 (m, 1H), 1.02-1.19 (m, 2H), 0.99 (s, 3H), 0.73 (s, 3H); LCMS (m/z): 468 (MH$^+$); Chiral HPLC Pk3 RT=28.18 min. (see protocol-5 in general methods).

Compound 14: Single Diastereomer; Single Enantiomer $^1$H NMR (DMSO d$_6$, 300 MHz) δ: 9.99 (s, 1H), 9.33 (s, 1H), 7.90 (s, 1H), 7.84 (d, J=3.9 Hz, 1H), 7.39 (s, 1H), 7.26 (d, J=8.5 Hz, 1H), 6.92 (s, 1H), 4.00-4.15 (br. m, 1H), 3.74 (s, 3H), 2.43 (s, 3H), 2.15-2.21 (m, 2H), 1.90-2.00 (m, 1H), 1.49-1.70 (m, 4H), 1.30-1.40 (m, 1H), 1.02-1.19 (m, 2H), 0.98 (s, 3H), 0.72 (s, 3H); LCMS (m/z): 468 (MH$^+$); Chiral HPLC Pk4 RT=33.19 min. (see protocol-5 in general methods).

Compounds 11 and 12 appear to be enantiomers of one another.

Compounds 13 and 14 appear to be enantiomers of one another.

Example 15

Synthesis of N2-{4-cyclopropyl-6-fluoro-[3-(4-methyl)-1,2,3,4-tetrazol-5-one-1-yl]}phenyl-5-fluoro-N4(7-amino-hexahydro-3,3-dimethylindolizin-5(1H)-one))2,4-pyrimidinediamine (Compound 30)

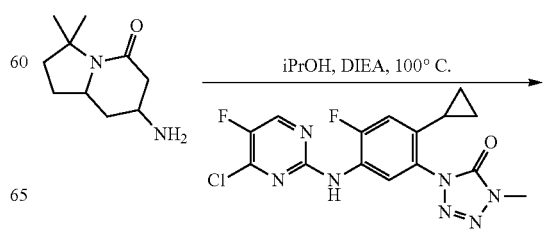

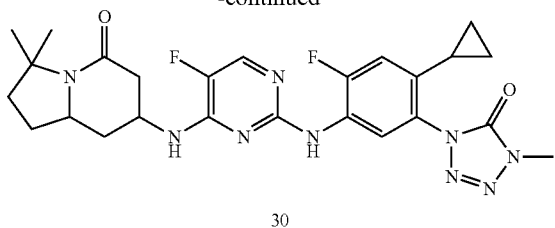

To a solution of 1-(5-(4-chloro-5-fluoropyrimidin-2-ylamino)-2-cyclopropyl-4-fluorophenyl)-4-methyl-1H-tetrazol-5(4H)-one (described in WO 2011/068898, published Jun. 9, 2011, which is hereby incorporated by reference in its entirety; 0.11 g, 0.3 mmol) in iPrOH (10 ml), diisopropyl ethyl amine (0.21 ml, 1.2 mmol) and 7-amino-hexahydro-3,3-dimethylindolizin-5(1H)-one (0.060 g, 0.329 mmol) were added. The reaction mixture was heated at 100° C. for 12 hours. LC-MS analysis indicated the completion of reaction. Volatiles were removed under vacuum and the crude product was adsorbed on silica gel. The crude product was purified by column chromatography to give the product white powder in 75% yield (0.12 g).

$^1$H NMR (DMSO d$_6$, 300 MHz) δ: 8.61 (s, 1H), 8.02 (d, J=7.6 Hz, 1H), 7.85 (d, J=3.8 Hz, 1H), 7.78 (d, J=6.7 Hz, 1H), 6.97 (d, J=12.3 Hz, 1H), 4.33 (br. s, 1H), 3.60-3.68 (m, 4H), 2.27 (d, J=17.0 Hz, 1H), 2.16 (d, J=12.0 Hz, 1H), 1.79-1.85 (m, 1H), 1.58-1.72 (m, 3H), 1.46 (s, 3H), 1.35-1.43 (m, 3H), 1.32 (s, 3H), 0.80-0.83 (m, 2H), 0.63-0.65 (m, 2H); $^{19}$F NMR (DMSO) δ: −165.08, −121.69. LCMS (m/z): 526 (MH$^+$).

Example 16

Synthesis of 1-(5-(4-((7R,8aS)-octahydro-5,5-dimethylindolizi-7-yl-amino)-5-fluoropyrimidin-2-yl-amino)-2-cyclopropyl-4-fluorophenyl)-4-methyl-1H-tetrazol-5-(4H)-one (Compound 17)

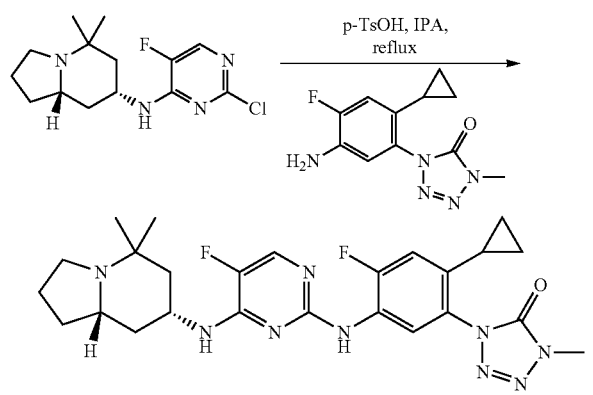

A mixture of (7R,8aS)—N-(2-chloro-5-fluoropyrimidin-4-yl)-octahydro-5,5-dimethylindolizin-7-amine (Compound 3-10 from Example 3) (10.8 g, 36.2 mmol), 1-(5-amino-2-cyclopropyl-4-fluorophenyl)-4-methyl-1H-tetrazol-5(4H)-one (12.6 g, 50.6 mmol) and para-toluenesulfonic acid monohydrate (12.4 g, 65.1 mmol) in $^i$PrOH (120 mL) was heated to reflux and stirred for 16 hours. After allowing the reaction mixture to cool, EtOAc (600 mL) was added and the resulting mixture was washed with 1N NaOH (200 mL). The organic and aqueous layers were partitioned and the aqueous layer extracted with EtOAc (200 mL). The combined organic extracts were dried (MgSO$_4$), filtered and the solvent removed in vacuo to leave a crude residue. The residue was purified by column chromatography on silica gel using CH$_2$Cl$_2$/2N NH$_3$ in MeOH (95:5) as eluent to give the product (12.7 g) containing a trace of TsOH. The product was dissolved in EtOAc (500 mL) and washed with 1N NaOH (100 mL) and H2O (100 mL). The organic layer was dried (MgSO$_4$) and concentrated in vacuo to give the product (12.1 g) as a solid.

[α]$_D$=−7.4 (c=0.25 in MeOH)

$^1$H NMR (DMSO-d$_6$, 300 MHz): δ 8.48 (br. s, 1H), 7.96 (d, J=7.8 Hz, 1H), 7.82 (d, J=3.6 Hz, 1H), 7.25 (d, J=8.4 Hz, 1H), 6.98 (d, J=12.3 Hz, 1H), 4.05-3.90 (m, 1H), 3.61 (s, 3H), 2.81 (td, J=8.4, 3.0 Hz, 1H), 2.21 (q, J=8.1 Hz, 1H), 2.20-2.10 (m, 1H), 2.00-1.90 (m, 1H), 1.75-1.48 (m, 5H), 1.38 (t, J=12.3 Hz, 1H), 1.22-1.12 (m, 1H), 1.03 (s, 3H), 1.08-1.00 (m, 1H), 0.83-0.77 (m, 2H), 0.75 (s, 3H), 0.63-0.57 (m, 2H)

$^{19}$F NMR (DMSO-d$_6$, 282 MHz): δ −121.04 (t), −166.01 (s)

m/z=511.0 (M+H)$^+$

The enantiomeric excess of the product is measured by chiral HPLC using the conditions detailed below.

Chiral HPLC Conditions:
Column: Daicel Chemical Industries, Chiralcel OJ, 4.6×250 mm
Mobile phase: 2:2:1 Methanol/Ethanol/Hexane 0.1% triethylamine (isocratic)
Flow rate: 0.5 ml/min
Run time: 15 minutes
Temperature: room temperature
Detection: Water 996 PDA
HPLC: Waters 2690 Separations Module Large-Scale Reaction Avoiding Use of Column Chromatography:

1-(5-Amino-2-cyclopropyl-4-fluorophenyl)-4-methyl-1H-tetrazol-5(4H)-one (26.7 g, 107.3 mmol) and para-toluene sulfonic acid monohydrate (30.6 g, 161.0 mmol) were added to a stirred mixture of chloro-pyrimidine (Compound 3-10 from Example 3) (23.0 g, 68.25 mmol) in $^i$PrOH (300 mL). The reaction mixture was heated to reflux and stirred for 16 hours, after which LC-MS analysis indicated completion of the reaction. The reaction mixture was cooled to room temperature and filtered to obtain a tan-colored solid. The filter cake was then washed with $^i$PrOH (1×25 mL). The filtrate was concentrated to ca. half volume in vacuo and the emerging precipitate was filtered. The combined filter cakes from the above procedures were air-dried then dissolved in EtOAc (300 mL) and washed with 1N NaOH (1×200 mL then 3×100 mL). The organic layer was dried over (MgSO$_4$), filtered and solvent removed in vacuo to leave the product (27.2 g, 78%) as a white powder.

Example 17

Synthesis of Octahydro-5,5-dimethylindolizin-7-ylamino)-5-fluoropyrimidin-2-yl-amino)-2-cyclopropyl-4-fluorophenyl)-4-methyl-1H-tetrazol-5(4H)-one (Compounds 16-21)

The synthesis of Compounds 16, 17, 18, 19, 20, and 21 is illustrated in the accompanying schemes. First the separation of diastereomers D1 and D2 was accomplished by column chromatography and both the diastereomers were taken to the SNAr reaction separately. The final products were separated by chiral HPLC provide individual enantiomers.

(R/S,S/R)—N-(2-chloro-5-fluoropyrimidin-4-yl)-octahydro-5,5-dimethylindolizin-7-amine (D1) is a racemic mixture of two enantiomers. D1 was taken to 2$^{nd}$ SNAr reaction to form Compound 16. Synthesis of Compound 16 (racemic) was described in the accompanying scheme. Compound 16 was separated by chiral HPLC to give Compound 17 (Single enantiomer) and Compound 18 (Single enantiomer).

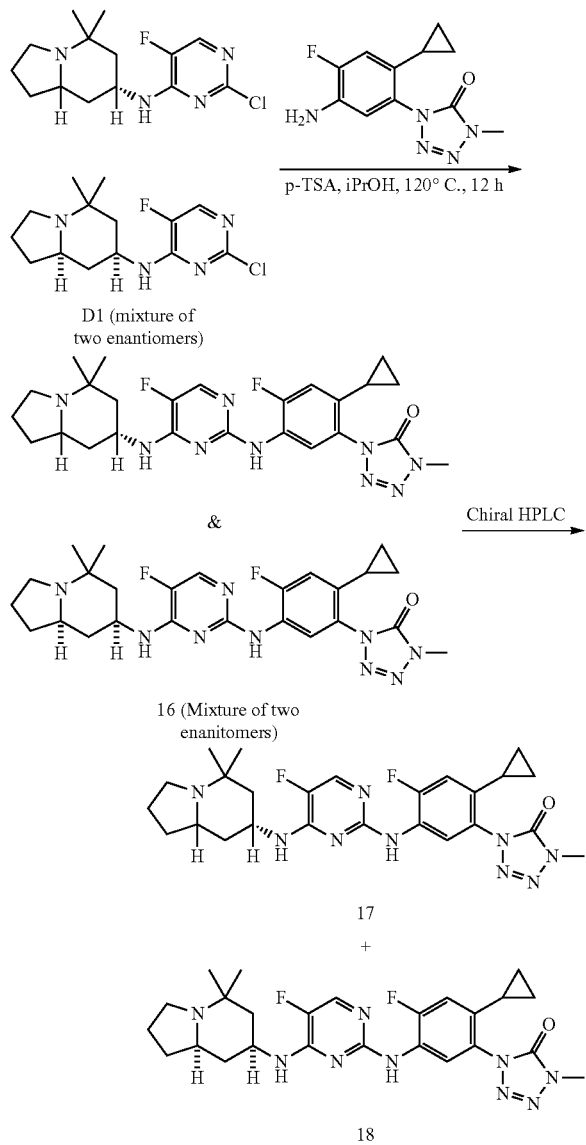

To a solution of (R/S,S/R)—N-(2-chloro-5-fluoropyrimidin-4-yl)-octahydro-5,5-dimethylindolizin-7-amine (D1) (0.1 g, 0.3 mmol) in 10 ml of iPrOH, 1-(5-amino-2-cyclopropyl-4-fluorophenyl)-4-methyl-1H-tetrazol-5(4H)-one (0.092 g, 0.37 mmol) and p-toluene sulfonicacid monohydrate (0.064 g, 0.3 mmol) were added. The reaction mixture was heated at 120° C. (bath temp.) for 16 hours. LC-MS analysis indicated the completion of the reaction. The reaction mixture was cooled to room temperature and filtered off to get tan solid. The filter cake was washed with 5 ml of iPrOH to get white solid. The filtrate was concentrated in vacuo to half the volume and the obtained solids were filtered off. The filtered solids were combined and dried under air. The dried solids were dissolved in 50 ml of EtOAc and partitioned with aqueous 1N NaOH (10 ml). Both the layers were separated and organic layer was washed (×3) with aqueous 1N NaOH (10 ml). Separated organic layer was dried over MgSO$_4$ and concentrated to give 0.12 g (yield=71%) of the product as white powder (Compound 16). Compound 16 was separated by chiral HPLC to give the corresponding enantiomers Compound 17 and Compound 18(see Protocol-3 in general methods).

1-(5-(4-(((7R,8aS)-Octahydro-5,5-dimethylindolizin-7ylamino)-5-fluoropyrimidin-2-yl-amino)-2-cyclopropyl-4-fluorophenyl)-4-methyl-1H-tetrazol-5(4H)-one (Compound 17)

(Single Enantiomer)

$^1$H NMR (DMSO d$_6$, 300 MHz) δ: 8.48 (s, 1H), 7.97 (d, J=7.6 Hz, 1H), 7.82 (d, J=3.8 Hz, 1H), 7.25 (d, J=7.9 Hz, 1H), 6.99 (d, J=12.0 Hz, 1H), 3.90-4.10 (br. m, 1H), 3.61 (s, 3H), 2.81 (dt, J=8.2, 2.9 Hz, 1H), 2.10-2.26 (m, 2H), 1.93 (d, J=11.7 Hz, 1H), 1.49-1.75 (m, 5H), 1.39 (t, J=12.3 Hz, 1H), 1.14-1.24 (m, 1H), 1.03 (s, 3H), 0.94-1.01 (m, 1H), 0.77-0.83 (m, 2H), 0.75 (s, 3H), 0.59-0.63 (m, 2H); $^{19}$F NMR (DMSO) δ: −165.99 (d), −121.09 (t).; LCMS (m/z): 512 (MH$^+$); Chiral HPLC RT=18.89 min. (see Protocol-4 in general methods).

1-(5-(4-(((7S,8aR)-Octahydro-5,5-dimethylindolizin-7ylamino)-5-fluoropyrimidin-2-yl amino)-2-cyclopropyl-4-fluorophenyl)-4-methyl-1H-tetrazol-5(4H)-one (Compound 18)

(Single Enantiomer)

$^1$H NMR (DMSO d$_6$, 300 MHz) δ: 8.48 (s, 1H), 7.97 (d, J=7.6 Hz, 1H), 7.83 (d, J=3.8 Hz, 1H), 7.25 (d, J=8.2 Hz, 1H), 6.99 (d, J=12.3 Hz, 1H), 3.90-4.05 (br. m, 1H), 3.61 (s, 3H), 2.81 (br. m, 1H), 2.10-2.26 (m, 2H), 1.93 (d, J=11.7 Hz, 1H), 1.49-1.75 (m, 5H), 1.39 (t, J=12.0 Hz, 1H), 1.14-1.24 (m, 1H), 1.03 (s, 3H), 0.94-1.01 (m, 1H), 0.77-0.82 (m, 2H), 0.75 (s, 3H), 0.58-0.63 (m, 2H); $^{19}$F NMR (DMSO) δ: −166.00 (d), −121.05 (t); LCMS (m/z): 512 (MH$^+$). Chiral HPLC RT=22.97 (see Protocol-4 in general methods).

(S/S, R/R)—N-(2-chloro-5-fluoropyrimidin-4-yl)-octahydro-5,5-dimethylindolizin-7-amine (D2) is a mixture of two enantiomers. D2 was taken to 2$^{nd}$ SNAr reaction to form Compound 19. Synthesis of Compound 19 (mixture of two enantiomers) was described in the accompanying scheme. Compound 19 was separated by chiral HPLC to give Compound 20 (Single enantiomer) and Compound 21 (Single enantiomer).

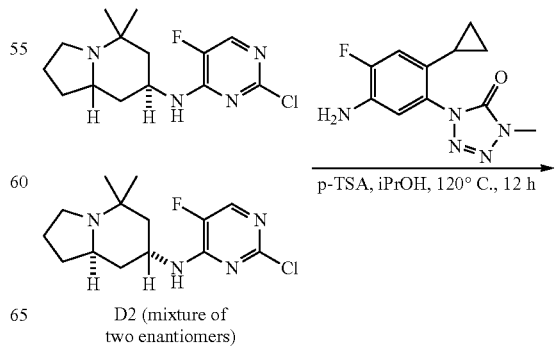

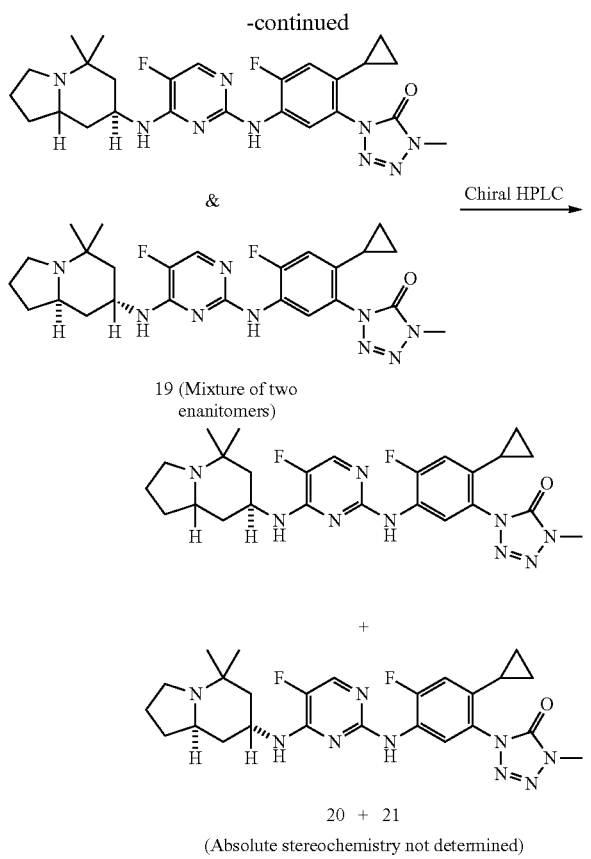

19 (Mixture of two enantiomers)

20 + 21
(Absolute stereochemistry not determined)

To a solution of (S/S, R/R)—N-(2-chloro-5-fluoropyrimidin-4-yl)-octahydro-5,5-dimethylindolizin-7-amine (D2) (0.10 g, 0.34 mmol) in 10 ml of iPrOH, 1-(5-amino-2-cyclopropyl-4-fluorophenyl)-4-methyl-1H-tetrazol-5(4H)-one (0.092 g, 0.4 mmol) and p-toluene sulfonic acid monohydrate (0.064 g, 0.3 mmol) were added. The reaction mixture was heated at 120° C. (bath temp.) for 16 hours. LC-MS analysis indicated the completion of the reaction. The reaction mixture was cooled to room temperature and filtered off to get tan solid. The filter cake was washed with 1 ml of iPrOH to get white solid. The filtered solids were combined and dried under air. The dried solids were dissolved in 50 ml of EtOAc and partitioned with aqueous 1N NaOH (10 ml). Both the layers were separated and organic layer was washed (×3) with aqueous 1N NaOH (10 ml). Separated organic layer was dried over MgSO$_4$ and concentrated to give 0.13 g (yield=74%) of the product as white powder (Compound 19). Compound 19 was separated by chiral HPLC to give the corresponding enantiomers Compound 20 and Compound 21 (see Protocol-4 in general methods).

Compound 20: (Single Enantiomer):

$^1$H NMR (DMSO d$_6$, 300 MHz) δ: 8.56 (s, 1H), 8.11 (d, J=7.6 Hz, 1H), 7.84 (d, J=3.8 Hz, 1H), 6.92-6.99 (m, 2H), 4.04 (br. s, 1H), 3.61 (s, 3H), 2.70-2.83 (m, 2H), 2.25-2.35 (m, 1H), 1.75-1.95 (m, 3H), 1.55-1.65 (m, 3H), 1.15-1.36 (m, 3H), 0.94 (s, 3H), 0.92 (s, 3H), 0.78-0.83 (m, 2H), 0.60-0.65 (m, 2H); $^{19}$F NMR (DMSO) δ: −165.78 (d), −122.24 (t); LCMS (m/z): 512 (MH$^+$); Chiral HPLC RT=29.88 min. (see Protocol-4 in general methods).

Compound 21: (Single Enantiomer):

$^1$H NMR (DMSO d$_6$, 300 MHz) δ: 8.57 (s, 1H), 8.11 (d, J=7.6 Hz, 1H), 7.84 (d, J=3.8 Hz, 1H), 6.92-6.99 (m, 2H), 4.04 (br. s, 1H), 3.61 (s, 3H), 2.71-2.83 (m, 2H), 2.25-2.35 (m, 1H), 1.76-1.95 (m, 3H), 1.56-1.68 (m, 3H), 1.15-1.35 (m, 3H), 0.94 (s, 3H), 0.92 (s, 3H), 0.78-0.83 (m, 2H), 0.60-0.65 (m, 2H); $^{19}$F NMR (DMSO) δ: −165.57 (d), −122.24 (t); LCMS (m/z): 512 (MH$^+$); Chiral HPLC RT=34.50 min. (see Protocol-4 in general methods).

Example 18

Synthesis of N2-(4,4-dimethyl-4H-benzo[b]tetrazolo[1,5-d][1,4]oxazin-8-yl)-5-fluoro-N4-(octahydro-5,5-dimethylindolizin-7-yl)pyrimidine-2,4-diamine (Compound 5)

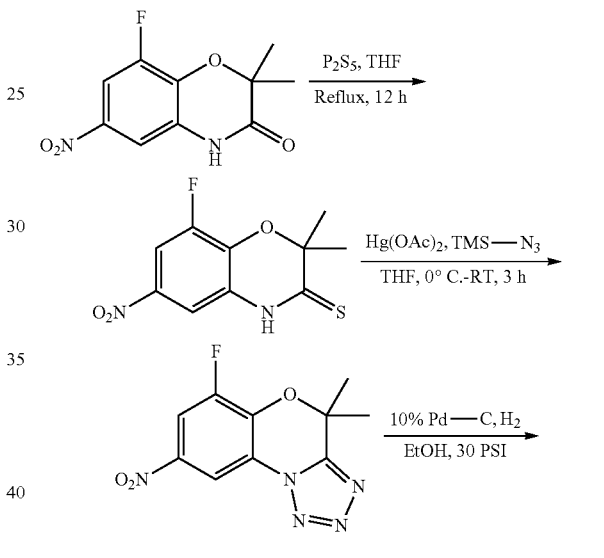

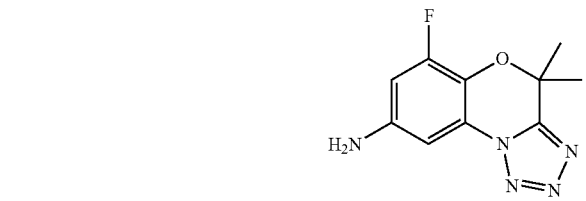

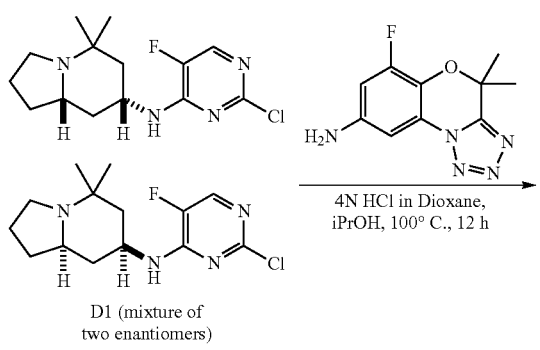

D1 (mixture of two enantiomers)

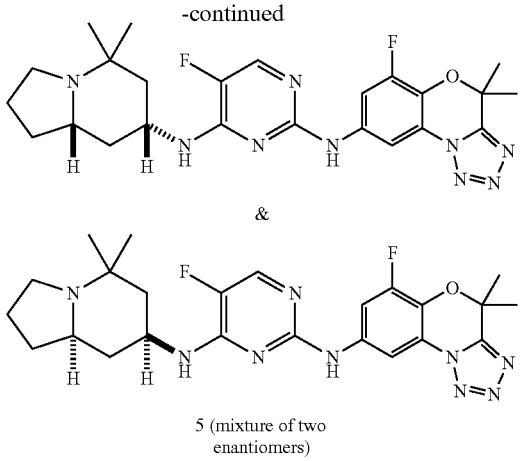

5 (mixture of two enantiomers)

Preparation of 8-Fluoro-2,2-dimethyl-6-nitro-2H-benzo[b][1,4]oxazin-3(4H)-thione To a solution of 8-Fluoro-2,2-dimethyl-6-nitro-2H-benzo[b][1,4]oxazin-3(4H)-one (0.75 g, 3.1 mmol) in 25 ml anhydrous THF, $P_2S_5$ (2.8 g, 6.25 mmol) was added and the reaction mixture was heated to reflux for 12 hours. Analysis of LC-MS indicated the completion of the reaction. Volatiles were removed in vacuo and the crude reaction mixture was partitioned in EtOAc (100 ml) and saturated aqueous $NH_4Cl$ (100 ml). Layers were separated and the organic layer was washed (×2) with saturated aqueous $NH_4Cl$ (50 ml). EtOAc layer was dried over $Na_2SO_4$ and concentrated to give the product in 69% yield (0.55 g). LCMS (m/z) 257 (MH$^+$).

Preparation of 4,4-dimethyl-6-fluoro-8-nitro-4H-benzo[b]tetrazolo[1,5-d][1,4]oxazine To a solution of 8-fluoro-2,2-dimethyl-6-nitro-2H-benzo[b][1,4]oxazin-3(4H)-thione (1.0 g, 3.9 mmol) in THF, Hg(OAc)$_2$ was added at 0° C. TMS-$N_3$ was added to the reaction mixture at 0° C. and stirred for 1 hour. Reaction mixture was allowed to warm to room temperature and stirred for 3 hours. LCMS analysis of the reaction mixture indicated completion of the reaction. After 3 hours, the reaction mixture was diluted with 100 ml of EtOAc and partitioned with saturated aqueous $NH_4Cl$ (100 ml). Layers were separated and the aqueous layer was washed twice with EtOAc (50 ml). Combined EtOAc layers were dried over $Na_2SO_4$ and concentrated. The crude product was purified by column chromatography to give the product in 57% yield (0.57 g). LCMS (m/z) 266 (MH$^+$).

Preparation of 4,4-dimethyl-6-fluoro-4H-benzo[b]tetrazolo[1,5-d][1,4]oxazin-8-amine 4,4-Dimethyl-6-fluoro-8-nitro-4H-benzo[b]tetrazolo[1,5-d][1,4]oxazine (0.82 g, 3.1 mmol) is dissolved in EtOH (20 ml). The clear solution is transferred to a Parr hydrogenation flask and placed under nitrogen. 10% Pd—C (0.25 g) was added to the Parr flask under nitrogen. The mixture was then transferred to a Parr hydrogenation apparatus, evacuated and filled with hydrogen (×3). The mixture was hydrogenated at 30 psi (optionally topping-up hydrogen) until LC/MS and TLC indicated complete reaction to the amine. After complete reaction, the mixture was placed under nitrogen and filtered through a small pad of Celite. The filter cake was washed with EtOH (×1) and the filtrate was concentrated in vacuo to leave the 4,4-dimethyl-6-fluoro-4H-benzo[b]tetrazolo[1,5-d][1,4]oxazin-8-amine in 72% yield (0.53 g). LCMS (m/z): 236 (MH$^+$).

Preparation of N2-(4,4-dimethyl-4H-benzo[b]tetrazolo[1,5-d][1,4]oxazin-8-yl)-5-fluoro-N4-(octahydro-5,5-dimethylindolizin-7-yl)pyrimidine-2,4-diamine (Compound 5)

A solution of (R/S,S/R)—N-(2-chloro-5-fluoropyrimidin-4-yl)-octahydro-5,5-dimethylindolizin-7-amine (D1) (0.1 g, 0.3 mmol, single diastereomer) in 3 ml of iPrOH, 4,4-dimethyl-6-fluoro-4H-benzo[b]tetrazolo[1,5-d][1,4]oxazin-8-amine (0.093 g, 0.4 mmol) and 4N HCl in dioxane (0.1 ml) were added. The reaction mixture was heated to 100° C. in a sealed vial for 12 hours. LCMS analysis of the crude reaction mixture indicated the completion of the reaction. The crude product was purified by column chromatography to give 0.12 g (Yield=72%) of the product as a mixture of two enantiomers.

$^1$H NMR (DMSO d$_6$, 300 MHz) δ: 9.58 (s, 1H), 8.40 (s, 1H), 7.90 (d, J=8.5 Hz, 1H), 7.75 (d, J=8.8 Hz, 1H), 7.10 (d, J=5.5 Hz, 1H), 4.25 (br. s, 1H), 2.85 (m, 2H), 2.23-2.335 (m, 1H), 2.15 (m, 2H), 1.88 (s, 6H), 1.40-1.60 (m, 4H), 1.22 (m, 2H), 1.05 (s, 3H), 0.99 (s, 3H); LCMS (m/z): 498 (MH$^+$).

Example 19

Synthesis of 4-((R/S,S/R)-Octahydro-5,5-dimethylindolizin-7-ylamino)-2-(4-cyclopropyl-2-fluoro-5-(4,5-dihydro-4-methyl-5-oxotetrazol-yl)phenylamino)pyrimidine-5-carbonitrile (Compound 66)

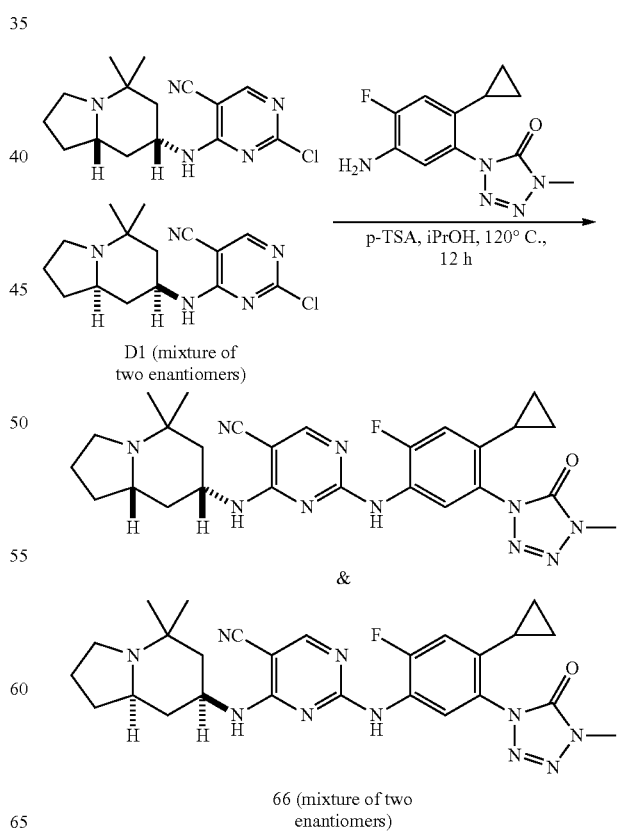

66 (mixture of two enantiomers)

To a solution of (±)-2-chloro-4-(octahydro-5,5-dimethylindolizin-7-ylamino)pyridimine-5-carbonitrile (70% pure, 0.068 g, 0.2 mmol) in iPrOH (10 ml), 1-(5-amino-2-cyclopropyl-4-fluorophenyl)-4-methyl-1H-tetrazol-5(4H)-one (0.078 g, 0.3 mmol) and p-TSA (0.04 g, 0.2 mmol) were added and the reaction mixture was heated to 82° C. for overnight. LCMS analysis indicated the completion of reaction. Purification of the crude product by column chromatography gave the product as p-toluene sulfonic acid salt. The salt was dissolved in 20 ml EtOAc and partitioned with aqueous 2N NaOH solution. The organic layers were separated and dried over $Na_2SO_4$. Removal of the solvents and lyophilization gave the product in 11% yield (0.015 g).

$^1$H NMR (DMSO $d_6$, 300 MHz) δ: 8.43 (s, 1H), 8.29 (s, 1H), 7.65 (d, J=7.3 Hz, 1H), 7.42 (d, J=7.6 Hz, 1H), 7.03 (d, J=11.7 Hz, 1H), 3.99 (br. s, 1H), 3.61 (s, 3H), 2.76-2.80 (m, 1H), 2.10-2.26 (m, 2H), 1.79-1.83 (m, 1H), 1.52-1.70 (m, 4H), 1.34-1.43 (m, 2H), 1.07-1.22 (m, 4H), 1.01 (s, 3H), 0.82-0.86 (m, 2H), 0.63-0.67 (m, 2H); LCMS (m/z): 519 (MH$^+$).

Example 20

Synthesis of (±)-$N^2$-(4-cyclopropyl-2-fluoro-5-(1H-tetrazol-1-yl)phenyl)-5-fluoro-$n^4$-(octahydroindolizin-7-yl)pyrimidine-2,4-diamine (Compound 24)

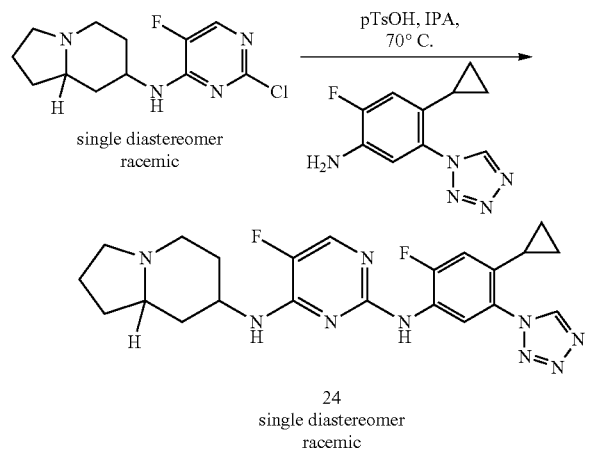

24
single diastereomer
racemic

A mixture of N-(2-chloro-5-fluoropyrimidin-4-yl)octahydroindolizin-7-amine (90 mg, 0.34 mmol), 4-cyclopropyl-2-fluoro-5-(1H-tetrazol-1-yl)benzeneamine (87 mg, 0.35 mmol; prepared according to U.S. patent application Ser. No. 13/188,222, filed Jul. 21, 2011, now U.S. patent application publication US2012/0022092, which is hereby incorporated by reference in its entirety) and para-toluenesulfonic acid monohydrate (63 mg, 0.34 mmol) in isopropyl alcohol (3 ml) were combined in a sealed vial, heated to 70° C. and stirred over a couple of days. After cooling, a precipitate emerged which was filtered to give a crude solid (50 mg). The crude solid was purified further by preparative high-performance liquid chromatography to give a solid. The solid was partitioned between EtOAc (20 ml) and 1N NaOH (20 ml). The aqueous layer was extracted with EtOAc (1×20 ml) and the combined organic extracts were dried (MgSO$_4$), filtered and the solvent removed under vacuum to leave the product (10 mg, 7%) as a solid.

$^1$H NMR (300 MHz; $d_6$-DMSO) δ 9.83 (t, J=0.9 Hz, 1H), 8.59 (s, 1H), 8.20 (d, J=7.7 Hz, 1H), 7.80 (d, J=6.5 Hz, 1H), 7.36 (d, J=8.1 Hz, 1H), 7.04 (d, J=12.2 Hz, 1H), 3.73-3.59 (m, 1H), 2.82-2.75 (m, 2H), 1.87 (q, J=8.4 Hz, 1H), 1.82-1.78 (m, 2H), 1.64-1.41 (m, 5H), 1.39-1.28 (m, 2H), 1.20-1.03 (m, 2H), 0.71-0.65 (m, 2H), 0.57-0.52 (m, 2H); $^{19}$F NMR (282 MHz; $d_6$-DMSO) δ −122.1 (t), −165.5 (d); m/z=454.29 (M+H)$^+$; rt=3.37 min (HPLC protocol-1).

Example 21

Synthesis of (±)-1-(5-(5-fluoro-4-(octahydroindolizin-7-ylamino)pyrimidin-2-ylamino)-2-cyclopropyl-4-fluorophenyl)-4-methyl-1H-tetrazol-5(4H)one (Compound 27)

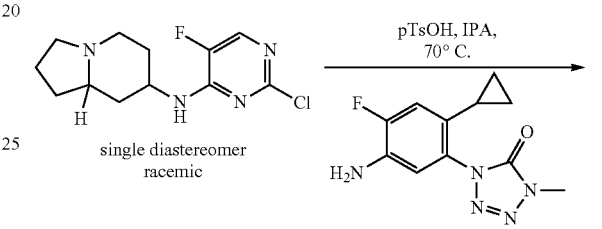

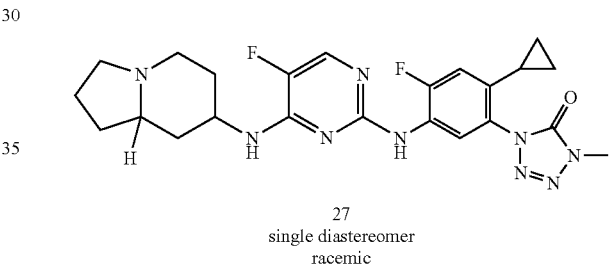

27
single diastereomer
racemic

A mixture of N-(2-chloro-5-fluoropyrimidin-4-yl)octahydroindolizin-7-amine (54 mg, 0.2 mmol), 1-(5-amino-2-cyclopropyl-4-fluorophenyl)-4-methyl-1H-tetrazol-5-one (52 mg, 0.21 mmol; prepared according to US20110130415 pages 43-48, which is hereby incorporated by reference in its entirety) and para-toluenesulfonic acid monohydrate (38 mg, 0.2 mmol) in isopropyl alcohol (3 ml) were combined in a sealed vial, heated to 70° C. and stirred for 2 days. After cooling, the mixture was concentrated under vacuum to leave a crude residue. The residue was purified by preparative high-performance liquid chromatography to give a solid. The solid was partitioned between EtOAc (20 ml) and 1N NaOH (20 ml). The aqueous layer was extracted with EtOAc (2×20 ml) and the combined organic extracts were dried (MgSO$_4$), filtered and the solvent removed in vacuo to leave the product (46 mg, 47%) as a solid after freeze-drying from MeCN/H$_2$O.

$^1$H NMR (300 MHz; $d_6$-DMSO) δ 8.52 (br. s, 1H), 8.08 (d, J=7.7 Hz, 1H), 7.83 (dd, J=3.8, 1.2 Hz, 1H), 7.38 (br. d, J=7.7 Hz, 1H), 6.97 (d, J=12.3 Hz, 1H), 3.85-3.71 (m, 1H), 3.62 (app. d, 3H), 2.97-2.87 (m, 2H), 1.93-1.89 (m, 2H), 1.75-1.50 (m, 7H), 1.31-1.15 (m, 3H), 0.83-0.77 (m, 2H), 0.64-0.59 (m, 2H); $^{19}$F NMR (282 MHz; $d_6$-DMSO) δ −122.0 (t), −165.8 (d); m/z=484.27 (M+H)$^+$; rt=3.22 min (HPLC protocol-1).

Example 22

Synthesis of (±)-N²-(4-cyclopropyl-2-fluoro-5-(5-methyl-1H-tetrazol-1-yl)phenyl)-5-fluoro-n⁴-(octahydroindolizin-7-yl)pyrimidine-2,4-diamine (Compound 28)

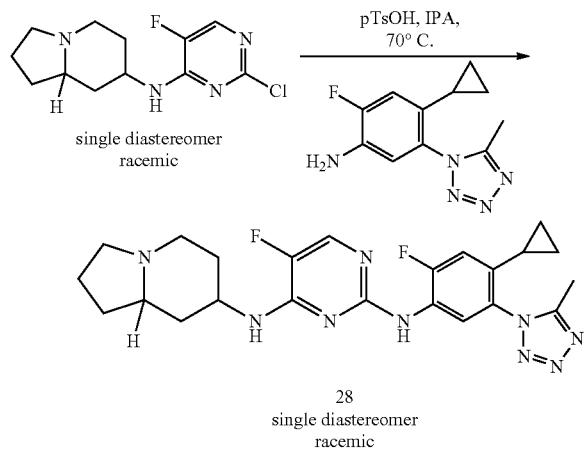

28
single diastereomer
racemic

A mixture of N-(2-chloro-5-fluoropyrimidin-4-yl)octahydroindolizin-7-amine (179 mg, 0.66 mmol), 1-(2-Cyclopropyl-4-fluoro-5-nitrophenyl)-5-methyl-1H-tetrazole (140 mg, 0.66 mmol; prepared according to U.S. patent application Ser. No. 13/188,222, now U.S. patent application publication US2012/0022092) and para-toluenesulfonic acid monohydrate (126 mg, 0.66 mol) in isopropyl alcohol (5 ml) were combined in a sealed vial, heated to 70° C. and stirred for 3 days. After cooling, the mixture was concentrated in vacuo and the crude residue partitioned between 1N NaOH (25 ml) and EtOAc (30 ml). The aqueous layer was extracted with EtOAc (1×30 ml) and the combined organic layers were dried (MgSO₄), filtered and the solvent removed under vacuum to leave a crude solid. The solid was purified by column chromatography on silica gel (ISCO System) using 2M NH₃ in MeOH/CH₂Cl₂ (gradient system from 0:1 to 1:9) as eluent to give the product (190 mg, 61%) as a solid after freeze-drying from MeCN/H₂O.

¹H NMR (300 MHz; d₆-DMSO) δ 8.61 (br. s, 1H), 8.15 (d, J=7.6 Hz, 1H), 7.86-7.84 (m, 1H), 7.41 (br. d, J=8.1 Hz, 1H), 7.04 (d, J=12.3 Hz, 1H), 3.75-3.64 (m, 1H), 2.92-2.82 (m, 2H), 2.41 (s, 3H), 2.05-2.91 (m, 1H), 1.88-1.85 (m, 2H), 1.71-1.40 (m, 6H), 1.27-1.08 (m, 3H), 0.79-0.70 (m, 2H), 0.68-0.62 (m, 2H); ¹⁹F NMR (282 MHz; d₆-DMSO) δ −122.4 (t), −165.6 (d); m/z=468.28 (M+H)⁺; rt=3.40 min (HPLC protocol-1).

Example 23

Synthesis of (±)-N²-(4-cyclopropyl-2-fluoro-5-(1H-tetrazol-1-yl)phenyl)-5-fluoro-n⁴-(octahydro-5,5-dimethylindolizin-7-yl)pyrimidine-2,4-diamine (Compound 53)

53
single diastereomer
racemic

A mixture of N-(2-chloro-5-fluoropyrimidin-4-yl)octahydro-5,5-dimethylindolizin-7-amine hydrochloride (168 mg, 0.5 mmol), 4-cyclopropyl-2-fluoro-5-(1H-tetrazol-1-yl)benzeneamine (153 mg, 0.7 mmol; prepared according to U.S. patent application Ser. No. 13/188,222, filed Jul. 21, 2011, now U.S. patent application publication US2012/0022092) and para-toluenesulfonic acid monohydrate (95 mg, 0.5 mmol) in isopropyl alcohol (3 ml) were combined in a sealed vial, heated to 70° C. and stirred for 4 days. After cooling, the mixture was filtered and the filter cake washed with cold isopropyl alcohol. The filter cake was suspended in EtOAc (50 ml) and 1N NaOH (50 ml) was added. The aqueous and organic layers were partitioned and the aqueous layer was extracted with EtOAc (30 ml). The combined organic extracts were dried (Na₂SO₄), filtered and the solvent removed under vacuum to leave a residue, which was freeze-dried from MeCN/H₂O to give the product (162 mg, 67%) as a solid.

¹H NMR (300 MHz; d₆-DMSO) δ 9.86 (m, 1H), 8.59 (s, 1H), 8.09 (d, J=7.6 Hz, 1H), 7.83 (d, J=3.8 Hz, 1H), 7.26 (br. d, J=8.0 Hz, 1H), 7.09 (d, J=12.1 Hz, 1H), 4.00-3.88 (m, 1H), 2.81-2.74 (m, 1H), 2.16 (q, J=8.2 Hz, 1H), 1.99-1.83 (m, 2H), 1.72-1.32 (m, 6H), 1.20-0.94 (m, 2H), 1.01 (s, 3H), 0.75-0.71 (m, 2H), 0.69 (s, 3H), 0.63-0.55 (m, 2H); ¹⁹F NMR (282 MHz; d₆-DMSO) δ −165.7 (s), −120.9 (t); m/z=482.33 (M+H)⁺; rt=3.44 min (HPLC protocol-1).

Example 24

Resolution of (±)-N²-(4-cyclopropyl-2-fluoro-5-(1H-tetrazol-1-yl)phenyl)-5-fluoro-n⁴-(octahydro-5,5-dimethylindolizin-7-yl)pyrimidine-2,4-diamine (Compounds 54 and 55)

A small quantity of racemic N²-(4-cyclopropyl-2-fluoro-5-(1H-tetraol-1-yl)phenyl)-5-fluoro-N⁴-(octahydro-5,5-dimethylindolizin-7-yl)pyrimidine-2,4-diamine (40 mg) was purified by chiral high-performance liquid chromatography using the conditions below to give individual enantiomers.

Chiral HPLC Conditions:
Column: Daicel Chemical Industries, Chiracel OJ 4.6×250 mm
Mobile phase: 1:1 MeOH/EtOH containing 0.1% diethylamine
Flow rate: 0.5 ml/min
Run time: 30 minutes
Temperature: room temperature
Detection: Waters 996 PDA
HPLC: Waters 2690 Separations Module
Compound 54
Retention time of first eluting isomer=9.30 min (15 mg);
Data for first eluting enantiomer from chiral column: ¹H NMR (300 MHz; d₆-DMSO) δ 9.87 (s, 1H), 8.59 (br. s, 1H), 8.08 (d, J=7.5 Hz, 1H), 7.83 (d, J=3.7 Hz, 1H), 7.33-7.24 (br. s, 1H), 7.09 (d, J=12.2 Hz, 1H), 4.03-3.87 (m, 1H), 2.86-2.72

(m, 1H), 2.29-2.14 (m, 1H), 2.00-1.83 (m, 2H), 1.73-1.36 (m, 6H), 1.22-1.03 (m, 5H), 0.78-0.66 (m, 5H), 0.64-0.56 (m, 2H); $^{19}$F NMR (282 MHz; d$_6$-DMSO) δ −165.7, −120.8; m/z=482.44 (M+H)$^+$; rt=3.58 min (HPLC protocol-1).

Compound 55

Retention time for second eluting isomer=11.74 min (18 mg); Data same as for 1$^{st}$ eluting isomer.

Example 25

Synthesis of (±)-2-(4-cyclopropyl-2-fluoro-5-(1H-tetrazol-1-yl)phenylamino)-4-(octahydro-5,5-dimethylindolizin-7-ylamino)pyrimidine-5-carbonitrile (Compound 56)

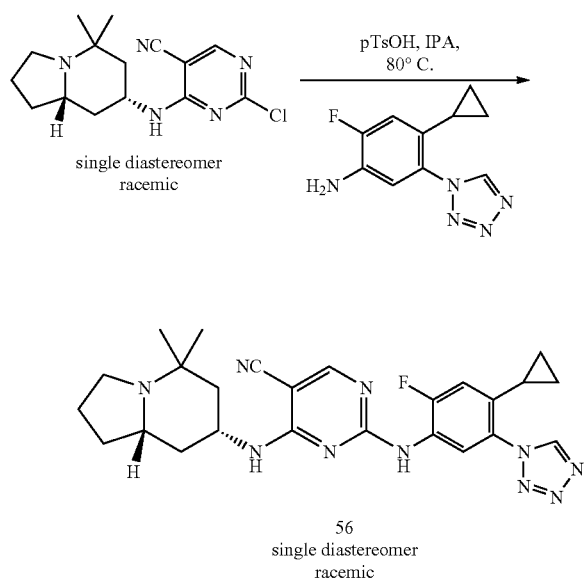

A mixture of (±)-2-chloro-4-(octahydro-5,5-dimethylindolizin-7-ylamino)pyrimidine-5-carbonitrile (60 mg of 70% pure material from previous step), 4-cyclopropyl-2-fluoro-5-(1H-tetrazol-1-yl)benzeneamine (65 mg, 0.3 mmol; prepared according to U.S. patent application Ser. No. 13/188,222, filed Jul. 21, 2011, now U.S. patent application publication US2012/0022092) and para-toluenesulfonic acid monohydrate (37 mg, 0.2 mmol) in isopropyl alcohol (3 ml) were combined in a sealed vial, heated to 80° C. and stirred for 4 hours. After cooling, a precipitate emerged which was filtered. The filter cake was suspended in EtOAc (30 ml) and 1N NaOH (50 ml). The aqueous and organic layers were partitioned and the aqueous layer was extracted with EtOAc (2×25 ml). The combined organic extracts were dried (MgSO$_4$), filtered and the solvent removed under vacuum to leave a solid. The solid was freeze-dried from MeCN/H$_2$O to give the product (26 mg) as a solid.

$^1$H NMR (300 MHz; d$_6$-DMSO) δ 9.85 (m, 1H), 9.51 (br. s, 1H), 8.30 (s, 1H), 7.80 (d, J=7.3 Hz, 1H), 7.44 (d, J=7.3 Hz, 1H), 7.14 (d, J=11.8 Hz, 1H), 4.08-3.89 (m, 1H), 2.83-2.71 (m, 1H), 2.28-2.13 (m, 1H), 2.06-1.88 (m, 1H), 1.84-1.73 (m, 1H), 1.71-1.50 (m, 3H), 1.47-1.34 (m, 2H), 1.21-1.07 (m, 3H), 1.00 (s, 3H), 0.75-0.59 (m, 7H); $^{19}$F NMR (282 MHz; d$_6$-DMSO) δ −117.3 (t); m/z=489.34 (M+H)$^+$; rt=4.01 min (HPLC protocol-1).

Example 26

Synthesis of N2-(4-cyclopropyl-2-fluoro-5-(4,5-dihydro-4-methyl-5-oxotetrazol-yl)phenylamino)-5-fluoro-N4-(Octahydro-5,5-dimethylindolizin-7-ylamino)pyrimidine-2,4-diamine (Compound 26)

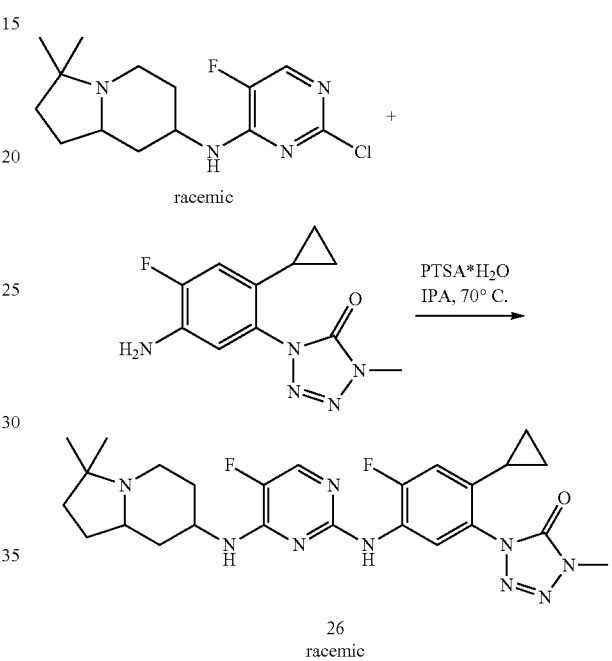

A mixture of N-(2-chloro-5-fluoropyrimidin-4-yl)-octahydro-3,3-dimethylindolizin-7-amine (Diastereomer D1 97% dr; 52 mg, 0.174 mmol, 1 equiv), 1-(5-amino-2-cyclopropyl-4-fluorophenyl)-4-methyl-1H-tetrazol-5(4H)-one (Described in: WO 2011/068898, which is hereby incorporated by reference in its entirety. 43 mg, 0.174 mmol, 1 equiv), and PTSA monohydrate (33 mg, 0.174 mmol, 1 equiv) in IPA (1 ml) were heated to 100° C. for 4 days. After cooling to ambient temperature, the crude mixture was concentrated to dryness and taken in water, EtOAc, and 1N NaOH. The layers were separated. The organic layer was washed with 1N NaOH (×2), dried over Na$_2$SO$_4$, filtered, and concentrated to dryness. The crude product was purified by flash chromatography and eluted with DCM:2M NH$_3$/MeOH=100:0 to 96:4 using 1% 2M NH$_3$/MeOH increments to give compound 1-(5-(5-fluoro-4-(octahydro-3,3-dimethylindolizin-7-ylamino)pyrimidin-2-ylamino)-2-cyclopropyl-4-fluorophenyl)-4-methyl-1H-tetrazol-5(4H)-one (Compound 26) (>90% dr, 53 mg, 60%) as a solid.

$^1$H NMR (300 MHz; d$_6$-DMSO) δ 8.59 (s, 1H), 8.10-8.09 (d, J=8.4 Hz), 7.85-7.86 (d, J=3.6 Hz), 6.95-7.00 (m, 2H), 4.11 (bs, 1H), 3.62 (s, 1H), 2.42-2.71 (m, 2H), 1.49-2.00 (m, 8H), 1.01-1.22 (m, 2H), 1.03-1.06 (m, 3H), 0.823-0.871 (m, 5H), 0.630-0.645 (m, 2H); $^{19}$F NMR (282 MHz; d$_6$-DMSO) δ −122.0 (t), −164.7 (s); m/z=512 (M+H)$^+$.

Example 27

Chiral HPLC resolution of 1-(5-(5-fluoro-4-(octahydro-3,3-dimethylindolizin-7-ylamino)pyrimidin-2-ylamino)-2-cyclopropyl-4-fluorophenyl)-4-methyl-1H-tetrazol-5(4H)-one (Compounds 34 and 35)

Chiral HPLC resolution of 1-(5-(5-fluoro-4-(octahydro-3,3-dimethylindolizin-7-ylamino)pyrimidin-2-ylamino)-2-cyclopropyl-4-fluorophenyl)-4-methyl-1H-tetrazol-5(4H)-one (Compound 26) (>90% dr, 35 mg) to enantiomers was performed.

Chiral HPLC method: Column: Chiralcel-OJ, 4.6×250 mm, with guard. Mobil phase: 95% Hexane, 2.4% methanol, 2.5% ethanol 0.1% triethylamine. Flow rate: 0.5 ml/min. Injection volume: 3 μL. Concentration: approx 5 mg/ml. Detection: UV at 254 nm.

Compound 34

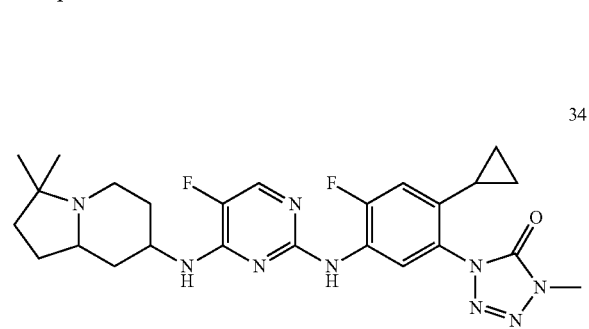

Single enantiomer#1

Compound 34: (>99% ee, 9.5 mg) has Rt=21.86 min.

$^{1}$H NMR (300 MHz; $d_6$-DMSO) δ 8.59 (s, 1H), 8.10-8.09 (d, J=8.4 Hz), 7.85-7.86 (d, J=3.6 Hz), 6.95-7.00 (m, 2H), 4.11 (bs, 1H), 3.62 (s, 1H), 2.42-2.71 (m, 2H), 1.49-2.00 (m, 8H), 1.01-1.22 (m, 2H), 1.03-1.06 (m, 3H), 0.823-0.871 (m, 5H), 0.630-0.645 (m, 2H); $^{19}$F NMR (282 MHz; $d_6$-DMSO) δ −122.0 (t), −164.7 (s); m/z=512 (M+H)$^+$.

Compound 35:

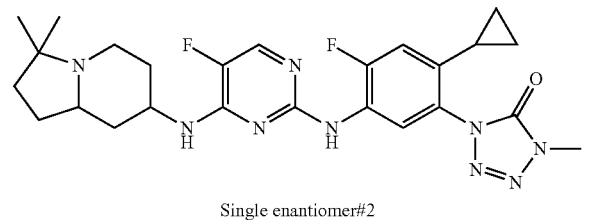

Single enantiomer#2

Compound 35: (>97% ee, 10.7 mg) has Rt=26.56 min.

$^{1}$H NMR (300 MHz; $d_6$-DMSO) δ 8.59 (s, 1H), 8.10-8.09 (d, 1H, J=8.4 Hz), 7.85-7.86 (d, 1H, J=3.6 Hz), 6.95-7.00 (m, 2H), 4.11 (bs, 1H), 3.62 (s, 1H), 2.42-2.71 (m, 2H), 1.49-2.00 (m, 8H), 1.01-1.22 (m, 2H), 1.03-1.06 (m, 3H), 0.823-0.871 (m, 5H), 0.630-0.645 (m, 2H); $^{19}$F NMR (282 MHz; $d_6$-DMSO) δ −122.0 (t), −164.7 (s); m/z=512 (M+H)$^+$.

Example 28

Synthesis of 1-(5-(5-fluoro-4-(hexahydro-5,5-dimethylindolizin-3(5H)-one-7-ylamino)pyrimidin-2-ylamino)-2-cyclopropyl-4-fluorophenyl)-4-methyl-1H-tetrazol-5(4H)-one (Compounds 31-33)

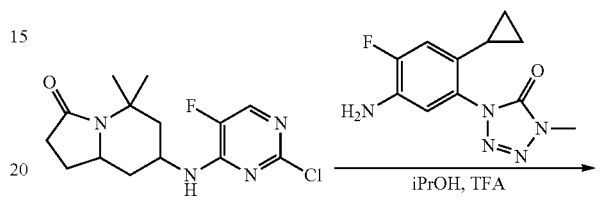

Preparation of 1-(5-(5-fluoro-4-(hexahydro-5,5-dimethylindolizin-3(5H)-one-7-ylamino)pyrimidin-2-ylamino)-2-cyclopropyl-4-fluorophenyl)-4-methyl-1H-tetrazol-5(4H)-one (Compound 31)

A mixture of 7-(2-chloro-5-fluoropyrimidin-4-ylamino)-hexahydro-5,5-dimethylindolizin-3(5H)-one isomer A (cis) (50 mg), 1-(5-amino-2-cyclopropyl-4-fluorophenyl)-4-methyl-1H-tetrazol-5(4H)-one (50 mg) and TFA (5 drops) in isopropanol (1 ml) was heated at 100° C. overnight in a sealed vial. After allowing to cool to room temperature, the solvent was removed in vacuo and the residue was purified by Combiflash chromatography (2.0 M ammonia methanol in dichloromethane=0-30%) to give product as racemic mixture.

$^{1}$H NMR (300 MHz; $d_6$-DMSO) δ 8.55 (s, 1H), 7.88 (d, J=7.8 Hz, 1H), 7.85 (d, J=3.9 Hz, 1H), 7.34 (d, J=7.8 Hz, 1H), 7.00 (d, J=12.0 Hz, 1H), 4.06-4.04 (m, 1H), 3.59 (s, 3H), 2.14-1.94 (m, 5H), 1.64-1.59 (m, 1H), 1.56 (s, 3H), 1.48-1.12 (m, 4H), 1.02 (s, 3H), 0.81 (dd, J=2.1, 8.7 Hz, 2H), 0.61 (q,

Preparation of 1-(5-(5-fluoro-4-(hexahydro-5,5-dimethylindolizin-3(5H)-one-7-ylamino)pyrimidin-2-ylamino)-2-cyclopropyl-4-fluorophenyl)-4-methyl-1H-tetrazol-5(4H)-one (Compound 32)

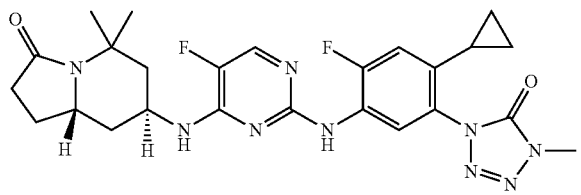 [SMILES: Cn1nnn(-c2cc(Nc3ncc(F)c(N[C@H]4C[C@@H]5CCC(=O)N5C(C)(C)C4)n3)c(F)cc2C2CC2)c1=O]

A mixture of 7-(2-chloro-5-fluoropyrimidin-4-ylamino)-hexahydro-5,5-dimethylindolizin-3(5H)-one isomer B (trans) (100 mg), 1-(5-amino-2-cyclopropyl-4-fluorophenyl)-4-methyl-1H-tetrazol-5(4H)-one (100 mg) and TFA (5 drops) in isopropanol (1 ml) was heated at 100° C. overnight in a sealed vial. After allowing to cool to room temperature, the solvent was removed in vacuo and the residue was purified by Combiflash chromatography (2.0 M ammonia methanol in dichloromethane=0-30%) to give product as racemic mixture.

$^1$H NMR (300 MHz; d$_6$-DMSO) δ 8.64 (s, 1H), 8.03 (d, J=7.8 Hz, 1H), 7.88 (d, J=3.9 Hz, 1H), 7.57 (d, J=5.7 Hz, 1H), 6.99 (d, J=12.3 Hz, 1H), 4.22 (m, 1H), 3.89 (m, 1H), 3.59 (s, 3H), 2.26-1.53 (m, 9H), 1.32 (s, 3H), 1.24 (s, 3H), 0.81 (d, J=8.4 Hz, 2H), 0.62 (d, J=3.3 Hz, 2H); LC-MS: purity: 98.22%; MS (m/e): 526.37 (M+H)$^+$; m/z=524.41 (M−H)$^+$.

Preparation of 1-(5-(5-fluoro-4-(hexahydro-5,5-dimethylindolizin-3(5H)-one-7-ylamino)pyrimidin-2-ylamino)-2-cyclopropyl-4-fluorophenyl)-4-methyl-1H-tetrazol-5(4H)-one formate (Compound 33)

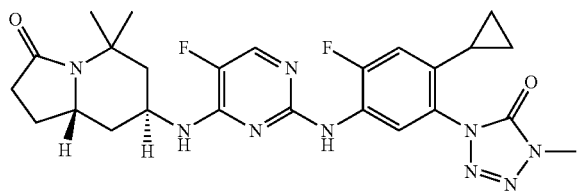 [SMILES: Cn1nnn(-c2cc(Nc3ncc(F)c(N[C@H]4C[C@@H]5CCC(=O)N5C(C)(C)C4)n3)c(F)cc2C2CC2)c1=O]

$^1$H NMR (300 MHz; d$_6$-DMSO) δ 8.58 (s, 1H), 8.04 (d, J=7.8 Hz, 1H), 7.86 (d, J=3.9 Hz, 1H), 7.50 (d, J=7.2 Hz, 1H), 6.99 (d, J=12.3 Hz, 1H), 4.21 (m, 1H), 3.90 (m, 1H), 3.59 (s, 3H), 2.26-1.54 (m, 9H), 1.32 (s, 3H), 1.25 (s, 3H), 0.81 (d, J=8.1 Hz, 2H), 0.61 (d, J=3.6 Hz, 2H); LC-MS: purity: 98.65%; MS (m/e): 526.37 (M+H)$^+$; m/z=524.37 (M−H)$^+$.

Example 29

Preparation of Anilines for Synthesis of Compounds

Certain anilines for the synthesis of the present compounds were prepared as illustrated in the scheme below:

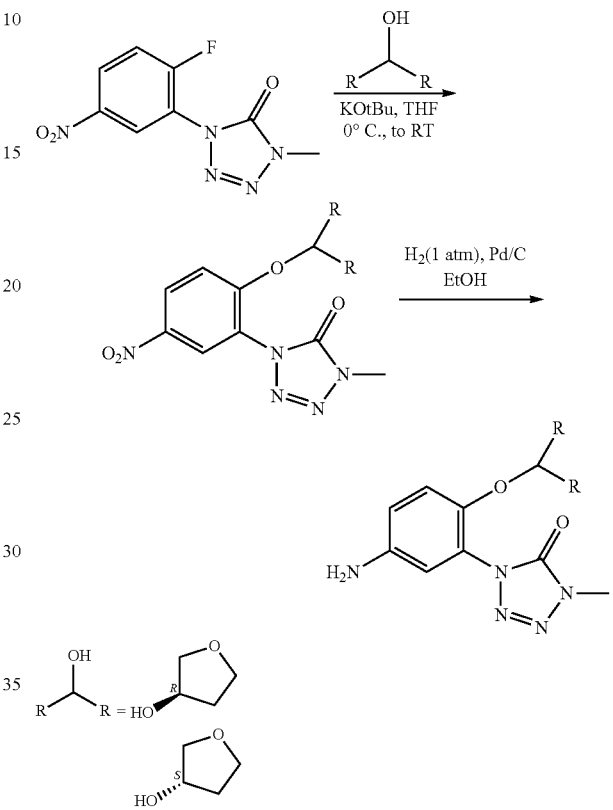

Preparation of 1-(2-((R)-Tetrahydrofuran-3-yloxy)-5-nitrophenyl)-4-methyl-1H-tetrazol-5(4H)-one (R)-(−)-3-Hydroxytetrahydrofuran (440 mg, 5 mmol, 2 equiv) in THF (15 ml) under argon gas, was cooled to 0° C. Potassium tert-butoxide (617 mg, 5.5 mmol, 2.2 equiv) was added in one portion, and the reaction mixture was stirred for 20 minutes at 0° C. Then 1-(2-fluoro-5-nitrophenyl)-4-methyl-1H-tetrazol-5(4H)-one (Described in: WO 2011/068898. 598 mg, 2.5 mmol, 1 equiv) was added in one portion, and the reaction mixture was stirred for 10 minutes at 0° C. and allowed to warm up to ambient temperature over 2 hours. The reaction mixture was concentrated, and the residue was taken in DCM and water. The layers were separated, and the organic layer was washed with water (×2), dried over Na$_2$SO$_4$, filtered, and concentrated to provide 1-(2-((R)-tetrahydrofuran-3-yloxy)-5-nitrophenyl)-4-methyl-1H-tetrazol-5(4H)-one (723 mg, 94%) as a yellow solid that was used without further purification.

$^1$H NMR (300 MHz; d$_6$-DMSO) δ 8.41-8.47 (m, 2H), 7.51-7.54 (d, 1H, J=9 Hz), 5.31-5.4 (t, 1H, J=3.6 Hz), 3.88-3.93 (dd, 1H, J=4.2 Hz, J=10.5 Hz), 3.70-3.74 (m, 3H), 3.62 (s, 3H), 2.20-2.27 (m, 1H), 1.89-1.93 (m, 1H); m/z=308 (M+H)$^+$.

Preparation of 1-(2-((S)-Tetrahydrofuran-3-yloxy)-5-nitrophenyl)-4-methyl-1H-tetrazol-5(4H)-one (S)-(+)-3-Hydroxytetrahydrofuran (440 mg, 5 mmol, 2 equiv) in THF (15 ml) under argon gas, was cooled to 0° C. Potassium tert-butoxide (617 mg, 5.5 mmol, 2.2 equiv) was added in one portion, and the reaction mixture was stirred for 20 minutes at 0° C. Then, fluoro tetrazole (598 mg, 2.5 mmol, 1 equiv) was added in one portion, and the reaction mixture was stirred for 10 minutes at 0° C. and allowed to warm up to ambient temperature over 2 hours. The reaction mixture was concentrated, and the residue was taken in DCM and water. The layers were separated, and the organic layer was washed with water (×2), dried over $Na_2SO_4$, filtered, and concentrated to provide 1-(2-((S)-tetrahydrofuran-3-yloxy)-5-nitrophenyl)-4-methyl-1H-tetrazol-5(4H)-one (764 mg, 98%) as a yellow solid that was used without further purification.

$^1$H NMR (300 MHz; $d_6$-DMSO) δ 8.41-8.47 (m, 2H), 7.51-7.54 (d, 1H, J=9 Hz), 5.31-5.4 (t, 1H, J=3.6 Hz), 3.88-3.93 (dd, 1H, J=4.2 Hz, J=10.5 Hz), 3.70-3.74 (m, 3H), 3.62 (s, 3H), 2.20-2.27 (m, 1H), 1.89-1.93 (m, 1H); m/z=308 (M+H)$^+$.

Preparation of 1-(2-((R)-Tetrahydrofuran-3-yloxy)-5-aminophenyl)-4-methyl-1H-tetrazol-5(4H)-one A round-bottom flask was charged with 1-(2-((R)-tetrahydrofuran-3-yloxy)-5-nitrophenyl)-4-methyl-1H-tetrazol-5(4H)-one (723 mg, 2.35 mmol), EtOH (25 ml), and 10% Pd/C (50% in water, Degussa type E101; 145 mg, 20 wt % by weight of the starting nitro compound) giving a suspension. The flask was sealed with a rubber septum, degassed, and back-filled with $H_2$ (×3) from a balloon filled with $H_2$. The reaction mixture was stirred for 2 hours using a $H_2$ filled balloon. The reaction mixture was filtered through a pad of Celite, and the pad of Celite was rinsed with MeOH. The filtrate was evaporated to dryness to provide 1-(2-((R)-tetrahydrofuran-3-yloxy)-5-aminophenyl)-4-methyl-1H-tetrazol-5(4H)-one (646 mg, 99%) as a dark-brown solid that was used without further purification.

$^1$H NMR (300 MHz; $d_6$-DMSO) δ 6.96-6.99 (m, 1H), 6.89-6.73 (m, 1H), 6.55-6.60 (m, 1H), 5.06 (bs, 2H), 4.77-4.85 (m, 1H), 3.55-3.77 (m, 7H), 1.94-2.03 (m, 1H), 1.78-1.86 (m, 1H); m/z=278 (M+H)$^+$.

Preparation of 1-(2-((S)-Tetrahydrofuran-3-yloxy)-5-aminophenyl)-4-methyl-1H-tetrazol-5(4H)-one A round-bottom flask was charged with 1-(2-((S)-tetrahydrofuran-3-yloxy)-5-nitrophenyl)-4-methyl-1H-tetrazol-5(4H)-one (764 mg, 2.49 mmol), EtOH (25 ml), and 10% Pd/C (50% in water, Degussa type E101; 153 mg, 20 wt % by weight of the starting nitro compound) giving a suspension. The flask was sealed with a rubber septum, degassed, and back-filled with $H_2$ (×3) from a balloon filled with $H_2$. The reaction mixture was stirred for 2 hours using a $H_2$ filled balloon. The reaction mixture was filtered through a pad of Celite, and the pad of Celite was rinsed with MeOH. The filtrate was evaporated to dryness to provide 1-(2-((S)-tetrahydrofuran-3-yloxy)-5-aminophenyl)-4-methyl-1H-tetrazol-5(4H)-one (677 mg, 98%) as a dark-brown solid that was used without further purification.

$^1$H NMR (300 MHz; $d_6$-DMSO) δ 6.96-6.99 (m, 1H), 6.89-6.73 (m, 1H), 6.55-6.60 (m, 1H), 5.06 (bs, 2H), 4.77-4.85 (m, 1H), 3.55-3.77 (m, 7H), 1.94-2.03 (m, 1H), 1.78-1.86 (m, 1H); m/z=278 (M+H)$^+$.

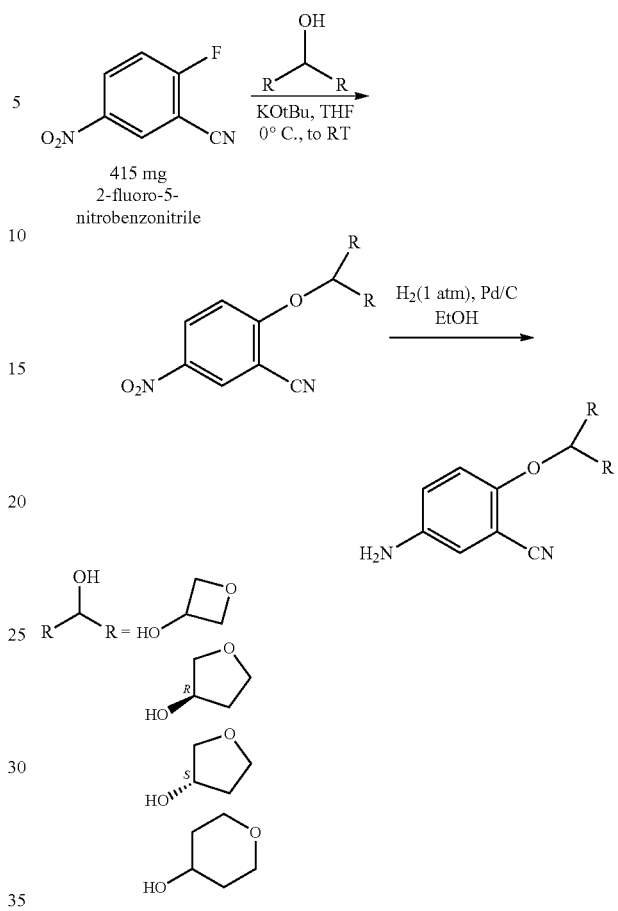

Preparation of 5-Nitro-2-(oxetan-3-yloxy)benzonitrile

General procedure: 3-Hydroxy oxetane (370 mg, 5 mmol, 2 equiv) in THF (15 ml) under argon gas, was cooled to 0° C. Potassium tert-butoxide (617 mg, 5.5 mmol, 2.2 equiv) was added in one portion, and the reaction mixture was stirred for 20 minutes at 0° C. Then 2-fluoro-5-nitrobenzonitrile (415 mg, 2.5 mmol, 1 equiv) was added in one portion, and the reaction mixture was stirred for 10 minutes at 0° C. and allowed to warm up to ambient temperature over 1 hour. The reaction mixture was concentrated, and the residue was taken in DCM and water. The layers were separated, and the organic layer was washed with water (×2), dried over $Na_2SO_4$, filtered, and concentrated to provide 5-nitro-2-(oxetan-3-yloxy)benzonitrile (495 mg, 90%) as a brown-yellow solid that was used without further purification.

$^1$H NMR (300 MHz; $d_6$-DMSO) δ 8.74-8.75 (m, 1H), 8.42-8.47 (m, 1H), 7.09-7.12 (dd, 1H, J=0.9 Hz, J=9.3 Hz), 5.56-5.63 (m, 1H), 4.96-5.00 (m, 2H), 4.59-4.63 (m, 2H); m/z=221 (M+H)$^+$.

Following the general procedure described above, the following compounds were prepared:

Preparation of 2-((R)-tetrahydrofuran-3-yloxy)-5-nitrobenzonitrile (544 mg, 93%) from (R)-(−)-3-hydroxytetrahydrofuran.
$^1$H NMR (300 MHz; $d_6$-DMSO) δ 8.67-8.71 (m, 1H), 8.46-

8.50 (m, 1H), 7.45-7.48 (d, 1H, J=9.6 Hz), 5.33-5.40 (m, 1H), 3.74-3.95 (m, 4H), 2.27-2.40 (m, 1H), 1.89-2.06 (m, 1H); m/z=235 (M+H)$^+$.

Preparation of 2-((S)-Tetrahydrofuran-3-yloxy)-5-nitrobenzonitrile (544 mg, 93%) from S)-(+)-3-hydroxytetrahydrofuran. $^1$H NMR (300 MHz; d$_6$-DMSO) δ 8.67-8.71 (m, 1H), 8.46-8.50 (m, 1H), 7.45-7.48 (d, 1H, J=9.6 Hz), 5.33-5.40 (m, 1H), 3.74-3.95 (m, 4H), 2.27-2.40 (m, 1H), 1.89-2.06 (m, 1H); m/z=235 (M+H)$^+$.

Preparation of 5-Nitro-2-(tetrahydro-2H-pyran-4-yloxy)benzonitrile (510 mg, 82%) from 4-hydroxytetrahydropyran. $^1$H NMR (300 MHz; d$_6$-DMSO) δ 8.68-8.69 (d, 1H, J=3 Hz), 8.43-8.47 (m, 1H), 7.56-7.59 (d, 1H, J=9.3 Hz), 4.97-5.05 (m, 1H), 3.82-3.87 (m, 2H), 3.50-3.60 (m, 2H), 1.99-2.06 (m, 2H), 1.62-1.72 (m, 2H); m/z=248 (M+H)$^+$.

Preparation of 5-Amino-2-(oxetan-3-yloxy)benzonitrile

General procedure: A round-bottom flask was charged with 5-nitro-2-(oxetan-3-yloxy)benzonitrile (495 mg, 2.25 mmol), EtOH (20 ml), and 10% Pd/C (50% in water, Degussa type E101; 100 mg, 20 wt % by weight of the starting nitro compound) giving a suspension. The flask was sealed with a rubber septum, degassed, and back-filled with H$_2$ (×3) from a balloon filled with H$_2$. The reaction mixture was stirred for 1 hour using a H$_2$ filled balloon. The reaction mixture was filtered through a pad of Celite, and the pad of Celite was rinsed with MeOH. The filtrate was evaporated to dryness to provide 5-amino-2-(oxetan-3-yloxy)benzonitrile (420 mg, 98%) as a pale yellow solid that was used without further purification.

$^1$H NMR (300 MHz; d$_6$-DMSO) δ 6.77-6.81 (m, 2H), 6.53-6.60 (m, 1H), 5.18-5.25 (p, 1H, J=6 Hz), 5.12 (bs, 2H), 4.84-4.89 (t, 2H, J=6.3 Hz), 4.50-4.51 (t, 2H, J=6.2 Hz); m/z=191 (M+H)$^+$.

Following the general procedure described above, the following compounds were prepared:

Preparation of 2-((R)-Tetrahydrofuran-3-yloxy)-5-aminobenzonitrile (465 mg, 98%) from 2-((R)-tetrahydrofuran-3-yloxy)-5-nitrobenzonitrile. $^1$H NMR (300 MHz; d$_6$-DMSO) δ 6.90-6.99 (m, 1H), 6.77-6.85 (m, 2H), 5.10 (bs, 2H), 4.93-4.99 (m, 1H), 3.70-3.87 (m, 4H), 2.07-2.19 (m, 1H), 1.89-1.96 (m, 1H); m/z=205 (M+H)$^+$.

Preparation of 2-((S)-Tetrahydrofuran-3-yloxy)-5-aminobenzonitrile (466 mg, 98%) from 2-((S)-tetrahydrofuran-3-yloxy)-5-nitrobenzonitrile. $^1$H NMR (300 MHz; d$_6$-DMSO) δ 6.90-6.99 (m, 1H), 6.77-6.85 (m, 2H), 5.10 (bs, 2H), 4.93-4.99 (m, 1H), 3.70-3.87 (m, 4H), 2.07-2.19 (m, 1H), 1.89-1.96 (m, 1H); m/z=205 (M+H)$^+$.

Preparation of 5-Amino-2-(tetrahydro-2H-pyran-4-yloxy)benzonitrile (361 mg, 81%) from 5-Nitro-2-(tetrahydro-2H-pyran-4-yloxy)benzonitrile. $^1$H NMR (300 MHz; d$_6$-DMSO) δ 7.00-7.03 (d, 1H, J=8.7 Hz), 6.73-6.84 (m, 2H), 5.11 (bs, 2H), 4.42-4.48 (m, 1H), 3.79-3.85 (m, 2H), 3.40-3.47 (m, 2H), 1.86-1.98 (m, 2H), 1.50-1.61 (m, 2H); m/z=219 (M+H)$^+$.

Preparation of 4-fluoro-2-isopropoxy-1-nitrobenzene

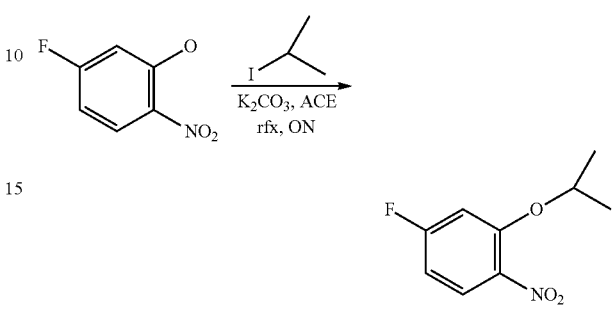

A mixture of 5-fluoro-2-nitrophenol (50.0 g, 318 mmol, 1 equiv), 2-iodopropane (96.0 mL, 955 mmol, 3 equiv), and K$_2$CO$_3$ (132.0 g, 955 mmol, 3 equiv) in acetone (1 L) was heated to reflux for ON. After cooling to RT, the solid was filtered-off and rinsed with DCM, then the filtrate was concentrated to dryness. The residue was taken in water, EtOAc, and 1N NaOH. The layers were separated, and the organic layer was washed with 1N NaOH 1×. The organic layer was dried over Na$_2$SO$_4$, filtered, and concentrated to dryness to provide 4-fluoro-2-isopropoxy-1-nitrobenzene (49.3 g, 78%) as a yellow-brown liquid that was used without further purification. $^1$H NMR (300 MHz; d$_6$-DMSO) δ 7.91-7.96 (dd, 1H, J=6.3 Hz, 9.0 Hz), 7.31-7.35 (dd, 1H, J=2.4 Hz, 11 Hz), 6.88-6.95 (m, 1H), 4.77-4.89 (hep, 1H, J=6.0 Hz), 1.27-1.29 (d, 6H, J=6.0 Hz); $^{19}$F NMR (282 MHz; d$_6$-DMSO) δ −102.4 (sextet); m/z=200 (M+H)$^+$.

Preparation of 4-fluoro-2-isopropoxybenzenamine

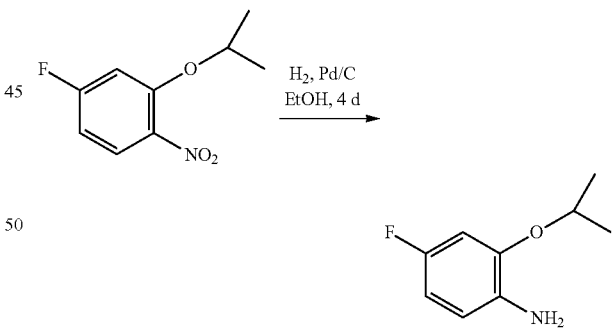

A round-bottom flask was charged with 4-fluoro-2-isopropoxy-1-nitrobenzene (49.3 g, 248 mmol), EtOH (600 mL), and 10% Pd/C (50% in water, Degussa type E101; 10 g, 20 wt % by weight of the starting nitro compound). The flask was sealed with a rubber septum, degassed, and back-filled with H$_2$ (×3) from a balloon filled with H$_2$. The reaction was stirred for 4 d using a H$_2$ filled balloon. The reaction mixture was filtered through a pad of celite, and the pad of celite was rinsed with MeOH. The filtrate was evaporated to dryness to provide 4-fluoro-2-isopropoxybenzenamine (41.0 g, 98%) as a brown liquid that was used without further purification. $^1$H NMR (300 MHz; d$_6$-DMSO) δ 6.67-6.72 (dd, 1H, J=2.7 Hz, 11 Hz), 6.55-6.60 (dd, 1H, J=6.0 Hz, 8.7 Hz), 6.43-6.49 (td, 1H, J=2.7 Hz, 8.4 Hz), 4.47-4.55 (m, 3H), 1.23-1.25 (d, 6H, J=6.0 Hz); $^{19}$F NMR (282 MHz; d$_6$-DMSO) δ −127.4 (sextet); m/z=170 (M+H)$^+$.

Preparation of 1-(4-fluoro-2-isopropoxyphenyl)-1H-tetrazol-5(4H)-one

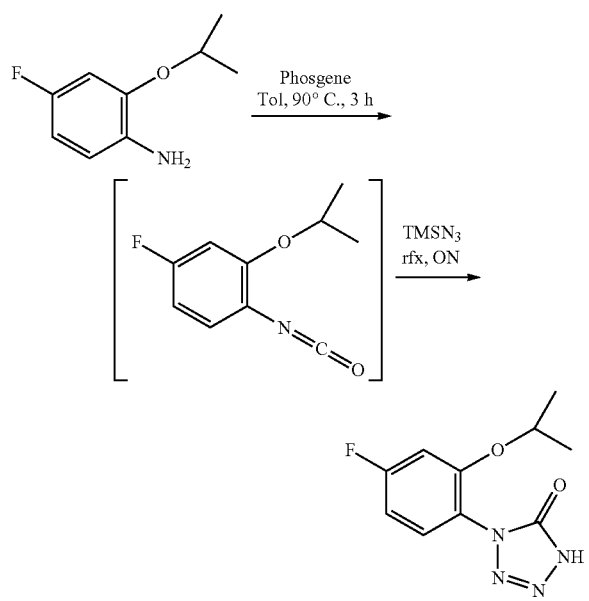

Step 1: Phosgene (20% in toluene; 63 mL, 118.2 mmol, 2 equiv) was cooled to −10° C. (ice/MeOH) under argon. Then 4-fluoro-2-isopropoxybenzenamine (10.0 g, 59.1 mmol, 1 equiv) was added dropwise, and the reaction mixture was stirred at −10° C. for 15 min then heated to 90° C. for 3 h under argon. After cooling, the reaction mixture was evaporated to dryness, and the crude 4-fluoro-1-isocyanato-2-isopropoxybenzene was dried in vacuo.

Step 2: This reaction with TMS-N$_3$ was performed behind a blast shield. The crude 4-fluoro-1-isocyanato-2-isopropoxybenzene was placed under argon and trimethylsilylazide (16 mL, 118.2 mmol, 2 equiv) was added. The reaction mixture was heated to refluxed for ON under argon. After cooling to RT, the reaction mixture was concentrated under vacuum, and the residue was charged with saturated NaHCO$_3$ (100 mL) and stirred vigorously for 5-10 min, then the basic reaction mixture was diluted with EtOAc. The layers were separated, and the organic layer was monitored by TLC to confirm that all the product had been extracted by the saturated NaHCO$_3$ solution. EtOAc was added to the combined basic aqueous extracts, and the pH was adjusted to <3 using 6N HCl. The aqueous and organic layers were partitioned, and the aqueous layer was extracted with EtOAc 3×. The combined organic layers were dried over Na$_2$SO$_4$, filtered, and the solvent removed under vacuum to provide 1-(4-fluoro-2-isopropoxyphenyl)-1H-tetrazol-5(4H)-one (11.4 g, 81%) as a brown oil that was used without further purification.

$^1$H NMR (300 MHz; d$_6$-DMSO) δ 7.47-7.52 (dd, 1H, J=6.0 Hz, 8.4 Hz), 7.19-7.24 (dd, 1H, J=2.7 Hz, 12 Hz), 6.87-6.94 (td, 1H, J=2.7 Hz, 8.1 Hz), 4.63-4.75 (d, 6H, J=6.0 Hz), 1.17-1.19 (d, 6H, J=6.0 Hz); $^{19}$F NMR (282 MHz; d$_6$-DMSO) δ −107.2 (q); m/z=238 (M+H)$^+$.

Preparation of 1-(4-fluoro-2-isopropoxyphenyl)-4-methyl-1H-tetrazol-5(4H)-one

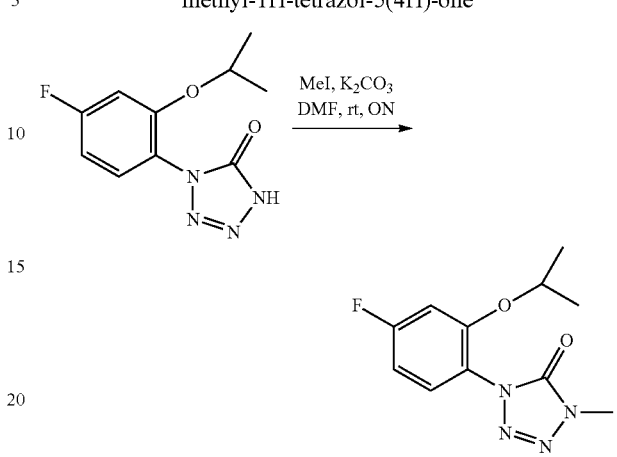

A mixture of 1-(4-fluoro-2-isopropoxyphenyl)-1H-tetrazol-5(4H)-one (4.10 g, 17.2 mmol, 1 equiv), K$_2$CO$_3$ (7.15 g, 52.0 mmol, 3 equiv), and iodomethane (3.25 mL, 52.0 mmol, 3 equiv) in DMF (40 mL) was stirred at RT ON. The reaction mixture was partitioned between water and EtOAc, then the layers were separated. The aqueous layer was extracted with EtOAc 2×, and the combined organic layer was washed with brine 1×. The organic layer was dried over Na$_2$SO$_4$, filtered, and concentrated to dryness to provide 1-(4-fluoro-2-isopropoxyphenyl)-4-methyl-1H-tetrazol-5(4H)-one (3.50 g, 81%) as a brown oil that was used without further purification. $^1$H NMR (300 MHz; d$_6$-DMSO) δ 7.46-7.51 (dd, 1H, J=6.3 Hz, 8.4 Hz), 7.20-7.25 (dd, 1H, J=2.7 Hz, 11 Hz), 6.87-6.94 (td, 1H, J=2.7 Hz, 8.1 Hz), 4.63-4.75 (hept, 1H, J=6.0 Hz), 3.59 (s, 3H), 1.16-1.18 (d, 6H, J=6.0 Hz); $^{19}$F NMR (282 MHz; d$_6$-DMSO) δ −107.0 (sextet); m/z=253 (M+H)$^+$.

Preparation of 1-(4-fluoro-2-hydroxy-5-nitrophenyl)-4-methyl-1H-tetrazol-5(4H)-one

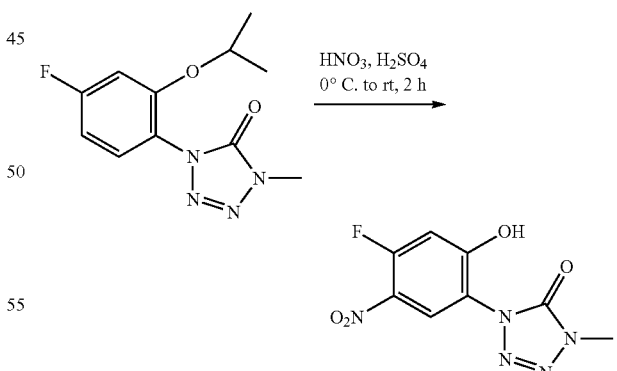

A solution of 1-(4-fluoro-2-isopropoxyphenyl)-4-methyl-1H-tetrazol-5(4H)-one (3.50 g, 13.9 mmol, 1 equiv) in H$_2$SO$_4$ (35 mL) was cooled in ice/water bath. To the cooled solution, was added HNO$_3$ (fuming >90%; 715 uL, 15.3 mmol, 1.1 equiv) dropwise, and the cooled reaction mixture was allowed to warm to RT over 2 h. The reaction mixture was quenched with ice, and extracted with EtOAc 3×. The organic layer was then extracted with saturated NaHCO$_3$ 3×. The basic aqueous layer was acidified to pH <3 with 6N HCl. Then, the acidic layer was extracted with EtOAc 3×, and the organic layer was dried over Na$_2$SO$_4$, filtered, and concentrated to dryness to provide 1-(4-fluoro-2-hydroxy-5-nitrophenyl)-4-methyl-1H-tetrazol-5(4H)-one (2.94 g, 83%) as brown solid that was used without further purification. $^1$H NMR (300 MHz; d$_6$-DMSO) δ 12.5 (bs, 1H), 8.41-8.44 (d, 1H, J=8.7 Hz), 7.04-7.08 (d, 1H, J=13 Hz), 3.59 (s, 3H); $^{19}$F NMR (282 MHz; d$_6$-DMSO) δ −111.3 (q); m/z=256 (M+H)$^+$.

Preparation of 1-(5-amino-4-fluoro-2-hydroxyphenyl)-4-methyl-1H-tetrazol-5(4H)-one

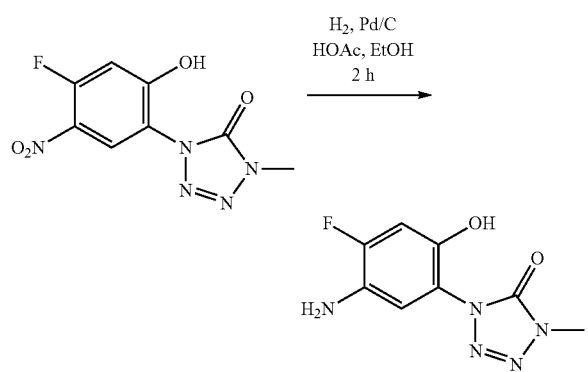

A round-bottom flask was charged with 1-(4-fluoro-2-hydroxy-5-nitrophenyl)-4-methyl-1H-tetrazol-5(4H)-one (500 mg, 1.96 mmol), EtOH (20 mL), HOAc (250 uL), and 10% Pd/C (50% in water, Degussa type E101; 100 mg, 20 wt % by weight of the starting nitro compound). The flask was sealed with a rubber septum, degassed, and back-filled with H$_2$ (×3) from a balloon filled with H$_2$. The reaction was stirred for 2 h using a H$_2$ filled balloon. The reaction mixture was filtered through a pad of celite, and the pad of celite was rinsed with MeOH. The filtrate was evaporated to dryness, and the product dried in vacuo with a water bath at 45° C. to remove any residual HOAc to provide 1-(5-amino-4-fluoro-2-hydroxyphenyl)-4-methyl-1H-tetrazol-5(4H)-one (437 mg, 99%) as a brown solid that was used without further purification. $^1$H NMR (300 MHz; d$_6$-DMSO) δ 9.46 (s, 1H), 6.67-6.72 (m, 2H), 4.80 (bs, 2H), 3.56 (s, 3H); $^{19}$F NMR (282 MHz; d$_6$-DMSO) δ −128.6 (t); m/z=225 (M+H)$^+$.

Example 30

Synthesis of 1-(5-(5-fluoro-4-(octahydro-5,5-dimethylindolizin-7-ylamino)pyrimidin-2-ylamino)-2-(oxetan-3-yloxy)phenyl)-4-methyl-1H-tetrazol-5(4H)-one (Compound 38)

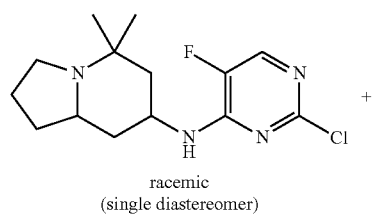
racemic
(single diastereomer)

+

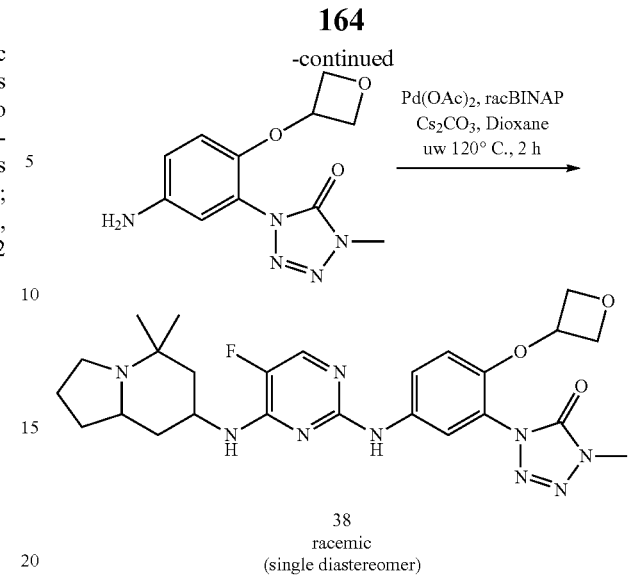

38
racemic
(single diastereomer)

To a microwave vial, was added N-(2-chloro-5-fluoropyrimidin-4-yl)-octahydro-5,5-dimethylindolizin-7-amine (Racemic, single diastereomer; 100 mg, 0.335 mmol, 1 equiv), 1-(5-amino-2-(oxetan-3-yloxy)phenyl)-4-methyl-1H-tetrazol-5(4H)-one (Described in: WO2011/068898 120 mg, 0.455 mmol, 1.36 equiv), rac-BINAP (45 mg, 0.0726 mmol, 0.217 equiv), Cs$_2$CO$_3$ (327 mg, 1.00 mmol, 3 equiv), Pd(OAc)$_2$ (7 mg, 0.0291 mmol, 0.0870 equiv), and dioxane (4 ml). The microwave vial was capped and sonicated under vacuum for 5 minutes. The reaction mixture was heated in the microwave at 120° C. for 2 hours. The cooled reaction mixture was filtered using a pad of Celite and rinsed with dioxane, and the filtrate was concentrated. The crude product was purified by flash chromatography and eluted with DCM:2M NH$_3$/MeOH=100:0 to 95:5 using 1% 2M NH$_3$/MeOH increments to provide the desired product 1-(5-(5-fluoro-4-(octahydro-5,5-dimethylindolizin-7-ylamino)pyrimidin-2-ylamino)-2-(oxetan-3-yloxy)phenyl)-4-methyl-1H-tetrazol-5(4H)-one (Compound 38) (Racemic, single diastereomer; 90 mg, 51%) as a solid.

$^1$H NMR (300 MHz; d$_6$-DMSO) δ 9.21 (s, 1H), 8.06 (s, 1H), 7.83-7.84 (d, 1H, J=3.9 Hz), 7.57-7.60 (dd, 1H, J=2.1 Hz, J=8.7 Hz), 7.23-7.26 (m, 1H), 6.80-6.83 (d, 1H, J=9.3 Hz), 5.34-5.27 (p, 1H, J=6.3 Hz), 4.79-4.84 (t, 2H, J=6 Hz), 4.38-4.42 (t, 2H, J=5.7 Hz), 4.04 (bs, 1H), 3.62 (s, 3H), 2.84 (bs, 1H), 1.89-2.42 (m, 4H), 1.13-1.74 (m, 5H), 1.06-1.13 (m, 4H), 0.815 (s, 3H); $^{19}$F NMR (282 MHz; d$_6$-DMSO) δ −166.5 (s); m/z=526 (M+H)$^+$.

Example 31

Chiral HPLC resolution of 1-(5-(5-fluoro-4-(octahydro-5,5-dimethylindolizin-7-ylamino)pyrimidin-2-ylamino)-2-(oxetan-3-yloxy)phenyl)-4-methyl-1H-tetrazol-5(4H)-one (Compounds 39-40)

Chiral HPLC resolution of compound 1-(5-(5-fluoro-4-(octahydro-5,5-dimethylindolizin-7-ylamino)pyrimidin-2-ylamino)-2-(oxetan-3-yloxy)phenyl)-4-methyl-1H-tetrazol-5(4H)-one (Compound 38) (Racemic, single diastereomer, 55 mg) to enantiomers was performed.

Chiral HPLC method: Column: Chiralcel OJ-H, 4.6×250 mm, with guard. Mobil phase: 90% CO$_2$, 10% methanol w/0.1% triethylamine. Flow rate: 4 ml/min. Injection volume: 10 µL. Concentration: approx 5 mg/ml. Detection: UV at 254 nm.

Compound 39

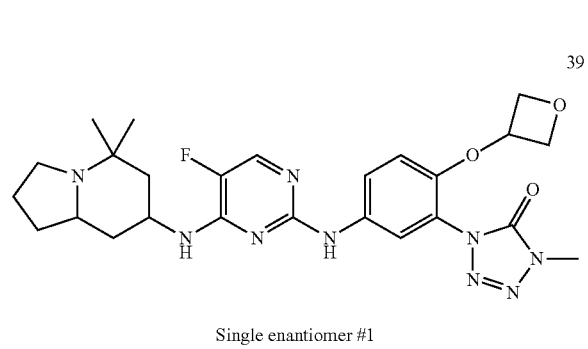 [SMILES: Cn1nnn(-c2cc(Nc3ncc(F)c(NC4CC5CCCN5C(C)(C)C4)n3)ccc2OC2COC2)c1=O]

Single enantiomer #1

Compound 39: (>99% ee, 15 mg) has Rt=6.14 min.
$^1$H NMR (300 MHz; $d_6$-DMSO) δ 9.21 (s, 1H), 8.06 (s, 1H), 7.83-7.84 (d, 1H, J=3.9 Hz), 7.57-7.60 (dd, 1H, J=2.1 Hz, J=8.7 Hz), 7.23-7.26 (m, 1H), 6.80-6.83 (d, 1H, J=9.3 Hz), 5.34-5.27 (p, 1H, J=6.3 Hz), 4.79-4.84 (t, 2H, J=6 Hz), 4.38-4.42 (t, 2H, J=5.7 Hz), 4.04 (bs, 1H), 3.62 (s, 3H), 2.84 (bs, 1H), 1.89-2.42 (m, 4H), 1.13-1.74 (m, 5H), 1.06-1.13 (m, 4H), 0.815 (s, 3H); $^{19}$F NMR (282 MHz; $d_6$-DMSO) δ −166.5 (s); m/z=526 (M+H)$^+$.

Compound 40

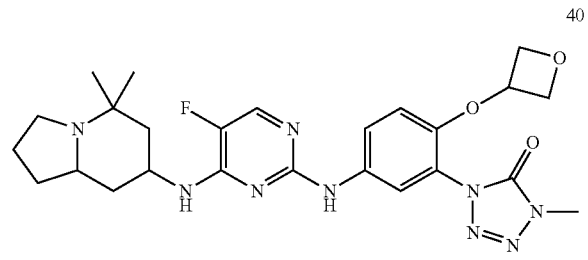

Single enantiomer #2

Compound 40: (>99% ee, 12 mg) has Rt=7.39 min.
$^1$H NMR (300 MHz; $d_6$-DMSO) δ 9.21 (s, 1H), 8.06 (s, 1H), 7.83-7.84 (d, 1H, J=3.9 Hz), 7.57-7.60 (dd, 1H, J=2.1 Hz, J=8.7 Hz), 7.23-7.26 (m, 1H), 6.80-6.83 (d, 1H, J=9.3 Hz), 5.34-5.27 (p, 1H, J=6.3 Hz), 4.79-4.84 (t, 2H, J=6 Hz), 4.38-4.42 (t, 2H, J=5.7 Hz), 4.04 (bs, 1H), 3.62 (s, 3H), 2.84 (bs, 1H), 1.89-2.42 (m, 4H), 1.13-1.74 (m, 5H), 1.06-1.13 (m, 4H), 0.815 (s, 3H); $^{19}$F NMR (282 MHz; $d_6$-DMSO) δ −166.5 (s); m/z=526 (M+H)$^+$.

Example 32

Synthesis of 5-(5-fluoro-4-(octahydro-5,5-dimethylindolizin-7-ylamino)pyrimidin-2-ylamino)-2-(tetrahydro-2H-pyran-4-yloxy)benzonitrile (Compound 41)

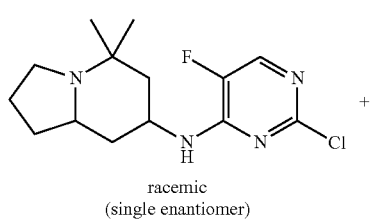

racemic
(single enantiomer)

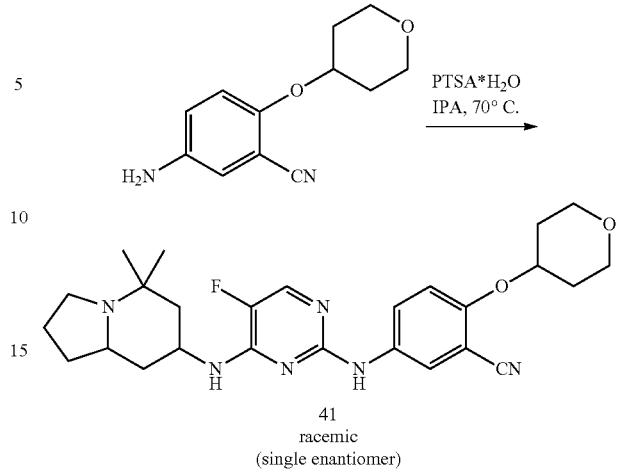

41
racemic
(single enantiomer)

A mixture of N-(2-chloro-5-fluoropyrimidin-4-yl)-octahydro-5,5-dimethylindolizin-7-amine (Racemic, single diastereomer; 150 mg, 0.502 mmol, 1 equiv), 5-amino-2-(tetrahydro-2H-pyran-4-yloxy)benzonitrile (153 mg, 0.703 mmol, 1.4 equiv), and PTSA monohydrate (95 mg, 0.502 mmol, 1 equiv) in IPA (5 ml) were heated to 70° C. for 3 days. After cooling to ambient temperature, the crude mixture was concentrated to dryness and taken in water, EtOAc, and 1N NaOH. The layers were separated. The organic layer was washed with 1N NaOH (×2), dried over Na$_2$SO$_4$, filtered, and concentrated to dryness. The crude product was purified by flash chromatography and eluted with DCM:2M NH$_3$/MeOH=100:0 to 96:4 using 1% 2M NH$_3$/MeOH increments to give compound 5-(5-fluoro-4-(octahydro-5,5-dimethylindolizin-7-ylamino)pyrimidin-2-ylamino)-2-(tetrahydro-2H-pyran-4-yloxy)benzonitrile (Compound 41)(Racemic, single diastereomer; 182 mg, 76%) as a solid.

$^1$H NMR (300 MHz; $d_6$-DMSO) δ 9.14 (s, 1H), 8.11-8.12 (d, 1H, J=2.4 Hz), 7.84-7.86 (d, 1H, J=3.9 Hz), 7.71-7.75 (dd, 2H, J=3 Hz, J=9.3 Hz), 7.28-7.19 (m, 2H), 4.62-4.67 (m, 1H), 4.14 (bs, 1H), 3.80-3.87 (m, 2H), 3.44-3.52 (m, 2H), 2.86 (bs, 1H), 2.31-2.55 (m, 1H), 1.08-2.06 (m, 15H), 0.985 (s, 3H); $^{19}$F NMR (282 MHz; $d_6$-DMSO) δ −166.3 (s); m/z=481 (M+H)$^+$.

Synthesis of Compounds with
2,2-Difluoro-5,5-dimethyloctahydroindolizine

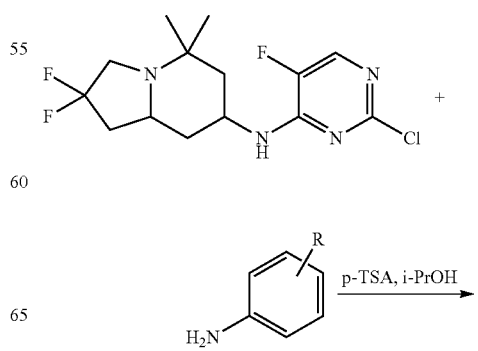

-continued

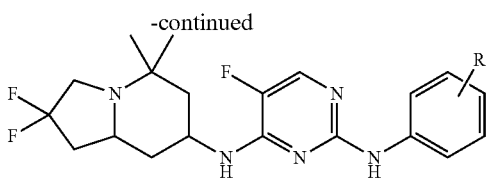

Typical procedures for final compounds synthesis: an i-PrOH (2 ml) solution of N-(2-chloro-5-fluoropyrimidin-4-yl)-2,2-difluoro-octahydro-5,5-dimethylindolizin-7-amine (33.5 mg, 0.1 mmol), aniline (0.14 mmol) and p-TSA.H$_2$O (28.5 mg, 0.15 mmol) was stirred at 90° C. for 15-96 hours until <5% of chloro-SM was detected by LC-MS. Solvent was removed in vacuo and the product was purified by RP-HPLC. Product was obtained as a formate salt and was free-based by following method: a MeOH solution of the salt was passed through a PL-HCO$_3$ column slowly, the column was further washed with MeOH, filtrate was collected and solvent was removed in vacuo to provide final desired products.

Example 33

Synthesis of 1-(5-(4-((7S,8aR)-2,2-difluoro-octahydro-5,5-dimethylindolizin-7-ylamino)-5-fluoropyrimidin-2-ylamino)-2-cyclopropyl-4-fluorophenyl)-4-methyl-1H-tetrazol-5(4H)-one (Compound 42)

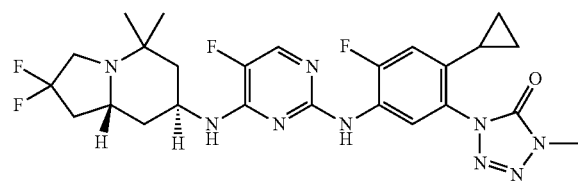 [SMILES: Cn1nnn(-c2cc(Nc3ncc(F)c(N[C@H]4C[C@@H]5CC(F)(F)CN5C(C)(C)C4)n3)c(F)cc2C2CC2)c1=O]

$^1$H NMR (300 MHz, CDCl$_3$) δ 8.57 (d, J=7.8 Hz, 1H), 7.80 (d, J=3.1 Hz, 1H), 7.06 (d, J=3.4 Hz, 1H), 6.87 (d, J=12.2 Hz, 1H), 5.08 (d, J=4.6 Hz, 1H), 4.35-4.29 (m, 1H), 3.74 (s, 3H), 3.34 (ddd, J=14.3, 10.6, 6.9 Hz, 1H), 3.01-2.92 (m, 1H), 2.81 (ddd, J=19.3, 15.3, 10.8 Hz, 1H), 2.42-2.28 (m, 1H), 2.11-2.07 (m, 1H), 2.02-1.79 (m, 3H), 1.70 (dd, J=14.4, 4.5 Hz, 1H), 1.59-1.49 (m, 1H, overlapped with water peak), 1.12 (s, 6H), 0.87-0.81 (m, 2H), 0.60-0.55 (m, 2H); LRMS (M+H) m/z 548.34.

Example 34

Synthesis of N$^2$-(4-cyclopropyl-2-fluoro-5-(1H-tetrazol-1-yl)phenyl)-5-fluoro-N$^4$-((7S,8aR)-2,2-difluoro-octahydro-5,5-dimethylindolizin-7-yl)pyrimidine-2,4-diamine (Compound 43)

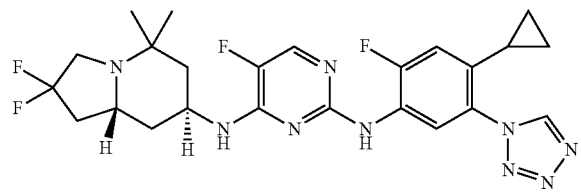 [SMILES: CC1(C)C[C@@H](Nc2nc(Nc3cc(-n4cnnn4)c(C4CC4)cc3F)ncc2F)C[C@@H]2CC(F)(F)CN21]

$^1$H NMR (300 MHz, CDCl$_3$) δ 8.90 (s, 1H), 8.73 (d, J=7.7 Hz, 1H), 7.80 (d, J=3.0 Hz, 1H), 7.10 (d, J=3.4 Hz, 1H), 6.90 (d, J=12.1 Hz, 1H), 5.13 (d, J=5.7 Hz, 1H), 4.31-4.24 (m, 1H), 3.34 (ddd, J=13.8, 10.7, 7.8 Hz, 1H), 3.00-2.88 (m, 1H), 2.81 (ddd, J=19.7, 14.9, 10.8 Hz, 1H), 2.39-2.26 (m, 1H), 2.08-1.80 (m, 4H), 1.69 (dd, J=14.4, 4.5 Hz, 1H), 1.62-1.49 (m, 1H, overlapped with water peak), 1.12 (s, 3H), 1.11 (s, 3H), 0.91-0.84 (m, 2H), 0.64-0.58 (m, 2H); LRMS (M+H) m/z 518.33.

Example 35

5-Synthesis of (4-((7S,8aR)-2,2-difluoro-octahydro-5,5-dimethylindolizin-7-ylamino)-5-fluoropyrimidin-2-ylamino)-2-methylbenzonitrile (Compound 44)

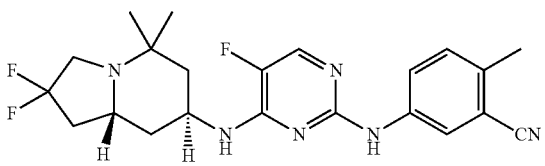 [SMILES: Cc1ccc(Nc2ncc(F)c(N[C@H]3C[C@@H]4CC(F)(F)CN4C(C)(C)C3)n2)cc1C#N]

$^1$H NMR (300 MHz, CDCl$_3$) δ 8.16 (d, J=2.4 Hz, 1H), 7.81 (d, J=3.1 Hz, 1H), 7.41 (dd, J=8.4, 2.4 Hz, 1H), 7.20 (d, J=12.1 Hz, 1H), 6.88-6.86 (m, 1H), 5.10 (d, J=5.6 Hz, 1H), 4.38-4.32 (m, 1H), 3.35 (ddd, J=13.8, 10.7, 7.1 Hz, 1H), 3.04-2.94 (m, 1H), 2.83 (ddd, J=19.6, 15.1, 10.8 Hz, 1H), 2.49 (s, 3H), 2.43-2.29 (m, 1H), 2.15 (br dd, J=13.6, 2.1 Hz, 1H), 2.07-1.82 (m, 3H), 1.70 (ddd, J=13.6, 11.8, 4.3 Hz, 1H), 1.15 (s, 3H), 1.14 (s, 3H); LRMS (M+H) m/z 431.26.

Example 36

Synthesis of 1-(5-(4-((7R,8aR)-2,2-difluoro-octahydro-5,5-dimethylindolizin-7-ylamino)-5-fluoropyrimidin-2-ylamino)-2-cyclopropyl-4-fluorophenyl)-4-methyl-1H-tetrazol-5(4H)-one (Compound 45)

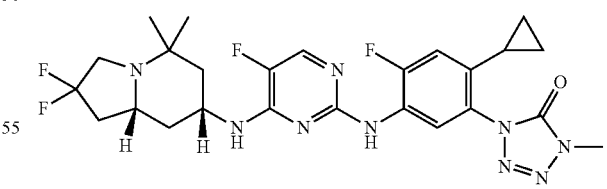

$^1$H NMR (300 MHz, CDCl$_3$) δ 8.53 (d, J=7.8 Hz, 1H), 7.79 (d, J=3.1 Hz, 1H), 7.05 (d, J=3.1 Hz, 1H), 6.89 (d, J=12.2 Hz, 1H), 4.74 (d, J=6.5 Hz, 1H), 4.17 (tdt, J=11.3, 7.3, 3.8 Hz, 1H), 3.72 (s, 3H), 3.30 (ddd, J=14.3, 10.7, 6.7 Hz, 1H), 2.85-2.68 (m, 2H), 2.40-2.26 (m, 2H), 2.00-1.75 (m, 3H), 1.41 (dd, J=12.3, 12.3 Hz, 1H), 1.12 (s, 3H), 1.17-1.06 (m, 1H), 0.98 (s, 3H), 0.85-0.79 (m, 2H), 0.59-0.53 (m, 2H); LRMS (M+H) m/z 548.35.

Example 37

Synthesis of N²-(4-cyclopropyl-2-fluoro-5-(1H-tetrazol-1-yl)phenyl)-5-fluoro-N⁴-((7R,8aR)-2,2-difluoro-octahydro-5,5-dimethylindolizin-7-yl)pyrimidine-2,4-diamine (Compound 46)

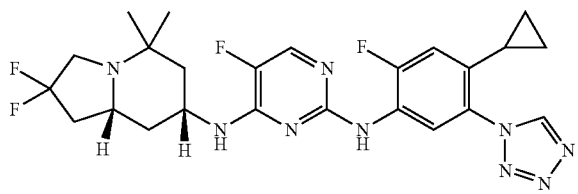 [SMILES: CC1(C)C[C@H](Nc2nc(Nc3cc(-n4cnnn4)c(C4CC4)cc3F)ncc2F)C[C@@H]2CC(F)(F)CN21]

¹H NMR (300 MHz, CDCl₃) δ 8.89 (s, 1H), 8.67 (d, J=7.7 Hz, 1H), 7.78 (d, J=3.0 Hz, 1H), 7.07 (d, J=3.5 Hz, 1H), 6.90 (d, J=12.1 Hz, 1H), 4.77 (d, J=8.3 Hz, 1H), 4.14 (tdt, J=13.0, 8.8, 4.3 Hz, 1H), 3.28 (ddd, J=14.5, 10.6, 5.8 Hz, 1H), 2.86-2.71 (m, 2H), 2.42-2.25 (m, 2H), 2.00-1.78 (m, 2H), 1.56-1.47 (m, 1H, overlapped with water peak), 1.41 (dd, J=12.3, 12.3 Hz, 1H), 1.14 (s, 3H), 1.18-1.06 (m, 1H), 0.95 (s, 3H), 0.89-0.83 (m, 2H), 0.63-0.57 (m, 2H); LRMS (M+H) m/z 518.34.

Example 38

Synthesis of 1-(2-((R)-tetrahydrofuran-3-yloxy)-5-(5-fluoro-4-(octahydro-5,5-dimethylindolizin-7-ylamino)pyrimidin-2-ylamino)phenyl)-4-methyl-1H-tetrazol-5(4H)-one (Compound 47)

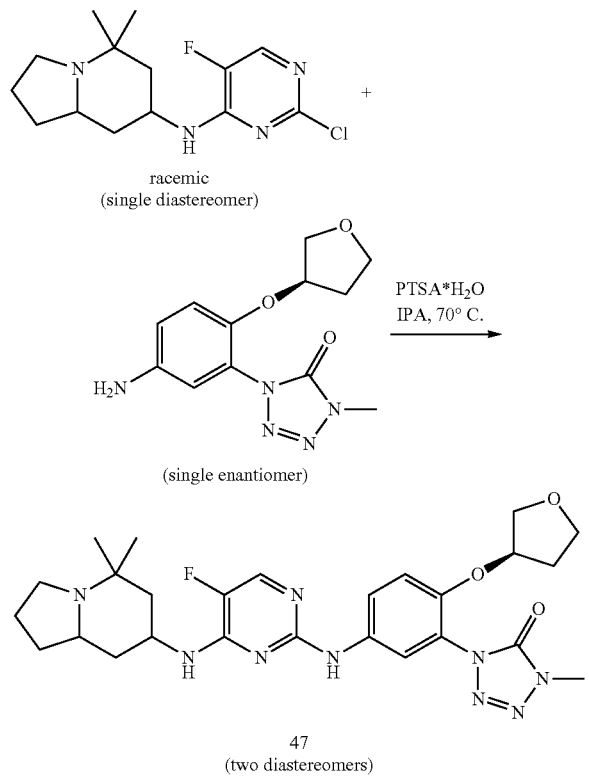

A mixture of N-(2-chloro-5-fluoropyrimidin-4-yl)-octahydro-5,5-dimethylindolizin-7-amine (racemic, single diastereomer; 200 mg, 0.669 mmol, 1 equiv), 1-(2-((R)-tetrahydrofuran-3-yloxy)-5-aminophenyl)-4-methyl-1H-tetrazol-5(4H)-one (260 mg, 0.937 mmol, 1.4 equiv), and PTSA monohydrate (127 mg, 0.669 mmol, 1 equiv) in IPA (7 ml) were heated to 70° C. for 3 days. After cooling to ambient temperature, the crude mixture was concentrated to dryness and taken in water, EtOAc, and 1N NaOH. The layers were separated. The organic layer was washed with 1N NaOH (×2), dried over Na₂SO₄, filtered, and concentrated to dryness. The crude product was purified by flash chromatography and eluted with DCM:2M NH₃/MeOH=100:0 to 96:4 using 1% 2M NH₃/MeOH increments to give compound 1-(2-((R)-tetrahydrofuran-3-yloxy)-5-(5-fluoro-4-(octahydro-5,5-dimethylindolizin-2-ylamino)pyrimidin-2-ylamino)phenyl)-4-methyl-1H-tetrazol-5(4H)-one (Compound 47) (Mixture of two diastereomers; 279 mg, 77%) as a solid.

¹H NMR (300 MHz; d₆-DMSO) δ 9.20 (s, 1H), 8.03 (s, 1H), 7.83-7.84 (d, 1H, J=3.9 Hz), 7.60-7.63 (dd, 1H, J=2.1 Hz, J=8.7 Hz), 7.22-7.25 (d, 1H, J=7.8 Hz), 7.14-7.17 (d, 1H, J=9 Hz), 4.94-5.07 (m, 1H), 3.99-4.11 (m, 1H), 3.79-3.83 (dd, 1H, J=4.5 Hz, J=9.9 Hz), 3.59-3.69 (m, 6H), 2.84 (bs, 1H), 1.41-2.24 (m, 11H), 1.06-1.22 (m, 4H), 0.813 (s, 3H); ¹⁹F NMR (282 MHz; d₆-DMSO) δ −166.6 (s); m/z=540 (M+H)⁺.

Example 39

Synthesis of 1-(2-((S)-tetrahydrofuran-3-yloxy)-5-(5-fluoro-4-(octahydro-5,5-dimethylindolizin-7-ylamino)pyrimidin-2-ylamino)phenyl)-4-methyl-1H-tetrazol-5(4H)-one (Compound 49)

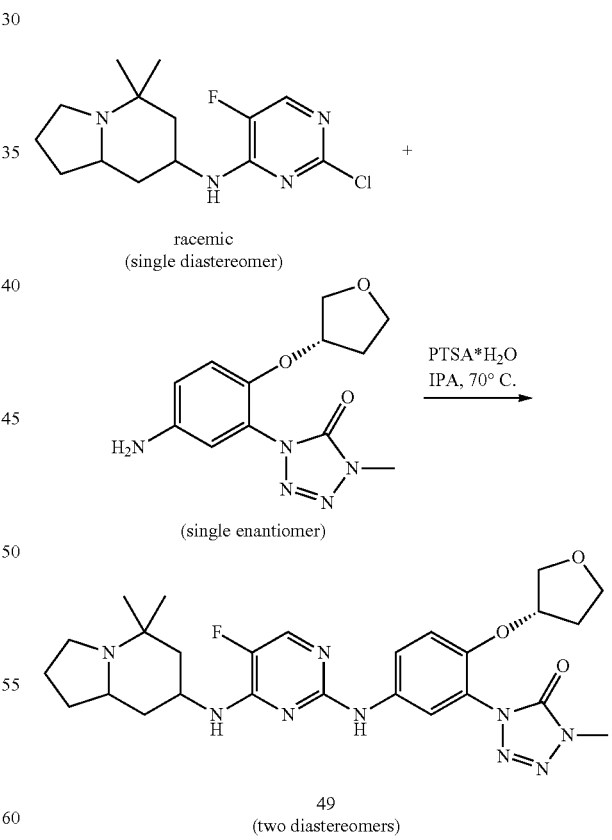

A mixture of N-(2-chloro-5-fluoropyrimidin-4-yl)-octahydro-5,5-dimethylindolizin-7-amine (Racemic, single diastereomer; 200 mg, 0.669 mmol, 1 equiv), 1-(2-((S)-tetrahydrofuran-3-yloxy)-5-aminophenyl)-4-methyl-1H-tetrazol-5(4H)-one (260 mg, 0.937 mmol, 1.4 equiv), and PTSA monohydrate (127 mg, 0.669 mmol, 1 equiv) in IPA (7 ml) were heated to 70° C. for 3 days. After cooling to ambient temperature, the crude mixture was concentrated to dryness and taken in water, EtOAc, and 1N NaOH. The layers were separated. The organic layer was washed with 1N NaOH (×2), dried over Na$_2$SO$_4$, filtered, and concentrated to dryness. The crude product was purified by flash chromatography and eluted with DCM:2M NH$_3$/MeOH=100:0 to 96:4 using 1% 2M NH$_3$/MeOH increments to give compound 1-(2-((S)-tetrahydrofuran-3-yloxy)-5-(5-fluoro-4-(octahydro-5,5-dimethylindolizin-7-ylamino)pyrimidin-2-ylamino)phenyl)-4-methyl-1H-tetrazol-5(4H)-one (Compound 49) (Mixture of two diastereomers; 315 mg, 87%) as a solid.

$^1$H NMR (300 MHz; d$_6$-DMSO) δ 9.20 (s, 1H), 8.03 (s, 1H), 7.83-7.84 (d, 1H, J=3.9 Hz), 7.60-7.63 (dd, 1H, J=2.1 Hz, J=8.7 Hz), 7.22-7.25 (d, 1H, J=7.8 Hz), 7.14-7.17 (d, 1H, J=9 Hz), 4.94-5.07 (m, 1H), 3.99-4.11 (m, 1H), 3.78-3.83 (dd, 1H, J=4.5 Hz, J=9.9 Hz), 3.59-3.69 (m, 6H), 2.84 (bs, 1H), 1.41-2.24 (m, 11H), 1.06-1.22 (m, 4H), 0.812 (s, 3H); $^{19}$F NMR (282 MHz; d$_6$-DMSO) δ −166.6 (s); m/z=540 (M+H)$^+$.

Example 40

Synthesis of 1-(5-(5-fluoro-4-(octahydro-5,5-dimethylindolizin-7-ylamino)pyrimidin-2-ylamino)-2-(tetrahydro-2H-pyran-4-yloxy)phenyl)-4-methyl-1H-tetrazol-5(4H)-one (Compound 51)

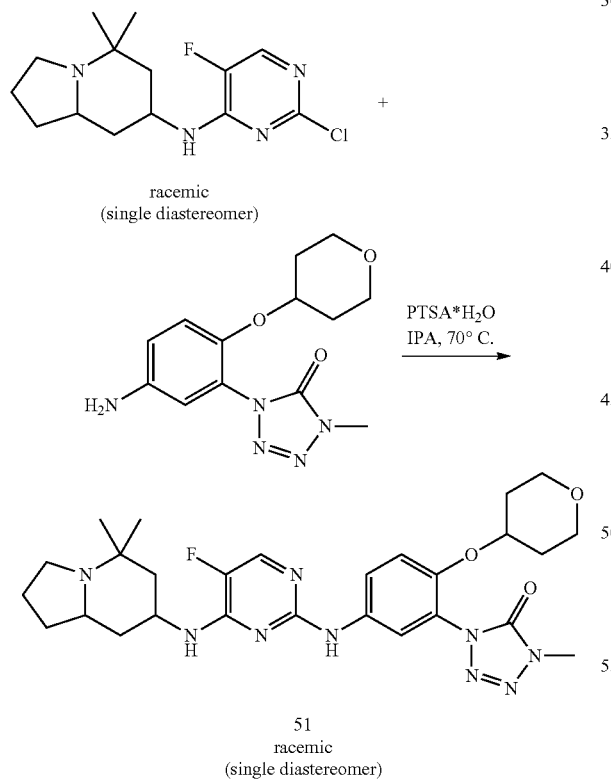

A mixture of N-(2-chloro-5-fluoropyrimidin-4-yl)-octahydro-5,5-dimethylindolizin-7-amine (Racemic, single diastereomer; 200 mg, 0.669 mmol, 1 equiv), 1-(5-amino-2-(tetrahydro-2H-pyran-4-yloxy)phenyl)-4-methyl-1H-tetrazol-5(4H)-one (Described in WO2011068898, 273 mg, 0.937 mmol, 1.4 equiv), and PTSA monohydrate (127 mg, 0.669 mmol, 1 equiv) in IPA (7 ml) were heated to 70° C. for 3 days. After cooling to ambient temperature, the crude mixture was concentrated to dryness and taken in water, EtOAc, and 1N NaOH. The layers were separated. The organic layer was washed with 1N NaOH (×2), dried over Na$_2$SO$_4$, filtered, and concentrated to dryness. The crude product was purified by flash chromatography and eluted with DCM:2M NH$_3$/MeOH=100:0 to 96:4 using 1% 2M NH$_3$/MeOH increments to give compound 1-(5-(5-fluoro-4-(octahydro-5,5-dimethylindolizin-7-ylamino)pyrimidin-2-ylamino)-2-(tetrahydro-2H-pyran-4-yloxy)phenyl)-4-methyl-1H-tetrazol-5(4H)-one (Compound 51) (racemic, single diastereomer; 321 mg, 87%) as a solid.

$^1$H NMR (300 MHz; d$_6$-DMSO) δ 9.19 (s, 1H), 8.06 (s, 1H), 7.83-7.84 (d, 1H, J=3.9 Hz), 7.57-7.61 (dd, 1H, J=2.1 Hz, J=8.7 Hz), 7.22-7.25 (d, 1H, J=7.8 Hz), 7.18-7.21 (d, 1H, J=9 Hz), 4.44-4.57 (m, 1H), 3.97-4.12 (m, 1H), 3.61-3.67 (m, 7H), 3.37-3.44 (m, 2H), 2.84 (bs, 1H), 1.42-2.24 (m, 11H), 1.06-1.22 (m, 4H), 0.812 (s, 3H); $^{19}$F NMR (282 MHz; d$_6$-DMSO) δ −166.7 (s); m/z=554 (M+H)$^+$.

Example 41

Synthesis of 2-((R)-tetrahydrofuran-3-yloxy)-5-(5-fluoro-4-(octahydro-5,5-dimethylindolizin-7-ylamino)pyrimidin-2-ylamino)benzonitrile (Compound 57)

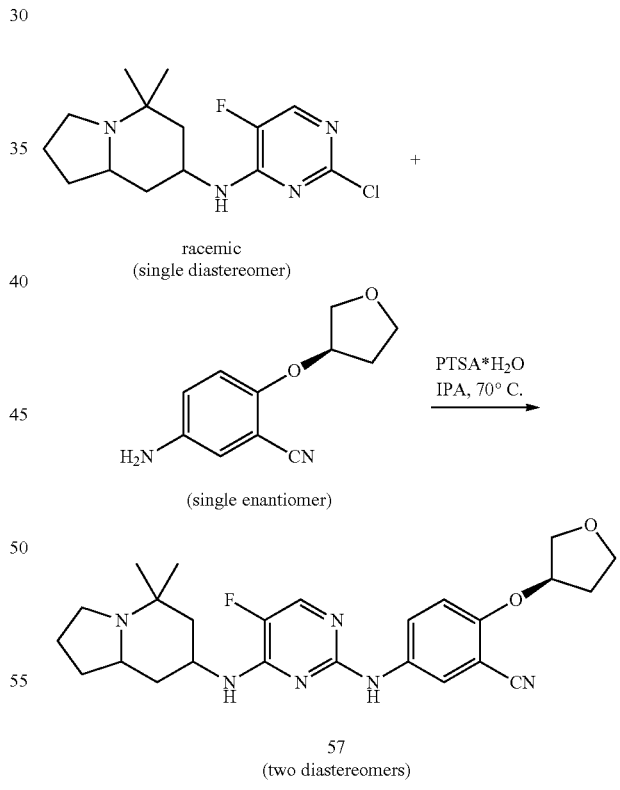

A mixture of N-(2-chloro-5-fluoropyrimidin-4-yl)-octahydro-5,5-dimethylindolizin-7-amine (racemic, single diastereomer; 200 mg, 0.669 mmol, 1 equiv), 2-((R)-tetrahydrofuran-3-yloxy)-5-aminobenzonitrile (191 mg, 0.937 mmol, 1.4 equiv), and PTSA monohydrate (127 mg, 0.669 mmol, 1 equiv) in IPA (7 ml) were heated to 70° C. for 3 days. After cooling to ambient temperature, the crude mixture was concentrated to dryness and taken in water, EtOAc, and 1N NaOH. The layers were separated. The organic layer was washed with 1N NaOH (×2), dried over Na₂SO₄, filtered, and concentrated to dryness. The crude product was purified by flash chromatography and eluted with DCM:2M NH₃/MeOH=100:0 to 96:4 using 1% 2M NH₃/MeOH increments to give compound 2-((R)-tetrahydrofuran-3-yloxy)-5-(5-fluoro-4-(octahydro-5,5-dimethylindolizin-7-ylamino)pyrimidin-2-ylamino)benzonitrile (Compound 57) (two diastereomers; 295 mg, 95%) as a solid.

¹H NMR (300 MHz; d₆-DMSO) δ 9.14 (s, 1H), 8.10-8.11 (d, 1H, J=2.7 Hz), 7.84-7.86 (d, 1H, J=3.9 Hz), 7.75-7.78 (dd, 1H, J=2.1 Hz, J=8.7 Hz), 7.25-7.28 (d, 1H, J=7.8 Hz), 7.09-7.12 (d, 1H, J=9 Hz), 5.02-5.11 (m, 1H), 4.11-4.21 (m, 1H), 3.71-3.91 (m, 4H), 2.85 (bs, 1H), 1.41-2.42 (m, 11H), 1.08-1.27 (m, 4H), 0.987 (s, 3H); ¹⁹F NMR (282 MHz; d₆-DMSO) δ −166.3 (s); m/z=467 (M+H)⁺.

Example 42

Chiral HPLC separation of 2-((R)-tetrahydrofuran-3-yloxy)-5-(5-fluoro-4-(octahydro-5,5-dimethylindolizin-7-ylamino)pyrimidin-2-ylamino)benzonitrile (Compounds 58-59)

Chiral HPLC separation of compound 2-((R)-tetrahydrofuran-3-yloxy)-5-(5-fluoro-4-(octahydro-5,5-dimethylindolizin-7-ylamino)pyrimidin-2-ylamino)benzonitrile (Compound 57) (two diastereomers 55 mg) to diastereomers (each a single enantiomer) was performed.

Chiral HPLC method: Column: Chiralcel OJ-H, 4.6×250 mm, with guard. Mobil phase: 90% CO₂, 10% methanol w/0.1% triethylamine. Flow rate: 4 ml/min. Injection volume: 10 μL. Concentration: approx 5 mg/ml. Detection: UV at 254 nm.

Compound 58

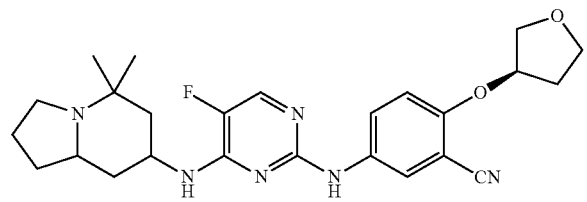 [SMILES: CC1(C)CC(Nc2nc(Nc3ccc(O[C@H]4CCOC4)c(C#N)c3)ncc2F)CC2CCCN21]

Compound 58: (>99% ee, 16 mg) has Rt=3.90 min.

¹H NMR (300 MHz; d₆-DMSO) δ 9.14 (s, 1H), 8.10-8.11 (d, 1H, J=2.7 Hz), 7.84-7.86 (d, 1H, J=3.9 Hz), 7.75-7.78 (dd, 1H, J=2.1 Hz, J=8.7 Hz), 7.25-7.28 (d, 1H, J=7.8 Hz), 7.09-7.12 (d, 1H, J=9 Hz), 5.02-5.11 (m, 1H), 4.11-4.21 (m, 1H), 3.71-3.91 (m, 4H), 2.85 (bs, 1H), 1.41-2.42 (m, 11H), 1.08-1.27 (m, 4H), 0.987 (s, 3H); ¹⁹F NMR (282 MHz; d₆-DMSO) δ −166.3 (s); m/z=467 (M+H)⁺.

Compound 59

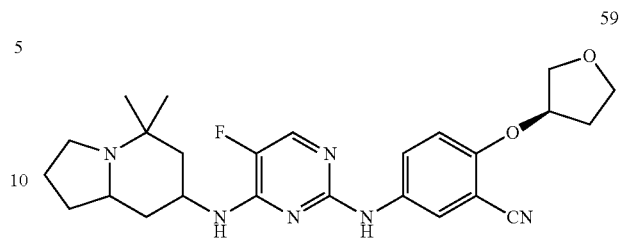

Compound 59: (>99% ee, 16 mg) has Rt=4.95 min.

¹H NMR (300 MHz; d₆-DMSO) δ 9.14 (s, 1H), 8.10-8.11 (d, 1H, J=2.7 Hz), 7.84-7.86 (d, 1H, J=3.9 Hz), 7.75-7.78 (dd, 1H, J=2.1 Hz, J=8.7 Hz), 7.25-7.28 (d, 1H, J=7.8 Hz), 7.09-7.12 (d, 1H, J=9 Hz), 5.02-5.11 (m, 1H), 4.11-4.21 (m, 1H), 3.71-3.91 (m, 4H), 2.85 (bs, 1H), 1.41-2.42 (m, 11H), 1.08-1.27 (m, 4H), 0.987 (s, 3H); ¹⁹F NMR (282 MHz; d₆-DMSO) δ −166.3 (s); m/z=467 (M+H)⁺

Example 43

Synthesis of 2-((S-tetrahydrofuran-3-yloxy)-5-(5-fluoro-4-(octahydro-5,5-dimethylindolizin-7-ylamino)pyrimidin-2-ylamino)benzonitrile (Compound 60)

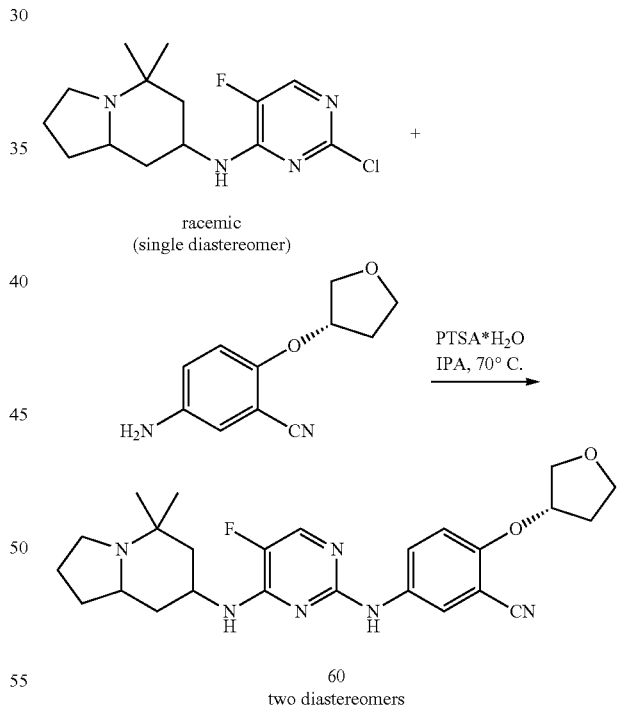

A mixture of N-(2-chloro-5-fluoropyrimidin-4-yl)-octahydro-5,5-dimethylindolizin-7-amine (Racemic, single diastereomer; 200 mg, 0.669 mmol, 1 equiv), 2-((S)-tetrahydrofuran-3-yloxy)-5-aminobenzonitrile (191 mg, 0.937 mmol, 1.4 equiv), and PTSA monohydrate (127 mg, 0.669 mmol, 1 equiv) in IPA (7 ml) were heated to 70° C. for 3 days. After cooling to ambient temperature, the crude mixture was concentrated to dryness and taken in water, EtOAc, and 1N NaOH. The layers were separated. The organic layer was washed with 1N NaOH (×2), dried over Na₂SO₄, filtered, and concentrated to dryness. The crude product was purified by flash chromatography and eluted with DCM:2M NH$_3$/MeOH=100:0 to 96:4 using 1% 2M NH$_3$/MeOH increments to give compound 2-((S)-tetrahydrofuran-3-yloxy)-5-(5-fluoro-4-(octahydro-5,5-dimethylindolizin-7-ylamino)pyrimidin-2-ylamino)benzonitrile (Compound 60) (two diastereomers; 294 mg, 95%) as a solid.

$^1$H NMR (300 MHz; d$_6$-DMSO) δ 9.14 (s, 1H), 8.10-8.11 (d, 1H, J=2.7 Hz), 7.84-7.86 (d, 1H, J=3.9 Hz), 7.75-7.78 (dd, 1H, J=2.1 Hz, J=8.7 Hz), 7.25-7.28 (d, 1H, J=7.8 Hz), 7.09-7.12 (d, 1H, J=9 Hz), 5.02-5.11 (m, 1H), 4.11-4.21 (m, 1H), 3.72-3.91 (m, 4H), 2.84 (bs, 1H), 1.40-2.42 (m, 11H), 1.08-1.27 (m, 4H), 0.982 (s, 3H); $^{19}$F NMR (282 MHz; d$_6$-DMSO) δ −166.3 (s); m/z=467 (M+H)$^+$.

Example 44

HPLC separation of compound 60 2-((S-tetrahydrofuran-3-yloxy)-5-(5-fluoro-4-(octahydro-5,5-dimethylindolizin-7-ylamino)pyrimidin-2-ylamino)benzonitrile (Compounds 61-62)

HPLC separation of compound 2-((S)-tetrahydrofuran-3-yloxy)-5-(5-fluoro-4-(octahydro-5,5-dimethylindolizin-7-ylamino)pyrimidin-2-ylamino)benzonitrile (Compound 60) (mixture of two diastereomers 55 mg) to constituent single diastereomers was performed.

HPLC method: Column: Chiralcel OJ-H, 4.6×250 mm, with guard. Mobil phase: 90% CO$_2$, 10% methanol w/0.1% triethylamine. Flow rate: 4 ml/min. Injection volume: 10 μL. Concentration: approx 5 mg/ml. Detection: UV at 254 nm.
Compound 61

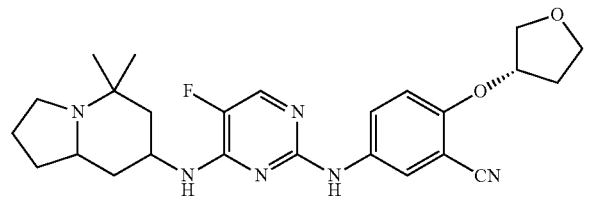 [SMILES: CC1(C)CC(Nc2nc(Nc3ccc(O[C@H]4CCOC4)c(C#N)c3)ncc2F)CC2CCCN21]

Compound 61: (>96% de, 17 mg) has Rt=6.01 min.
$^1$H NMR (300 MHz; d$_6$-DMSO) δ 9.14 (s, 1H), 8.10-8.11 (d, 1H, J=2.7 Hz), 7.84-7.86 (d, 1H, J=3.9 Hz), 7.75-7.78 (dd, 1H, J=2.1 Hz, J=8.7 Hz), 7.25-7.28 (d, 1H, J=7.8 Hz), 7.09-7.12 (d, 1H, J=9 Hz), 5.02-5.11 (m, 1H), 4.11-4.21 (m, 1H), 3.71-3.91 (m, 4H), 2.85 (bs, 1H), 1.41-2.42 (m, 11H), 1.08-1.27 (m, 4H), 0.987 (s, 3H); $^{19}$F NMR (282 MHz; d$_6$-DMSO) δ −166.3 (s); m/z=467 (M+H)$^+$.
Compound 62

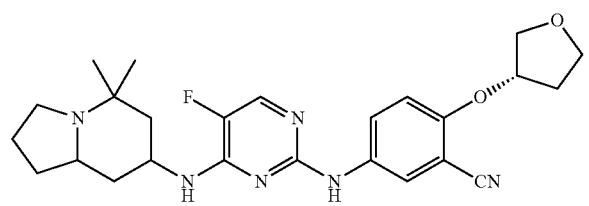

Compound 62: (>97% de, 18 mg) has Rt=6.90 min.
$^1$H NMR (300 MHz; d$_6$-DMSO) δ 9.14 (s, 1H), 8.10-8.11 (d, 1H, J=2.7 Hz), 7.84-7.86 (d, 1H, J=3.9 Hz), 7.75-7.78 (dd, 1H, J=2.1 Hz, J=8.7 Hz), 7.25-7.28 (d, 1H, J=7.8 Hz), 7.09-7.12 (d, 1H, J=9 Hz), 5.02-5.11 (m, 1H), 4.11-4.21 (m, 1H), 3.71-3.91 (m, 4H), 2.85 (bs, 1H), 1.41-2.42 (m, 11H), 1.08-1.27 (m, 4H), 0.987 (s, 3H); $^{19}$F NMR (282 MHz; d$_6$-DMSO) δ −166.3 (s); m/z=467 (M+H)$^+$.

Example 45

Synthesis of 5-(5-Fluoro-4-(octahydro-5,5-dimethylindolizin-7-ylamino)pyrimidin-2-ylamino)-2-(oxetan-3-yloxy)benzonitrile (Compound 63)

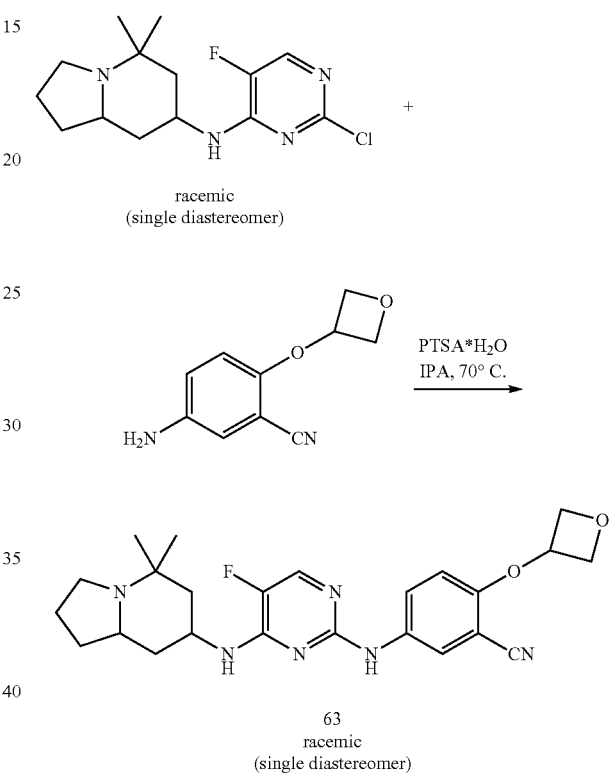

A mixture of N-(2-chloro-5-fluoropyrimidin-4-yl)-octahydro-5,5-dimethylindolizin-7-amine (racemic, single diastereomer; 200 mg, 0.669 mmol, 1 equiv), 5-amino-2-(oxetan-3-yloxy)benzonitrile (178 mg, 0.937 mmol, 1.4 equiv), and PTSA monohydrate (127 mg, 0.669 mmol, 1 equiv) in IPA (7 ml) were heated to 70° C. for 3 days. After cooling to ambient temperature, the crude mixture was concentrated to dryness and taken in water, EtOAc, and 1N NaOH. The layers were separated. The organic layer was washed with 1N NaOH (×2), dried over Na$_2$SO$_4$, filtered, and concentrated to dryness. The crude product was purified by flash chromatography and eluted with DCM:2M NH$_3$/MeOH=100:0 to 96:4 using 1% 2M NH$_3$/MeOH increments to give compound 5-(5-fluoro-4-(octahydro-5,5-dimethylindolizin-7-ylamino)pyrimidin-2-ylamino)-2-(oxetan-3-yloxy)benzonitrile (Compound 63)(Racemic, single enantiomer; 163 mg, 54%) as a solid.

$^1$H NMR (300 MHz; d$_6$-DMSO) δ 9.16 (s, 1H), 8.14 (s, 1H), 7.83-7.84 (d, 1H, J=3.9 Hz), 7.71-7.74 (dd, 1H, J=2.1 Hz, J=8.7 Hz), 7.23-7.26 (m, 1H), 6.74-6.77 (d, 1H, J=9.3 Hz), 5.24-5.39 (p, 1H, J=6.3 Hz), 4.88-4.94 (t, 2H, J=6 Hz), 4.49-4.58 (t, 2H, J=5.7 Hz), 4.15 (bs, 1H), 2.84 (bs, 1H), 1.42-2.42 (m, 9H), 1.06-1.28 (m, 4H), 0.974 (s, 3H); $^{19}$F NMR (282 MHz; d$_6$-DMSO) δ −166.2 (s); m/z=453 (M+H)$^+$.

Example 46

Synthesis of 1-(2-((R)-tetrahydrofuran-3-yloxy)-5-(5-fluoro-4-(octahydro-5,5-dimethylindolizin-7-ylamino)pyrimidin-2-ylamino)phenyl)-4-methyl-1H-tetrazol-5(4H)-one (Compound 48)

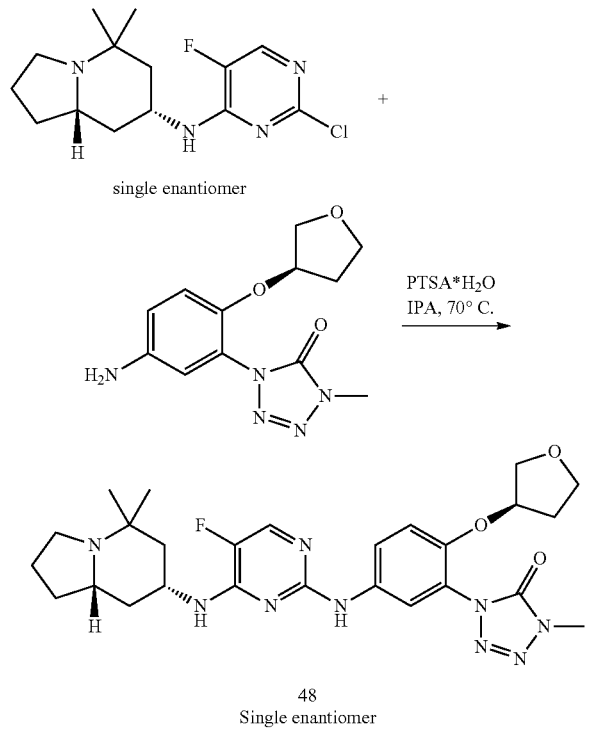

A mixture of N-(2-chloro-5-fluoropyrimidin-4-yl)-octahydro-5,5-dimethylindolizin-7-amine (single enantiomer; 35 mg, 0.116 mmol, 1 equiv), 1-(2-((R)-tetrahydrofuran-3-yloxy)-5-aminophenyl)-4-methyl-1H-tetrazol-5(4H)-one (45 mg, 0.162 mmol, 1.4 equiv), and PTSA monohydrate (22 mg, 0.116 mmol, 1 equiv) in IPA (1.5 ml) were heated to 70° C. for 3 days. After cooling to ambient temperature, the crude mixture was concentrated to dryness and taken in water, EtOAc, and 1N NaOH. The layers were separated. The organic layer was washed with 1N NaOH (×2), dried over Na$_2$SO$_4$, filtered, and concentrated to dryness. The crude product was purified by flash chromatography and eluted with DCM:2M NH$_3$/MeOH=100:0 to 96:4 using 1% 2M NH$_3$/MeOH increments to give compound 1-(2-((R)-tetrahydrofuran-3-yloxy)-5-(5-fluoro-4-(octahydro-5,5-dimethylindolizin-7-ylamino)pyrimidin-2-ylamino)phenyl)-4-methyl-1H-tetrazol-5(4H)-one (Compound 48) (49 mg, 78%) as a solid.

$^1$H NMR (300 MHz; d$_6$-DMSO) δ 9.20 (s, 1H), 8.03 (s, 1H), 7.83-7.84 (d, 1H, J=3.9 Hz), 7.60-7.63 (dd, 1H, J=2.1 Hz, J=8.7 Hz), 7.22-7.25 (d, 1H, J=7.8 Hz), 7.14-7.17 (d, 1H, J=9 Hz), 4.94-5.07 (m, 1H), 3.99-4.11 (m, 1H), 3.79-3.83 (dd, 1H, J=4.5 Hz, J=9.9 Hz), 3.59-3.69 (m, 6H), 2.84 (bs, 1H), 1.41-2.24 (m, 11H), 1.06-1.22 (m, 4H), 0.813 (s, 3H); $^{19}$F NMR (282 MHz; d$_6$-DMSO) δ −166.6 (s); m/z=540 (M+H)$^+$.

Example 47

Synthesis of 1-(2-((S)-tetrahydrofuran-3-yloxy)-5-(5-fluoro-4-(octahydro-5,5-dimethylindolizin-7-ylamino)pyrimidin-2-ylamino)phenyl)-4-methyl-1H-tetrazol-5(4H)-one (Compound 50)

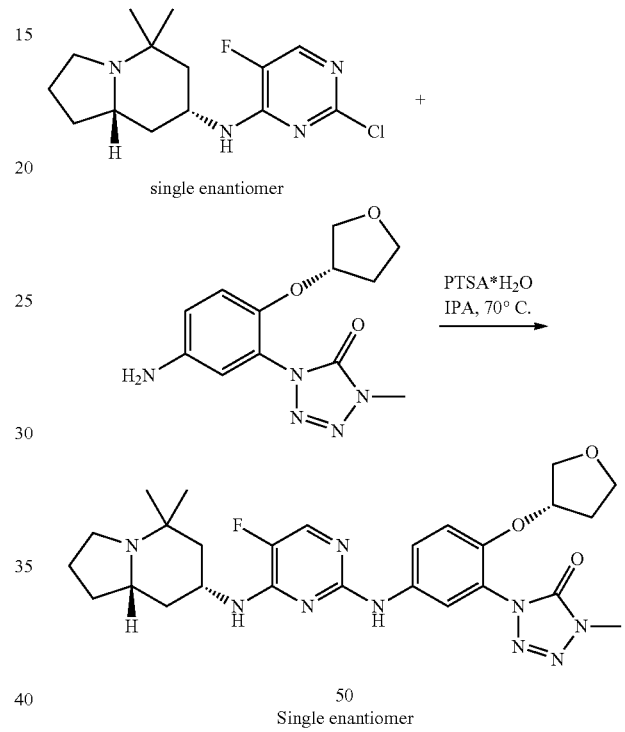

A mixture of N-(2-chloro-5-fluoropyrimidin-4-yl)-octahydro-5,5-dimethylindolizin-7-amine (Single diastereomer, single enantiomer; 53 mg, 0.178 mmol, 1 equiv), 1-(2-((S)-tetrahydrofuran-3-yloxy)-5-aminophenyl)-4-methyl-1H-tetrazol-5(4H)-one (69 mg, 0.249 mmol, 1.4 equiv), and PTSA monohydrate (34 mg, 0.178 mmol, 1 equiv) in IPA (2 ml) were heated to 70° C. for 3 days. After cooling to ambient temperature, the crude mixture was concentrated to dryness and taken in water, EtOAc, and 1N NaOH. The layers were separated. The organic layer was washed with 1N NaOH (×2), dried over Na$_2$SO$_4$, filtered, and concentrated to dryness. The crude product was purified by flash chromatography and eluted with DCM:2M NH$_3$/MeOH=100:0 to 96:4 using 1% 2M NH$_3$/MeOH increments to give compound 1-(2-((S)-tetrahydrofuran-3-yloxy)-5-(5-fluoro-4-(octahydro-5,5-dimethylindolizin-7-ylamino)pyrimidin-2-ylamino)phenyl)-4-methyl-1H-tetrazol-5(4H)-one (Compound 50) (75 mg, 78%) as a solid.

$^1$H NMR (300 MHz; d$_6$-DMSO) δ 9.20 (s, 1H), 8.03 (s, 1H), 7.83-7.84 (d, 1H, J=3.9 Hz), 7.60-7.63 (dd, 1H, J=2.1 Hz, J=8.7 Hz), 7.22-7.25 (d, 1H, J=7.8 Hz), 7.14-7.17 (d, 1H, J=9 Hz), 4.94-5.07 (m, 1H), 3.99-4.11 (m, 1H), 3.78-3.83 (dd, 1H, J=4.5 Hz, J=9.9 Hz), 3.59-3.69 (m, 6H), 2.84 (bs, 1H), 1.41-2.24 (m, 11H), 1.06-1.22 (m, 4H), 0.812 (s, 3H); $^{19}$F NMR (282 MHz; d$_6$-DMSO) δ −166.6 (s); m/z=540 (M+H)$^+$.

Example 48

Synthesis of 1-(5-(5-fluoro-4-(octahydro-5,5-dimethylindolizin-7-ylamino)pyrimidin-2-ylamino)-2-(tetrahydro-2H-pyran-4-yloxy)phenyl)-4-methyl-1H-tetrazol-5(4H)-one (Compound 52)

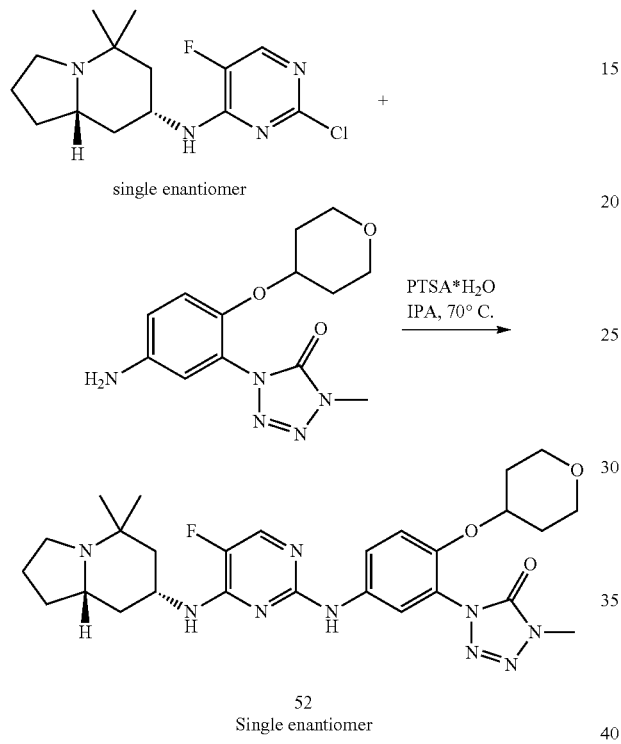

52
Single enantiomer

A mixture of N-(2-chloro-5-fluoropyrimidin-4-yl)-octahydro-5,5-dimethylindolizin-7-amine (Single diastereomer, single enantiomer; 53 mg, 0.178 mmol, 1 equiv), 1-(5-amino-2-(tetrahydro-2H-pyran-4-yloxy)phenyl)-4-methyl-1H-tetrazol-5(4H)-one (Described in: WO 2011/068898, 73 mg, 0.249 mmol, 1.4 equiv), and PTSA monohydrate (34 mg, 0.178 mmol, 1 equiv) in IPA (2 ml) were heated to 70° C. for 3 days. After cooling to ambient temperature, the crude mixture was concentrated to dryness and taken in water, EtOAc, and 1N NaOH. The layers were separated. The organic layer was washed with 1N NaOH (×2), dried over Na$_2$SO$_4$, filtered, and concentrated to dryness. The crude product was purified by flash chromatography and eluted with DCM:2M NH$_3$/MeOH=100:0 to 96:4 using 1% 2M NH$_3$/MeOH increments to give compound 1-(5-(5-fluoro-4-(octahydro-5,5-dimethylindolizin-7-ylamino)pyrimidin-2-ylamino)-2-(tetrahydro-2H-pyran-4-yloxy)phenyl)-4-methyl-1H-tetrazol-5(4H)-one (Compound 52) (48 mg, 50%) as a solid.

$^1$H NMR (300 MHz; d$_6$-DMSO) δ 9.19 (s, 1H), 8.06 (s, 1H), 7.83-7.84 (d, 1H, J=3.9 Hz), 7.57-7.61 (dd, 1H, J=2.1 Hz, J=8.7 Hz), 7.22-7.25 (d, 1H, J=7.8 Hz), 7.18-7.21 (d, 1H, J=9 Hz), 4.44-4.57 (m, 1H), 3.97-4.12 (m, 1H), 3.61-3.67 (m, 7H), 3.37-3.44 (m, 2H), 2.84 (bs, 1H), 1.42-2.24 (m, 11H), 1.06-1.22 (m, 4H), 0.812 (s, 3H); $^{19}$F NMR (282 MHz; d$_6$-DMSO) δ −166.7 (s); m/z=554 (M+H)$^+$.

Example 49

Synthesis of 1-(5-(4-((2R,7R,8aR)-2-fluoro-octahydro-5,5-dimethylindolizin-7-ylamino)-5-fluoropyrimidin-2-ylamino)-2-cyclopropyl-4-fluorophenyl)-4-methyl-1H-tetrazol-5(4H)-one (Compound 64)

$^1$H NMR (300 MHz, CDCl$_3$) δ 8.57 (d, J=7.8 Hz, 1H), 7.78 (s, 1H), 7.09 (s, 1H), 6.89 (d, J=12.2 Hz, 1H), 5.18 (dt, J=11.9, 5.7 Hz, 1H), 4.75 (d, J=8.2 Hz, 1H), 4.28-4.12 (m, 1H), 3.73 (s, 3H), 3.52-3.35 (m, 1H), 2.78 (t, J=13.3 Hz, 1H), 2.71-2.52 (m, 1H), 2.33 (d, J=11.8 Hz, 1H), 2.19-1.99 (m, 1H), 1.89-1.75 (m, 2H), 1.74-1.48 (m, 3H), 1.30 (t, J=12.2 Hz, 1H), 1.15 (s, 3H), 1.00 (s, 3H), 0.87-0.78 (m, 2H), 0.61-0.51 (m, 2H).
$^{19}$F NMR (282 MHz, CDCl$_3$) δ −129.42 (s), −167.50 (s), −168.35-−169.04 (m).
LCMS (m/z): 530.5 (MH$^+$).

Example 50

Synthesis of 1-(5-(4-((2R,7S,8aR)-2-fluoro-octahydro-5,5-dimethylindolizin-7-ylamino)-5-fluoropyrimidin-2-ylamino)-2-cyclopropyl-4-fluorophenyl)-4-methyl-1H-tetrazol-5(4H)-one (Compound 65)

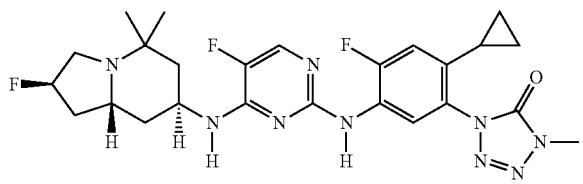 [SMILES: Cn1nnn(-c2cc(Nc3ncc(F)c(N[C@H]4C[C@@H]5C[C@@H](F)CN5C(C)(C)C4)n3)c(F)cc2C2CC2)c1=O]

$^1$H NMR (300 MHz, CDCl$_3$) δ 8.59 (d, J=7.8 Hz, 1H), 7.79 (d, J=3.1 Hz, 1H), 7.10 (d, J=3.2 Hz, 1H), 6.86 (d, J=12.2 Hz, 1H), 5.30-5.04 (m, 2H), 4.32 (s, 1H), 3.72 (s, 3H), 3.55-3.37 (m, 1H), 3.01-2.86 (m, 1H), 2.80-2.60 (m, 1H), 2.08 (d, J=13.6 Hz, 2H), 1.92-1.75 (m, 3H), 1.63-1.37 (m, 2H), 1.13 (s, 3H), 1.12 (s, 3H), 0.87-0.79 (m, 2H), 0.60-0.53 (m, 2H).
$^{19}$F NMR (282 MHz, CDCl3$_3$) δ −129.67 (s), −167.84 (s), −168.37-−168.79 (m).
LCMS (m/z): 530.5 (MH$^+$).

Example 51

Synthesis of 1-(5-(4-((2S,7R,8aR)-2-fluoro-octahydro-5,5-dimethylindolizin-7-ylamino)-5-fluoropyrimidin-2-ylamino)-2-cyclopropyl-4-fluorophenyl)-4-methyl-1H-tetrazol-5(4H)-one (Compound 67)

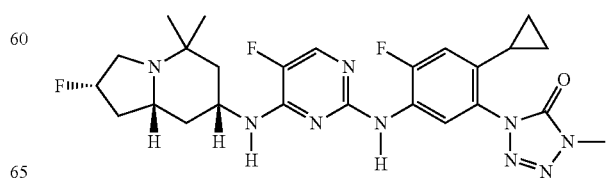

¹H NMR (300 MHz, CDCl₃) δ 8.54 (d, J=7.8 Hz, 1H), 7.78 (s, 1H), 7.05 (s, 1H), 6.88 (d, J=12.2 Hz, 1H), 5.23-5.00 (m, 1H), 4.77 (d, J=8.0 Hz, 1H), 4.19-4.08 (m, 1H), 3.71 (s, 3H), 3.18 (dd, J=22.9, 11.3 Hz, 1H), 2.46-2.27 (m, 4H), 1.84-1.64 (m, 4H), 1.48 (t, J=12.3 Hz, 1H), 1.26-1.15 (m, 3H), 0.93 (s, 3H), 0.86-0.78 (m, 2H), 0.59-0.53 (m, 2H).
¹⁹F NMR (282 MHz, CDCl₃) δ −129.23 (s), −164.71-−165.30 (m), −167.34 (s).
LCMS (m/z): 530.5 (MH⁺).

Example 52

Synthesis of 1-(5-(4-((2R,7R,8aR)-2-hydroxy-octahydro-5,5-dimethylindolizin-7-ylamino)-5-fluoropyrimidin-2-ylamino)-2-cyclopropyl-4-fluorophenyl)-4-methyl-1H-tetrazol-5(4H)-one (Compound 68)

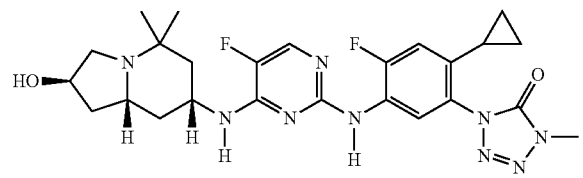 [SMILES: Cn1nnn(-c2cc(Nc3ncc(F)c(N[C@@H]4C[C@@H]5C[C@@H](O)CN5C(C)(C)C4)n3)c(F)cc2C2CC2)c1=O]

¹H NMR (300 MHz, CDCl₃) δ 8.56 (d, J=7.7 Hz, 1H), 7.78 (s, 1H), 7.12 (s, 1H), 6.90 (d, J=12.2 Hz, 1H), 4.79 (d, J=8.0 Hz, 1H), 4.40 (s, 1H), 4.21-4.07 (m, 1H), 3.76 (s, 3H), 3.49 (s, 1H), 3.41 (dd, J=9.9, 6.8 Hz, 1H), 2.70 (dd, J=16.6, 10.3 Hz, 1H), 2.32 (dd, J=9.8, 4.0 Hz, 2H), 2.08 (s, 1H), 1.85-1.63 (m, 4H), 1.35 (t, J=12.3 Hz, 1H), 1.16 (s, 3H), 1.01-0.88 (m, 3H), 0.81 (d, J=8.3 Hz, 2H), 0.57 (d, J=4.0 Hz, 2H).
LCMS (m/z): 528.4 (MH⁺).

Example 53

Synthesis of 5-Fluoro-N2-(4-fluoro-3-(5-methyl-1H-tetrazol-1-yl)phenyl)-N4-(octahydro-5,5,8-trimethylindolizin-7-yl)pyrimidine-2,4-diamine (Compounds 69-70)

Synthesis of Compounds 69 and 70

The mono-S$_N$Ar product (50.0 mg, 0.159 mmol) was dissolved in 4 ml of isopropyl alcohol in a 2 dram vial. PTSA-monohydrate (45.3 mg, 0.238 mmol) and the desired aniline (1.5 eq) were added and the vial was sealed. After heating over night at 105° C. using an anodized aluminum heating block the solvent was boiled off by removing the cap. The product was isolated by preparative HPLC eluting with an acetonitrile/water gradient. Analysis by NMR showed that the isolated product is a single diastereomer of unknown configuration.

Synthesis of 5-Fluoro-N2-(4-fluoro-3-(5-methyl-1H-tetrazol-1-yl)phenyl)-N4-(octahydro-5,5,8-trimethylindolizin-7-yl)pyrimidine-2,4-diamine (Compound 70)

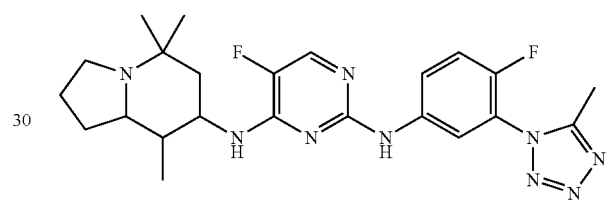

¹H NMR (300 MHz, d6-DMSO) δ 8.05-7.88 (m, 1H), 7.87-7.71 (m, 1H), 7.70-7.50 (m, 2H), 6.50 (s, 1H), 5.46 (s, 1H), 4.17 (s, 1H), 3.70 (s, 1H), 3.02 (s, 1H), 2.61-2.50 (m, 4H), 2.44 (t, J=0.9 Hz, 1H), 2.23 (d, J=20.1 Hz, 2H), 2.14 (d, J=14.0 Hz, 1H), 1.89 (s, 2H), 1.43 (d, J=12.9 Hz, 1H), 1.35 (s, 3H), 1.24 (s, 3H), 1.20 (d, J=23.5 Hz, 3H), 0.97 (d, J=6.8 Hz, 2H); MS (ES) 470 (M+H), 468 (M−H).

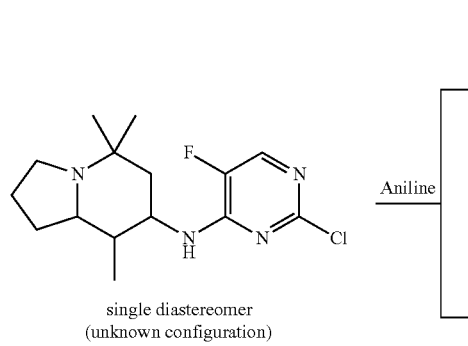

single diastereomer
(unknown configuration)

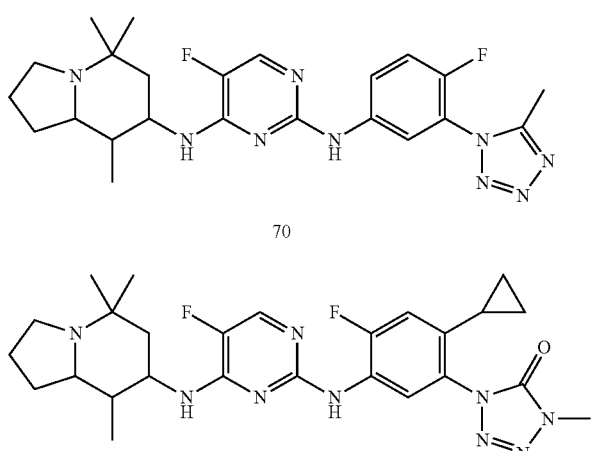

Aniline

70

69

183

Synthesis of 1-(5-(5-Fluoro-4-(octahydro-5,5,8-trimethylindolizin-7-ylamino)pyrimidin-2-ylamino)-2-cyclopropyl-4-fluorophenyl)-4-methyl-1H-tetrazol-5(4H)-one (Compound 69)

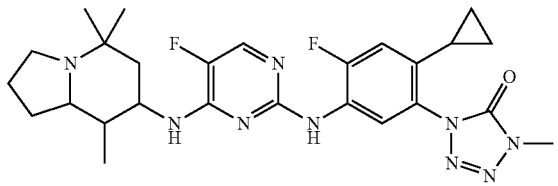 [SMILES: CC1C(Nc2nc(Nc3cc(-n4nnn(C)c4=O)c(C4CC4)cc3F)ncc2F)CC(C)(C)N2CCCC12]

$^1$H NMR (300 MHz, CDCl$_3$) δ 8.45 (d, J=7.8 Hz, 1H), 8.36 (s, 1H), 7.78-7.72 (s br, 1H), 7.21 (s, 1H), 6.81 (d, J=12.1 Hz, 1H), 5.95 (s br, 2H), 5.18 (s, 1H), 4.34 (s, 1H), 3.67 (s, 3H), 3.13 (m, 1H), 2.84 (m, 1H), 2.60-2.45 (m, 1H), 2.28 (s, 1H), 2.24-2.03 (m, 4H), 2.05-1.66 (m, 3H), 1.39 (s, 3H), 1.27 (s, 3H), 0.98 (d, J=7.0 Hz, 3H), 0.78 (d, J=8.3 Hz, 1H), 0.56-0.46 (m, 2H); MS (ES) 526 (M+H), 524 (M−H).

Example 54

Synthesis of 1-(5-(4-((7R,8aS)-5,5-dimethyl-octahydroindolizin-7-ylamino)-5-fluoropyrimidin-2-ylamino)-4-fluoro-2-methoxyphenyl)-4-methyl-1H-tetrazol-5(4H)-one (Compound 22)

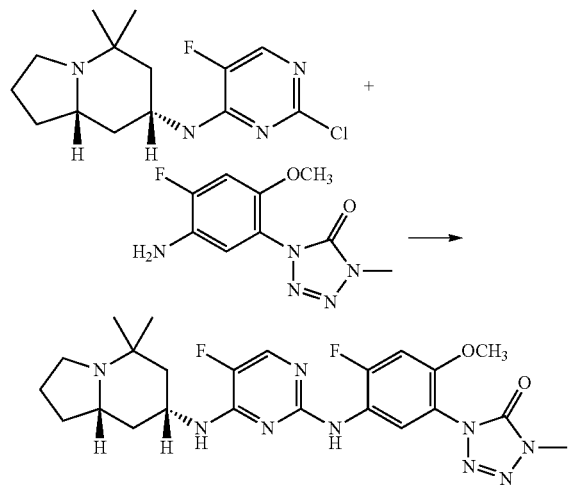

A mixture of (7R,8aS)—N-(2-choro-5-fluoropyrimidin-4-yl)-octahydro-5,5-dimethylindolizin-7-amine (49 mg, 0.16 mmol, 1 equiv), 1-(5-amino-4-fluoro-2-methoxyphenyl)-4-methyl-1H-tetrazol-5(4H)-one (59 mg, 0.25 mmol, 1.5 equiv) and pTsOH.H$_2$O (25 mg, 0.13 mmol, 0.8 equiv) in isopropanol (1.5 ml) was heated at 100° C. overnight in a sealed vial. After allowing to cool to room temperature, the solvent was removed and the residue was purified by HPLC to give the product as a solid.

$^1$H NMR (300 MHz; d$_6$-DMSO) δ 8.39 (s, 1H), 7.85 (d, J=8.1 Hz, 1H), 7.78 (d, J=3.9 Hz, 1H), 7.25 (d, J=12.6 Hz, 1H), 7.18 (d, J=8.1 Hz, 1H), 4.05-3.90 (m, 1H), 3.75 (s, 3H), 3.59 (s, 3H), 2.85-2.75 (m, 1H), 2.27-2.15 (m, 2H), 1.93-1.89 (m, 1H), 1.70-1.50 (m, 3H), 1.41-1.32 (m, 1H), 1.24-1.15 (m, 1H), 1.11-0.95 (m, 2H), 1.04 (s, 3H), 0.76 (s, 3H); $^{19}$F NMR (282 MHz; d$_6$-DMSO) δ −115.9 (s), −166.9 (s); m/z=502.1 (M+H)$^+$; m/z=500.4 (M−H)$^+$.

Example 55

Synthesis of 1-(5-(4-((7R,8aS)-5,5-dimethyl-octahydroindolizin-7-ylamino)-5-fluoropyrimidin-2-ylamino)-4-fluoro-2-isopropoxyphenyl)-4-methyl-1H-tetrazol-5(4H)-one (Compound 23)

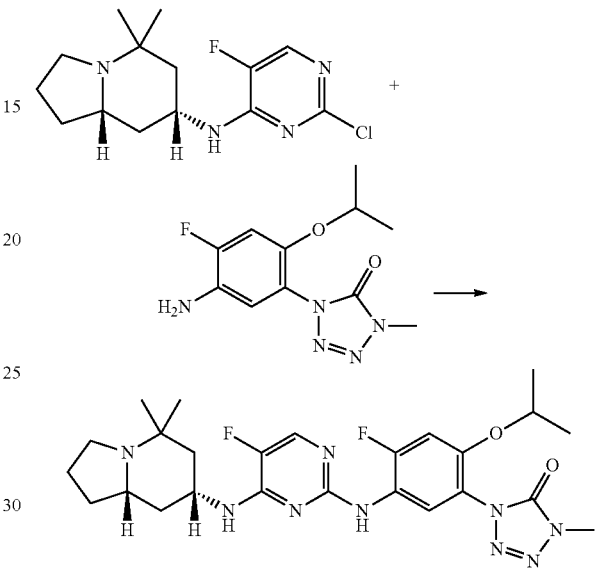

23

A mixture of (7R,8aS)—N-(2-choro-5-fluoropyrimidin-4-yl)-octahydro-5,5-dimethylindolizin-7-amine (52 mg, 0.18 mmol, 1 equiv), 1-(5-amino-4-fluoro-2-methoxyphenyl)-4-methyl-1H-tetrazol-5(4H)-one (94 mg, 0.36 mmol, 2 equiv) and pTsOH.H$_2$O (27 mg, 0.14 mmol, 0.8 equiv) in isopropanol (1.5 ml) was heated at 100° C. overnight in a sealed vial. After allowing to cool to room temperature, the solvent was removed and the residue was purified by HPLC to give the product as a solid.

$^1$H NMR (300 MHz; d$_6$-DMSO) δ 8.38 (s, 1H), 7.82 (d, J=8.4 Hz, 1H), 7.78 (d, J=3.9 Hz, 1H), 7.26 (d, J=12.6 Hz, 1H), 7.20 (d, J=8.1 Hz, 1H), 4.59 (q, J=6.0 Hz, 1H), 4.05-3.90 (m, 1H), 3.59 (s, 3H), 2.90-2.80 (m, 1H), 2.30-2.20 (m, 2H), 1.95-1.91 (m, 1H), 1.72-1.52 (m, 3H), 1.43-1.35 (m, 1H), 1.22-1.00 (m, 3H), 1.55 (d, J=6.0 Hz, 6H), 1.05 (s, 3H), 0.78 (s, 3H); $^{19}$F NMR (282 MHz; d$_6$-DMSO) δ −116.2 (s), −167.0 (s); m/z=530.2 (M+H)$^+$; m/z=528.5 (M−H)$^+$.

Example 56

Synthesis of Compound 71

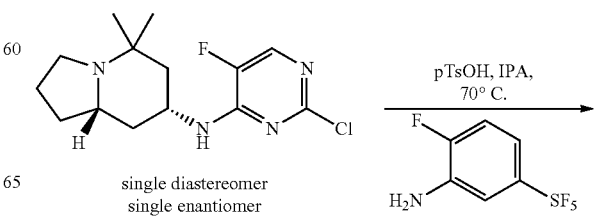

single diastereomer
single enantiomer

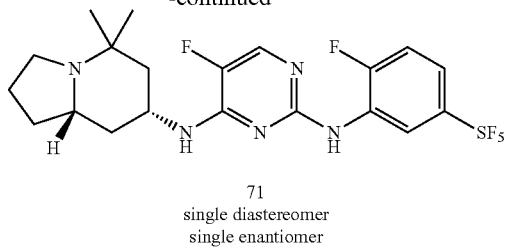

71
single diastereomer
single enantiomer $^1$H NMR (300 MHz; d$_6$-DMSO) δ 8.76 (s, 1H), 8.42-8.39 (m, 1H), 7.86 (d, J=3.6 Hz, 1H), 7.58-7.53 (m, 1H), 7.41 (t, J=6.5 Hz, 1H), 7.27 (br. d, 1H), 4.04 (m, 1H), 2.81 (m, 1H), 2.42-2.20 (m, 2H), 1.98-1.89 (m, 1H), 1.74-1.48 (m, 4H), 1.43-1.35 (m, 1H), 1.30-1.11 (m, 2H), 1.04 (s, 3H), 0.83 (s, 3H); $^{19}$F NMR (282 MHz; d$_6$-DMSO) δ −165.3 (s), −135.6 (s), −135.1 (s), −116.7 (s), −112.5 (m); m/z=500.25 (M+H)$^+$; rt=4.13 min (HPLC conditions-Protocol 1).

Example 57

Synthesis of Compound 72

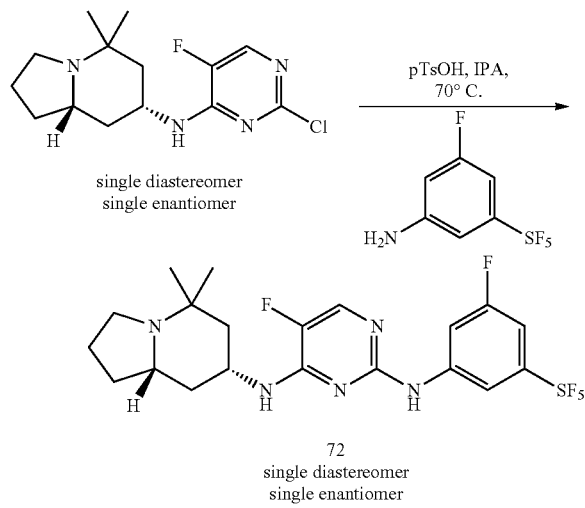

72
single diastereomer
single enantiomer $^1$H NMR (300 MHz; d$_6$-DMSO) δ 9.66 (s, 1H), 8.17 (d, J=11.9 Hz, 1H), 7.94-7.92 (m, 2H), 7.43 (br. d, J=7.4 Hz, 1H), 7.27 (d, J=8.8 Hz, 1H), 4.24-4.10 (m, 1H), 2.90-2.79 (m, 1H), 2.36-2.23 (m, 1H), 2.05-2.10 (m, 1H), 1.70-1.44 (m, 4H), 1.30-1.15 (m, 3H), 1.09 (s, 3H), 0.98 (s, 3H); $^{19}$F NMR (282 MHz; d$_6$-DMSO) δ −164.3 (s), −136.7 (s), −136.1 (s), −113.7 (m), −109.5 (s); m/z=500.37 (M+H)$^+$; rt=4.57 min (HPLC conditions-Protocol 1).

Example 58

Synthesis of Compound 76

Synthesis of 4-(R,S)-Octahydro-5,5-dimethylindolizin-7-ylamino)-2-(4-cyclopropyl-2-fluoro-5-(4,5-dihydro-4-methyl-5-oxotetrazol-yl)phenylamino)pyrimidine-5-carbonitrile (Compound 76)

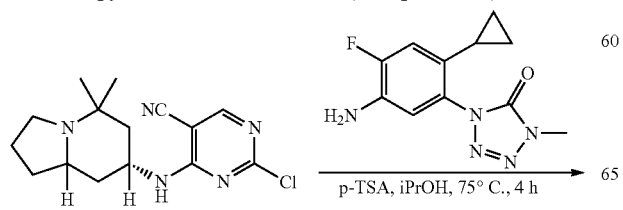

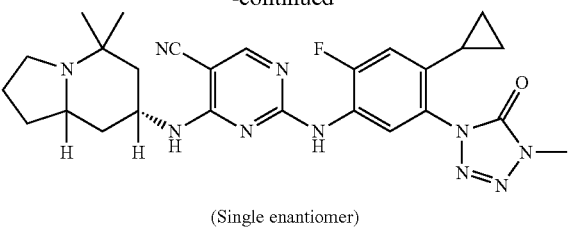

(Single enantiomer)

To a solution of (R,S)-2-chloro-4-(octahydro-5,5-dimethylindolizin-7-ylamino)pyridimine-5-carbonitrile (Example 7; 0.300 g, 1.0 mmol) in iPrOH (25 mL), 1-(5-amino-2-cyclopropyl-4-fluorophenyl)-4-methyl-1H-tetrazol-5(4H)-one (0.34 g, 1.4 mmol) and p-TSA (0.20 g, 1.1 mmol) were added and the reaction mixture was heated to 75° C. for 4 h. LCMS analysis indicated the completion of reaction. Removal of volatiles and purification of the crude by column chromatography gave the desired product as p-toluene sulfonic acid salt. The salt was dissolved in 50 mL EtOAc and partitioned with aq. 2N NaOH solution. The organic layers were separated and dried over Na$_2$SO$_4$. Removal of the solvents under vacuum gave the desired product in 78% yield (0.40 g).

$^1$H NMR (DMSO d$_6$, 300 MHz) δ: 9.43 (s, 1H), 8.29 (s, 1H), 7.65 (d, J=7.2 Hz, 1H), 7.42 (d, J=8.1 Hz, 1H), 7.02 (d, J=12.0 Hz, 1H), 4.02 (br. s, 1H), 3.60 (s, 3H), 2.76-2.81 (m, 1H), 2.15-2.24 (m, 2H), 1.79-1.83 (m, 1H), 1.50-1.68 (m, 4H), 1.34-1.43 (m, 2H), 1.07-1.22 (m, 5H), 1.01 (s, 3H), 0.82-0.86 (m, 2H), 0.63-0.67 (m, 2H); LCMS (m/z): 519 (MH$^+$).

Example 59

Synthesis of 1-(2-((S)-2-hydroxypropoxy)-5-(4-((7R,8aS)-octahydro-5,5-dimethylindolizin-7-ylamino)-5-fluoropyrimidin-2-ylamino)-4-fluorophenyl)-4-methyl-1H-tetrazol-5(4H)-one (Compound 81)

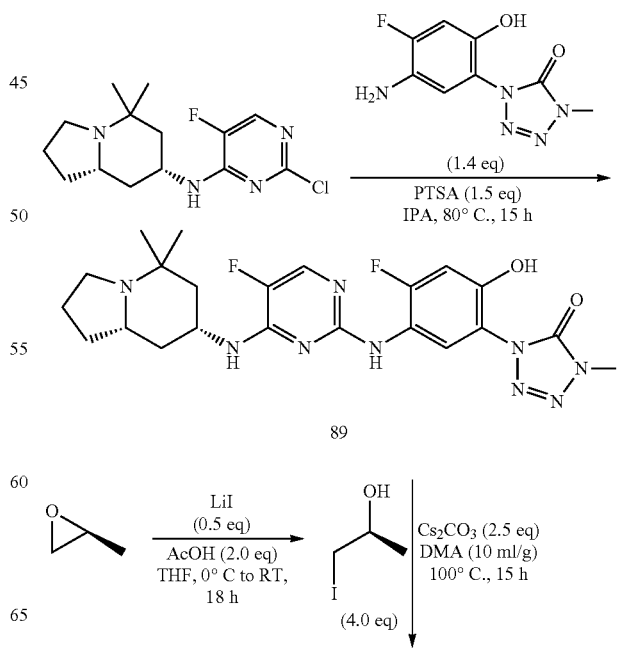

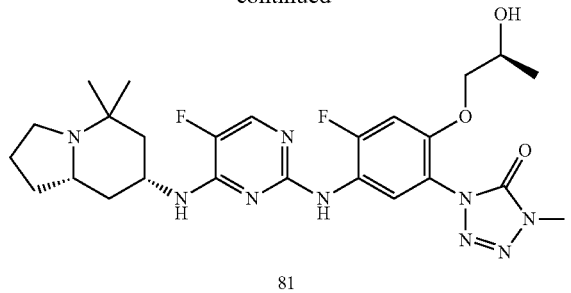

81

Other Reaction Products:

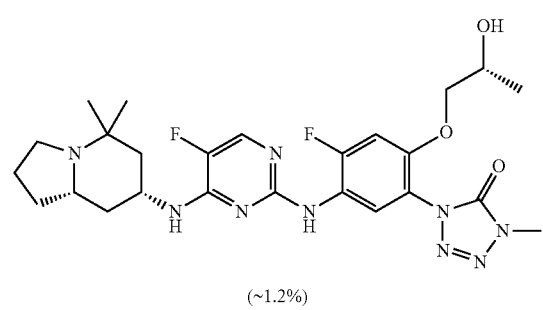

(~1.2%)

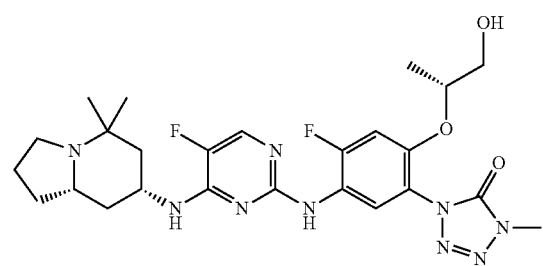

(~1.0%)

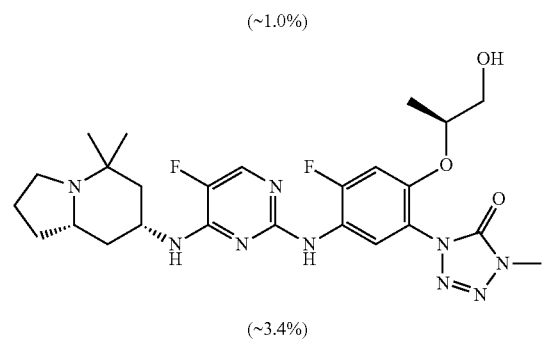

(~3.4%)

1-(5-amino-4-fluoro-2-hydroxyphenyl)-4-methyl-1H-tetrazol-5(4H)-one was prepared according to Example 29 above. N-(2-chloro-5-fluoropyrimidin-4-yl)-octahydro-5,5-dimethylindolizin-7-amine and 1-(5-amino-4-fluoro-2-hydroxyphenyl)-4-methyl-1H-tetrazol-5(4H)-one were conjugated to form the phenol (compound 89). The phenol (4.61 g, 9.45 mmol), (S)-1-iodopropan-2-ol (7.02 g, 37.7 mmol) (synthesized according to U.S. Application Publication No. 2005/0054701) and Cs$_2$CO$_3$ (7.68 g, 23.6 mmol) were placed in a pressure vessel. DMA (dimethylacetamide) (50 ml) was added and the vessel was sealed. The pale grey suspension was heated to 100° C. and stirred at this temperature for 15 hours. After cooling down to room temperature, the reaction mixture was analyzed by TLC and HPLC to check for completion. The DMA was distilled off and water (100 ml) was added to the crude reaction mixture. The crude reaction mixture was extracted with DCM (2×100 ml) and EtOAc (1×100 ml), filtered through Na$_2$SO$_4$ and solvents were evaporated under reduced pressure to yield 6.6 gram of crude product. The crude product was re-dissolved in DCM and absorbed on silica gel. Further purification was carried out with a CombiFlash Gold column (spherical silica, 220 gram) eluted with DCM and MeOH (2M NH$_3$) (gradient 0% to 6%). The clean fractions were combined to yield 3.04 gram (59%, off-white solid) of compound 81. Reverse phase HPLC and $^1$H-NMR indicated a substantially pure product. Analysis by chiral SFC (12 min method) showed that the product also contained ~1.2% of the other diastereomer and two diastereomeric regioisomers (~1.0% and ~3.4%).

$^1$H NMR (300 MHz, d6-DMSO) δ 8.41 (s, 1H), 7.88 (d, J=8.4 Hz, 1H), 7.80 (d, J=3.8 Hz, 1H), 7.27 (d, J=12.5 Hz, 1H), 7.20 (d, J=7.8 Hz, 1H), 4.74 (d, J=4.1 Hz, 1H), 4.08-3.94 (m, 1H), 3.93-3.76 (m, 3H), 3.60 (s, 3H), 3.32 (m, 1H), 2.90-2.75 (m, 1H), 2.30-2.11 (m, 2H), 1.94 (d, J=11.0 Hz, 1H), 1.78-1.47 (m, 4H), 1.47-1.33 (m, 1H), 1.30-1.09 (m, 2H), 1.09-0.99 (m, 6H), 0.77 (s, 3H); MS (ES) m/z 546 (M+H)$^+$.

Example 60

Synthesis of 1-(2-(2-hydroxyethoxy)-5-(4-((7R,8aS)-octahydro-5,5-dimethylindolizin-7-ylamino)-5-fluoropyrimidin-2-ylamino)-4-fluorophenyl)-4-methyl-1H-tetrazol-5(4H)-one (Compound 77)

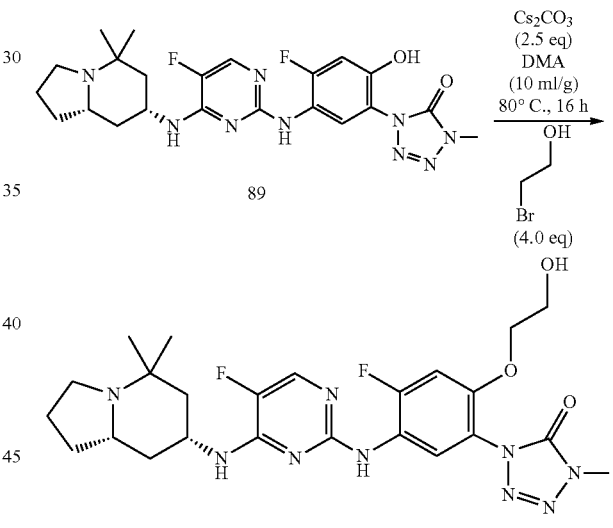

The phenol (compound 89) (9.90 g, 20.3 mmol), 2-bromoethanol (10.2 g, 81.2 mmol) and Cs$_2$CO$_3$ (16.5 g, 50.7 mmol) were placed in a pressure vessel. DMA (dimethylacetamide) (100 ml) was added and the vessel was sealed. The reaction mixture was heated to 80° C. and stirred at this temperature for 16 hours. The reaction was then analyzed by TLC and HPLC to check for completion. The DMA was distilled off, water (150 ml) was added and the crude reaction mixture was extracted with DCM (3×150 ml). The organic layers were combined, filtered through Na$_2$SO$_4$ and solvents were evaporated under reduced pressure. The crude product was further purified using CombiFlash chromatography (regular silica gel, 330 gram) eluted with DCM and MeOH (2M NH$_3$) (gradient 0% to 6%). The clean fractions were combined to yield 6.40 gram (59%) of compound 77 in the form of an off-white solid. Slightly less pure factions were also combined to yield another 3.35 gram (31%) of the product.

¹H NMR (300 MHz, d6-DMSO) δ 8.39 (s, 1H), 7.89 (d, J=8.4 Hz, 1H), 7.79 (d, J=3.8 Hz, 1H), 7.28 (d, J=12.5 Hz, 1H), 7.18 (d, J=7.9 Hz, 1H), 4.71 (t, J=5.6 Hz, 1H), 4.03 (t, J=4.9 Hz, 2H), 3.97 (dd, J=7.8, 4.0 Hz, 1H), 3.65-3.53 (m, 5H), 3.34 (m, 1H), 2.80 (dd, J=8.4, 5.4 Hz, 1H), 2.27-2.09 (m, 2H), 2.05 (s, 1H), 1.92 (d, J=11.4 Hz, 1H), 1.68 (dd, J=11.1, 6.6 Hz, 1H), 1.62-1.45 (m, 3H), 1.37 (t, J=12.2 Hz, 1H), 1.27-1.05 (m, 1H), 1.03 (s, 3H), 0.75 (s, 3H); ¹⁹F NMR (300 MHz, d6-DMSO) δ −116.5, −166.8; MS (ES) m/z 532 (M+H)⁺.

Example 61

Synthesis of Compound 80

Preparation of (7R,8aS)—N-(5-aminocarbonyl-2-chloropyrimidin-4-yl)-octahydro-5,5-dimethylindolizin-7-amine

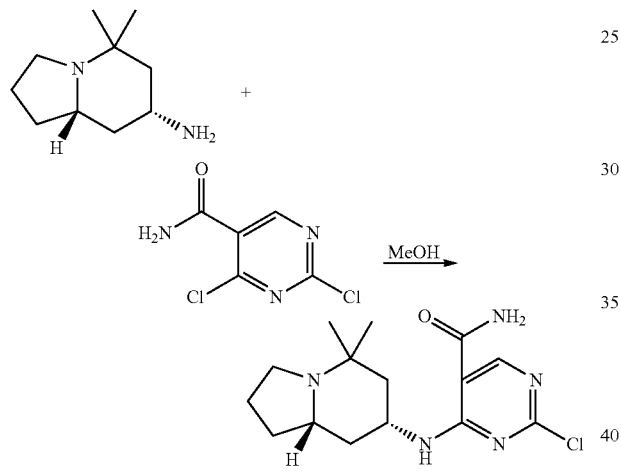

A mixture of (7R,8aS)-octahydro-5,5-dimethylindolizin-7-amine (1.25 g) and 5-aminocarbonyl-2,4-dichloropyrimidine (2.14 g, 1.5 eq.) in iPrOH (50 mL) was stirred at −10° C. to rt for 3 d. The solid was filtered off and washed with methanol (3×10 mL). The filtrate was evaporated under vacuum and the residue was purified by CombiFlash chromatography on silica gel (2N NH₃ in MeOH/CH₂Cl₂=0-30%) to give the desired product (1.3 g, 54% over 3 steps).

m/z=324.11 (M+H)⁺.

Preparation of (7R,8aS)—N-(2-chloro-5-cyanopyrimidin-4-yl)-octahydro-5,5-dimethylindolizin-7-amine

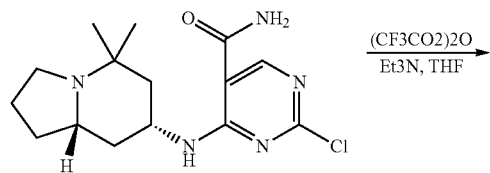

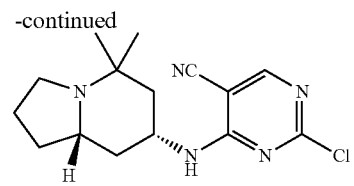

To a mixture of (7R,8aS)—N-(5-aminocarbonyl-2-chloropyrimidin-4-yl)-octahydro-5,5-dimethylindolizin-7-amine (1.3 g) and triethylamine (1.72 mL) in THF (50 mL) was added trifluoroacetic anhydride (1.33 mL) at −78° C. After stifling for 2 h, the reaction was quenched with ice (150 mL). The aqueous solution was extracted with EtOAc (6×150 mL). The organic layers were evaporated under vacuum and the residue was purified by CombiFlash chromatography on silica gel (2N NH₃ in MeOH/CH₂Cl₂=0-20%) to give the desired product (1.1 g, 89%).

¹H NMR (CDCl₃, 300 MHz): δ 8.29 (s, 1H), 5.41 (d, J=6.0 Hz, 1H), 4.34-4.29 (m, 1H), 3.01-2.94 (m, 1H), 2.57-2.52 (m, 1H), 2.39 (q, J=8.7 Hz, 1H), 2.27-2.20 (m, 1H), 1.94-1.62 (m, 5H), 1.48-1.35 (m, 2H), 1.21 (s, 3H), 1.06 (s, 3H); m/z=306.06 (M+H)⁺.

Synthesis of 4-((7R,8aS)-octahydro-5,5-dimethylindolizin-7-ylamino)-2-(4-(2-hydroxy-2-methylpropoxy)-2-fluoro-5-(4,5-dihydro-4-methyl-5-oxotetrazol-1-yl)phenylamino)pyrimidine-5-carbonitrile (Compound 80)

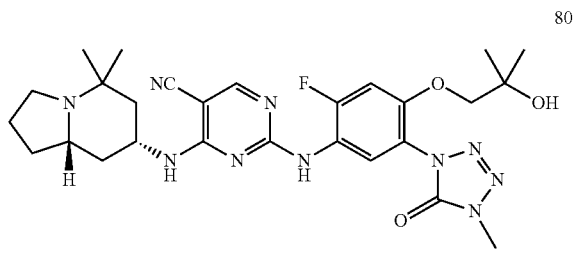 [SMILES: Cn1nnn(-c2cc(Nc3ncc(C#N)c(N[C@@H]4C[C@@H]5CCCN5C(C)(C)C4)n3)c(F)cc2OCC(C)(C)O)c1=O]

A mixture of 1-(5-amino-2-(2-hydroxy-2-methylpropoxy)-4-fluorophenyl)-4-methyl-1H-tetrazol-5(4H)-one (305 mg), (7R,8aS)—N-(2-chloro-5-cyanopyrimidin-4-yl)-octahydro-5,5-dimethylindolizin-7-amine (262 mg), and benzenesulfonic acid (160 mg) in IPA (2 mL) were heated to 80° C. overnight. After cooling to ambient temperature, the crude mixture was concentrated to dryness. The crude product was absorbed onto silica gel and purified by CombiFlash chromatography (2N NH₃ in MeOH/CH₂Cl₂=0-30%) to give desired product (386 mg, 80%).

¹H NMR (300 MHz; d₆-DMSO) δ 9.32 (bs, 1H), 8.26 (s, 1H), 7.68 (d, 1H, J=7.8 Hz), 7.38 (d, 1H, J=7.2 Hz), 7.27 (d, 1H, J=12.0 Hz), 4.57 (s, 1H), 3.96 (br, 1H), 3.72 (s, 2H), 3.58 (s, 3H), 2.78 (m, 1H), 2.16 (m, 2H), 1.82-1.42 (m, 6H), 1.22-1.01 (m, 5H), 0.67 (bs, 3H); m/z=567.10 (M+H)⁺.

Example 62

Synthesis of 4-((7R,8aS)-octahydro-5,5-dimethylindolizin-7-ylamino)-2-(4-((S)-2-hydroxypropoxy)-2-fluoro-5-(4,5-dihydro-4-methyl-5-oxotetrazol-1-yl)phenylamino)pyrimidine-5-carbonitrile (Compound 79)

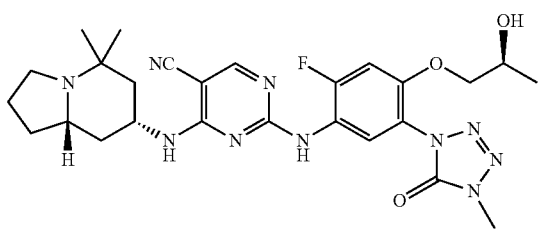

A mixture of 1-(5-amino-4-fluoro-2-hydroxyphenyl)-4-methyl-1H-tetrazol-5(4H)-one (210 mg), (7R,8aS)—N-(2-chloro-5-cyanopyrimidin-4-yl)-octahydro-5,5-dimethylindolizin-7-amine (220 mg), and benzenesulfonic acid (200 mg) in IPA (2 mL) were heated to 80° C. for overnight. After cooling to ambient temperature, the crude mixture was concentrated to dryness. The crude product was absorbed onto silica gel and purified by CombiFlash chromatography (2N $NH_3$ in $MeOH/CH_2Cl_2$=0-30%) to give compound 1-(5-(4-((7R,8aS)-octahydro-5,5-dimethylindolizin-7-ylamino)-5-cyanopyrimidin-2-ylamino)-4-fluoro-2-hydroxyphenyl)-4-methyl-1H-tetrazol-5(4H)-one (540 mg with some benzenesulfonic acid).

m/z=495.08 $(M+H)^+$.

A mixture of 1-(5-(4-((7R,8aS)-octahydro-5,5-dimethylindolizin-7-ylamino)-5-cyanopyrimidin-2-ylamino)-4-fluoro-2-hydroxyphenyl)-4-methyl-1H-tetrazol-5(4H)-one (600 mg), (S)-1-iodopropan-2-ol (1.13 g) and cesium carbonate (1.19 g) in DMA (5 mL) were heated to 100° C. for overnight. The reaction mixture was diluted with water (100 mL), and extracted with EtOAc (2×100 mL). The organic layers were evaporated and purified by CombiFlash chromatography (2N $NH_3$ in $MeOH/CH_2Cl_2$=0-30%) to give compound 79 (400 mg, 78%).

$^1$H NMR (300 MHz; $d_6$-DMSO) δ 9.32 (bs, 1H), 8.26 (s, 1H), 7.64 (d, 1H, J=8.7 Hz), 7.37 (d, 1H, J=7.8 Hz), 7.30 (d, 1H, J=12.3 Hz), 4.74 (d, 1H, J=4.2 Hz), 3.90-3.81 (m, 5H), 3.58 (s, 3H), 2.78 (m, 1H), 2.17 (m, 2H), 1.82-1.42 (m, 6H), 1.18-1.01 (m, 5H), 0.68 (bs, 3H); m/z=553.06 $(M+H)^+$.

Example 63

Synthesis of 4-((7R,8aS)-octahydro-5,5-dimethylindolizin-7-ylamino)-2-(4-(2-hydroxyethoxy)-2-fluoro-5-(4,5-dihydro-4-methyl-5-oxotetrazol-1-yl)phenylamino)pyrimidine-5-carbonitrile (Compound 78)

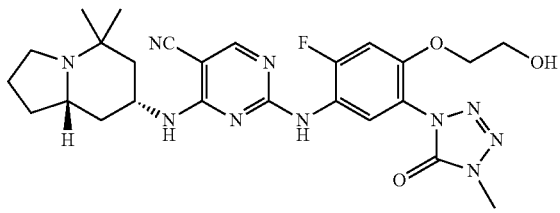

A mixture of 1-(5-amino-2-(2-(tert-butyldimethylsilyl)oxyethoxy)-4-fluorophenyl)-4-methyl-1H-tetrazol-5(4H)-one (200 mg), (7R,8aS)—N-(2-chloro-5-cyanopyrimidin-4-yl)-octahydro-5,5-dimethylindolizin-7-amine (120 mg), and benzenesulfonic acid (120 mg) in IPA (2 mL) was heated to 80° C. overnight. After cooling to ambient temperature, the crude mixture was concentrated to dryness. The crude product was absorbed onto silica gel and purified by CombiFlash chromatography (2N $NH_3$ in $MeOH/CH_2Cl_2$=0-20%) to give desired product with benzenesulfonic acid. The methanol solution of the salt was passed through an ion-exchange resin column to remove acid to give the free base of compound 78 (120 mg, 57%).

$^1$H NMR (300 MHz; $d_6$-DMSO) δ 9.33 (bs, 1H), 8.26 (s, 1H), 7.64 (d, 1H, J=7.5 Hz), 7.37 (d, 1H, J=7.5 Hz), 7.32 (d, 1H, J=12.3 Hz), 4.71 (t, 1H, J=5.4 Hz), 4.05 (t, 2H, J=4.8 Hz), 4.01 (br, 1H), 3.58 (m, 5H), 2.78 (m, 1H), 2.17 (m, 2H), 1.79-1.42 (m, 6H), 1.16-1.08 (m, 2H), 1.01 (s, 3H), 0.69 (bs, 3H); m/z=539.11 $(M+H)^+$.

Example 64

Synthesis of 1-(5-(4-((7R,8aS)-5,5-dimethyloctahydroindolizin-7-ylamino)-5-fluoropyrimidin-2-ylamino)-4-fluoro-2-((R)-2-hydroxypropoxy)phenyl)-4-methyl-1H-tetrazol-5(4H)-one (Compound 82)

Method 1:

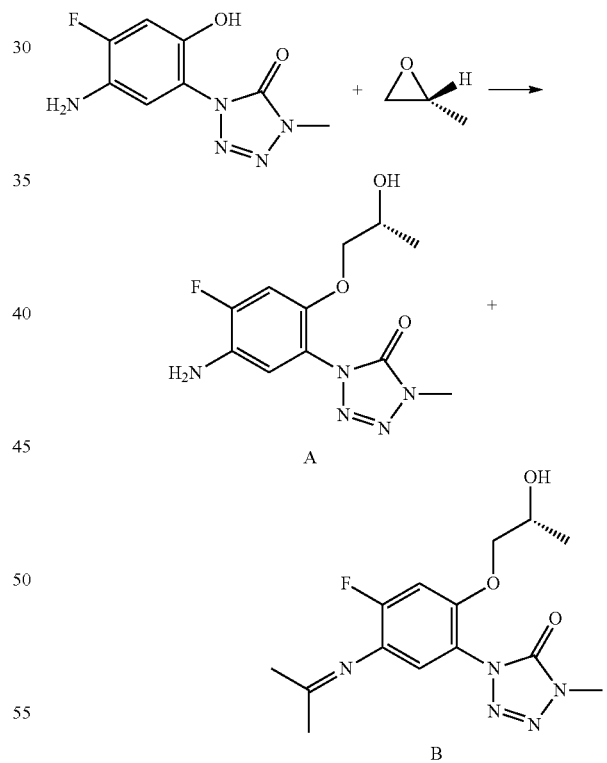

A mixture of anilino-phenol (300 mg, 1.33 mmol, 1 equiv), (R)-propylene oxide (387 mg, 6.66 mmol, 5.0 equiv), $K_2CO_3$ (221 mg, 1.60 mmol, 1.2 equiv) and $^nBu_4NBr$ (43 mg, 0.13 mmol, 0.1 equiv) in 6 mL of acetone was heated in a sealed vessel at 70° C. for 16 h. The mixture was cooled to room temperature, filtered and washed with EtOAc (~50 mL). The filtrate was concentrated and the resulting residue was purified by column chromatography on silica gel using hexane/EtOAc (1:4) as eluent to give 280 mg (Y=74%) of product A and B (~3:1). This mixture was directly used in the next step.

¹H NMR (CDCl₃, 300 MHz) of mixture: δ 6.92 (d, J=8.1 Hz, 1H, compound B), 6.86 (d, J=9.0 Hz, 1H, compound A), 6.80 (d, J=11.1 Hz, 1H, compound B), 6.77 (d, J=12.0 Hz, 1H, compound A), 4.12-4.05 (m, 3H, compound A), 3.85-3.70 (m, 3H, compound B), 3.71 (s, 3H, compound B), 3.70 (s, 3H, compound A), 2.24 (s, 3H, compound B), 2.18 (s, 3H, compound B), 1.21 (d, J=6.3 Hz, 3H, compound B), 1.19 (d, J=6.3 Hz, 3H, compound A); m/z=283.93 (M+H)⁺.

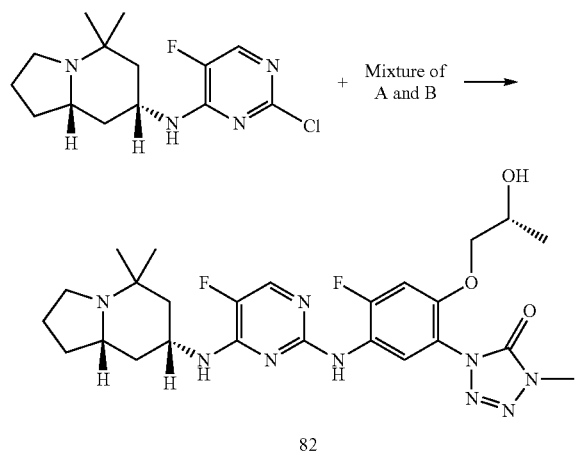

82

A mixture of above A and B (98 mg, 0.35 mmol, 1.3 equiv), mono-SNAr product (80 mg, 0.27 mmol, 1 equiv), Pd(OAc)₂ (6 mg, 0.03 mmol, 0.1 equiv), (±)BINAP (34 mg, 0.05 mmol, 0.2 equiv) and Cs₂CO₃ (264 mg, 0.81 mmol, 3 equiv) in 2 mL of dioxane was microwaved at 120° C. for 2 hours. The mixture was filtered and washed with EtOAc (10 mL). The filtrate was concentrated and the residue was purified by HPLC to give compound 82.

¹H NMR (DMSO-d₆, 300 MHz): δ 8.39 (s, 1H), 7.86 (d, J=8.1 Hz, 1H), 7.78 (d, J=3.9 Hz, 1H), 7.25 (d, J=12.6 Hz, 1H), 7.18 (d, J=7.2 Hz, 1H), 4.05-3.90 (m, 1H), 3.88-3.78 (m, 3H), 3.59 (s, 3H), 2.80 (td, J=8.4, 3.0 Hz, 1H), 2.26-2.16 (m, 3H), 1.93-1.89 (m, 1H), 1.69-1.50 (m, 4H), 1.37 (t, J=12.6 Hz, 1H), 1.19-1.14 (m, 1H), 1.03 (s, 3H), 1.01 (d, J=5.7 Hz, 3H), 0.75 (s, 3H); ¹⁹F NMR (DMSO-d₆, 282 MHz): δ −116.18 (s), −166.94 (s); m/z=546.05 (M+H)⁺.

Method 2:

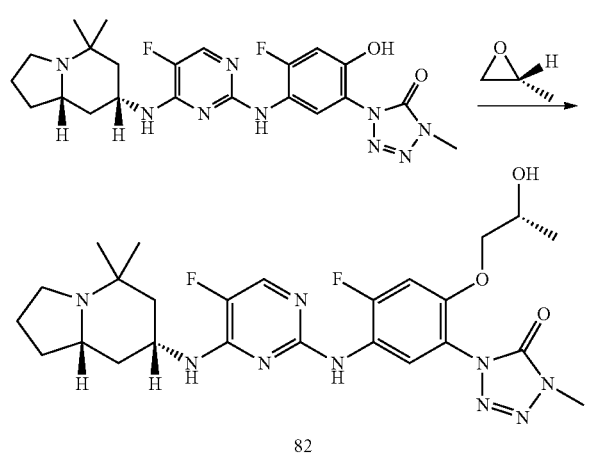

82

A mixture of the starting phenol (1.8 g, 3.69 mmol, 1 equiv), (R)-propylene oxide (1.1 mL, 14.77 mmol, 4.0 equiv), K₂CO₃ (1.0 g, 7.38 mmol, 2.0 equiv) and ⁿBu₄NBr (0.12 g, 0.37 mmol, 0.1 equiv) in 15 mL of acetone was heated in a sealed vessel at 70° C. for 4 days. The mixture was cooled to room temperature, filtered and washed with EtOAc (~100 mL). The filtrated was washed with brine and concentrated. The resulting residue was purified by column chromatography on silica gel using DCM/2N NH₃ in MeOH (95:5) as eluent to give 1.4 g (Y=71%) of compound 82.

Example 65

Synthesis of Compound 86

Preparation of 1-(tert-butyldimethylsilyloxy)-2-methylpropan-2-ol

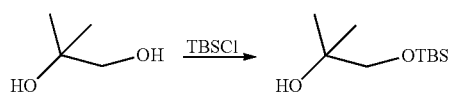

2-Methylpropane-1,2-diol (1.08 g, 12.0 mmol, 1.0 equiv) in DCM (40 mL) under argon was cooled to 0° C. TEA (2.50 mL, 18.0 mmol, 1.5 equiv), DMAP (75.0 mg, 0.600 mmol, 0.05 equiv), and TBSCl (2.00 g, 13.2 mmol, 1.1 equiv) were added sequentially, and the reaction was allowed to warm up to ambient temperature overnight. Complete conversion of reactant to product was confirmed by TLC eluted with EtOAc and visualized with KMnO₄. The solvent was removed in vacuo, and the residue was partitioned between water and EtOAc. The aqueous layer was extracted with EtOAc 2×, and the combined organics were dried with Na₂SO₄, filtered, and concentrated to provide 1-(tertbutyldimethylsilyloxy)-2-methylpropan-2-ol (2.05 g, 84%) as a light brown oil that was used without further purification.

¹H NMR (300 MHz; d₆-DMSO) δ 3.46 (s, 1H), 3.31 (s, 2H), 1.08 (s, 6H), 0.920 (s, 9H), 0.0710 (s, 6H).

Preparation of 1-(2-(1-(tert-butyldimethylsilyloxy)-2-methylpropan-2-yloxy)-5-nitrophenyl)-4-methyl-1H-tetrazol-5(4H)-one

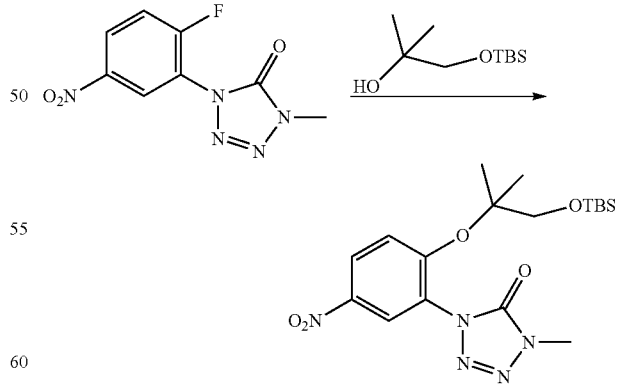

1-(Tertbutyldimethylsilyloxy)-2-methylpropan-2-ol (1.80 g, 8.81 mmol, 1.10 equiv) in THF (30 mL) under argon gas, was cooled to −78° C. Potassium tert-butoxide (1.165 g, 9.61 mmol, 1.20 equiv) was added in one portion, and the reaction mixture was stirred for 15 min at −78° C. Then a solution of 1-(2-fluoro-5-nitrophenyl)-4-methyl-1H-tetrazol-5(4H)-one (prepared according to WO2011068898, which is incorporated herein by reference; 1.915 g, 8.00 mmol, 1.00 equiv) in THF (10 mL) was added slowly, and the reaction mixture was stirred for 30 min at −78° C. and allowed to warm up to ambient temperature over 1 h. The reaction mixture was concentrated, and the residue was taken in EtOAc and water. The layers were separated, and the aqueous layer was extracted with EtOAc 2×. The organic layer was dried over Na$_2$SO$_4$, filtered, and concentrated. The crude product was absorbed onto silica gel and purified by flash chromatography and eluted with heptane:EtOAc=100:0 to 30% EtOAc using 10% EtOAc increments to provide 1-(2-(1-(tert-butyldimethylsilyloxy)-2-methylpropan-2-yloxy)-5-nitrophenyl)-4-methyl-1H-tetrazol-5(4H)-one (2.28 g, 67%) as a yellow oil.

$^1$H NMR (300 MHz; d$_6$-DMSO) δ 8.44-8.53 (m, 2H), 7.54-7.57 (d, J=9.3 Hz, 1H), 4.04 (s, 2H), 3.63 (s, 3H), 1.23 (s, 6H), 0.770 (s, 9H), 0.00300 (s, 6H); m/z=424 (M+H)$^+$.

Preparation of 1-(5-amino-2-(1-(tert-butyldimethylsilyloxy)-2-methylpropan-2-yloxy)phenyl)-4-methyl-1H-tetrazol-5(4H)-one

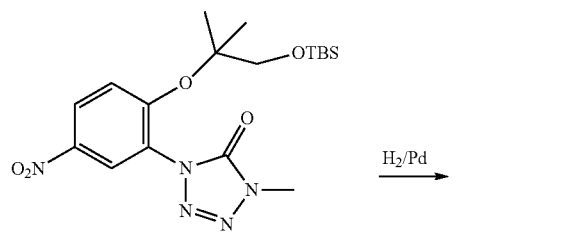

A round-bottom flask was charged with 1-(2-(1-(tert-butyldimethylsilyloxy)-2-methylpropan-2-yloxy)-5-nitrophenyl)-4-methyl-1H-tetrazol-5(4H)-one (2.54 g, 6.00 mmol), EtOH (60 mL), and 10% Pd/C (50% in water, Degussa type E101; 510 mg, 20 wt % by weight of the starting nitro compound). The flask was sealed with a rubber septum, degassed, and back-filled with H$_2$ (3×) from a balloon filled with H$_2$. The reaction was stirred for 4 h using a H$_2$ filled balloon. The reaction mixture was filtered through a pad of celite, and the pad of celite was rinsed with EtOAc/MeOH. The filtrate was evaporated to dryness to provide 1-(5-amino-2-(1-(tert-butyldimethylsilyloxy)-2-methylpropan-2-yloxy)phenyl)-4-methyl-1H-tetrazol-5(4H)-one (2.26 g, 96%) as a light brown solid that was used without further purification.

$^1$H NMR (300 MHz; d$_6$-DMSO) δ 6.97-7.00 (d, J=9.0 Hz, 1H), 6.74-6.78 (m, 1H), 6.64-6.68 (m, 1H), 5.04 (bs, 2H), 3.66 (s, 2H), 3.60 (s, 3H), 1.17 (s, 6H), 0.803 (s, 9H), 0.00300 (s, 6H); m/z=394 (M+H)$^+$.

Preparation of 1-(2-(1-hydroxy-2-methylpropan-2-yloxy)-5-(4-((7R,8aS)-octahydro-5,5-dimethylindolizin-7-ylamino)-5-fluoropyrimidin-2-ylamino)phenyl)-4-methyl-1H-tetrazol-5(4H)-one (Compound 86)

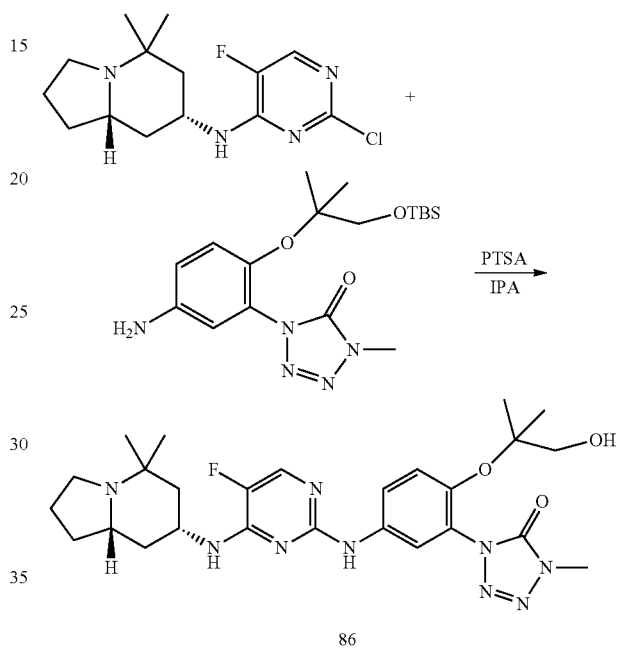

86

A mixture of (7R,8aS)—N-(2-chloro-5-fluoropyrimidin-4-yl)-octahydro-5,5-dimethylindolizin-7-amine hydrochloride (775 mg, 2.31 mmol, 1.00 equiv), 1-(5-amino-2-(1-(tert-butyldimethylsilyloxy)-2-methylpropan-2-yloxy)phenyl)-4-methyl-1H-tetrazol-5(4H)-one (1.00 g, 2.54 mmol, 1.10 equiv), and PTSA monohydrate (880 mg, 4.62 mmol, 2.00 equiv) in IPA (80 mL) was heated to reflux for 3 d as monitored by LCMS. After the first day, in the morning, LCMS indicated a ratio of OTBS-protected product:product=1.5:1. Thus, more PTSA monohydrate (220 mg, 1.16 mmol, 0.50 equiv) was added and refluxing was continued. The reaction was checked by LCMS in the afternoon, which indicated a ratio of OTBS-protected product:product=1:1.2. Thus, more PTSA monohydrate (220 mg, 1.16 mmol, 0.50 equiv) was added and refluxing was continued. On the second day, in the morning, LCMS indicated a ratio of OTBS-protected product:product=1:6.5. Thus, more PTSA monohydrate (220 mg, 1.16 mmol, 0.50 equiv) was added and refluxing was continued. The reaction was checked by LCMS in the afternoon, which indicated a ratio of OTBS-protected product:product=1:9. Thus, more PTSA monohydrate (220 mg, 1.16 mmol, 0.50 equiv) was added and refluxing was continued. On the third day, LCMS indicated the reaction was completed. After cooling to ambient temperature, the crude mixture was concentrated to dryness. The residue was taken in water, EtOAc, and aqueous 1N NaOH. The aqueous and organic layers were partitioned, and the aqueous layer was extracted with EtOAc 2×. The organic layer was dried (Na$_2$SO$_4$), filtered, and the solvent removed under vacuum. The crude product was purified by flash chromatography and eluted with DCM:2M NH$_3$/MeOH=100:0 to 94:6 using 1% 2M NH$_3$/MeOH increments to give compound 1-(2-(1-hydroxy-2-methylpropan-2-yloxy)-5-(4-((7R,8aS)-octahydro-5,5-dimethylindolizin-7-ylamino)-5-fluoropyrimidin-2-ylamino)phenyl)-4-methyl-1H-tetrazol-5(4H)-one (compound 86) (870 mg, 70%) as a solid.

$^1$H NMR (300 MHz; d$_6$-DMSO) δ 9.82 (s, 1H), 8.07 (s, 1H), 7.83-7.84 (d, J=3.6 Hz, 1H), 7.58-7.61 (m, 1H), 7.21-7.24 (m, 1H), 7.09-7.12 (d, J=9.3 Hz, 1H), 4.51 (s, 1H), 4.05 (bs, 1H), 3.65 (s, 2H), 3.59 (s, 3H), 2.83 (m, 1H), 0.803-2.26 (m, 22H); $^{19}$F NMR (282 MHz; d$_6$-DMSO) δ −166.7 (s); m/z=542 (M+H)$^+$.

Example 66

Preparation of 4-((7R,8aS)-octahydro-5,5-dimethylindolizin-7-ylamino)-2-(4-(1-hydroxy-2-methylpropan-2-yloxy)-3-(4,5-dihydro-4-methyl-5-oxotetrazol-1-yl)phenylamino)pyrimidine-5-carbonitrile (Compound 83)

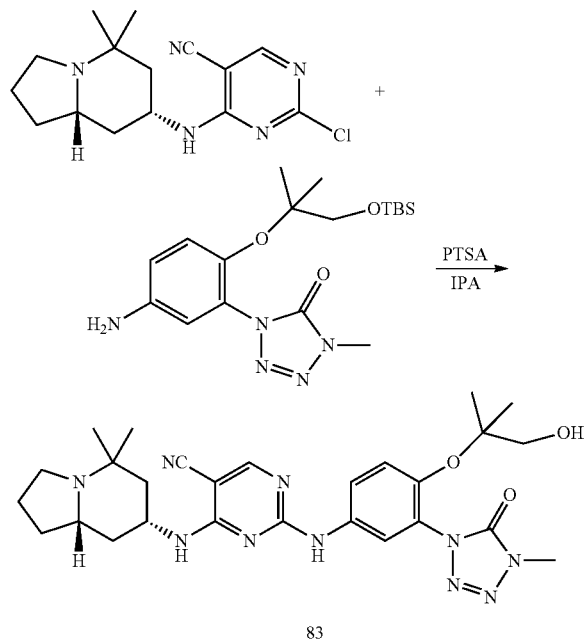

A mixture of 4-((7R,8aS)-octahydro-5,5-dimethylindolizin-7-ylamino)-2-chloropyrimidine-5-carbonitrile hydrochloride (200 mg, 0.584 mmol, 1.00 equiv), 1-(5-amino-2-(1-(tert-butyldimethylsilyloxy)-2-methylpropan-2-yloxy)phenyl)-4-methyl-1H-tetrazol-5(4H)-one (255 mg, 0.643 mmol, 1.10 equiv), and PTSA monohydrate (225 mg, 1.17 mmol, 2.00 equiv) in IPA (20 mL) was heated at 70° C. overnight. After the first day, in the morning, LCMS indicated a ratio of OTBS-protected product:product=3:1. Thus, more PTSA monohydrate (56 mg, 0.292 mmol, 0.50 equiv) was added and temperature was raised to reflux. The reaction was checked by LCMS in the afternoon, which indicated a ratio of OTBS-protected product:product=1.5:1. Thus, more PTSA monohydrate (56 mg, 0.292 mmol, 0.50 equiv) was added and refluxing was continued. On the second day, in the morning, LCMS indicated a ratio of OTBS-protected product:product=1:4.5. Thus, more PTSA monohydrate (112 mg, 0.585 mmol, 1.00 equiv) was added and refluxing was continued. The reaction awas checked by LCMS in the afternoon, which indicated a ratio of OTBS-protected product:product=1:8. Thus, more PTSA monohydrate (56 mg, 0.292 mmol, 0.50 equiv) was added and refluxing was continued. On the third day, LCMS indicated the reaction was completed. After cooling to ambient temperature, the crude mixture was concentrated to dryness. The residue was taken in water, EtOAc, and aqueous 1N NaOH. The aqueous and organic layers were partitioned, and the aqueous layer was extracted with EtOAc 2×. The organic layer was dried (Na$_2$SO$_4$), filtered, and the solvent removed under vacuum. The crude product was purified by flash chromatography and eluted with DCM:2M NH$_3$/MeOH=100:0 to 94:6 using 1% 2M NH$_3$/MeOH increments to give compound 4-((7R,8aS)-octahydro-5,5-dimethylindolizin-7-ylamino)-2-(4-(1-hydroxy-2-methylpropan-2-yloxy)-3-(4,5-dihydro-4-methyl-5-oxotetrazol-1-yl)phenylamino)pyrimidine-5-carbonitrile (compound 83) (252 mg, 79%) as a solid.

$^1$H NMR (300 MHz; d$_6$-DMSO) δ 9.56 (bs, 1H), 8.30 (s, 1H), 8.04 (bs, 1H), 7.63-7.66 (m, 1H), 7.46 (bs, 1H), 7.16-7.19 (d, J=9.3 Hz, 1H), 4.56 (s, 1H), 4.15 (bs, 1H), 3.68 (s, 2H), 3.59 (s, 3H), 2.81 (m, 1H), 0.760-2.26 (m, 22H); m/z=549 (M+H)$^+$.

Example 67

Synthesis of Compound 84

Preparation of ethyl 2-(4-amino-5-fluoro-2-(4-methyl-5-oxo-4,5-dihydro-1H-tetrazol-1-yl)phenoxy)-2-methylpropanoate

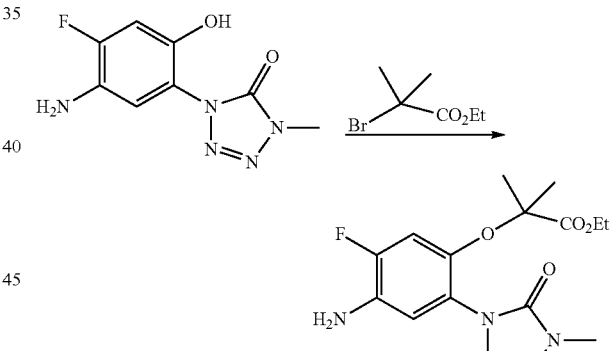

A mixture of 1-(5-amino-4-fluoro-2-hydroxyphenyl)-4-methyl-1H-tetrazol-5(4H)-one (5.00 g, 22.2 mmol, 1.00 equiv), ethyl 2-bromo-2-methylpropanoate (6.50 g, 4.94 mL, 33.3 mmol, 1.50 equiv), K$_2$CO$_3$ (6.15 g, 44.4 mmol, 2.00 equiv), and tetra-n-butylammonium bromide (716 mg, 2.22 mmol, 0.10 equiv) in acetone (220 mL) was heated at reflux overnight. After cooling to RT, the reaction mixture was concentrated to dryness. The crude product was taken in excess water and EtOAc. The layers were separated, and the aqueous layer was extracted with EtOAc 2×. The organic layer was dried over Na$_2$SO$_4$, filtered, and concentrated to dryness. The crude product was absorbed onto silica gel and purified by flash chromatography and eluted with DCM:MeOH=100:0 to 98% MeOH using 1% MeOH increments to provide ethyl 2-(4-amino-5-fluoro-2-(4-methyl-5-oxo-4,5-dihydro-1H-tetrazol-1-yl)phenoxy)-2-methylpropanoate (5.60 g, 74%) as a clear brown oil.

¹H NMR (300 MHz; d₆-DMSO) δ 6.81-6.82 (d, J=5.7 Hz, 1H), 6.76-6.79 (d, J=8.4 Hz, 1H), 5.26 (bs, 2H), 4.11-4.18 (q, J=7.2 Hz, 2H), 3.58 (s, 3H), 1.31 (s, 6H), 1.16-1.21 (t, J=6.9 Hz, 3H); ¹⁹F NMR (282 MHz; d₆-DMSO) δ −128.5 (q); m/z=340 (M+H)⁺.

Preparation of 1-(5-amino-4-fluoro-2-(1-hydroxy-2-methylpropan-2-yloxy)phenyl)-4-methyl-1H-tetrazol-5(4H)-one

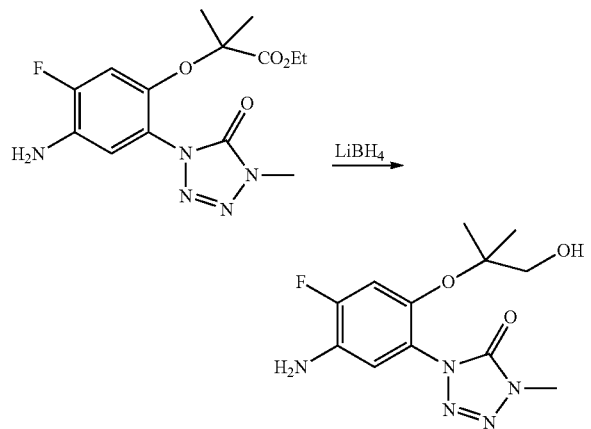

A solution of ethyl 2-(4-amino-5-fluoro-2-(4-methyl-5-oxo-4,5-dihydro-1H-tetrazol-1-yl)phenoxy)-2-methylpropanoate (5.60 g, 16.5 mmol, 1.00 equiv) in Et₂O (155 mL) under argon was cooled to 0° C. The ice-cooled solution was charged with lithium borohydride (791 mg, 36.3 mmol, 2.20 equiv) followed by MeOH (1.540 mL), which resulted in the formation of a free-flowing precipitate. The reaction was stirred at 0° C. for 30 min, then the ice-bath was removed, and the reaction was stirred at ambient temperature for 1 h. At ambient temperature, the reaction was slowly quenched with aqueous 1 N NaOH (100 mL, 100 mmol, 6.00 equiv), which dissolved the free-flowing precipitate. The layers were separated, and the aqueous layer was extracted with DCM 2×. The organic layer was dried over Na₂SO₄, filtered, and concentrated to dryness to give 1-(5-amino-4-fluoro-2-(1-hydroxy-2-methylpropan-2-yloxy)phenyl)-4-methyl-1H-tetrazol-5(4H)-one (4.60 g, 94%) as a white solid that was used without further purification.

¹H NMR (300 MHz; d₆-DMSO) δ 7.05-7.11 (dd, J=3.9 Hz, 12.6 Hz, 1H), 6.73-6.77 (d, J=3.9 Hz, 9.3 Hz, 1H), 5.20 (bs, 2H), 4.81 (bs, 1H), 3.58 (s, 3H), 3.21 (s, 2H), 0.965 (s, 3H); ¹⁹F NMR (282 MHz; d₆-DMSO) δ −129.1 (q); m/z=298 (M+H)⁺.

Preparation of 4-((7R,8aS)-octahydro-5,5-dimethylindolizin-7-ylamino)-2-(4-(1-hydroxy-2-methylpropan-2-yloxy)-2-fluoro-5-(4,5-dihydro-4-methyl-5-oxotetrazol-1-yl)phenylamino)pyrimidine-5-carbonitrile (Compound 84)

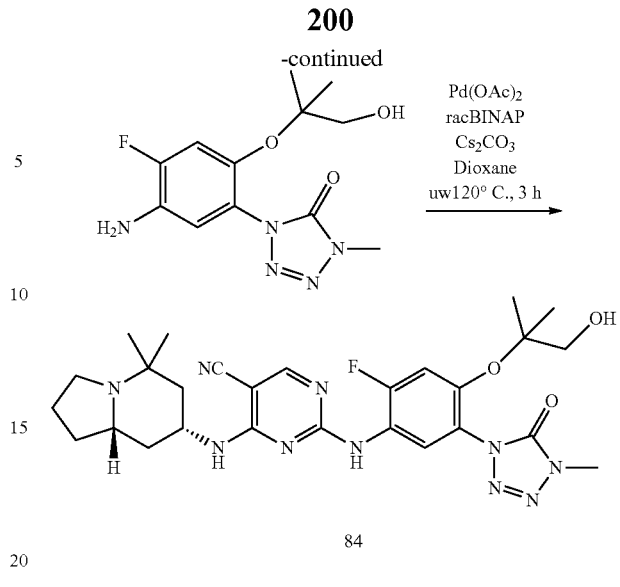

To a microwave vial, was added 4-((7R,8aS)-octahydro-5,5-dimethylindolizin-7-ylamino)-2-chloropyrimidine-5-carbonitrile hydrochloride (100 mg, 0.292 mmol, 1.00 equiv), 1-(5-amino-4-fluoro-2-(1-hydroxy-2-methylpropan-2-yloxy)phenyl)-4-methyl-1H-tetrazol-5(4H)-one (130 mg, 0.438 mmol, 1.50 equiv), rac-BINAP (37 mg, 0.0584 mmol, 0.200 equiv), Cs₂CO₃ (286 mg, 0.877 mmol, 3.00 equiv), Pd(OAc)₂ (7 mg, 0.0292 mmol, 0.100 equiv), and dioxane (3 mL). The microwave vial was capped and sonicated under vacuum for 5 min. The reaction mixture was heated in the microwave at 120° C. for 3 h. The cooled reaction mixture was filtered using a pad of celite and rinsed with dioxane, and the filtrate was concentrated. The crude product was purified by flash chromatography and eluted with DCM:2M NH₃/MeOH=100:0 to 95:5 using 1% 2M NH₃/MeOH increments to provide 4-((7R,8aS)-octahydro-5,5-dimethylindolizin-7-ylamino)-2-(4-(1-hydroxy-2-methylpropan-2-yloxy)-2-fluoro-5-(4,5-dihydro-4-methyl-5-oxotetrazol-1-yl)phenylamino)pyrimidine-5-carbonitrile (compound 84) (65 mg, 39%) as a solid.

¹H NMR (300 MHz; d₆-DMSO) δ 9.32 (bs, 1H), 8.27 (s, 1H), 7.66-7.69 (d, J=8.4 Hz, 1H), 7.37-7.41 (m, 1H), 7.25-7.29 (d, J=12 Hz, 1H), 4.57 (s, 1H), 3.98 (bs, 1H), 3.73 (s, 2H), 3.59 (s, 3H), 2.79 (m, 1H), 0.692-2.21 (m, 22H); ¹⁹F NMR (282 MHz; d₆-DMSO) δ −113.6 (s); m/z=567 (M+H)⁺.

Example 68

Synthesis of 1-(2-(1-hydroxy-2-methylpropan-2-yloxy)-5-(4-((7R,8aS)-octahydro-5,5-dimethylindolizin-7-ylamino)-5-fluoropyrimidin-2-ylamino)-4-fluorophenyl)-4-methyl-1H-tetrazol-5(4H)-one (Compound 85)

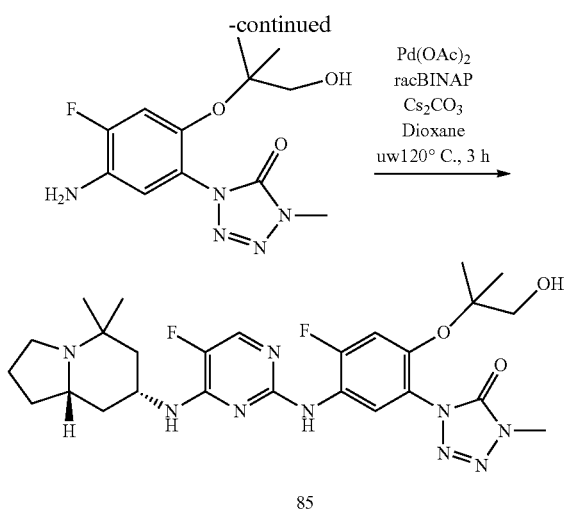

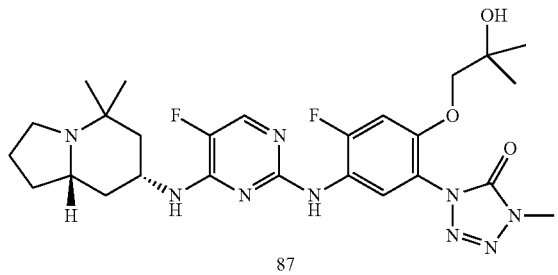

To a microwave vial, was added (7R,8aS)—N-(2-chloro-5-fluoropyrimidin-4-yl)-octahydro-5,5-dimethylindolizin-7-amine hydrochloride (100 mg, 0.298 mmol, 1.00 equiv), 1-(5-amino-4-fluoro-2-(1-hydroxy-2-methylpropan-2-yloxy)phenyl)-4-methyl-1H-tetrazol-5(4H)-one (133 mg, 0.447 mmol, 1.50 equiv), rac-BINAP (38 mg, 0.0597 mmol, 0.200 equiv), Cs$_2$CO$_3$ (292 mg, 0.895 mmol, 3.00 equiv), Pd(OAc)$_2$ (7 mg, 0.0298 mmol, 0.100 equiv), and dioxane (3 mL). The microwave vial was capped and sonicated under vacuum for 5 min. The reaction mixture was heated in the microwave at 120° C. for 3 h. The cooled reaction mixture was filtered using a pad of celite and rinsed with dioxane, and the filtrate was concentrated. The crude product was purified by flash chromatography and eluted with DCM:2M NH$_3$/MeOH=100:0 to 95:5 using 1% 2M NH$_3$/MeOH increments to provide 1-(2-(1-hydroxy-2-methylpropan-2-yloxy)-5-(4-((7R,8aS)-octahydro-5,5-dimethylindolizin-7-ylamino)-5-fluoropyrimidin-2-ylamino)-4-fluorophenyl)-4-methyl-1H-tetrazol-5(4H)-one (compound 85) (85 mg, 51%) as a solid.

$^1$H NMR (300 MHz; d$_6$-DMSO) δ 8.47 (s, 1H), 7.94-7.97 (d, J=8.7 Hz, 1H), 7.81-7.82 (d, J=3.6 Hz, 1H), 7.31-7.35 (d, J=12.3 Hz, 1H), 7.20-7.25 (m, 1H), 4.91-4.95 (t, J=5.7 Hz, 1H), 3.98 (bs, 1H), 3.58 (s, 3H), 3.29 (s, 2H), 2.81 (m, 1H), 0.767-2.21 (m, 22H); $^{19}$F NMR (282 MHz; d$_6$-DMSO) δ −117.8 (s), −166.4 (s); m/z=560 (M+H)$^+$.

Example 69

Synthesis of 1-(5-(4-((7R,8aS)-5,5-dimethyloctahydroindolizin-7-ylamino)-5-fluoropyrimidin-2-ylamino)-4-fluoro-2-(2-hydroxy-2-methylpropoxy)phenyl)-4-methyl-1H-tetrazol-5(4H)-one (Compound 87)

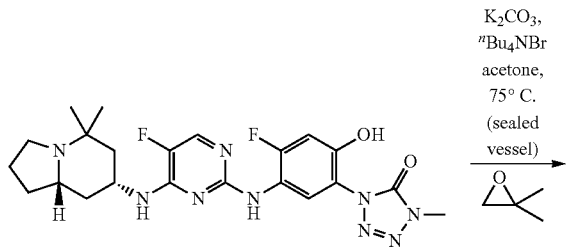

Into a vessel was weighed compound 89 (10.2 g, 20.9 mmol), K$_2$CO$_3$ (3.5 g, 25.1 mmol) and tetra-butylammonium bromide (674 mg, 2.09 mmol). Acetone (100 mL) then isobutylene oxide (5.6 mL, 62.8 mmol) was added and the vessel sealed. The mixture was then heated to a bath temperature of 78° C. for 5 days. The mixture was allowed to cool, then filtered and the filter cake was washed with acetone (2×30 mL). The filtrate was concentrated under vacuum and the residue was partitioned between EtOAc (100 mL) and H$_2$O (100 mL). The aqueous layer was extracted with EtOAc (2×75 mL) and the combined organic extracts were dried (Na$_2$SO$_4$), filtered and the solvent removed under vacuum to leave a crude residue. The residue was dry-loaded on to silica gel and then purified by column chromatography on silica gel using EtOAc/2M NH$_3$ in MeOH (1:0 to 9:1 in increments of 0.02 2M NH$_3$ in MeOH) to give compound 87 (8.0 g, 68%) as a solid. Super-critical fluid chromatography using a chiral stationary phase indicated that the product material contained ~1.2% of an impurity, which may correspond to a regio-isomeric product arising from ring-opening of the epoxide at the more hindered terminus. Also obtained from the column were mixed fractions containing the desired product (~2 g).

$^1$H NMR (300 MHz; d$_6$-DMSO): δ 8.39 (br. s, 1H), 7.91 (d, J=8.4 Hz, 1H), 7.79 (d, J=3.8 Hz, 1H), 7.24 (d, J=12.5 Hz, 1H), 7.18 (br. s, 1H), 4.54 (s, 1H), 4.03-4.90 (m, 1H), 3.71 (s, 2H), 3.58 (s, 3H), 2.83 (br. t, J=8.7 Hz, 1H), 2.24-2.10 (m, 2H), 1.94 (m, 1H), 1.74-1.50 (m, 5H), 1.38 (t, J=12.2 Hz, 1H), 1.24-1.11 (m, 1H), 1.03 (s, 9H), 0.75 (s, 3H); $^{19}$F NMR (287 MHz; d$_6$-DMSO): δ −166.9 (d), −116.2 (s); m/z=560.15 [M+H]$^+$.

Example 70

Synthesis of 1-(5-(4-((7R,8aS)-octahydro-5,5-dimethylindolizin-7-ylamino)-5-fluoropyrimidin-2-ylamino)-4-fluoro-2-(oxetan-3-yloxy)phenyl)-4-methyl-1H-tetrazol-5(4H)-one (Compound 88)

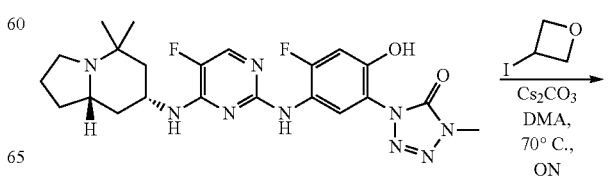

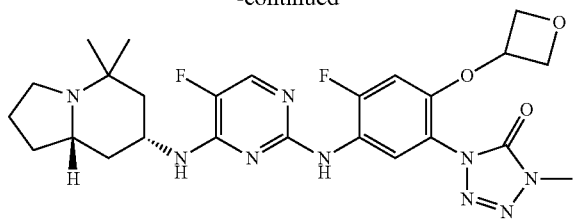

A mixture of 1-(5-(4-((7R,8aS)-octahydro-5,5-dimethylindolizin-7-ylamino)-5-fluoropyrimidin-2-ylamino)-4-fluoro-2-hydroxyphenyl)-4-methyl-1H-tetrazol-5(4H)-one (900 mg, 1.85 mmol, 1 equiv), 3-iodooxetane (1.02 g, 5.54 mmol, 3 equiv), and Cs$_2$CO$_3$ (665 mg, 2.03 mmol, 1.1 equiv) in DMA was heated to 70° C. overnight. After cooling to RT, the reaction mixture was diluted with excess water (200 mL) and EtOAc (200 mL). The layers were separated, and the aqueous layer extracted with EtOAc 3×. The combined organics were dried over Na$_2$SO$_4$, filtered, and concentrated to dryness. The crude product was absorbed onto silica gel and purified by flash chromatography and eluted with DCM: 2M NH$_3$/MeOH=100:0 to 95:5 using 1% 2M NH$_3$/MeOH increments to give compound 88 as a solid.

$^1$H NMR (300 MHz; d$_6$-DMSO) δ 8.44 (s, 1H), 7.90-7.93 (d, 1H, J=8.7 Hz), 7.78-7.79 (d, 1H, J=3.9 Hz), 7.19-7.21 (s, 1H, J=8.1 Hz), 6.95-6.99 (s, 1H, J=12 Hz), 5.28-5.36 (p, 1H, J=5.7 Hz), 4.83-4.88 (m, 2H), 4.39-4.43 (m, 2H), 3.91-4.09 (m, 1H), 3.61 (s, 3H), 2.75-2.99 (m, 1H), 0.974-2.25 (m, 13H), 0.750 (bs, 3H); $^{19}$F NMR (282 MHz; d$_6$-DMSO) δ −115.8 (t), −166.8 (s); m/z=544 (M+H)$^+$.

Example 71

Synthesis of 4-((7R,8aS)-octahydro-5,5-dimethylindolizin-7-ylamino)-2-(5-(4,5-dihydro-4-methyl-5-oxotetrazol-1-yl)-2-fluoro-4-hydroxyl-phenylamino)pyrimidine-5-carbonitrile

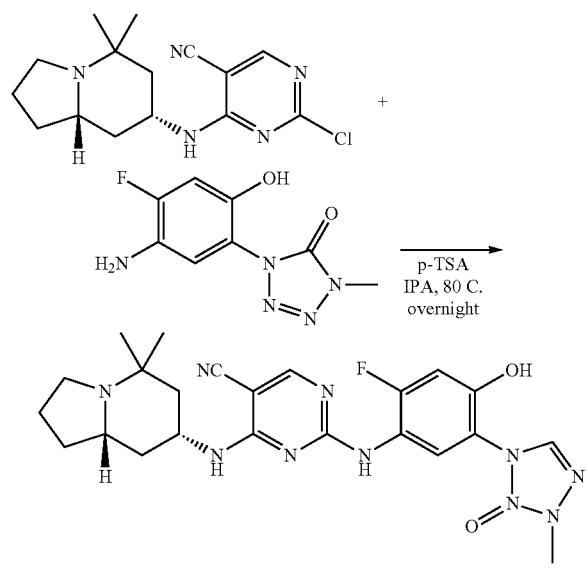

To a mixture of (7R,8aS)—N-(2-chloro-5-cyanopyrimidinal-4-yl)-octahydro-5,5-dimethylindolizin-7-amine (150 mg, 1.0 eq.) in isopropyl alcohol (2.45 ml, 0.2M), 5-(4,5-dihydro-4-methyl-5-oxotetrazol-1-yl)-2-fluoro-4-hydroxylphenyamine (144 mg, 1.3 eq.) was added, followed by p-toluenesulfonic acid (112 mg, 1.2 eq.), and was heated at 80° C. overnight under nitrogen. Upon completion of the reaction indicated by LC/MS, the mixture was cooled to room temperature, and concentrated under reduced pressure. The residue was dissolved into ethyl acetate, absorbed into silica gel and purified by Combi-flash chromatography (2N NH$_3$ in MeOH/EtOAc=0-20%), yield 160 mg of desired product as a light yellow solid.

$^1$H NMR (300 MHz; d$_6$-DMSO) δ 9.24 (bs, 1H), 8.25 (s, 1H), 7.5 (d, J=7.5 Hz, 1H), 7.33 bs, 1H), 6.87 (d, J=11.7 Hz, 1H), 3.57 (s, 3H), 2.82 (bs, 1H), 1.96-1.67 (m, 8H), 1.13 (m, 6H), 0.76 (m, 2H); m/z=495.01 (M+H)$^+$.

Synthesis of 4-((7R,8aS)-octahydro-5,5-dimethylindolizin-7-ylamino)-2-(4-((R)-2-hydroxypropoxy)-2-fluoro-5-(4,5-dihydro-4-methyl-5-oxotetrazol-1-yl)phenylamino)pyrimidine-5-carbonitrile (Compound 90)

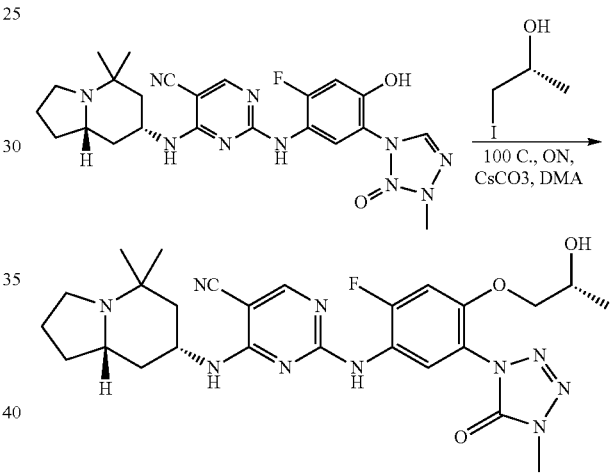

4-((7R,8aS)-octahydro-5,5-dimethylindolizin-7-ylamino)-2-(5-(4,5-dihydro-4-methyl-5-oxotetrazol-1-yl)-2-fluoro-4-hydroxyl-phenylamino)pyrimidine-5-carbonitrile (467 mg, 1.0 eq.) was added to N,N-dimethylacetamide (4.7 ml, 0.2M), followed by Cs$_2$CO$_3$ (922 mg, 3.0 eq.) and 3-iodo-2-(R)-propanol (0.88 g, 5.0 eq.) and heated at 100° C. under nitrogen overnight. It was cooled to room temperature and concentrated under reduced pressure. The residue was treated with ethyl acetate (10 ml) and treated with saturated NaHCO$_3$ (10 ml). The aqueous layer was extracted with ethyl acetate (2×10 ml), and the combined organic solution was washed with brine (10 ml), and dried with Na$_2$SO$_4$. Solid was filtered off, and the organic solution was concentrated under reduced pressure. 5 ml of ethyl acetate was added to the residue, silica gel was added to form a thick paste, and was concentrated under reduced pressure. This silica gel mixture was loaded onto the Combiflash chromatography and product was eluted using 2N NH$_3$ in MeOH (0-20%)/Ethyl Acetate (100%-80%) gradient to yield 124 mg of product as a light beige solid.

$^1$H NMR (300 MHz; d$_6$-DMSO) δ 9.33 (s, 1H), 8.26 (s, 1H), 7.65 (d, J=8.1 Hz, 1H), 7.37 (d, J=7.5 Hz, 1H), 7.3 (d, J=12 Hz, 1H), 4.75 (d, J=4.2 Hz, 1H), 3.97-3.8 (m, 3H), 3.58

(s, 3H), 2.76 (m, 1H), 2.20 (m, 2H), 1.83-1.4 (m, 8H), 1.22-1.07 (m, 2H), 1.03 (m, 6H), 1.0 (bs, 1H); m/z=553.04 (M+H)$^+$.

BIOLOGICAL EXAMPLES

Example 72

PKC Assay

The inhibition of PKC-alpha, PKC-beta, PKC-delta, PKC epsilon and PKC-theta activity is determined via ELISA as follows: NUNC MAXISORP (#436110) or Costar High Binding (#3922) plates are coated with 0.01 mg/ml Neutravidin (Pierce #PI-31000) in 1×PBS (100 µL/well) for 18-24 hours at 4° C. When ready to be used, plates are washed with 1×PBST and then blocked with 2% BSA in 1×PBST (100 µL/well) for a minimum of 1 hour at room temperature. The reactions are conducted in a volume of 60 µL/well. When ready to begin, the plates are washed with 1×PBST to remove the 2% BSA blocking solution. Reaction solution containing the necessary buffer components as well as the appropriate concentrations of ATP and peptide substrate is then added to each well (see Table 3). Appropriate concentrations of test compound is then added—with the volume added should taking into consideration the DMSO tolerance of the kinases being about 0.2%. The reaction is then initiated by the addition of kinase—the approximate final concentration of which is listed in Table 3 (note that this will vary depending on the batch to batch variability in the activity of enzymes). After allowing the reaction to stand at room temperature for 20 minutes, the plates are then washed with 1×PBST.

TABLE 3

| Kinase | Buffer components | [ATP] (uM) | [peptide] (uM) | Time (min) | 1° and 2° antibodies | Notes |
|---|---|---|---|---|---|---|
| PKCs<br>α: ~8 ng/ml<br>β: ~16 ng/ml<br>δ: ~13 ng/ml<br>ε: ~13 ng/ml<br>θ: ~8 ng/ml | 20 mM Hepes pH 7.4<br>5 mM MgCl$_2$<br>0.2 mM CaCl$_2$<br>1 mM DTT<br>0.05% Chaps | 1 µM | 1 µM PKC peptide (biotin-RFARKGSLRQKNV) (Invitrogen #P2760) | 20 min | Rabbit pSer PKC substrate Ab (Cell Signaling #2261); HRP-goat a-rabbit (Jackson Immunoresearch #111-035-003) | 0.15 mg/ml DAG (Sigma #D0138) 0.75 mg/ml Phosphoserine (Sigma #P6641) DMSO tolerance ~0.2% |

After removal of the reaction mixture from the plate and washing with 1×PBST, an antibody developing solution containing a 1:10,000 dilution of the appropriate primary and secondary antibodies (Table 3) in a 0.1% BSA solution in 1×PBST is then added to each well (100 µL/well). This is then allowed to stand at room temperature for a minimum of 1 hour. After this time, the plates are once again washed with 1×PBST. The SuperSignal ELISA Pico Chemiluminescent substrate (Pierce #PI-37069) is then added (100 µL/well) and the plate is read on a luminescence plate reader.

Example 73

PKC Assay

Alternatively, the inhibition of PKC activity is measured by monitoring the production of phosphorylated peptide by fluorescence polarization at different concentrations of the inhibitor. Reactions are carried out in 96-well plate format with a total volume of 20 µL containing 20 mM HEPES, pH 7.4, 5 mM MgCl$_2$, 0.2 mM CaCl$_2$, 1 mM DTT, 0.02% Brij-35, 0.1 mg/ml phosphatidylserine, 0.02 mg/ml dioleoyl-sn-glycerol and 5 µM each of ATP and the peptide substrate. Compounds are first diluted serially in DMSO and then transferred to a solution containing the above concentrations of HEPES, MgCl$_2$, CaCl$_2$, DTT, and Brij-35 to yield 5× compound solutions in 2% DMSO, which is then added to the reaction solution. Reactions are initiated by the addition of PKC at a typical concentration as described in Table 4, and then allowed to incubate at room temperature for 20 minutes. At the end of this time, a combination of quench (EDTA) and detection (peptide tracer and antibody) reagents is added using the protocol of Invitrogen P2748. After a 30 minutes period of incubation, the amount of phosphorylated peptide generated is measured by fluorescence polarization (Ex=485 nm, Em=535 nm) using a Tecan Polarian instrument.

TABLE 4

| | Peptide substrate | SEQ ID | Enzyme source | Typical enzyme concentration |
|---|---|---|---|---|
| PKC theta | RFARKGSLRQ KNV | Seq ID No. 1 | Upstate Biotechnologies, Temecula, CA, cat. #14-444 | 40 ng/ml |
| PKC epsilon | RFARKGSLRQ KNV | Seq ID No. 1 | Upstate Biotechnologies, Temecula, CA, cat. #14-518 | 50 ng/ml |

Example 74

Calcium Influx

HEK-FLPTREX cells are stably transfected with pcDNA5/FRT/TO+hTRPV4a, rat TRPV1-HA or rTRPA1-HA are grown in Dulbecco's Modified Eagle's Medium (DMEM) containing 10% tetracycline-free fetal bovine serum, hygromycin (50 µg/ml) and blasticidin (10 µg/ml). Cells are treated with tetracycline (0.1 µg/ml, 20 h) to induce TRP expression. DRG from thoracic and lumbar spinal cord of rats or mice are minced in cold Hank's Balanced Salt Solution (HBSS) and incubated for 60 at 37° C. in DMEM containing 1 mg/ml of collagenase type IA and 0.1 mg/ml of DNAse type IV, pelleted and incubated with 0.25% trypsin for 30 minutes. Neurons are pelleted, suspended in DMEM containing 10% fetal bovine serum, 10% horse serum, 100 U/ml penicillin, 0.1 mg/ml streptomycin, 2 mM glutamine, dissociated by gentle trituration until the solution appears cloudy and homogeneous and plated on glass coverslips coated with PolyOnitine/laminin. Neurons are cultured for 3-4 days before the experiment.

Cells grown on coverslips or on a 96 multiwell plate are incubated in HBSS (pH 7.4) containing Ca2+ and Mg2+, 20 mM HEPES buffer, 0.1% BSA, 100 U/ml penicillin, 100 µg/ml streptomycin, with 2.5-5 µM Fura-2AM (Invitrogen) for 20-45 minutes at 37° C. Cells are washed and fluorescence is measured at 340 nm and 380 nm excitation and 510 nm emission in a F-2500 spectrophotometer, or in a Flexstation 3 Microplate Reader III (for the measurement of the calcium in the cell population) or using a Zeiss Axiovert microscope, an ICCD video camera and a video microscopy acquisition program (for the measurement of the calcium influx in the single neurons). Substances are injected directly into the chamber (20 ml into 2 ml, for the spectrophotometer; 20 ml in 200 ml for the Flexstation, 50 ml in 350 ml in the chamber for the single cells).

Example 75

In Vivo Hyperplasia

Mechanical pain is quantified as the number of times the hind paw is withdrawn in response to 5 applications of a 0.173 mN von Frey hair. Responses are expressed as a percentage (e.g. 3 withdrawals out of 5 are recorded as 60%) and mechanical hyperalgesia defined as increase in the percentage of withdrawal compared to basal measurement. 2) Mechanical pain is quantified using the 'up-down paradigm', determining the 50% response threshold to the von Frey filaments applied to the mid-plantar surface for 5 s or until a withdrawal response occurred. Von Frey filaments are in this range of intensities: 1.65, 2.44, 2.83, 3.22, 3.61, 3.84, 4.08.

Thermal hyperalgesia is assessed in mice using a plantar test apparatus and quantified as the latency of paw withdrawal to a radiant heat. Thermal hyperalgesia is defined as a decrease in the withdrawal latency compared to the basal measurement. After measuring basal level mice, under light halothane anesthesia (5%), are injected with testing compound into the left or right paws (5-10 µl intraplantar injection) and paw withdrawal measurements repeated at different time point. To assess PAR2 TRPV1, TRPV4 and TRPA1 mediated hyperalgesia and potentiation of TRPV-mediated responses, mice are treated with PAR2-AP for 15 minutes followed by capsaicin, 4αPDD or HNE. To assess the role of protein kinases, the antagonists or the corresponding vehicles are injected 20-30 minutes before the challenge with agonists. The effects induced by the different treatments are evaluated within the same rat comparing the responses recorded in the right paw (receiving for example saline, or vehicle) with the responses obtained in the left paw (receiving for example PAR2-AP or 4αPDD).

Formalin induced hyperalgeisa is assessed using 5% solution of formalin administered by intradermal injection into the dorsal surface of the mouse or rat forepaw to induce a painful behavior. Pain is accessed on a four-level scale related to posture: 0, normal posture; 1, with the injected paw remaining on the ground but not supporting the animal; 2, with the injected paw clearly raised; and 3, with the injected paw being licked, nibbled, or shaken. Animals are observed and scored for behavior at 3 minutes after the injection (defined as initial phase that results from the direct stimulation of nociceptors), and then at 30-60 minutes after the injection (defined as second phase that involves a period of sensitization during which inflammatory phenomena occur). The nociceptive behavioral score for each 3-minutes interval is calculated as the weighted average of the number of seconds spent in each behavior. 2.5% solution of formalin is administered by intraplantar injection and thermal and mechanical pain measured as described above after 30-60 minutes. To assess the role of protein kinases, antagonists or their vehicles (control) are injected into the right paws 20-30 minutes before formalin. Nociceptive behavior will be scored for each rats and compared to control.

Exemplary compounds exhibited in vivo activity in one or more disease models. For example Compound 17 had an ED50 of 30 mg/kg in both pretreatment and treatment dosing in an PLP induced experimental autoimmune encephalomyelitis (EAE) model in SJL mice. As is known to those of skill in the art, EAE is considered to be a model of multiple sclerosis in humans. Other exemplary compounds demonstrated in vivo efficacy in rodents in contact dermatitis and/or adjuvant induced arthritis models.

Example 76

IL-2 ELISA, Human Primary T Cell, Anti CD3+CD28+

Compounds 1-90 were tested in a whole cell functional assay for PKC mediated IL-2 production as follows. Human primary T cell isolation and culture: Human primary T cells were prepared as follows. Whole blood was obtained from a healthy volunteer, mixed 1:1 with PBS, layered on to Ficoll Hypaque (Amersham Pharmacia Biotech, Piscataway, N.J., Catalog #17-1440-03) in 2:1 blood/PBS:ficoll ratio and centrifuged for 30 minutes at 4° C. at 1750 rpm. The cells at the serum: ficoll interface were recovered and washed twice with 5 volumes of PBS. These freshly isolated human peripheral blood mononuclear cells were cultured in Yssel's medium containing 40 U/ml IL2 in a flask pre-coated with 1 µg/ml αCD3 and 5 µg/ml αCD28 (Anti-Human CD3, BD Pharmingen Catalog #555336, Anti-Human CD28, Beckman Coulter Catalog #IM1376). The cells were stimulated for 3-4 days, then transferred to a fresh flask and maintained in RPMI (RPMI-1640 with L-Glutamine; Mediatech, Inc., Herndon Va., cat. #10-040-CM) with 10% FBS and 40 U/ml IL-2. The primary T-cells were then washed twice with PBS to remove the IL-2.

Primary T cell stimulation and IL2 ELISA: Human primary T cells (100,000 cells per well) were pre-incubated with or without test compound in Yssel's medium for 1 hour at 37° C. Cells were then stimulated by transferring them to round-bottom 96-well plates pre-coated with 1 µg/ml αCD3 and 5 µg/ml αCD28. For counter assay, cells were instead stimulated by adding 8× stock solutions of PMA and ionomycin in Yssels (for final concentrations of 0.5 ng/ml PMA and 0.1 uM ionomycin, both from Calbiochem). Cells were incubated at 37° C. for 24 hours before 100 µL supernatants were harvested for quantification of IL-2 by ELISA using Human IL-2 Duoset ELISA Kit from R and D Systems, Cat. #DY202E. Compounds 1-90 blocked IL-2 production with an EC50 of less than 10 micromolar.

Table 5 shows the EC50 values of Compounds 1-90 according to the above assay. In Table 5, an EC50 of A is less than 0.1 µM, B<0.5 µM, C<1 µM, D<10 µM, and E>10 µM.

TABLE 5

| Compound | EC50 (µM) |
| --- | --- |
| 1 | B |
| 2 | A |
| 3 | C |
| 4 | D |
| 5 | B |

TABLE 5-continued

| Compound | EC50 (µM) |
|---|---|
| 6 | B |
| 7 | D |
| 8 | C |
| 9 | B |
| 10 | B |
| 11 | D |
| 12 | C |
| 13 | A |
| 14 | A |
| 15 | B |
| 16 | A |
| 17 | A |
| 18 | C |
| 19 | C |
| 20 | D |
| 21 | D |
| 22 | B |
| 23) | A |
| 24 | B |
| 25 | D |
| 26 | D |
| 27 | D |
| 28 | A |
| 29 | D |
| 30 | E |
| 31 | D |
| 32 | D |
| 33 | D |
| 34 | D |
| 35 | D |
| 36 | D |
| 37 | D |
| 38 | B |
| 39 | B |
| 40 | A |
| 41 | B |
| 42 | D |
| 43 | D |
| 44 | D |
| 45 | D |
| 46 | C |
| 47 | A |
| 48 | A |
| 49 | A |
| 50 | A |
| 51 | B |
| 52 | B |
| 53 | A |
| 54 | A |
| 55 | B |
| 56 | A |
| 57 | B |
| 58 | D |
| 59 | B |
| 60 | B |
| 61 | C |
| 62 | B |
| 63 | B |
| 64 | B |
| 65 | D |
| 66 | A |
| 67 | B |
| 68 | B |
| 69 | C |
| 70 | D |
| 71 | C |
| 72 | C |
| 73 | B |
| 74 | B |
| 75 | B |
| 76 | A |
| 77 | A |
| 78 | A |
| 79 | A |
| 80 | A |
| 81 | A |
| 82 | A |
| 83 | A |
| 84 | B |
| 85 | B |
| 86 | A |
| 87 | A |
| 88 | B |
| 89 | D |
| 90 | A |

While the present invention has been described with reference to the specific embodiments thereof, it should be understood by those skilled in the art that various changes may be made and equivalents may be substituted without departing from the true spirit and scope of the invention. In addition, many modifications may be made to adapt a particular situation, material, composition of matter, process, process step or steps, to the objective, spirit and scope of the present invention. All such modifications are intended to be within the scope of the claims appended hereto.

What is claimed is:

1. A compound selected from:
   Compound 77: 1-(2-(2-hydroxyethoxy)-5-(4-((7R,8aS)-octahydro-5,5-dimethylindolizin-7-ylamino)-5-fluoropyrimidin-2-ylamino)-4-fluorophenyl)-4-methyl-1H-tetrazol-5(4H)-one;
   Compound 78: 4-((7R,8aS)-octahydro-5,5-dimethylindolizin-7-ylamino)-2-(4-(2-hydroxyethoxy)-2-fluoro-5-(4,5-dihydro-4-methyl-5-oxotetrazol-1-yl)phenylamino)pyrimidine-5-carbonitrile;
   Compound 79: 4-((7R,8aS)-octahydro-5,5-dimethylindolizin-7-ylamino)-2-(4-((S)-2-hydroxypropoxy)-2-fluoro-5-(4,5-dihydro-4-methyl-5-oxotetrazol-1-yl)phenylamino)pyrimidine-5-carbonitrile;
   Compound 80: 4-((7R,8aS)-octahydro-5,5-dimethylindolizin-7-ylamino)-2-(4-(2-hydroxy-2-methylpropoxy)-2-fluoro-5-(4,5-dihydro-4-methyl-5-oxotetrazol-1-yl)phenylamino)pyrimidine-5-carbonitrile;
   Compound 81: 1-(2-((S)-2-hydroxypropoxy)-5-(4-((7R,8aS)-octahydro-5,5-dimethylindolizin-7-ylamino)-5-fluoropyrimidin-2-ylamino)-4-fluorophenyl)-4-methyl-1H-tetrazol-5(4H)-one;
   Compound 82: 1-(5-(4-((7R,8aS)-5,5-dimethyloctahydroindolizin-7-ylamino)-5-fluoropyrimidin-2-ylamino)-4-fluoro-2-((R)-2-hydroxypropoxy)phenyl)-4-methyl-1H-tetrazol-5(4H)-one;
   Compound 83: 4-((7R,8aS)-octahydro-5,5-dimethylindolizin-7-ylamino)-2-(4-(1-hydroxy-2-methylpropan-2-yloxy)-3-(4,5-dihydro-4-methyl-5-oxotetrazol-1-yl)phenylamino)pyrimidine-5-carbonitrile;
   Compound 84: 4-((7R,8aS)-5,5-dimethyloctahydroindolizin-7-ylamino)-2-(2-fluoro-4-(1-hydroxy-2-methylpropan-2-yloxy)-5-(4-methyl-5-oxo-4,5-dihydro-1H-tetrazol-1-yl)phenylamino)pyrimidine-5-carbonitrile;
   Compound 85: 1-(5-(4-((7R,8aS)-5,5-dimethyloctahydroindolizin-7-ylamino)-5-fluoropyrimidin-2-ylamino)-4-fluoro-2-(1-hydroxy-2-methylpropan-2-yloxy)phenyl)-4-methyl-1H-tetrazol-5(4H)-one;
   Compound 86: 1-(5-(4-((7R,8aS)-5,5-dimethyloctahydroindolizin-7-ylamino)-5-fluoropyrimidin-2-ylamino)-2-(1-hydroxy-2-methylpropan-2-yloxy)phenyl)-4-methyl-1H-tetrazol-5(4H)-one;
   Compound 87: 1-(5-(4-((7R,8aS)-5,5-dimethyloctahydroindolizin-7-ylamino)-5-fluoropyrimidin-2-ylamino)-4-fluoro-2-(2-hydroxy-2-methylpropoxy)phenyl)-4-methyl-1H-tetrazol-5(4H)-one; and
   Compound 90: 4-((7R,8aS)-octahydro-5,5-dimethylindolizin-7-ylamino)-2-(4-((R)-2-hydroxypropoxy)-2-fluoro-5-(4,5-dihydro-4-methyl-5-oxotetrazol-1-yl)phenylamino)pyrimindine-5-carbonitrile.

2. The compound of claim 1, wherein the compound is 1-(2-(2-hydroxyethoxy)-5-(4-((7R,8aS)-octahydro-5,5-dimethylindolizin-7-ylamino)-5-fluoropyrimidin-2-ylamino)-4-fluorophenyl)-4-methyl-1H-tetrazol-5(4H)-one (Compound 77).

3. The compound of claim 1, wherein the compound is 4-((7R,8aS)-octahydro-5,5-dimethylindolizin-7-ylamino)-2-(4-(2-hydroxyethoxy)-2-fluoro-5-(4,5-dihydro-4-methyl-5-oxotetrazol-1-yl)phenylamino)pyrimidine-5-carbonitrile (Compound 78).

4. The compound of claim 1, wherein the compound is 4-((7R,8aS)-octahydro-5,5-dimethylindolizin-7-ylamino)-2-(4-((S)-2-hydroxypropoxy)-2-fluoro-5-(4,5-dihydro-4-methyl-5-oxotetrazol-1-yl)phenylamino)pyrimidine-5-carbonitrile (Compound 79).

5. The compound of claim 1, wherein the compound is 4-((7R,8aS)-octahydro-5,5-dimethylindolizin-7-ylamino)-2-(4-(2-hydroxy-2-methylpropoxy)-2-fluoro-5-(4,5-dihydro-4-methyl-5-oxotetrazol-1-yl)phenylamino)pyrimidine-5-carbonitrile (Compound 80).

6. The compound of claim 1, wherein the compound is 1-(2-((S)-2-hydroxypropoxy)-5-(4-((7R,8aS)-octahydro-5,5-dimethylindolizin-7-ylamino)-5-fluoropyrimidin-2-ylamino)-4-fluorophenyl)-4-methyl-1H-tetrazol-5 (4H)-one (Compound 81).

7. The compound of claim 1, wherein the compound is 1-(5-(4-((7R,8aS)-5,5-dimethyloctahydroindolizin-7-ylamino)-5-fluoropyrimidin-2-ylamino)-4-fluoro-2-((R)-2-hydroxypropoxy)phenyl)-4-methyl-1H-tetrazol-5(4H)-one (Compound 82).

8. The compound of claim 1, wherein the compound is 4-((7R,8aS)-octahydro-5,5-dimethylindolizin-7-ylamino)-2-(4-(1-hydroxy-2-methylpropan-2-yloxy)-3-(4,5-dihydro-4-methyl-5-oxotetrazol-1-yl)phenylamino)pyrimidine-5-carbonitrile (Compound 83).

9. The compound of claim 1, wherein the compound is 4-((7R,8aS)-5,5-dimethyloctahydroindolizin-7-ylamino)-2-(2-fluoro-4-(1-hydroxy-2-methylpropan-2-yloxy)-5-(4-methyl-5-oxo-4,5-dihydro-1H-tetrazol-1-yl)phenylamino)pyrimidine-5-carbonitrile (Compound 84).

10. The compound of claim 1, wherein the compound is 1-(5-(4-((7R,8aS)-5,5-dimethyloctahydroindolizin-7-ylamino)-5-fluoropyrimidin-2-ylamino)-4-fluoro-2-(1-hydroxy-2-methylpropan-2-yloxy)phenyl)-4-methyl-1H-tetrazol-5(4H)-one (Compound 85).

11. The compound of claim 1, wherein the compound is 1-(5-(4-((7R,8aS)-5,5-dimethyloctahydroindolizin-7-ylamino)-5-fluoropyrimidin-2-ylamino)-2-(1-hydroxy-2-methylpropan-2-yloxy)phenyl)-4-methyl-1H-tetrazol-5 (4H)-one (Compound 86).

12. The compound of claim 1, wherein the compound is 1-(5-(4-((7R,8aS)-5,5-dimethyloctahydroindolizin-7-ylamino)-5-fluoropyrimidin-2-ylamino)-4-fluoro-2-(2-hydroxy-2-methylpropoxy)phenyl)-4-methyl-1H-tetrazol-5 (4H)-one (Compound 87).

13. The compound of claim 1, wherein the compound is 4-((7R,8aS)-octahydro-5,5-dimethylindolizin-7-ylamino)-2-(4-((R)-2-hydroxypropoxy)-2-fluoro-5-(4,5-dihydro-4-methyl-5-oxotetrazol-1-yl)phenylamino)pyrimindine-5-carbonitrile (Compound 90).

14. A pharmaceutical composition comprising a compound of claim 1 and a pharmaceutically acceptable carrier.

15. A compound selected from:
   Compound 88: 1-(5-(4-((7R,8aS)-octahydro-5,5-dimethylindolizin-7-ylamino)-5-fluoropyrimidin-2-ylamino)-4-fluoro-2-(oxetan-3-yloxy)phenyl)-4-methyl-1H-tetrazol-5(4H)-one; and
   Compound 89: 1-(5-(4-((7R,8aS)-5,5-dimethyloctahydroindolizin-7-ylamino)-5-fluoropyrimidin-2-ylamino)-4-fluoro-2-hydroxyphenyl)-4-methyl-1H-tetrazol-5(4H)-one.

16. The compound of claim 15, wherein the compound is 1-(5-(4-((7R,8aS)-octahydro-5,5-dimethylindolizin-7-ylamino)-5-fluoropyrimidin-2-ylamino)-4-fluoro-2-(oxetan-3-yloxy)phenyl)-4-methyl-1H-tetrazol-5(4H)-one (Compound 88).

17. A pharmaceutical composition comprising a compound of claim 15 and a pharmaceutically acceptable carrier.

* * * * *